US00RE47996E

(19) United States
(12) Reissued Patent
Turner et al.

(10) Patent Number: US RE47,996 E
(45) Date of Reissued Patent: *May 19, 2020

(54) SURGICAL GENERATOR FOR ULTRASONIC AND ELECTROSURGICAL DEVICES

(71) Applicant: Ethicon LLC, Guaynabo, PR (US)

(72) Inventors: Douglas J. Turner, Cincinnati, OH (US); Jeffrey L. Aldridge, Lebanon, OH (US); Vincent P. Battaglia, Jr., Lebanon, OH (US)

(73) Assignee: Ethicon LLC, Guaynabo, PR (US)

( * ) Notice: This patent is subject to a terminal disclaimer.

(21) Appl. No.: 15/795,156

(22) Filed: Oct. 26, 2017

Related U.S. Patent Documents

Reissue of:
(64) Patent No.: 9,168,054
Issued: Oct. 27, 2015
Appl. No.: 13/448,175
Filed: Apr. 16, 2012

U.S. Applications:
(63) Continuation-in-part of application No. 13/251,766, filed on Oct. 3, 2011, now Pat. No. 10,441,345, which
(Continued)

(51) Int. Cl.
*A61H 1/00* (2006.01)
*A61B 17/32* (2006.01)
(Continued)

(52) U.S. Cl.
CPC ..... *A61N 1/08* (2013.01); *A61B 18/1206* (2013.01); *A61N 7/00* (2013.01); *H01H 1/00* (2013.01); *H03M 11/24* (2013.01); *A61B 18/1233* (2013.01); *A61B 18/14* (2013.01); *A61B 18/1445* (2013.01); *A61B 2017/00154* (2013.01); *A61B 2017/00477* (2013.01); *A61B 2017/00486* (2013.01);
(Continued)

(58) Field of Classification Search
None
See application file for complete search history.

(56) References Cited

U.S. PATENT DOCUMENTS 969,528 A 9/1910 Disbrow
1,570,025 A 1/1926 Young
(Continued)

FOREIGN PATENT DOCUMENTS

AU 2003241752 A1 9/2003
CA 2535467 A1 4/1993
(Continued)

OTHER PUBLICATIONS

Incropera el al., "Fundamentals of Heat and Mass Transfer", Wiley, New York (1990). (Book—not attached).
(Continued)

*Primary Examiner* — Robert L Nasser

(57) ABSTRACT

A control circuit of a surgical device is disclosed. The control circuit includes a first circuit portion coupled to at least one switch operable between an open state and a closed state. The first circuit portion communicates with a surgical generator over a conductor pair to receive a control signal to determine a state of the at least one switch.

28 Claims, 77 Drawing Sheets

Related U.S. Application Data is a continuation-in-part of application No. 12/896,360, filed on Oct. 1, 2010, now Pat. No. 9,060,775.

(60) Provisional application No. 61/250,217, filed on Oct. 9, 2009.

(51) Int. Cl.

| | |
|---|---|
| ***A61B 18/12*** | (2006.01) |
| ***A61B 18/14*** | (2006.01) |
| ***A61B 17/00*** | (2006.01) |
| ***A61B 17/29*** | (2006.01) |
| ***A61B 18/00*** | (2006.01) |
| ***A61N 1/08*** | (2006.01) |
| ***A61N 7/00*** | (2006.01) |
| ***H01H 1/00*** | (2006.01) |
| ***H03M 11/24*** | (2006.01) |

(52) U.S. Cl.

CPC ..... *A61B 2017/00973* (2013.01); *A61B 2017/2933* (2013.01); *A61B 2017/2934* (2013.01); *A61B 2017/2936* (2013.01); *A61B 2017/320069* (2017.08); *A61B 2017/320093* (2017.08); *A61B 2017/320094* (2017.08); *A61B 2017/320095* (2017.08); *A61B 2018/00178* (2013.01); *A61B 2018/00666* (2013.01); *A61B 2018/00678* (2013.01); *A61B 2018/00714* (2013.01); *A61B 2018/00779* (2013.01); *A61B 2018/00791* (2013.01); *A61B 2018/00875* (2013.01); *A61B 2018/00988* (2013.01); *A61B 2018/00994* (2013.01); *A61B 2018/1273* (2013.01); *H01H 2239/012* (2013.01)

(56) References Cited

U.S. PATENT DOCUMENTS

| | | | |
|---|---|---|---|
| 1,813,902 | A | 7/1931 | Bovie |
| 2,188,497 | A | 1/1940 | Calva |
| 2,425,245 | A | 8/1947 | Johnson |
| 2,597,564 | A | 8/1947 | Bugg |
| 2,442,966 | A | 6/1948 | Wallace |
| 2,704,333 | A | 3/1955 | Calosi et al. |
| 2,736,960 | A | 3/1956 | Armstrong |
| 2,748,967 | A | 6/1956 | Roach |
| 2,845,072 | A | 7/1958 | Shafer |
| 2,849,788 | A | 9/1958 | Creek |
| 2,874,470 | A | 2/1959 | Richards |
| 2,990,616 | A | 7/1961 | Balamuth et al. |
| RE25,033 | E | 8/1961 | Balamuth et al. |
| 3,015,961 | A | 1/1962 | Roney |
| 3,033,407 | A | 5/1962 | Alfons |
| 3,053,124 | A | 9/1962 | Balamuth et al. |
| 3,082,805 | A | 3/1963 | Royce |
| 3,432,691 | A | 3/1969 | Shoh |
| 3,433,226 | A | 3/1969 | Boyd |
| 3,489,930 | A | 1/1970 | Shoh |
| 3,513,848 | A | 5/1970 | Winston et al. |
| 3,514,856 | A | 6/1970 | Camp et al. |
| 3,526,219 | A | 9/1970 | Balamuth |
| 3,554,198 | A | 1/1971 | Tatoian et al. |
| 3,606,682 | A | 9/1971 | Camp et al. |
| 3,614,484 | A | 10/1971 | Shoh |
| 3,616,375 | A | 10/1971 | Inoue |
| 3,629,726 | A | 12/1971 | Popescu |
| 3,636,943 | A | 1/1972 | Balamuth |
| 3,668,486 | A | 6/1972 | Silver |
| 3,702,948 | A | 11/1972 | Balamuth |
| 3,776,238 | A | 12/1973 | Peyman et al. |
| 3,805,787 | A | 4/1974 | Banko |
| 3,809,977 | A | 5/1974 | Balamuth et al. |
| 3,830,098 | A | 8/1974 | Antonevich |
| 3,854,737 | A | 12/1974 | Gilliam, Sr. |
| 3,862,630 | A | 1/1975 | Balamuth |
| 3,875,945 | A | 4/1975 | Friedman |
| 3,885,438 | A | 5/1975 | Harris, Sr. et al. |
| 3,900,823 | A | 8/1975 | Sokal et al. |
| 3,918,442 | A | 11/1975 | Nikolaev et al. |
| 3,924,335 | A | 12/1975 | Balamuth et al. |
| 3,946,738 | A | 3/1976 | Newton et al. |
| 3,955,859 | A | 5/1976 | Stella et al. |
| 3,956,826 | A | 5/1976 | Perdreaux, Jr. |
| 4,012,647 | A | 3/1977 | Balamuth et al. |
| 4,074,719 | A | 2/1978 | Semm |
| 4,156,187 | A | 5/1979 | Murry et al. |
| 4,167,944 | A | 9/1979 | Banko |
| 4,188,927 | A | 2/1980 | Harris |
| 4,200,106 | A | 4/1980 | Douvas et al. |
| 4,203,444 | A | 5/1980 | Bonnell et al. |
| 4,300,083 | A | 11/1981 | Heiges |
| 4,302,728 | A | 11/1981 | Nakamura |
| 4,306,570 | A | 12/1981 | Matthews |
| 4,445,063 | A | 4/1984 | Smith |
| 4,491,132 | A | 1/1985 | Aikins |
| 4,494,759 | A | 1/1985 | Kieffer |
| 4,504,264 | A | 3/1985 | Kelman |
| 4,512,344 | A | 4/1985 | Barber |
| 4,526,571 | A | 7/1985 | Wuchinich |
| 4,541,638 | A | 9/1985 | Ogawa et al. |
| 4,545,374 | A | 10/1985 | Jacobson |
| 4,574,615 | A | 3/1986 | Bower et al. |
| 4,617,927 | A | 10/1986 | Manes |
| 4,633,119 | A | 12/1986 | Thompson |
| 4,634,420 | A | 1/1987 | Spinosa et al. |
| 4,640,279 | A | 2/1987 | Beard |
| 4,641,053 | A | 2/1987 | Takeda |
| 4,646,738 | A | 3/1987 | Trott |
| 4,646,756 | A | 3/1987 | Watmough et al. |
| 4,649,919 | A | 3/1987 | Thimsen et al. |
| 4,662,068 | A | 5/1987 | Polonsky |
| 4,674,502 | A | 6/1987 | Imonti |
| 4,708,127 | A | 11/1987 | Abdelghani |
| 4,712,722 | A | 12/1987 | Hood et al. |
| 4,808,154 | A | 2/1989 | Freeman |
| 4,819,635 | A | 4/1989 | Shapiro |
| 4,827,911 | A | 5/1989 | Broadwin et al. |
| 4,832,683 | A | 5/1989 | Idemoto et al. |
| 4,836,186 | A | 6/1989 | Scholz |
| 4,838,853 | A | 6/1989 | Parisi |
| 4,844,064 | A | 7/1989 | Thimsen et al. |
| 4,850,354 | A | 7/1989 | McGurk-Burleson et al. |
| 4,852,578 | A | 8/1989 | Companion et al. |
| 4,860,745 | A | 8/1989 | Farin et al. |
| 4,862,890 | A | 9/1989 | Stasz et al. |
| 4,865,159 | A | 9/1989 | Jamison |
| 4,867,157 | A | 9/1989 | McGurk-Burleson et al. |
| 4,831,550 | A | 11/1989 | Kothe |
| 4,878,493 | A | 11/1989 | Pasternak et al. |
| 4,896,009 | A | 1/1990 | Pawlowski |
| 4,903,696 | A | 2/1990 | Stasz |
| 4,915,643 | A | 4/1990 | Samejima et al. |
| 4,922,902 | A | 5/1990 | Wuchinich et al. |
| 4,965,532 | A | 10/1990 | Sakurai |
| 4,979,952 | A | 12/1990 | Kubota et al. |
| 4,981,756 | A | 1/1991 | Rhandhawa |
| 5,013,956 | A | 5/1991 | Kurozumi et al. |
| 5,015,227 | A | 5/1991 | Broadwin et al. |
| 5,026,370 | A | 6/1991 | Lottick |
| 5,026,387 | A | 6/1991 | Thomas |
| 5,035,695 | A | 7/1991 | Weber, Jr. et al. |
| 5,042,707 | A | 8/1991 | Taheri |
| 5,084,052 | A | 1/1992 | Jacobs |
| 5,105,117 | A | 4/1992 | Yamaguchi |
| 5,109,819 | A | 5/1992 | Custer et al. |
| 5,112,300 | A | 5/1992 | Ureche |
| 5,123,903 | A | 6/1992 | Quaid et al. |
| 5,126,618 | A | 6/1992 | Takahashi et al. |
| D327,872 | S | 7/1992 | McMills et al. |
| 5,152,762 | A | 10/1992 | McElhenney |
| 5,162,044 | A | 11/1992 | Gahn et al. |
| 5,163,421 | A | 11/1992 | Bernstein et al. |

(56) References Cited

U.S. PATENT DOCUMENTS 5,163,537 A 11/1992 Radev
5,167,725 A 12/1992 Clark et al.
5,172,344 A 12/1992 Ehrlich
5,174,276 A 12/1992 Crockard
D332,660 S 1/1993 Rawson et al.
5,176,677 A 1/1993 Wuchinich
5,176,695 A 1/1993 Dulebohn
5,184,605 A 2/1993 Grzeszykowski
5,188,102 A 2/1993 Idemoto et al.
D334,173 S 3/1993 Liu et al.
5,209,719 A 5/1993 Baruch et al.
5,213,569 A 5/1993 Davis
5,214,339 A 5/1993 Naito
5,218,529 A 6/1993 Meyer et al.
5,221,282 A 6/1993 Wuchinich
5,222,937 A 6/1993 Kagawa
5,226,909 A 7/1993 Evans et al.
5,226,910 A 7/1993 Kajiyama et al.
5,241,236 A 8/1993 Sasaki et al.
5,241,968 A 9/1993 Slater
5,242,460 A 9/1993 Klein et al.
5,254,129 A 10/1993 Alexander
5,257,988 A 11/1993 L'Esperance, Jr.
5,261,922 A 11/1993 Hood
5,263,957 A 11/1993 Davison
5,264,925 A 11/1993 Shipp et al.
5,275,166 A 1/1994 Vaitekunas et al.
5,275,607 A 1/1994 Lo et al.
5,275,609 A 1/1994 Pingleton et al.
5,282,800 A 2/1994 Foshee et al.
5,282,817 A 2/1994 Hoogeboom et al.
5,285,795 A 2/1994 Ryan et al.
5,300,068 A 4/1994 Rosar et al.
5,304,115 A 4/1994 Pflueger et al.
D347,474 S 5/1994 Olson
5,307,976 A 5/1994 Olson et al.
5,312,023 A 5/1994 Green et al.
5,312,425 A 5/1994 Evans et al.
5,322,055 A 6/1994 Davison et al.
5,324,299 A 6/1994 Davison et al.
5,326,013 A 7/1994 Green et al.
5,326,342 A 7/1994 Pflueger et al.
5,344,420 A 9/1994 Hilal et al.
5,345,937 A 9/1994 Middleman et al.
5,346,502 A 9/1994 Estabrook et al.
5,353,474 A 10/1994 Good et al.
5,357,164 A 10/1994 Imabayashi et al.
5,357,423 A 10/1994 Weaver et al.
5,359,994 A 11/1994 Krauter et al.
5,366,466 A 11/1994 Christian et al.
5,368,557 A 11/1994 Nita et al.
5,370,645 A 12/1994 Klicek et al.
5,371,429 A 12/1994 Manna
5,374,813 A 12/1994 Shipp
D354,564 S 1/1995 Medema
5,381,067 A 1/1995 Greenstein et al.
5,387,215 A 2/1995 Fisher
5,389,098 A 2/1995 Tsuruta et al.
5,394,187 A 2/1995 Shipp
5,396,266 A 3/1995 Brimhall
5,403,312 A 4/1995 Yates et al.
5,403,334 A 4/1995 Evans et al.
5,408,268 A 4/1995 Shipp
D358,887 S 5/1995 Feinberg
5,411,481 A 5/1995 Allen et al.
5,419,761 A 5/1995 Narayanan et al.
5,421,829 A 6/1995 Olichney et al.
5,423,844 A 6/1995 Miller
5,438,997 A 8/1995 Sieben et al.
5,445,639 A 8/1995 Kuslich et al.
5,449,370 A 9/1995 Vaitekunas
5,451,161 A * 9/1995 Sharp ..... A61B 17/32006 433/119
5,451,220 A 9/1995 Ciervo
5,456,684 A 10/1995 Schmidt et al.
5,471,988 A 12/1995 Fujio et al.
5,472,443 A 12/1995 Cordis et al.
5,478,003 A 12/1995 Green et al.
5,483,501 A 1/1996 Park et al.
5,486,162 A 1/1996 Brumbach
5,490,860 A 2/1996 Middle et al.
5,500,216 A 3/1996 Julian et al.
5,501,654 A 3/1996 Bauman
5,505,693 A 4/1996 Mackool
5,507,738 A 4/1996 Ciervo
5,527,331 A 6/1996 Kresch et al.
5,540,693 A 7/1996 Fisher
5,553,675 A 9/1996 Pitzen et al.
5,558,671 A 9/1996 Yates
5,562,609 A 10/1996 Brumbach
5,562,610 A 10/1996 Brumbach
5,562,659 A 10/1996 Morris
5,573,424 A 11/1996 Poppe
5,577,654 A 11/1996 Bishop
5,591,187 A 1/1997 Dekel
5,593,414 A 1/1997 Shipp et al.
5,601,601 A 2/1997 Tal et al.
5,603,773 A 2/1997 Campbell
5,607,436 A 3/1997 Pratt et al.
5,609,573 A 3/1997 Sandock
5,618,304 A 4/1997 Hart et al.
5,618,492 A 4/1997 Auten et al.
5,620,447 A 4/1997 Smith et al.
5,626,587 A 5/1997 Bishop et al.
5,626,595 A 5/1997 Sklar et al.
5,628,760 A 5/1997 Knoepfler
5,630,420 A 5/1997 Vaitekunas
5,632,717 A 5/1997 Yoon
5,640,741 A 6/1997 Yano
D381,077 S 7/1997 Hunt
5,649,937 A 7/1997 Bito et al.
5,651,780 A 7/1997 Jackson et al.
5,653,713 A 8/1997 Michelson
5,662,662 A 9/1997 Bishop et al.
5,669,922 A 9/1997 Hood
5,674,235 A 10/1997 Parisi
5,678,568 A 10/1997 Uchikubo et al.
5,690,269 A 11/1997 Bolanos et al.
5,694,936 A 12/1997 Fujimoto et al.
5,695,510 A 12/1997 Hood
5,700,261 A 12/1997 Brinkerhoff
5,704,534 A 1/1998 Huitema et al.
5,709,680 A 1/1998 Yates et al.
5,711,472 A 1/1998 Bryan
5,713,896 A 2/1998 Nardella
5,715,817 A 2/1998 Stevens-Wright et al.
5,717,306 A 2/1998 Shipp
5,728,130 A 3/1998 Ishikawa et al.
5,730,752 A 3/1998 Alden et al.
5,733,074 A 3/1998 Stöck et al.
5,741,226 A 4/1998 Strukel et al.
5,766,164 A 6/1998 Mueller et al.
5,772,659 A 6/1998 Becker et al.
5,776,155 A 7/1998 Beaupre et al.
5,792,135 A 8/1998 Madhani et al.
5,792,138 A 8/1998 Shipp
5,792,165 A 8/1998 Klieman et al.
5,797,959 A 8/1998 Castro et al.
5,805,140 A 9/1998 Rosenberg et al.
5,807,393 A 9/1998 Williamson, IV et al.
5,808,396 A 9/1998 Boukhny
5,810,859 A 9/1998 DiMatteo et al.
5,817,084 A 10/1998 Jensen
5,817,119 A 10/1998 Klieman et al.
5,823,197 A 10/1998 Edwards
5,827,323 A 10/1998 Klieman et al.
5,828,160 A 10/1998 Sugishita
5,833,696 A 11/1998 Whitfield et al.
5,836,897 A 11/1998 Sakurai et al.
5,836,957 A 11/1998 Schulz et al.
5,843,109 A 12/1998 Mehta et al.
5,851,212 A 12/1998 Zirps et al.
5,858,018 A 1/1999 Shipp et al.
5,865,361 A 2/1999 Milliman et al.

(56) References Cited

U.S. PATENT DOCUMENTS 5,873,873 A 2/1999 Smith et al.
5,873,882 A 2/1999 Straub et al.
5,878,193 A 3/1999 Wang et al.
5,879,364 A 3/1999 Bromfield et al.
5,883,615 A 3/1999 Fago et al.
5,893,835 A 4/1999 Witt et al.
5,897,523 A 4/1999 Wright et al.
5,897,569 A 4/1999 Kellogg et al.
5,903,607 A 5/1999 Tailliet
5,904,681 A 5/1999 West, Jr.
5,906,627 A 5/1999 Spaulding
5,906,628 A 5/1999 Miyawaki et al.
5,911,699 A 6/1999 Anis et al.
5,916,229 A 6/1999 Evans
5,929,846 A 7/1999 Rosenberg et al.
5,935,143 A 8/1999 Hood
5,935,144 A 8/1999 Estabrook
5,938,633 A 8/1999 Beaupre
5,944,718 A 8/1999 Austin et al.
5,944,737 A 8/1999 Tsonton et al.
5,947,984 A 9/1999 Whipple
5,954,736 A 9/1999 Bishop et al.
5,954,746 A 9/1999 Holthaus et al.
5,957,882 A 9/1999 Nita et al.
5,957,943 A 9/1999 Vaitekunas
5,968,007 A 10/1999 Simon et al.
5,968,060 A 10/1999 Kellogg
5,974,342 A * 10/1999 Petrofsky ..... 607/50
D416,089 S 11/1999 Barton et al.
5,980,510 A 11/1999 Tsonton et al.
5,980,546 A 11/1999 Hood
5,989,274 A 11/1999 Davison et al.
5,989,275 A 11/1999 Estabrook et al.
5,993,465 A 11/1999 Shipp et al.
5,993,972 A 11/1999 Reich et al.
5,994,855 A 11/1999 Lundell et al.
6,024,741 A 2/2000 Williamson, IV et al.
6,024,750 A 2/2000 Mastri et al.
6,027,515 A 2/2000 Cimino
6,031,526 A 2/2000 Shipp
6,033,375 A 3/2000 Brumbach
6,033,399 A 3/2000 Gines
6,036,667 A 3/2000 Manna et al.
6,036,707 A 3/2000 Spaulding
6,048,224 A 4/2000 Kay
6,050,943 A 4/2000 Slayton et al.
6,051,010 A 4/2000 DiMatteo et al.
6,056,735 A 5/2000 Okada et al.
6,063,098 A 5/2000 Houser et al.
6,066,132 A 5/2000 Chen et al.
6,066,151 A 5/2000 Miyawaki et al.
6,068,627 A 5/2000 Orszulak et al.
6,068,647 A 5/2000 Witt et al.
6,077,285 A 6/2000 Boukhny
6,083,191 A 7/2000 Rose
6,086,584 A 7/2000 Miller
6,090,120 A 7/2000 Wright et al.
6,096,033 A 8/2000 Tu et al.
6,099,542 A 8/2000 Cohn et al.
6,109,500 A 8/2000 Alli et al.
6,110,127 A 8/2000 Suzuki
6,113,594 A 9/2000 Savage
6,117,152 A 9/2000 Huitema
6,126,629 A 10/2000 Perkins
6,129,735 A 10/2000 Okada et al.
6,129,740 A 10/2000 Michelson
6,132,368 A 10/2000 Cooper
6,132,427 A 10/2000 Jones et al.
6,132,448 A 10/2000 Perez et al.
6,139,320 A 10/2000 Hahn
6,139,561 A 10/2000 Shibata et al.
6,142,615 A 11/2000 Qiu et al.
6,142,994 A 11/2000 Swanson et al.
6,147,560 A 11/2000 Erhage et al.
6,152,902 A 11/2000 Christian et al.
6,154,198 A 11/2000 Rosenberg
6,159,160 A 12/2000 Hsei et al.
6,159,175 A 12/2000 Strukel et al.
6,162,194 A 12/2000 Shipp
6,165,150 A 12/2000 Banko
6,174,310 B1 1/2001 Kirwan, Jr.
6,179,853 B1 1/2001 Sachse et al.
6,183,426 B1 2/2001 Akisada et al.
6,193,709 B1 2/2001 Miyawaki et al.
6,204,592 B1 3/2001 Hur
6,205,383 B1 * 3/2001 Hermann ..... B60R 21/01 280/728.1
6,205,855 B1 3/2001 Pfeiffer
6,206,844 B1 3/2001 Reichel et al.
6,210,337 B1 4/2001 Dunham et al.
6,210,402 B1 4/2001 Olsen et al.
6,210,403 B1 4/2001 Klicek
6,214,023 B1 4/2001 Whipple et al.
6,228,080 B1 5/2001 Gines
6,231,565 B1 5/2001 Tovey et al.
6,233,476 B1 5/2001 Strommer et al.
6,238,366 B1 5/2001 Savage et al.
6,245,065 B1 6/2001 Panescu et al.
6,251,110 B1 6/2001 Wampler
6,252,110 B1 6/2001 Uemura et al.
D444,365 S 7/2001 Bass et al.
D445,092 S 7/2001 Lee
D445,764 S 7/2001 Lee
6,254,623 B1 7/2001 Haibel, Jr. et al.
6,257,241 B1 7/2001 Wampler
6,258,034 B1 7/2001 Hanafy
6,267,761 B1 7/2001 Ryan
6,270,831 B2 8/2001 Kumar et al.
6,273,852 B1 8/2001 Lehe et al.
6,274,963 B1 8/2001 Estabrook et al.
6,277,115 B1 8/2001 Saadat
6,278,218 B1 8/2001 Madan et al.
6,280,407 B1 8/2001 Manna et al.
6,283,981 B1 9/2001 Beaupre
6,287,344 B1 9/2001 Wampler et al.
6,290,575 B1 9/2001 Shipp
6,299,591 B1 10/2001 Banko
6,306,131 B1 10/2001 Hareyarna
6,306,157 B1 10/2001 Shchervinsky
6,309,400 B2 10/2001 Beaupre
6,311,783 B1 11/2001 Harpell
6,319,221 B1 11/2001 Savage et al.
6,325,795 B1 12/2001 Lindemann et al.
6,325,799 B1 12/2001 Goble
6,325,811 B1 12/2001 Messerly
6,328,751 B1 12/2001 Beaupre
6,332,891 B1 12/2001 Himes
6,338,657 B1 1/2002 Harper et al.
6,340,352 B1 1/2002 Okada et al.
6,350,269 B1 2/2002 Shipp et al.
6,352,532 B1 3/2002 Kramer et al.
6,358,264 B2 3/2002 Banko
6,364,888 B1 4/2002 Niemeyer et al.
6,379,320 B1 4/2002 Lafon et al.
D457,958 S 5/2002 Dycus et al.
6,383,194 B1 5/2002 Pothula
6,384,690 B1 5/2002 Wilhelmsson et al.
6,387,109 B1 5/2002 Davison et al.
6,388,657 B1 5/2002 Natoli
6,391,042 B1 5/2002 Cimino
6,398,779 B1 6/2002 Buysse et al.
6,402,743 B1 6/2002 Orszulak et al.
6,402,748 B1 6/2002 Schoenman et al.
6,405,733 B1 6/2002 Fogarty et al.
6,416,486 B1 7/2002 Wampler
6,423,073 B2 7/2002 Bowman
6,423,082 B1 7/2002 Houser et al.
6,425,906 B1 7/2002 Young et al.
6,428,538 B1 8/2002 Blewett et al.
6,428,539 B1 8/2002 Baxter et al.
6,432,118 B1 8/2002 Messerly
6,436,114 B1 8/2002 Novak et al.
6,436,115 B1 8/2002 Beaupre
6,440,062 B1 8/2002 Ouchi

(56) References Cited

U.S. PATENT DOCUMENTS

| | | | |
|---|---|---|---|
| 6,443,968 | B1 | 9/2002 | Holthaus et al. |
| 6,443,969 | B1 | 9/2002 | Novak et al. |
| 6,449,006 | B1 | 9/2002 | Shipp |
| 6,454,781 | B1 | 9/2002 | Witt et al. |
| 6,454,782 | B1 | 9/2002 | Schwemberger |
| 6,458,142 | B1 | 10/2002 | Faller et al. |
| 6,475,215 | B1 | 11/2002 | Tanrisever |
| 6,480,796 | B2 | 11/2002 | Wiener |
| 6,485,490 | B2 | 11/2002 | Wampler et al. |
| 6,491,701 | B2 | 12/2002 | Tierney et al. |
| 6,491,708 | B2 | 12/2002 | Madan et al. |
| 6,497,715 | B2 | 12/2002 | Satou |
| 6,500,176 | B1 | 12/2002 | Truckai et al. |
| 6,500,188 | B2 | 12/2002 | Harper et al. |
| 6,500,312 | B2 | 12/2002 | Wedekamp |
| 6,506,208 | B2 | 1/2003 | Hunt et al. |
| 6,511,478 | B1 | 1/2003 | Burnside et al. |
| 6,511,493 | B1 | 1/2003 | Moutafis et al. |
| 6,514,267 | B2 | 2/2003 | Jewett |
| 6,524,251 | B2 | 2/2003 | Rabiner et al. |
| 6,524,316 | B1 | 2/2003 | Nicholson et al. |
| 6,527,736 | B1 | 3/2003 | Attinger et al. |
| 6,533,784 | B2 | 3/2003 | Truckai et al. |
| 6,537,272 | B2 | 3/2003 | Christopherson et al. |
| 6,537,291 | B2 | 3/2003 | Friedman et al. |
| 6,543,452 | B1 | 4/2003 | Lavigne |
| 6,543,456 | B1 | 4/2003 | Freeman |
| 6,544,260 | B1 | 4/2003 | Markel et al. |
| 6,558,376 | B2 | 5/2003 | Bishop |
| 6,561,983 | B2 | 5/2003 | Cronin et al. |
| 6,562,035 | B1 | 5/2003 | Levin |
| 6,565,558 | B1 | 5/2003 | Lindenmeier et al. |
| 6,572,563 | B2 | 6/2003 | Ouchi |
| 6,572,632 | B2 | 6/2003 | Zisterer et al. |
| 6,575,969 | B1 | 6/2003 | Rittman, III et al. |
| 6,582,427 | B1 | 6/2003 | Goble et al. |
| 6,582,451 | B1 | 6/2003 | Marucci et al. |
| D477,408 | S | 7/2003 | Bromley |
| 6,588,277 | B2 | 7/2003 | Giordano et al. |
| 6,589,200 | B1 | 7/2003 | Schwemberger et al. |
| 6,589,239 | B2 | 7/2003 | Khandkar et al. |
| 6,599,288 | B2 | 7/2003 | Maguire et al. |
| 6,607,540 | B1 | 8/2003 | Shipp |
| 6,610,059 | B1 | 8/2003 | West, Jr. |
| 6,616,450 | B2 | 9/2003 | Mossle et al. |
| 6,619,529 | B2 | 9/2003 | Green et al. |
| 6,623,500 | B1 | 9/2003 | Cook et al. |
| 6,623,501 | B2 | 9/2003 | Heller et al. |
| 6,626,848 | B2 | 9/2003 | Neuenfeldt |
| 6,626,926 | B2 | 9/2003 | Friedman et al. |
| 6,629,974 | B2 | 10/2003 | Penny et al. |
| 6,633,234 | B2 | 10/2003 | Wiener et al. |
| 6,644,532 | B2 | 11/2003 | Green et al. |
| 6,651,669 | B1 | 11/2003 | Burnside |
| 6,652,513 | B2 | 11/2003 | Panescu et al. |
| 6,652,539 | B2 | 11/2003 | Shipp et al. |
| 6,652,545 | B2 | 11/2003 | Shipp et al. |
| 6,656,132 | B1 | 12/2003 | Ouchi |
| 6,656,177 | B2 | 12/2003 | Truckai et al. |
| 6,660,017 | B2 | 12/2003 | Beaupre |
| 6,662,127 | B2 | 12/2003 | Wiener et al. |
| 6,663,941 | B2 | 12/2003 | Brown et al. |
| 6,666,860 | B1 | 12/2003 | Takahashi |
| 6,666,875 | B1 | 12/2003 | Sakurai et al. |
| 6,669,690 | B1 | 12/2003 | Okada et al. |
| 6,669,710 | B2 | 12/2003 | Moutafis et al. |
| 6,676,660 | B2 | 1/2004 | Wampler et al. |
| 6,678,621 | B2 | 1/2004 | Wiener et al. |
| 6,679,875 | B2 | 1/2004 | Honda et al. |
| 6,679,899 | B2 | 1/2004 | Wiener et al. |
| 6,682,544 | B2 | 1/2004 | Mastri et al. |
| 6,685,701 | B2 | 2/2004 | Orszulak et al. |
| 6,685,703 | B2 | 2/2004 | Pearson et al. |
| 6,689,145 | B2 | 2/2004 | Lee et al. |
| 6,689,146 | B1 | 2/2004 | Himes |
| 6,702,821 | B2 | 3/2004 | Bonutti |
| 6,716,215 | B1 | 4/2004 | David et al. |
| 6,719,692 | B2 | 4/2004 | Kleffner et al. |
| 6,719,776 | B2 | 4/2004 | Baxter |
| 6,723,091 | B2 | 4/2004 | Goble et al. |
| D490,059 | S | 5/2004 | Conway et al. |
| 6,731,047 | B2 | 5/2004 | Kauf et al. |
| 6,733,506 | B1 | 5/2004 | McDevitt et al. |
| 6,736,813 | B2 | 5/2004 | Yamauchi et al. |
| 6,739,872 | B1 | 5/2004 | Turri |
| 6,740,079 | B1 | 5/2004 | Eggers et al. |
| D491,666 | S | 6/2004 | Kimmell et al. |
| 6,743,245 | B2 | 6/2004 | Lobdell |
| 6,746,284 | B1 | 6/2004 | Spink, Jr. |
| 6,746,443 | B1 | 6/2004 | Morley et al. |
| 6,752,815 | B2 | 6/2004 | Beaupre |
| 6,755,825 | B2 | 6/2004 | Shoenman et al. |
| 6,761,698 | B2 | 7/2004 | Shibata et al. |
| 6,762,535 | B2 | 7/2004 | Take et al. |
| 6,770,072 | B1 | 8/2004 | Truckai et al. |
| 6,773,409 | B2 | 8/2004 | Truckai et al. |
| 6,773,443 | B2 | 8/2004 | Truwit et al. |
| 6,773,444 | B2 | 8/2004 | Messerly |
| 6,778,023 | B2 | 8/2004 | Christensen |
| 6,783,524 | B2 | 8/2004 | Anderson et al. |
| 6,786,382 | B1 | 9/2004 | Hoffman |
| 6,786,383 | B2 | 9/2004 | Stegelmann |
| 6,790,173 | B2 | 9/2004 | Saadat et al. |
| 6,790,216 | B1 | 9/2004 | Ishikawa |
| 6,796,981 | B2 | 9/2004 | Wham et al. |
| D496,997 | S | 10/2004 | Dycus et al. |
| 6,802,843 | B2 | 10/2004 | Truckai et al. |
| 6,808,525 | B2 | 10/2004 | Latterell et al. |
| 6,809,508 | B2 | 10/2004 | Donofrio |
| 6,810,281 | B2 | 10/2004 | Brock et al. |
| 6,827,712 | B2 | 12/2004 | Tovey et al. |
| 6,828,712 | B2 | 12/2004 | Battaglin et al. |
| 6,835,082 | B2 | 12/2004 | Gonnering |
| 6,849,073 | B2 | 2/2005 | Hoey et al. |
| 6,860,878 | B2 | 3/2005 | Brock |
| 6,863,676 | B2 | 3/2005 | Lee et al. |
| 6,869,439 | B2 | 3/2005 | White et al. |
| 6,875,220 | B2 | 4/2005 | Du et al. |
| 6,877,647 | B2 | 4/2005 | Green et al. |
| 6,882,439 | B2 | 4/2005 | Ishijima |
| 6,887,209 | B2 | 5/2005 | Kadziauskas et al. |
| 6,887,252 | B1 | 5/2005 | Okada et al. |
| 6,899,685 | B2 | 5/2005 | Kermode et al. |
| 6,905,497 | B2 | 6/2005 | Truckai et al. |
| 6,908,472 | B2 | 6/2005 | Wiener et al. |
| 6,913,579 | B2 | 7/2005 | Truckai et al. |
| 6,915,623 | B2 | 7/2005 | Dey et al. |
| 6,923,804 | B2 | 8/2005 | Eggers et al. |
| 6,926,712 | B2 | 8/2005 | Phan |
| 6,926,716 | B2 | 8/2005 | Baker et al. |
| 6,929,602 | B2 | 8/2005 | Hirakui et al. |
| 6,929,632 | B2 | 8/2005 | Nita et al. |
| 6,929,644 | B2 | 8/2005 | Truckai et al. |
| 6,933,656 | B2 | 8/2005 | Matsushita et al. |
| D509,589 | S | 9/2005 | Wells |
| 6,942,660 | B2 | 9/2005 | Pantera et al. |
| 6,942,677 | B2 | 9/2005 | Nita et al. |
| 6,945,981 | B2 | 9/2005 | Donofrio et al. |
| 6,946,779 | B2 | 9/2005 | Birgel |
| 6,948,503 | B2 | 9/2005 | Refior et al. |
| D511,145 | S | 11/2005 | Donofrio et al. |
| 6,974,450 | B2 | 12/2005 | Weber et al. |
| 6,976,844 | B2 | 12/2005 | Hickok et al. |
| 6,976,969 | B2 | 12/2005 | Messerly |
| 6,977,495 | B2 | 12/2005 | Donofrio |
| 6,979,332 | B2 | 12/2005 | Adams |
| 6,981,628 | B2 | 1/2006 | Wales |
| 6,984,220 | B2 | 1/2006 | Wuchinich |
| 6,988,295 | B2 | 1/2006 | Tillim |
| 6,994,708 | B2 | 2/2006 | Manzo |
| 7,001,335 | B2 | 2/2006 | Adachi et al. |
| 7,011,657 | B2 | 3/2006 | Truckai et al. |
| 7,014,638 | B2 | 3/2006 | Michelson |
| 7,033,357 | B2 | 4/2006 | Baxter et al. |

(56) References Cited

U.S. PATENT DOCUMENTS

| | | | |
|---|---|---|---|
| 7,037,306 | B2 | 5/2006 | Podany |
| 7,041,083 | B2 | 5/2006 | Chu et al. |
| 7,041,088 | B2 | 5/2006 | Nawrocki et al. |
| 7,041,102 | B2 | 5/2006 | Truckai et al. |
| 7,044,949 | B2 | 5/2006 | Orszulak et al. |
| 7,066,893 | B2 | 6/2006 | Hibner et al. |
| 7,066,895 | B2 | 6/2006 | Podany |
| 7,070,597 | B2 | 7/2006 | Truckai et al. |
| 7,074,218 | B2 | 7/2006 | Washington et al. |
| 7,074,219 | B2 | 7/2006 | Levine et al. |
| 7,077,039 | B2 | 7/2006 | Gass et al. |
| 7,077,845 | B2 | 7/2006 | Hacker et al. |
| 7,077,853 | B2 | 7/2006 | Kramer et al. |
| 7,083,618 | B2 | 8/2006 | Couture |
| 7,083,619 | B2 | 8/2006 | Truckai et al. |
| 7,087,054 | B2 | 8/2006 | Truckai et al. |
| 7,090,672 | B2 | 8/2006 | Underwood et al. |
| 7,101,371 | B2 | 9/2006 | Dycus et al. |
| 7,101,378 | B2 | 9/2006 | Salameh et al. |
| 7,104,834 | B2 | 9/2006 | Robinson et al. |
| 7,108,695 | B2 | 9/2006 | Witt et al. |
| 7,111,769 | B2 | 9/2006 | Wales et al. |
| 7,112,201 | B2 | 9/2006 | Truckai et al. |
| D531,311 | S | 10/2006 | Guerra et al. |
| 7,117,034 | B2 | 10/2006 | Kronberg |
| 7,118,564 | B2 | 10/2006 | Ritchie et al. |
| 7,124,932 | B2 | 10/2006 | Isaacson et al. |
| 7,125,409 | B2 | 10/2006 | Truckai et al. |
| 7,128,720 | B2 | 10/2006 | Podany |
| 7,131,860 | B2 | 11/2006 | Sartor et al. |
| 7,135,018 | B2 | 11/2006 | Ryan et al. |
| 7,135,030 | B2 | 11/2006 | Schwemberger et al. |
| 7,137,980 | B2 | 11/2006 | Buysse et al. |
| 7,144,403 | B2 | 12/2006 | Booth |
| 7,153,315 | B2 | 12/2006 | Miller |
| D536,093 | S | 1/2007 | Nakajima et al. |
| 7,156,189 | B1 | 1/2007 | Bar-Cohen et al. |
| 7,156,853 | B2 | 1/2007 | Muratsu |
| 7,157,058 | B2 | 1/2007 | Marhasin et al. |
| 7,159,750 | B2 | 1/2007 | Racenet et al. |
| 7,160,296 | B2 | 1/2007 | Pearson et al. |
| 7,160,299 | B2 | 1/2007 | Baily |
| 7,163,548 | B2 | 1/2007 | Stulen et al. |
| 7,169,144 | B2 | 1/2007 | Hoey et al. |
| 7,169,146 | B2 | 1/2007 | Truckai et al. |
| 7,179,254 | B2 | 2/2007 | Pendekanti et al. |
| 7,179,271 | B2 | 2/2007 | Friedman et al. |
| 7,186,253 | B2 | 3/2007 | Truckai et al. |
| 7,189,233 | B2 | 3/2007 | Truckai et al. |
| D541,418 | S | 4/2007 | Schechter et al. |
| 7,198,635 | B2 | 4/2007 | Danek et al. |
| 7,204,820 | B2 | 4/2007 | Akahoshi |
| 7,207,997 | B2 | 4/2007 | Shipp et al. |
| 7,210,881 | B2 | 5/2007 | Greenberg |
| 7,211,079 | B2 | 5/2007 | Treat |
| 7,217,128 | B2 | 5/2007 | Atkin et al. |
| 7,217,269 | B2 | 5/2007 | El-Galley et al. |
| 7,220,951 | B2 | 5/2007 | Truckai et al. |
| 7,223,229 | B2 | 5/2007 | Inman et al. |
| 7,229,455 | B2 | 6/2007 | Sakurai et al. |
| 7,235,071 | B2 | 6/2007 | Gonnering |
| 7,244,262 | B2 | 7/2007 | Wiener et al. |
| 7,258,688 | B1 | 8/2007 | Shah et al. |
| 7,269,873 | B2 | 9/2007 | Brewer et al. |
| 7,273,483 | B2 | 9/2007 | Wiener et al. |
| D552,241 | S | 10/2007 | Bromley et al. |
| 7,282,048 | B2 | 10/2007 | Goble et al. |
| 7,285,895 | B2 | 10/2007 | Beaupre |
| 7,300,431 | B2 | 11/2007 | Dubrovsky |
| 7,300,435 | B2 | 11/2007 | Wham et al. |
| 7,300,446 | B2 | 11/2007 | Beaupre |
| 7,303,531 | B2 | 12/2007 | Lee et al. |
| 7,303,557 | B2 | 12/2007 | Wham et al. |
| 7,306,597 | B2 | 12/2007 | Manzo |
| 7,309,849 | B2 | 12/2007 | Truckai et al. |
| 7,311,706 | B2 | 12/2007 | Schoenman et al. |
| 7,311,709 | B2 | 12/2007 | Truckai et al. |
| 7,317,955 | B2 | 1/2008 | McGreevy |
| 7,318,831 | B2 | 1/2008 | Alvarez et al. |
| 7,326,236 | B2 | 2/2008 | Andreas et al. |
| 7,331,410 | B2 | 2/2008 | Yong et al. |
| 7,335,165 | B2 | 2/2008 | Truwit et al. |
| 7,335,997 | B2 | 2/2008 | Wiener |
| 7,337,010 | B2 | 2/2008 | Howard et al. |
| 7,353,068 | B2 | 4/2008 | Tanaka et al. |
| 7,354,440 | B2 | 4/2008 | Truckal et al. |
| 7,361,172 | B2 | 4/2008 | Cimino |
| 7,364,577 | B2 | 4/2008 | Wham et al. |
| RE40,388 | E | 6/2008 | Gines |
| 7,380,695 | B2 | 6/2008 | Doll et al. |
| 7,380,696 | B2 | 6/2008 | Shelton, IV et al. |
| 7,381,209 | B2 | 6/2008 | Truckai et al. |
| 7,390,317 | B2 | 6/2008 | Taylor et al. |
| 7,404,508 | B2 | 7/2008 | Smith et al. |
| 7,408,288 | B2 | 8/2008 | Hara |
| 7,416,101 | B2 | 8/2008 | Shelton, IV et al. |
| 7,416,437 | B2 | 8/2008 | Sartor et al. |
| D576,725 | S | 9/2008 | Shumer et al. |
| 7,419,490 | B2 | 9/2008 | Falkenstein et al. |
| 7,422,139 | B2 | 9/2008 | Shelton, IV et al. |
| 7,422,463 | B2 | 9/2008 | Kuo |
| D578,643 | S | 10/2008 | Shumer et al. |
| D578,644 | S | 10/2008 | Shumer et al. |
| D578,645 | S | 10/2008 | Shumer et al. |
| 7,431,704 | B2 | 10/2008 | Babaev |
| 7,441,684 | B2 | 10/2008 | Shelton, IV et al. |
| 7,455,208 | B2 | 11/2008 | Wales et al. |
| 7,462,181 | B2 | 12/2008 | Kraft et al. |
| 7,464,846 | B2 | 12/2008 | Shelton, IV et al. |
| 7,472,815 | B2 | 1/2009 | Shelton, IV et al. |
| 7,473,263 | B2 | 1/2009 | Johnston et al. |
| 7,479,148 | B2 | 1/2009 | Beaupre |
| 7,479,160 | B2 | 1/2009 | Branch et al. |
| 7,481,775 | B2 | 1/2009 | Weikel, Jr. et al. |
| 7,488,285 | B2 | 2/2009 | Honda et al. |
| 7,494,468 | B2 | 2/2009 | Rabiner et al. |
| 7,502,234 | B2 | 3/2009 | Goliszek et al. |
| 7,503,893 | B2 | 3/2009 | Kucklick |
| 7,503,895 | B2 | 3/2009 | Rabiner et al. |
| 7,506,790 | B2 | 3/2009 | Shelton, IV |
| 7,506,791 | B2 | 3/2009 | Omaits et al. |
| 7,524,320 | B2 | 4/2009 | Tierney et al. |
| 7,530,986 | B2 | 5/2009 | Beaupre et al. |
| 7,534,243 | B1 | 5/2009 | Chin et al. |
| D594,983 | S | 6/2009 | Price et al. |
| 7,540,871 | B2 | 6/2009 | Gonnering |
| 7,544,200 | B2 | 6/2009 | Houser |
| 7,549,564 | B2 | 6/2009 | Boudreaux |
| 7,559,450 | B2 | 7/2009 | Wales et al. |
| 7,567,012 | B2 | 7/2009 | Namikawa |
| 7,568,603 | B2 | 8/2009 | Shelton, IV et al. |
| 7,569,057 | B2 | 8/2009 | Liu et al. |
| 7,572,266 | B2 | 8/2009 | Young et al. |
| 7,572,268 | B2 | 8/2009 | Babaev |
| 7,578,820 | B2 | 8/2009 | Moore et al. |
| 7,582,084 | B2 | 9/2009 | Swanson et al. |
| 7,582,095 | B2 | 9/2009 | Shipp et al. |
| 7,585,181 | B2 | 9/2009 | Olsen |
| 7,588,176 | B2 | 9/2009 | Timm et al. |
| 7,601,119 | B2 | 10/2009 | Shahinian |
| 7,607,557 | B2 | 10/2009 | Shelton, IV et al. |
| 7,621,930 | B2 | 11/2009 | Houser |
| 7,641,653 | B2 | 1/2010 | Della Bette et al. |
| 7,645,278 | B2 | 1/2010 | Ichihashi et al. |
| 7,654,431 | B2 | 2/2010 | Hueil et al. |
| 7,659,833 | B2 | 2/2010 | Warner et al. |
| 7,665,647 | B2 | 2/2010 | Shelton, IV et al. |
| 7,670,334 | B2 | 3/2010 | Hueil et al. |
| 7,670,338 | B2 | 3/2010 | Albrecht et al. |
| 7,674,263 | B2 | 3/2010 | Ryan |
| 7,678,069 | B1 | 3/2010 | Baker et al. |
| 7,678,125 | B2 | 3/2010 | Shipp |
| 7,682,366 | B2 | 3/2010 | Sakurai et al. |
| 7,686,770 | B2 | 3/2010 | Cohen |

(56) References Cited

U.S. PATENT DOCUMENTS 7,686,826 B2 3/2010 Lee et al.
7,688,028 B2 3/2010 Phillips et al.
7,691,098 B2 4/2010 Wallace et al.
7,699,846 B2 4/2010 Ryan
7,713,202 B2 5/2010 Boukhny et al.
7,714,481 B2 5/2010 Sakai
7,717,312 B2 5/2010 Beetel
7,717,915 B2 5/2010 Miyazawa
7,721,935 B2 5/2010 Racenet et al.
D618,797 S 6/2010 Price et al.
7,726,537 B2 6/2010 Olson et al.
7,727,177 B2 6/2010 Bayat
7,738,969 B2 6/2010 Bleich
7,740,594 B2 6/2010 Hibner
7,751,115 B2 7/2010 Song
D621,503 S 8/2010 Otten et al.
7,766,210 B2 8/2010 Shelton, IV et al.
7,766,693 B2 8/2010 Sartor et al.
7,770,774 B2 8/2010 Mastri et al.
7,770,775 B2 8/2010 Shelton, IV et al.
7,771,425 B2 8/2010 Dycus et al.
7,771,444 B2 8/2010 Patel et al.
7,775,972 B2 8/2010 Brock et al.
7,776,036 B2 8/2010 Schechter et al.
7,778,733 B2 8/2010 Nowlin et al.
7,780,054 B2 8/2010 Wales
7,780,593 B2 8/2010 Ueno et al.
7,780,651 B2 8/2010 Madhani et al.
7,780,659 B2 8/2010 Okada et al.
7,784,662 B2 8/2010 Wales et al.
7,796,969 B2 9/2010 Kelly et al.
7,798,386 B2 9/2010 Schall et al.
7,799,020 B2 9/2010 Shores et al.
7,799,045 B2 9/2010 Masuda
7,803,152 B2 9/2010 Honda et al.
7,806,891 B2 10/2010 Nowlin et al.
7,810,693 B2 10/2010 Broehl et al.
7,811,283 B2 10/2010 Moses et al.
7,819,819 B2 10/2010 Quick et al.
7,821,143 B2 10/2010 Wiener
D627,066 S 11/2010 Romero
7,824,401 B2 11/2010 Manzo et al.
7,832,611 B2 11/2010 Boyden et al.
7,834,484 B2 11/2010 Sartor
7,837,699 B2 11/2010 Yamada et al.
7,845,537 B2 12/2010 Shelton, IV et al.
7,846,155 B2 12/2010 Houser et al.
7,846,161 B2 12/2010 Dumbauld et al.
7,854,735 B2 12/2010 Houser et al.
D631,155 S 1/2011 Peine et al.
7,861,906 B2 1/2011 Doll et al.
7,862,560 B2 1/2011 Marion
7,876,030 B2 1/2011 Taki et al.
D631,965 S 2/2011 Price et al.
7,878,991 B2 2/2011 Babaev
7,879,033 B2 2/2011 Sartor et al.
7,892,606 B2 2/2011 Thies et al.
7,901,400 B2 3/2011 Wham et al.
7,901,423 B2 3/2011 Stulen et al.
7,905,881 B2 3/2011 Masuda et al.
7,909,824 B2 3/2011 Masuda et al.
7,922,061 B2 4/2011 Shelton, IV et al.
7,922,651 B2 4/2011 Yamada et al.
D637,288 S 5/2011 Houghton
D638,540 S 5/2011 Ijiri et al.
7,936,203 B2 * 5/2011 Zimlich ..... 327/512
7,951,095 B2 5/2011 Makin et al.
7,951,165 B2 5/2011 Golden et al.
7,959,050 B2 6/2011 Smith et al.
7,959,626 B2 6/2011 Hong et al.
7,972,329 B2 7/2011 Refior et al.
7,976,544 B2 7/2011 McClurken et al.
7,981,050 B2 7/2011 Ritchart et al.
7,998,157 B2 8/2011 Culp et al.
8,038,693 B2 10/2011 Allen
8,057,498 B2 11/2011 Robertson
8,058,771 B2 11/2011 Giordano et al.
8,061,014 B2 11/2011 Smith et al.
8,070,711 B2 12/2011 Bassinger et al.
8,070,762 B2 12/2011 Escudero et al.
8,075,558 B2 12/2011 Truckai et al.
8,089,197 B2 1/2012 Rinner et al.
8,097,012 B2 1/2012 Kagarise
8,105,323 B2 1/2012 Buysse et al.
8,142,461 B2 3/2012 Houser et al.
8,152,801 B2 4/2012 Goldberg et al.
8,152,825 B2 4/2012 Madan et al.
8,157,145 B2 4/2012 Shelton, IV et al.
8,161,977 B2 4/2012 Shelton, IV et al.
8,162,966 B2 4/2012 Connor et al.
8,172,846 B2 5/2012 Brunnett et al.
8,172,870 B2 5/2012 Shipp
8,177,800 B2 5/2012 Spitz et al.
8,182,502 B2 5/2012 Stulen et al.
8,186,877 B2 5/2012 Klimovitch et al.
D661,801 S 6/2012 Price et al.
D661,802 S 6/2012 Price et al.
D661,803 S 6/2012 Price et al.
D661,804 S 6/2012 Price et al.
8,197,472 B2 6/2012 Lau et al.
8,197,502 B2 6/2012 Smith et al.
8,207,651 B2 6/2012 Gilbert
8,210,411 B2 7/2012 Yates et al.
8,226,675 B2 7/2012 Houser et al.
8,235,917 B2 8/2012 Joseph et al.
8,236,019 B2 8/2012 Houser
8,236,020 B2 8/2012 Smith et al.
8,241,271 B2 8/2012 Millman et al.
8,246,575 B2 8/2012 Viola
8,246,615 B2 8/2012 Behnke
8,252,012 B2 8/2012 Stulen
8,253,303 B2 8/2012 Giordano et al.
8,257,377 B2 9/2012 Wiener et al.
8,257,387 B2 9/2012 Cunningham
8,273,087 B2 9/2012 Kimura et al.
D669,992 S 10/2012 Schafer et al.
D669,993 S 10/2012 Merchant et al.
8,286,846 B2 10/2012 Smith et al.
8,287,485 B2 10/2012 Kimura et al.
8,287,528 B2 10/2012 Wham et al.
8,287,532 B2 10/2012 Carroll et al.
8,292,888 B2 10/2012 Whitman
8,293,223 B2 10/2012 Wham et al.
8,298,223 B2 10/2012 Wham et al.
8,298,225 B2 10/2012 Gilbert
8,303,576 B2 11/2012 Brock
8,303,580 B2 11/2012 Wham et al.
8,303,583 B2 11/2012 Hosier et al.
8,319,400 B2 11/2012 Houser et al.
8,323,302 B2 12/2012 Robertson et al.
8,328,833 B2 12/2012 Cuny
8,333,778 B2 12/2012 Smith et al.
8,333,779 B2 12/2012 Smith et al.
8,334,468 B2 12/2012 Palmer et al.
8,334,635 B2 12/2012 Voegele et al.
8,337,407 B2 12/2012 Quistgaard et al.
8,338,726 B2 12/2012 Palmer et al.
8,344,596 B2 1/2013 Nield et al.
8,348,967 B2 1/2013 Stulen
8,357,103 B2 1/2013 Mark et al.
8,366,727 B2 2/2013 Witt et al.
8,372,099 B2 2/2013 Deville et al.
8,372,101 B2 2/2013 Smith et al.
8,372,102 B2 2/2013 Stulen et al.
8,374,670 B2 2/2013 Selkee
8,377,059 B2 2/2013 Deville et al.
8,377,085 B2 2/2013 Smith et al.
8,382,748 B2 2/2013 Geisel
8,382,775 B1 2/2013 Bender et al.
8,382,782 B2 2/2013 Robertson et al.
8,403,948 B2 3/2013 Deville et al.
8,403,949 B2 3/2013 Palmer et al.
8,403,950 B2 3/2013 Palmer et al.
8,418,073 B2 4/2013 Mohr et al.

(56) References Cited

U.S. PATENT DOCUMENTS

| | | | |
|---|---|---|---|
| 8,418,349 | B2 | 4/2013 | Smith et al. |
| 8,419,757 | B2 | 4/2013 | Smith et al. |
| 8,419,758 | B2 | 4/2013 | Smith et al. |
| 8,419,759 | B2 | 4/2013 | Dietz |
| 8,425,545 | B2 | 4/2013 | Smith et al. |
| 8,430,898 | B2 | 4/2013 | Wiener et al. |
| 8,435,257 | B2 | 5/2013 | Smith et al. |
| 8,439,912 | B2 | 5/2013 | Cunningham et al. |
| 8,439,939 | B2 | 5/2013 | Deville et al. |
| 8,444,637 | B2 | 5/2013 | Podmore et al. |
| 8,444,662 | B2 | 5/2013 | Palmer et al. |
| 8,444,664 | B2 | 5/2013 | Balanev et al. |
| 8,460,288 | B2 | 6/2013 | Tamai et al. |
| 8,461,744 | B2 | 6/2013 | Wiener et al. |
| 8,469,981 | B2 | 6/2013 | Robertson et al. |
| 8,479,969 | B2 | 7/2013 | Shelton, IV |
| 8,480,703 | B2 | 7/2013 | Nicholas et al. |
| 8,485,413 | B2 | 7/2013 | Scheib et al. |
| 8,486,057 | B2 | 7/2013 | Behnke, II |
| 8,486,096 | B2 | 7/2013 | Robertson et al. |
| 8,491,578 | B2 | 7/2013 | Manwaring et al. |
| D687,549 | S | 8/2013 | Johnson et al. |
| 8,506,555 | B2 | 8/2013 | Ruiz Morales |
| 8,509,318 | B2 | 8/2013 | Tailliet |
| 8,512,359 | B2 | 8/2013 | Whitman et al. |
| 8,512,365 | B2 | 8/2013 | Wiener et al. |
| 8,523,889 | B2 | 9/2013 | Stulen et al. |
| 8,531,064 | B2 | 9/2013 | Robertson et al. |
| 8,535,340 | B2 | 9/2013 | Allen |
| 8,535,341 | B2 | 9/2013 | Allen |
| 8,546,996 | B2 | 10/2013 | Messerly et al. |
| 8,546,999 | B2 | 10/2013 | Houser et al. |
| 8,551,086 | B2 | 10/2013 | Kimura et al. |
| 8,568,400 | B2 | 10/2013 | Gilbert |
| 8,573,461 | B2 | 11/2013 | Shelton, IV et al. |
| 8,573,465 | B2 | 11/2013 | Shelton, IV |
| 8,579,928 | B2 | 11/2013 | Robertson et al. |
| 8,591,459 | B2 | 11/2013 | Clymer et al. |
| 8,591,506 | B2 | 11/2013 | Wham et al. |
| 8,591,536 | B2 | 11/2013 | Robertson |
| D695,407 | S | 12/2013 | Price et al. |
| D696,631 | S | 12/2013 | Price et al. |
| 8,602,031 | B2 | 12/2013 | Reis et al. |
| 8,602,288 | B2 | 12/2013 | Shelton, IV et al. |
| 8,608,745 | B2 | 12/2013 | Guzman et al. |
| 8,616,431 | B2 | 12/2013 | Timm et al. |
| 8,623,027 | B2 | 1/2014 | Price et al. |
| 8,650,728 | B2 | 2/2014 | Wan et al. |
| 8,652,155 | B2 | 2/2014 | Houser et al. |
| 8,659,208 | B1 | 2/2014 | Rose et al. |
| 8,663,220 | B2 | 3/2014 | Wiener et al. |
| 8,690,582 | B2 | 4/2014 | Rohrbach et al. |
| 8,696,366 | B2 | 4/2014 | Chen et al. |
| 8,704,425 | B2 | 4/2014 | Giordano et al. |
| 8,709,031 | B2 | 4/2014 | Stulen |
| 8,747,351 | B2 | 6/2014 | Schultz |
| 8,749,116 | B2 | 6/2014 | Messerly et al. |
| 8,752,749 | B2 | 6/2014 | Moore et al. |
| 8,753,338 | B2 | 6/2014 | Widenhouse et al. |
| 8,754,570 | B2 | 6/2014 | Voegele et al. |
| 8,758,352 | B2 | 6/2014 | Cooper et al. |
| 8,764,735 | B2 | 7/2014 | Coe et al. |
| 8,771,270 | B2 | 7/2014 | Burbank |
| 8,773,001 | B2 | 7/2014 | Wiener et al. |
| 8,779,648 | B2 | 7/2014 | Giordano et al. |
| 8,784,418 | B2 | 7/2014 | Romero |
| 8,808,319 | B2 | 8/2014 | Houser et al. |
| 8,827,992 | B2 | 9/2014 | Koss et al. |
| 8,845,537 | B2 | 9/2014 | Tanaka et al. |
| 8,882,791 | B2 | 11/2014 | Stulen |
| 8,888,776 | B2 | 11/2014 | Dietz et al. |
| 8,888,809 | B2 | 11/2014 | Davison et al. |
| 8,899,462 | B2 | 12/2014 | Kostrzewski et al. |
| 8,900,259 | B2 | 12/2014 | Houser et al. |
| 8,911,460 | B2 | 12/2014 | Neurohr et al. |
| 8,951,248 | B2 | 2/2015 | Messerly et al. |
| 8,951,272 | B2 | 2/2015 | Robertson et al. |
| 8,956,349 | B2 | 2/2015 | Aldridge et al. |
| 8,961,547 | B2 | 2/2015 | Dietz et al. |
| 8,968,283 | B2 | 3/2015 | Kharin |
| 8,968,355 | B2 | 3/2015 | Malkowski et al. |
| 8,974,477 | B2 | 3/2015 | Yamada |
| 8,979,890 | B2 | 3/2015 | Boudreaux |
| 8,986,287 | B2 | 3/2015 | Park et al. |
| 8,986,302 | B2 | 3/2015 | Aldridge et al. |
| 8,989,903 | B2 | 3/2015 | Weir et al. |
| 9,017,326 | B2 | 4/2015 | DiNardo et al. |
| 9,039,695 | B2 | 5/2015 | Giordano et al. |
| 9,043,018 | B2 | 5/2015 | Mohr |
| 9,044,261 | B2 | 6/2015 | Houser |
| 9,050,093 | B2 | 6/2015 | Aldridge et al. |
| 9,050,124 | B2 | 6/2015 | Houser |
| 9,060,775 | B2 | 6/2015 | Wiener et al. |
| 9,060,776 | B2 | 6/2015 | Yates et al. |
| 9,066,747 | B2 | 6/2015 | Robertson |
| 9,072,539 | B2 | 7/2015 | Messerly et al. |
| 9,089,360 | B2 | 7/2015 | Messerly et al. |
| 9,095,367 | B2 | 8/2015 | Olson et al. |
| 9,107,689 | B2 | 8/2015 | Robertson et al. |
| 9,113,940 | B2 | 8/2015 | Twomey |
| 9,168,054 | B2 | 10/2015 | Turner et al. |
| 9,198,714 | B2 | 12/2015 | Worrell et al. |
| 9,220,527 | B2 | 12/2015 | Houser et al. |
| 9,226,766 | B2 | 1/2016 | Aldridge et al. |
| 9,226,767 | B2 | 1/2016 | Stulen et al. |
| 9,232,979 | B2 | 1/2016 | Parihar et al. |
| 9,237,921 | B2 | 1/2016 | Messerly et al. |
| 9,241,728 | B2 | 1/2016 | Price et al. |
| 9,241,731 | B2 | 1/2016 | Boudreaux et al. |
| 9,259,234 | B2 | 2/2016 | Robertson et al. |
| 9,283,045 | B2 | 3/2016 | Rhee et al. |
| 9,326,788 | B2 | 5/2016 | Batross et al. |
| 9,339,289 | B2 | 5/2016 | Robertson |
| 9,351,754 | B2 | 5/2016 | Vakharia et al. |
| 9,393,037 | B2 | 7/2016 | Olson et al. |
| 9,408,622 | B2 | 8/2016 | Stulen et al. |
| 9,414,853 | B2 | 8/2016 | Stulen et al. |
| 9,421,060 | B2 | 8/2016 | Monson et al. |
| 9,427,249 | B2 | 8/2016 | Robertson et al. |
| 9,439,668 | B2 | 9/2016 | Timm et al. |
| 9,439,669 | B2 | 9/2016 | Wiener et al. |
| 9,445,832 | B2 | 9/2016 | Wiener et al. |
| 2001/0025173 | A1 | 9/2001 | Ritchie et al. |
| 2001/0025183 | A1 | 9/2001 | Shahidi et al. |
| 2001/0025184 | A1 | 9/2001 | Messerly |
| 2001/0031950 | A1 | 10/2001 | Ryan |
| 2001/0039419 | A1 | 11/2001 | Francischelli et al. |
| 2002/0002377 | A1 | 1/2002 | Cimino |
| 2002/0019649 | A1 | 2/2002 | Sikora et al. |
| 2002/0022836 | A1 | 2/2002 | Goble et al. |
| 2002/0029055 | A1 | 3/2002 | Bonutti |
| 2002/0049551 | A1 | 4/2002 | Friedman et al. |
| 2002/0052617 | A1 | 5/2002 | Anis et al. |
| 2002/0077550 | A1 | 6/2002 | Rabiner et al. |
| 2002/0156466 | A1 | 10/2002 | Sakurai et al. |
| 2002/0156493 | A1 | 10/2002 | Houser et al. |
| 2003/0014087 | A1* | 1/2003 | Fang et al. ..... 607/48 |
| 2003/0036705 | A1 | 2/2003 | Hare et al. |
| 2003/0050572 | A1 | 3/2003 | Brautigam et al. |
| 2003/0055443 | A1 | 3/2003 | Spotnitz |
| 2003/0114851 | A1 | 6/2003 | Truckai et al. |
| 2003/0144680 | A1 | 7/2003 | Kellogg et al. |
| 2003/0199794 | A1 | 10/2003 | Sakurai et al. |
| 2003/0204199 | A1 | 10/2003 | Novak et al. |
| 2003/0212332 | A1 | 11/2003 | Fenton et al. |
| 2003/0212363 | A1 | 11/2003 | Shipp |
| 2003/0212392 | A1 | 11/2003 | Fenton et al. |
| 2003/0212422 | A1 | 11/2003 | Fenton et al. |
| 2003/0229344 | A1 | 12/2003 | Dycus et al. |
| 2004/0030254 | A1 | 2/2004 | Babaev |
| 2004/0030330 | A1 | 2/2004 | Brassell et al. |
| 2004/0047485 | A1 | 3/2004 | Sherrit et al. |
| 2004/0054364 | A1 | 3/2004 | Aranyi et al. |
| 2004/0064151 | A1 | 4/2004 | Mollenauer |

(56) References Cited

U.S. PATENT DOCUMENTS

2004/0092921 A1 5/2004 Kadziauskas et al.
2004/0092992 A1 5/2004 Adams et al.
2004/0097911 A1 5/2004 Murakami et al.
2004/0097912 A1 5/2004 Gonnering
2004/0097919 A1 5/2004 Wellman et al.
2004/0097996 A1 5/2004 Rabiner et al.
2004/0116952 A1 6/2004 Sakurai et al.
2004/0132383 A1 7/2004 Langford et al.
2004/0147934 A1 7/2004 Kiester
2004/0167508 A1 8/2004 Wham et al.
2004/0176686 A1 9/2004 Hare et al.
2004/0176751 A1 9/2004 Weitzner et al.
2004/0199193 A1 10/2004 Hayashi et al.
2004/0204728 A1 10/2004 Haefner
2004/0215132 A1 10/2004 Yoon
2004/0243147 A1 12/2004 Lipow
2004/0243157 A1 12/2004 Connor et al.
2004/0260300 A1 12/2004 Gorensek et al.
2004/0267333 A1* 12/2004 Kronberg ..... 607/72
2005/0020967 A1 1/2005 Ono
2005/0021018 A1 1/2005 Anderson et al.
2005/0021065 A1 1/2005 Yamada et al.
2005/0033337 A1 2/2005 Muir et al.
2005/0049546 A1 3/2005 Messerly et al.
2005/0070800 A1 3/2005 Takahashi
2005/0096683 A1 5/2005 Ellins et al.
2005/0099824 A1 5/2005 Dowling et al.
2005/0103819 A1 5/2005 Racenet et al.
2005/0143769 A1 6/2005 White et al.
2005/0149108 A1 7/2005 Cox
2005/0165345 A1 7/2005 Laufer et al.
2005/0177184 A1 8/2005 Easley
2005/0182339 A1 8/2005 Lee et al.
2005/0188743 A1 9/2005 Land
2005/0192610 A1 9/2005 Houser et al.
2005/0209620 A1 9/2005 Du et al.
2005/0222598 A1 10/2005 Ho et al.
2005/0234484 A1 10/2005 Houser et al.
2005/0249667 A1 11/2005 Tuszynski et al.
2005/0256405 A1 11/2005 Makin et al.
2005/0261581 A1 11/2005 Hughes et al.
2005/0261588 A1 11/2005 Makin et al.
2005/0273090 A1 12/2005 Nieman et al.
2005/0288659 A1 12/2005 Kimura et al.
2006/0030797 A1 2/2006 Zhou et al.
2006/0058825 A1 3/2006 Ogura et al.
2006/0063130 A1 3/2006 Hayman et al.
2006/0066181 A1 3/2006 Bromfield et al.
2006/0074442 A1 4/2006 Noriega et al.
2006/0079874 A1 4/2006 Faller et al.
2006/0079876 A1 4/2006 Houser et al.
2006/0079878 A1 4/2006 Houser
2006/0079879 A1 4/2006 Faller et al.
2006/0084963 A1 4/2006 Messerly
2006/0095046 A1 5/2006 Trieu et al.
2006/0190034 A1 8/2006 Nishizawa et al.
2006/0206100 A1 9/2006 Eskridge et al.
2006/0206115 A1 9/2006 Schomer et al.
2006/0211943 A1 9/2006 Beaupre
2006/0217729 A1 9/2006 Eskridge et al.
2006/0224160 A1 10/2006 Trieu et al.
2006/0235306 A1 10/2006 Cotter et al.
2006/0247558 A1 11/2006 Yamada
2006/0253050 A1 11/2006 Yoshimine et al.
2006/0264809 A1 11/2006 Hansmann et al.
2006/0271030 A1 11/2006 Francis et al.
2007/0016235 A1 1/2007 Tanaka et al.
2007/0016236 A1 1/2007 Beaupre
2007/0055228 A1 3/2007 Berg et al.
2007/0056596 A1 3/2007 Fanney et al.
2007/0060915 A1 3/2007 Kucklick
2007/0060935 A1 3/2007 Schwardt et al.
2007/0063618 A1 3/2007 Bromfield
2007/0074584 A1 4/2007 Talarico et al.
2007/0078458 A1 4/2007 Dumbauld et al.
2007/0106317 A1 5/2007 Shelton, IV et al.
2007/0129716 A1 6/2007 Daw et al.
2007/0130771 A1 6/2007 Ehlert et al.
2007/0131034 A1 6/2007 Ehlert et al.
2007/0149881 A1 6/2007 Rabin
2007/0156163 A1 7/2007 Davison et al.
2007/0162050 A1 7/2007 Sartor
2007/0166663 A1 7/2007 Telles et al.
2007/0173803 A1 7/2007 Wham et al.
2007/0173813 A1 7/2007 Odom
2007/0173872 A1 7/2007 Neuenfeldt
2007/0175949 A1 8/2007 Shelton, IV et al.
2007/0185380 A1 8/2007 Kucklick
2007/0191712 A1 8/2007 Messerly et al.
2007/0219481 A1 9/2007 Babaev
2007/0239028 A1 10/2007 Houser et al.
2007/0239101 A1 10/2007 Kellogg
2007/0249941 A1 10/2007 Salehi et al.
2007/0260234 A1 11/2007 McCullagh et al.
2007/0265560 A1 11/2007 Soltani et al.
2007/0275348 A1 11/2007 Lemon
2007/0282335 A1 12/2007 Young et al.
2007/0287933 A1 12/2007 Phan et al.
2007/0288055 A1 12/2007 Lee
2008/0009848 A1 1/2008 Paraschiv et al.
2008/0013809 A1 1/2008 Zhu et al.
2008/0051812 A1 2/2008 Schmitz et al.
2008/0058585 A1 3/2008 Novak et al.
2008/0058775 A1 3/2008 Darian et al.
2008/0058845 A1 3/2008 Shimizu et al.
2008/0077145 A1 3/2008 Boyden et al.
2008/0082039 A1 4/2008 Babaev
2008/0082098 A1 4/2008 Tanaka et al.
2008/0097501 A1 4/2008 Blier
2008/0114364 A1 5/2008 Goldin et al.
2008/0125768 A1 5/2008 Tahara et al.
2008/0140158 A1 6/2008 Hamel et al.
2008/0147092 A1 6/2008 Rogge et al.
2008/0171938 A1 7/2008 Masuda et al.
2008/0172051 A1 7/2008 Masuda et al.
2008/0177268 A1 7/2008 Daum et al.
2008/0188878 A1 8/2008 Young
2008/0200940 A1 8/2008 Eichmann et al.
2008/0208108 A1 8/2008 Kimura
2008/0208231 A1 8/2008 Ota et al.
2008/0214967 A1 9/2008 Aranyi et al.
2008/0234709 A1 9/2008 Houser
2008/0234710 A1 9/2008 Neurohr et al.
2008/0234711 A1 9/2008 Houser et al.
2008/0243106 A1 10/2008 Coe et al.
2008/0243162 A1 10/2008 Shibata et al.
2008/0245371 A1 10/2008 Gruber
2008/0249553 A1 10/2008 Gruber et al.
2008/0255423 A1 10/2008 Kondo et al.
2008/0262490 A1 10/2008 Williams
2008/0281200 A1 11/2008 Voic et al.
2008/0281315 A1 11/2008 Gines
2008/0281322 A1 11/2008 Sherman et al.
2008/0287948 A1 11/2008 Newton et al.
2009/0023985 A1 1/2009 Ewers
2009/0024141 A1 1/2009 Stahler et al.
2009/0030311 A1 1/2009 Stulen et al.
2009/0030351 A1 1/2009 Wiener et al.
2009/0030437 A1 1/2009 Houser et al.
2009/0030438 A1 1/2009 Stulen
2009/0030439 A1 1/2009 Stulen
2009/0036911 A1 2/2009 Stulen
2009/0036912 A1 2/2009 Wiener et al.
2009/0036913 A1 2/2009 Wiener et al.
2009/0036914 A1 2/2009 Houser
2009/0048537 A1 2/2009 Lydon et al.
2009/0054886 A1 2/2009 Yachi et al.
2009/0054894 A1 2/2009 Yachi
2009/0076506 A1 3/2009 Baker
2009/0082716 A1 3/2009 Akahoshi
2009/0088738 A1 4/2009 Guerra et al.
2009/0088785 A1 4/2009 Masuda
2009/0105750 A1 4/2009 Price et al.
2009/0112229 A1 4/2009 Omori et al.

(56) References Cited

U.S. PATENT DOCUMENTS

2009/0118751 A1 5/2009 Wiener et al.
2009/0118802 A1 5/2009 Mioduski et al.
2009/0138006 A1 5/2009 Bales et al.
2009/0143797 A1 6/2009 Smith et al.
2009/0143798 A1 6/2009 Smith et al.
2009/0143799 A1 6/2009 Smith et al.
2009/0143800 A1 6/2009 Deville et al.
2009/0143801 A1 6/2009 Deville et al.
2009/0143802 A1 6/2009 Deville et al.
2009/0143803 A1 6/2009 Palmer et al.
2009/0143804 A1 6/2009 Palmer et al.
2009/0143805 A1 6/2009 Palmer et al.
2009/0143806 A1 6/2009 Witt et al.
2009/0149801 A1 6/2009 Crandall et al.
2009/0163807 A1 6/2009 Sliwa
2009/0207923 A1 8/2009 Dress
2009/0216157 A1 8/2009 Yamada
2009/0223033 A1 9/2009 Houser
2009/0254077 A1 10/2009 Craig
2009/0254080 A1 10/2009 Honda
2009/0264909 A1 10/2009 Beaupre
2009/0270771 A1 10/2009 Takahashi
2009/0270812 A1 10/2009 Litscher et al.
2009/0270853 A1 10/2009 Yachi et al.
2009/0270891 A1 10/2009 Beupre
2009/0270899 A1 10/2009 Carusillo et al.
2009/0275940 A1* 11/2009 Malackowski et al. ..... 606/42
2009/0299141 A1 12/2009 Downey et al.
2009/0318945 A1 12/2009 Yoshimine et al.
2009/0327715 A1 12/2009 Smith et al.
2010/0004508 A1 1/2010 Naito et al.
2010/0004668 A1 1/2010 Smith et al.
2010/0004669 A1 1/2010 Smith et al.
2010/0016785 A1 1/2010 Takuma
2010/0016852 A1 1/2010 Manzo et al.
2010/0022825 A1 1/2010 Yoshie
2010/0030233 A1 2/2010 Whitman et al.
2010/0030248 A1 2/2010 Palmer et al.
2010/0036370 A1 2/2010 Mirel et al.
2010/0042077 A1 2/2010 Okada
2010/0049180 A1 2/2010 Wells et al.
2010/0057118 A1 3/2010 Dietz et al.
2010/0063525 A1 3/2010 Beaupre et al.
2010/0063528 A1 3/2010 Beaupré
2010/0069940 A1 3/2010 Miller et al.
2010/0106173 A1 4/2010 Yoshimine
2010/0158307 A1 6/2010 Kubota et al.
2010/0168741 A1 7/2010 Sanai et al.
2010/0179577 A1 7/2010 Houser
2010/0187283 A1 7/2010 Crainich et al.
2010/0193567 A1 8/2010 Scheib et al.
2010/0222714 A1 9/2010 Muir et al.
2010/0228264 A1 9/2010 Robinson et al.
2010/0234906 A1 9/2010 Koh
2010/0262134 A1 10/2010 Jensen et al.
2010/0268211 A1 10/2010 Manwaring et al.
2010/0274160 A1 10/2010 Yachi et al.
2010/0280407 A1 11/2010 Polster
2010/0292691 A1 11/2010 Brogna
2010/0298743 A1 11/2010 Nield et al.
2010/0298851 A1 11/2010 Nield
2010/0331742 A1 12/2010 Masuda
2010/0331869 A1 12/2010 Voegele et al.
2010/0331870 A1 12/2010 Wan et al.
2010/0331871 A1 12/2010 Nield et al.
2010/0331872 A1 12/2010 Houser et al.
2011/0004233 A1 1/2011 Muir et al.
2011/0009850 A1 1/2011 Main et al.
2011/0015627 A1 1/2011 DiNardo et al.
2011/0015631 A1 1/2011 Wiener et al.
2011/0015660 A1 1/2011 Wiener et al.
2011/0077648 A1 3/2011 Lee et al.
2011/0082486 A1 4/2011 Messerly et al.
2011/0087212 A1 4/2011 Aldridge et al.
2011/0087213 A1 4/2011 Messerly et al.
2011/0087214 A1 4/2011 Giordano et al.
2011/0087215 A1 4/2011 Aldridge et al.
2011/0087216 A1 4/2011 Aldridge et al.
2011/0087217 A1 4/2011 Yates et al.
2011/0087218 A1 4/2011 Boudreaux et al.
2011/0087256 A1 4/2011 Wiener et al.
2011/0112526 A1 5/2011 Fritz et al.
2011/0125151 A1 5/2011 Strauss et al.
2011/0125174 A1 5/2011 Babaev
2011/0125175 A1 5/2011 Stulen et al.
2011/0140863 A1* 6/2011 Shingai ..... G06K 7/0008 340/10.6
2011/0144806 A1 6/2011 Sandhu et al.
2011/0196286 A1 8/2011 Robertson et al.
2011/0196287 A1 8/2011 Robertson et al.
2011/0196398 A1 8/2011 Robertson et al.
2011/0196399 A1 8/2011 Robertson et al.
2011/0196400 A1 8/2011 Robertson et al.
2011/0196401 A1 8/2011 Robertson et al.
2011/0196402 A1 8/2011 Robertson et al.
2011/0196403 A1 8/2011 Robertson et al.
2011/0196404 A1 8/2011 Dietz et al.
2011/0196405 A1 8/2011 Dietz
2011/0224689 A1 9/2011 Larkin et al.
2011/0238065 A1 9/2011 Hunt et al.
2011/0257650 A1 10/2011 Deville et al.
2011/0270126 A1 11/2011 Gunday et al.
2011/0288452 A1 11/2011 Houser et al.
2011/0290853 A1 12/2011 Shelton, IV et al.
2011/0290856 A1 12/2011 Shelton, IV et al.
2011/0295242 A1 12/2011 Spivey et al.
2012/0004655 A1 1/2012 Kim et al.
2012/0022525 A1 1/2012 Dietz et al.
2012/0022530 A1 1/2012 Woodruff et al.
2012/0022583 A1 1/2012 Sugalski et al.
2012/0029546 A1 2/2012 Robertson
2012/0059289 A1 3/2012 Nield et al.
2012/0065628 A1 3/2012 Naito
2012/0071863 A1 3/2012 Lee et al.
2012/0078139 A1 3/2012 Aldridge et al.
2012/0078243 A1 3/2012 Worrell et al.
2012/0078244 A1 3/2012 Worrell et al.
2012/0078247 A1 3/2012 Worrell et al.
2012/0078278 A1 3/2012 Bales, Jr. et al.
2012/0080332 A1 4/2012 Shelton, IV et al.
2012/0083783 A1 4/2012 Davison et al.
2012/0083784 A1 4/2012 Davison et al.
2012/0101495 A1 4/2012 Young et al.
2012/0101501 A1 4/2012 Nishimura et al.
2012/0109159 A1 5/2012 Jordan et al.
2012/0116379 A1 5/2012 Yates et al.
2012/0116391 A1 5/2012 Houser et al.
2012/0116394 A1 5/2012 Timm et al.
2012/0116395 A1 5/2012 Madan et al.
2012/0123458 A1 5/2012 Giordano et al.
2012/0130256 A1 5/2012 Buysse et al.
2012/0130365 A1 5/2012 McLawhorn
2012/0132450 A1 5/2012 Timm et al.
2012/0136354 A1 5/2012 Rupp
2012/0138660 A1 6/2012 Shelton, IV
2012/0143211 A1 6/2012 Kishi
2012/0150170 A1 6/2012 Buysse et al.
2012/0165816 A1 6/2012 Kersten et al.
2012/0172873 A1 7/2012 Artale et al.
2012/0172904 A1 7/2012 Muir et al.
2012/0177005 A1 7/2012 Liang et al.
2012/0184946 A1 7/2012 Price et al.
2012/0199630 A1 8/2012 Shelton, IV
2012/0199631 A1 8/2012 Shelton, IV et al.
2012/0199632 A1 8/2012 Spivey et al.
2012/0199633 A1 8/2012 Shelton, IV et al.
2012/0203143 A1 8/2012 Sanai et al.
2012/0203247 A1 8/2012 Shelton, IV et al.
2012/0205421 A1 8/2012 Shelton, IV
2012/0209289 A1 8/2012 Duque et al.
2012/0209303 A1 8/2012 Frankhouser et al.
2012/0210223 A1 8/2012 Eppolito
2012/0211546 A1 8/2012 Shelton, IV
2012/0215220 A1 8/2012 Manzo et al.

(56) References Cited

U.S. PATENT DOCUMENTS

| | | | |
|---|---|---|---|
| 2012/0245582 | A1 | 9/2012 | Kimball et al. |
| 2012/0253370 | A1 | 10/2012 | Ross et al. |
| 2012/0259353 | A1 | 10/2012 | Houser et al. |
| 2012/0269676 | A1 | 10/2012 | Houser et al. |
| 2012/0289984 | A1 | 11/2012 | Houser et al. |
| 2012/0310262 | A1 | 12/2012 | Messerly et al. |
| 2012/0310263 | A1 | 12/2012 | Messerly et al. |
| 2012/0310264 | A1 | 12/2012 | Messerly et al. |
| 2012/0323265 | A1 | 12/2012 | Stulen |
| 2012/0330307 | A1 | 12/2012 | Ladtkow et al. |
| 2013/0012957 | A1 | 1/2013 | Shelton, IV et al. |
| 2013/0012970 | A1 | 1/2013 | Houser |
| 2013/0030433 | A1 | 1/2013 | Heard |
| 2013/0035680 | A1 | 2/2013 | Ben-Haim et al. |
| 2013/0053840 | A1 | 2/2013 | Krapohl et al. |
| 2013/0072856 | A1 | 3/2013 | Frankhouser et al. |
| 2013/0072857 | A1 | 3/2013 | Frankhouser et al. |
| 2013/0079762 | A1 | 3/2013 | Twomey et al. |
| 2013/0103023 | A1 | 4/2013 | Monson et al. |
| 2013/0103024 | A1 | 4/2013 | Monson et al. |
| 2013/0110145 | A1 | 5/2013 | Weitzman |
| 2013/0123776 | A1 | 5/2013 | Monson et al. |
| 2013/0123777 | A1 | 5/2013 | Monson et al. |
| 2013/0123782 | A1 | 5/2013 | Trees et al. |
| 2013/0123822 | A1 | 5/2013 | Wellman et al. |
| 2013/0131660 | A1 | 5/2013 | Monson et al. |
| 2013/0165929 | A1 | 6/2013 | Muir et al. |
| 2013/0217967 | A1 | 8/2013 | Mohr et al. |
| 2013/0253498 | A1 | 9/2013 | Germain et al. |
| 2013/0274734 | A1 | 10/2013 | Maass et al. |
| 2013/0282038 | A1 | 10/2013 | Dannaher et al. |
| 2013/0296908 | A1 | 11/2013 | Schulte et al. |
| 2013/0338661 | A1 | 12/2013 | Behnke, II |
| 2013/0345689 | A1 | 12/2013 | Ruddenklau et al. |
| 2014/0005640 | A1 | 1/2014 | Shelton, IV et al. |
| 2014/0005653 | A1 | 1/2014 | Shelton, IV et al. |
| 2014/0005656 | A1 | 1/2014 | Mucilli et al. |
| 2014/0005661 | A1 | 1/2014 | Shelton, IV et al. |
| 2014/0005662 | A1 | 1/2014 | Shelton, IV et al. |
| 2014/0005676 | A1 | 1/2014 | Shelton, IV et al. |
| 2014/0005680 | A1 | 1/2014 | Shelton, IV et al. |
| 2014/0005681 | A1 | 1/2014 | Gee et al. |
| 2014/0005702 | A1 | 1/2014 | Timm et al. |
| 2014/0005705 | A1 | 1/2014 | Weir et al. |
| 2014/0005708 | A1 | 1/2014 | Shelton, IV et al. |
| 2014/0005718 | A1 | 1/2014 | Shelton, IV et al. |
| 2014/0012299 | A1 | 1/2014 | Stoddard et al. |
| 2014/0066962 | A1 | 3/2014 | Robertson et al. |
| 2014/0087569 | A1 | 3/2014 | Lee |
| 2014/0107538 | A1 | 4/2014 | Wiener et al. |
| 2014/0114327 | A1 | 4/2014 | Boudreaux et al. |
| 2014/0135804 | A1 | 5/2014 | Weisenburgh, II et al. |
| 2014/0155921 | A1 | 6/2014 | Price et al. |
| 2014/0180280 | A1 | 6/2014 | Sigmon, Jr. |
| 2014/0243864 | A1 | 8/2014 | Voegele et al. |
| 2014/0276970 | A1 | 9/2014 | Messerly et al. |
| 2015/0045819 | A1 | 2/2015 | Houser et al. |
| 2015/0066067 | A1 | 3/2015 | Stulen |
| 2015/0073460 | A1 | 3/2015 | Stulen |
| 2015/0112335 | A1 | 4/2015 | Boudreaux et al. |
| 2015/0119914 | A1 | 4/2015 | Neurohr et al. |
| 2015/0119915 | A1 | 4/2015 | Neurohr et al. |
| 2015/0119916 | A1 | 4/2015 | Dietz et al. |
| 2015/0123348 | A1 | 5/2015 | Robertson et al. |
| 2015/0157355 | A1 | 6/2015 | Price et al. |
| 2015/0157356 | A1 | 6/2015 | Gee |
| 2015/0164533 | A1 | 6/2015 | Felder et al. |
| 2015/0164534 | A1 | 6/2015 | Felder et al. |
| 2015/0164535 | A1 | 6/2015 | Felder et al. |
| 2015/0164536 | A1 | 6/2015 | Czarnecki et al. |
| 2015/0164537 | A1 | 6/2015 | Cagle et al. |
| 2015/0164538 | A1 | 6/2015 | Aldridge et al. |
| 2015/0182251 | A1 | 7/2015 | Messerly et al. |
| 2015/0182276 | A1 | 7/2015 | Wiener et al. |
| 2015/0182277 | A1 | 7/2015 | Wiener et al. |
| 2015/0196318 | A1 | 7/2015 | Messerly et al. |
| 2015/0250495 | A1 | 9/2015 | Robertson et al. |
| 2015/0257780 | A1 | 9/2015 | Houser |
| 2015/0257781 | A1 | 9/2015 | Houser et al. |
| 2015/0265308 | A1 | 9/2015 | Houser et al. |
| 2015/0327883 | A1 | 11/2015 | Messerly et al. |
| 2015/0328484 | A1 | 11/2015 | Messerly et al. |
| 2015/0340586 | A1 | 11/2015 | Wiener et al. |
| 2015/0351789 | A1 | 12/2015 | Robertson et al. |
| 2016/0030076 | A1 | 2/2016 | Faller et al. |
| 2016/0089209 | A1 | 3/2016 | Parihar et al. |
| 2016/0089533 | A1 | 3/2016 | Turner et al. |
| 2016/0095617 | A1 | 4/2016 | Price et al. |
| 2016/0106509 | A1 | 4/2016 | Worrell et al. |
| 2016/0120563 | A1 | 5/2016 | Messerly et al. |
| 2016/0144204 | A1 | 5/2016 | Akagane |
| 2016/0192999 | A1 | 7/2016 | Stulen et al. |
| 2016/0206342 | A1 | 7/2016 | Robertson et al. |
| 2016/0262786 | A1 | 9/2016 | Madan et al. |
| 2016/0296249 | A1 | 10/2016 | Robertson |
| 2016/0296250 | A1 | 10/2016 | Olson et al. |
| 2016/0296251 | A1 | 10/2016 | Olson et al. |
| 2016/0296252 | A1 | 10/2016 | Olson et al. |
| 2016/0317217 | A1 | 11/2016 | Batross et al. |
| 2016/0367281 | A1 | 12/2016 | Gee et al. |
| 2017/0143371 | A1 | 5/2017 | Witt et al. |
| 2017/0143877 | A1 | 5/2017 | Witt et al. |
| 2017/0196586 | A1 | 7/2017 | Witt et al. |
| 2017/0196587 | A1 | 7/2017 | Witt et al. |
| 2017/0202573 | A1 | 7/2017 | Witt et al. |

FOREIGN PATENT DOCUMENTS

| | | | |
|---|---|---|---|
| CN | 1253485 | A | 5/2000 |
| CN | 2460047 | Y | 11/2001 |
| CN | 1634601 | A | 7/2005 |
| CN | 1640365 | A | 7/2005 |
| CN | 1694649 | A | 11/2005 |
| CN | 1775323 | A | 5/2006 |
| CN | 1922563 | A | 2/2007 |
| CN | 1951333 | A | 4/2007 |
| CN | 101035482 | A | 9/2007 |
| CN | 101040799 | A | 9/2007 |
| CN | 101467917 | A | 1/2009 |
| CN | 101396300 | A | 4/2009 |
| CN | 101674782 | A | 3/2010 |
| CN | 101883531 | A | 11/2010 |
| CN | 202027624 | U | 11/2011 |
| CN | 101313865 | A | 1/2013 |
| CN | 1233944 | A | 8/2017 |
| CN | 102160045 | A | 8/2017 |
| DE | 3904558 | A1 | 8/1990 |
| DE | 4323585 | A1 | 1/1995 |
| DE | 9210327 | U1 | 1/1995 |
| DE | 19608716 | C1 | 4/1997 |
| DE | 20021619 | U1 | 3/2001 |
| DE | 10042606 | A1 | 8/2001 |
| EP | 0136855 | B1 | 9/1984 |
| EP | 0171967 | A2 | 2/1986 |
| EP | 1839599 | A1 | 10/1987 |
| EP | 0336742 | A2 | 4/1989 |
| EP | 0342448 | A1 | 11/1989 |
| EP | 0424685 | B1 | 5/1991 |
| EP | 0443256 | A1 | 8/1991 |
| EP | 0456470 | A1 | 11/1991 |
| EP | 0238667 | B1 | 11/1992 |
| EP | 0677275 | A2 | 3/1995 |
| EP | 0482195 | B1 | 1/1996 |
| EP | 0598976 | A2 | 1/1996 |
| EP | 0695535 | A1 | 2/1996 |
| EP | 0741996 | A2 | 11/1996 |
| EP | 0612570 | B1 | 6/1997 |
| EP | 0612570 | B1 | 9/1997 |
| EP | 1138264 | A1 | 10/2001 |
| EP | 0908148 81 | | 1/2002 |
| EP | 0908148 | B1 | 1/2002 |
| EP | 1229515 | A2 | 8/2002 |
| EP | 2002-263579 | A | 9/2002 |
| EP | 1285634 | A1 | 2/2003 |

(56) References Cited

FOREIGN PATENT DOCUMENTS

| | | | |
|---|---|---|---|
| EP | 0908155 | B1 | 6/2003 |
| EP | 1108394 | A2 | 6/2003 |
| EP | 0705570 | B1 | 4/2004 |
| EP | 0765637 | B1 | 7/2004 |
| EP | 0870473 | B1 | 9/2005 |
| EP | 0624346 | B1 | 11/2005 |
| EP | 1594209 | A1 | 11/2005 |
| EP | 1199044 | B1 | 12/2005 |
| EP | 1609428 | A1 | 12/2005 |
| EP | 1199043 | B1 | 3/2006 |
| EP | 1433425 | B1 | 6/2006 |
| EP | 1256323 | B1 | 9/2006 |
| EP | 1698289 | A2 | 9/2006 |
| EP | 1704824 | A1 | 9/2006 |
| EP | 1749479 | A1 | 2/2007 |
| EP | 1815950 | A1 | 8/2007 |
| EP | 1844720 | A1 | 10/2007 |
| EP | 1862133 | A1 | 12/2007 |
| EP | 1875875 | A1 | 1/2008 |
| EP | 1199045 | B1 | 6/2008 |
| EP | 1964530 | A1 | 9/2008 |
| EP | 1972264 | A1 | 9/2008 |
| EP | 1974771 | A1 | 10/2008 |
| EP | 1435852 | B1 | 12/2008 |
| EP | 1498082 | B1 | 12/2008 |
| EP | 1707131 | B1 | 12/2008 |
| EP | 1997438 | A2 | 12/2008 |
| EP | 1477104 | B1 | 1/2009 |
| EP | 2014218 | A2 | 1/2009 |
| EP | 2042112 | A2 | 4/2009 |
| EP | 1832259 | B1 | 6/2009 |
| EP | 2074959 | A1 | 7/2009 |
| EP | 2106758 | A1 | 10/2009 |
| EP | 2111813 | A1 | 10/2009 |
| EP | 2200145 | A1 | 6/2010 |
| EP | 1214913 | B1 | 7/2010 |
| EP | 2238938 | A1 | 10/2010 |
| EP | 2298154 | A2 | 3/2011 |
| EP | 1510178 | B1 | 6/2011 |
| EP | 1946708 | B1 | 6/2011 |
| EP | 2305144 | A1 | 6/2011 |
| EP | 2335630 | A1 | 6/2011 |
| EP | 1502551 | B1 | 7/2011 |
| EP | 2361562 | A1 | 8/2011 |
| EP | 2365608 | A2 | 9/2011 |
| EP | 2420197 | A2 | 2/2012 |
| EP | 2422721 | A2 | 2/2012 |
| EP | 1927321 | B1 | 4/2012 |
| EP | 2510891 | A1 | 10/2012 |
| EP | 2316359 | B1 | 3/2013 |
| EP | 1586275 | B1 | 5/2013 |
| EP | 1616529 | B1 | 9/2013 |
| EP | 2583633 | B1 | 10/2014 |
| EP | 2113210 | B1 | 3/2016 |
| EP | 2227155 | B1 | 7/2016 |
| EP | 2859858 | B1 | 12/2016 |
| ES | 2115068 | T3 | 6/1998 |
| GB | 1482943 | A | 8/1977 |
| GB | 2032221 | A | 4/1980 |
| GB | S 59141938 | A | 8/1984 |
| GB | 2317566 | A | 4/1998 |
| GB | 2379878 | B | 11/2004 |
| GB | 2447767 | B | 8/2011 |
| JP | S 50-100891 | A | 8/1975 |
| JP | S 59-68513 | U | 5/1984 |
| JP | S 62-221343 | A | 9/1987 |
| JP | S 62-227343 | A | 10/1987 |
| JP | 62-292153 | A | 12/1987 |
| JP | 62-2292153 | A | 12/1987 |
| JP | S 62-292154 | A | 12/1987 |
| JP | 63-109386 | A | 5/1988 |
| JP | S 63-109386 | A | 5/1988 |
| JP | 63-315049 | A | 12/1988 |
| JP | S 63-315049 | A | 12/1988 |
| JP | H 01-151452 | A | 6/1989 |
| JP | H 01-198540 | A | 8/1989 |
| JP | 02-71510 | U | 5/1990 |
| JP | H 02-71510 | U | 5/1990 |
| JP | 2-286149 | A | 11/1990 |
| JP | H 02-286149 | A | 11/1990 |
| JP | H 02-292193 | A | 12/1990 |
| JP | H 03-37061 | A | 2/1991 |
| JP | 04-25707 | U | 2/1992 |
| JP | H 04-25707 | U | 2/1992 |
| JP | H 04-64351 | A | 2/1992 |
| JP | 4-30508 | U | 3/1992 |
| JP | H 04-30508 | U | 3/1992 |
| JP | H 04-150847 | A | 5/1992 |
| JP | H 04-152942 | A | 5/1992 |
| JP | 05-095955 | A | 4/1993 |
| JP | H 05-115490 | A | 5/1993 |
| JP | H 06-70938 | A | 3/1994 |
| JP | 6-104503 | A | 4/1994 |
| JP | H 06-104503 | A | 4/1994 |
| JP | 6-507081 | A | 8/1994 |
| JP | H 06-217988 | A | 8/1994 |
| JP | H 06-507081 | A | 8/1994 |
| JP | H 07-500514 | A | 1/1995 |
| JP | H 7-508910 | A | 10/1995 |
| JP | 7-308323 | A | 11/1995 |
| JP | H 07-308323 | A | 11/1995 |
| JP | 8-24266 | A | 1/1996 |
| JP | H 08-24266 | A | 1/1996 |
| JP | 8-275951 | A | 10/1996 |
| JP | H 08-275951 | A | 10/1996 |
| JP | H 08-299351 | A | 11/1996 |
| JP | H 08-336544 | A | 12/1996 |
| JP | H 08-336545 | A | 12/1996 |
| JP | H 09-503146 | A | 3/1997 |
| JP | H 09-135553 | A | 5/1997 |
| JP | H 09-140722 | A | 6/1997 |
| JP | H 09-503146 | A | 6/1997 |
| JP | H 10-5237 | A | 1/1998 |
| JP | 10-295700 | A | 11/1998 |
| JP | H 10-295700 | A | 11/1998 |
| JP | H 11-501543 | A | 2/1999 |
| JP | H 11-128238 | A | 5/1999 |
| JP | H 11-192235 | A | 7/1999 |
| JP | 11-253451 | A | 9/1999 |
| JP | H 11-253451 | A | 9/1999 |
| JP | H 11-318918 | A | 11/1999 |
| JP | 2000-041991 | A | 2/2000 |
| JP | 2000-070279 | A | 3/2000 |
| JP | 2000-210299 | A | 8/2000 |
| JP | 2000-271145 | A | 10/2000 |
| JP | 2000-287987 | A | 10/2000 |
| JP | 2001-029353 | A | 2/2001 |
| JP | 2001-502216 | A | 2/2001 |
| JP | 2001-309925 | A | 11/2001 |
| JP | 2002-177295 | A | 6/2002 |
| JP | 2002-186901 | A | 7/2002 |
| JP | 2002-204808 | A | 7/2002 |
| JP | 2002-238919 | A | 8/2002 |
| JP | 2002-263579 | A | 9/2002 |
| JP | 2002-301086 | A | 10/2002 |
| JP | 2002-306504 | A | 10/2002 |
| JP | 2002-330977 | A | 11/2002 |
| JP | 2002-542690 | A | 12/2002 |
| JP | 2003-000612 | A | 1/2003 |
| JP | 2003-010201 | | 1/2003 |
| JP | 2003-510158 | A | 3/2003 |
| JP | 2003-116870 | A | 4/2003 |
| JP | 2003-126104 | A | 5/2003 |
| JP | 2003-126110 | A | 5/2003 |
| JP | 2003-153919 | A | 5/2003 |
| JP | 2003-310627 | A | 5/2003 |
| JP | 2003-530921 | A | 10/2003 |
| JP | 2003-339730 | A | 12/2003 |
| JP | 2004-129871 | A | 4/2004 |
| JP | 2004-147701 | A | 5/2004 |
| JP | 2005027026 | | 1/2005 |
| JP | 2005027026 | A | 1/2005 |
| JP | 2005-040222 | A | 2/2005 |
| JP | 2005-066316 | A | 3/2005 |

(56) References Cited

FOREIGN PATENT DOCUMENTS

| | | | |
|---|---|---|---|
| JP | 2005-074088 | A | 3/2005 |
| JP | 2005-507679 | A | 3/2005 |
| JP | 2005-534451 | A | 11/2005 |
| JP | 2006-006410 | A | 1/2006 |
| JP | 2006-512149 | A | 4/2006 |
| JP | 2006-116194 | A | 5/2006 |
| JP | 2006-158525 | A | 6/2006 |
| JP | 2006-218296 | A | 8/2006 |
| JP | 2006217716 | | 8/2006 |
| JP | 2006217716 | A | 8/2006 |
| JP | 2006-288431 | A | 10/2006 |
| JP | 2007-050181 | A | 3/2007 |
| JP | 2007-524459 | A | 8/2007 |
| JP | 2007-229454 | A | 9/2007 |
| JP | 2007-527747 | A | 10/2007 |
| JP | 2007-296369 | A | 11/2007 |
| JP | 2008-036390 | A | 2/2008 |
| JP | 2008-508065 | A | 3/2008 |
| JP | 2008-119250 | A | 5/2008 |
| JP | 2008-515562 | A | 5/2008 |
| JP | 2008-521503 | A | 5/2008 |
| JP | 2008-536562 | A | 6/2008 |
| JP | D1339835 | S | 8/2008 |
| JP | 2008-212679 | A | 9/2008 |
| JP | 2008-284374 | A | 11/2008 |
| JP | 2009-511206 | A | 3/2009 |
| JP | 2009-082711 | A | 4/2009 |
| JP | 2009-517181 | A | 4/2009 |
| JP | 4262923 | B2 | 5/2009 |
| JP | 2009-523567 | A | 6/2009 |
| JP | 2009-148557 | A | 7/2009 |
| JP | 2009-236177 | A | 10/2009 |
| JP | 2009-254819 | A | 11/2009 |
| JP | 2010-000336 | A | 1/2010 |
| JP | 2010-009686 | A | 1/2010 |
| JP | 2010-514923 | A | 5/2010 |
| JP | 2010-121865 | A | 6/2010 |
| JP | 2010-534522 | A | 11/2010 |
| JP | 2010-540186 | A | 12/2010 |
| JP | 2011-505198 | A | 2/2011 |
| JP | 2012/075899 | A | 4/2012 |
| JP | 2012-235658 | A | 11/2012 |
| JP | 5208761 | B2 | 6/2013 |
| JP | 2015-515339 | A | 5/2015 |
| JP | 5714508 | B2 | 5/2015 |
| JP | 5836543 | B1 | 12/2015 |
| KR | 100789356 | B1 | 12/2007 |
| RU | 2154437 | C1 | 8/2000 |
| RU | 22035 | U1 | 3/2002 |
| RU | 2304934 | C2 | 8/2007 |
| RU | 2405603 | C1 | 12/2010 |
| SU | 850068 | A1 | 7/1981 |
| WO | WO 92/22259 | A2 | 12/1992 |
| WO | WO 93/08757 | | 5/1993 |
| WO | WO 93/08757 | A1 | 5/1993 |
| WO | WO 93/14708 | A1 | 8/1993 |
| WO | WO 93/16646 | A1 | 9/1993 |
| WO | WO 93/20877 | A1 | 10/1993 |
| WO | WO 9400059 | A1 | 1/1994 |
| WO | WO 94/21183 | | 9/1994 |
| WO | WO 94/21183 | A1 | 9/1994 |
| WO | W0 94/24949 | | 11/1994 |
| WO | WO 94/24949 | A1 | 11/1994 |
| WO | WO 95/09572 | A1 | 4/1995 |
| WO | WO 95/34259 | A1 | 12/1995 |
| WO | WO 96/30885 | A1 | 10/1996 |
| WO | WO 96/39086 | | 12/1996 |
| WO | WO 96/39086 | A1 | 12/1996 |
| WO | WO 98/16156 | A1 | 4/1998 |
| WO | WO 98/26739 | A1 | 6/1998 |
| WO | WO 98/35621 | A1 | 8/1998 |
| WO | WO 98/37815 | A1 | 9/1998 |
| WO | WO 98/47436 | A1 | 10/1998 |
| WO | WO 99/20213 | | 4/1999 |
| WO | WO 99/20213 | A1 | 4/1999 |
| WO | WO 99/52489 | A1 | 10/1999 |
| WO | WO 00/64358 | A2 | 11/2000 |
| WO | WO 00/745585 | A2 | 12/2000 |
| WO | WO 01/24713 | A1 | 4/2001 |
| WO | WO 01/54590 | A1 | 8/2001 |
| WO | WO 01/67970 | A1 | 9/2001 |
| WO | WO 01/95810 | A2 | 12/2001 |
| WO | WO 02/24080 | A2 | 3/2002 |
| WO | WO 02/38057 | A1 | 5/2002 |
| WO | WO 02/062241 | A1 | 8/2002 |
| WO | WO 03/082133 | A1 | 10/2003 |
| WO | WO 2004/012615 | A1 | 2/2004 |
| WO | WO 2004/032754 | A2 | 2/2004 |
| WO | WO 2004/026104 | A2 | 4/2004 |
| WO | WO 2004/032762 | A1 | 4/2004 |
| WO | WO 2004/032763 | A2 | 4/2004 |
| WO | WO 2004/037095 | A2 | 5/2004 |
| WO | WO 2004/060141 | A2 | 7/2004 |
| WO | WO 2004/098426 | A1 | 11/2004 |
| WO | WO 2004/112618 | A2 | 12/2004 |
| WO | WO 2005/117735 | A1 | 12/2005 |
| WO | WO 2005/122917 | A1 | 12/2005 |
| WO | WO 2006/012797 | A1 | 2/2006 |
| WO | WO 2006/042210 | A2 | 4/2006 |
| WO | WO 2006/058223 | A2 | 6/2006 |
| WO | WO 2006/063199 | A2 | 6/2006 |
| WO | WO 2006/083988 | A1 | 8/2006 |
| WO | WO 2006/101661 | A2 | 9/2006 |
| WO | WO 2006/119139 | A2 | 11/2006 |
| WO | WO 2006/119376 | A2 | 11/2006 |
| WO | WO 2006/129465 | A1 | 12/2006 |
| WO | WO 2007/008703 | A2 | 1/2007 |
| WO | WO 2007/008710 | A2 | 1/2007 |
| WO | WO 2007/038538 | A1 | 4/2007 |
| WO | WO 2007/040818 | A1 | 4/2007 |
| WO | WO 2007/047380 | A2 | 4/2007 |
| WO | WO 2007/047531 | A2 | 4/2007 |
| WO | WO 2007/056590 | A1 | 5/2007 |
| WO | WO 2007/087272 | A2 | 8/2007 |
| WO | WO 2007/089724 | A2 | 8/2007 |
| WO | WO 2007/143665 | A2 | 12/2007 |
| WO | WO 2008/016886 | A2 | 2/2008 |
| WO | WO 2008/042021 | A1 | 4/2008 |
| WO | WO 2008/049084 | A2 | 4/2008 |
| WO | WO 2008/051764 | A2 | 5/2008 |
| WO | WO 2008/089174 | A2 | 7/2008 |
| WO | WO 2008/118709 | A1 | 10/2008 |
| WO | WO 2008/130793 | A1 | 10/2008 |
| WO | WO 2009/010565 | A1 | 1/2009 |
| WO | WO 2009/018067 | A1 | 2/2009 |
| WO | WO 2009/018406 | A2 | 2/2009 |
| WO | WO 2009/027065 | A1 | 3/2009 |
| WO | WO 2009/046234 | A2 | 4/2009 |
| WO | WO 2009/073402 | A2 | 6/2009 |
| WO | WO 2009/088550 | A2 | 7/2009 |
| WO | WO 2009/120992 | A2 | 10/2009 |
| WO | WO 2009/141616 | A1 | 11/2009 |
| WO | WO 2010/017149 | A1 | 2/2010 |
| WO | WO 2010/068783 | A1 | 6/2010 |
| WO | WO 2011/008672 | A2 | 1/2011 |
| WO | WO 2011/044338 | A2 | 4/2011 |
| WO | WO 2011/052939 | A2 | 5/2011 |
| WO | WO 2011/060031 | A1 | 5/2011 |
| WO | WO 2011/100321 | A2 | 8/2011 |
| WO | WO 2011/144911 | A1 | 11/2011 |
| WO | WO 2012/044597 | A1 | 4/2012 |
| WO | WO 2012/061722 | A2 | 5/2012 |
| WO | WO 2012/128362 | A1 | 9/2012 |
| WO | WO 2012/135705 | A1 | 10/2012 |
| WO | WO 2012/135721 | A1 | 10/2012 |
| WO | WO 2013/018934 | A1 | 2/2013 |
| WO | WO 2013/062978 | A2 | 5/2013 |
| WO | WO 2014/092108 | A1 | 6/2014 |
| WO | WO 2016/009921 | A1 | 12/2016 |

OTHER PUBLICATIONS http://www.dotmed.com/listing/electrosurical-unit/ethicon/ultracision-g110-/1466724.

(56) References Cited

OTHER PUBLICATIONS

Sullivan, "Cost-Constrained Selection of Strand Diameter and Number in a Litz-Wire Transformer Winding," IEEE Transactions on Power Electronics, vol. 16, No. 2, Mar. 2001, pp. 281-288.
Sullivan, "Optimal Choice for No. of Strands in a Litz-Wire Transformer Winding," IEEE Transactions on Power Electronics, vol. 14, No. 2, Mar. 1999, pp. 283-291.
Graff, K.F., "Elastic Wave Propagation in a Curved Sonic Transmission Line," IEEE Transactions on Sonics and Ultrasonics, SU-17(1), 1-6 (1970).
Makarov, S. N., Ochmann, M., Desinger, K., "The longitudinal vibration response of a curved fiber used for laser ultrasound surgical therapy," Journal of the Acoustical Society of America 102, 1191-1199 (1997).
Morley, L. S. D., "Elastic Waves in a Naturally Curved Rod," Quarterly Journal of Mechanics and Applied Mathematics, 14: 155-172 (1961).
Walsh, S. J., White, R. G., "Vibrational Power Transmission in Curved Beams," Journal of Sound and Vibration, 233(3), 455-488 (2000).
Covidien 501(k) Summary Sonicision, dated Feb. 24, 2011 (7 pages).
Gerhard, Glen C., "Surgical Electrotechnology: Quo Vadis?," IEEE Transactions on Biomedical Engineering, vol. BME-31, No. 12, pp. 787-792, Dec. 1984.
Fowler, K.R., "A Programmable, Arbitrary Waveform Electrosurgical Device," IEEE Engineering in Medicine and Biology Society 10th Annual International Conference, pp. 1324, 1325 (1988).
LaCourse, J.R.; Vogt, M.C.; Miller, W.T., III; Selikowitz, S.M., "Spectral Analysis Interpretation of Electrosurgical Generator Nerve and Muscle Stimulation," IEEE Transactions on Biomedical Engineering, vol. 35, No. 7, pp. 505-509, Jul. 1988.
Partial European Search Report for 12187105.7, dated Jan. 31, 2013 (7 pages).
U.S. Appl. No. 13/151,181, filed Jun. 2, 2011.
U.S. Appl. No. 13/369,561, filed Feb. 9, 2012.
U.S. Appl. No. 13/369,569, filed Feb. 9, 2012.
U.S. Appl. No. 13/369,578, filed Feb. 9, 2012.
U.S. Appl. No. 13/369,584, filed Feb. 9, 2012.
U.S. Appl. No. 13/369,588, filed Feb. 9, 2012.
U.S. Appl. No. 13/369,594, filed Feb. 9, 2012.
U.S. Appl. No. 13/369,601, filed Feb. 9, 2012.
U.S. Appl. No. 13/369,609, filed Feb. 9, 2012.
U.S. Appl. No. 13/369,629, filed Feb. 9, 2012.
U.S. Appl. No. 13/369,666, filed Feb. 9, 2012.
U.S. Appl. No. 13/584,020, filed Aug. 13, 2012.
U.S. Appl. No. 13/584,445, filed Aug. 13, 2012.
Partial International Search Report for PCT/US2010/051787, Feb. 17, 2011 (3 pages).
International Search Report for PCT/US2010/051787, Aug. 26, 2011 (11 pages).
Technology Overview, printed from www.harmonicscalpel.com, Internet site, website accessed on Jun. 13, 2007, (3 pages).
Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.
AST Products, Inc., "Principles of Video Contact Angle Analysis," 20 pages, (2006).
Lim et al., "A Review of Mechanism Used in Laparoscopic Surgical Instruments," Mechanism and Machine Theory, vol. 38, pp. 1133-1147, (2003).
Gooch et al., "Recommended Infection-Control Practices for Dentistry, 1993," Published: May 28, 1993; [retrieved on Aug. 23, 2008]. Retrieved from the internet: URL: http//wonder.cdc.gov/wonder/prevguid/p0000191/p0000191.asp (15 pages).
Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).
Incropera et al., Fundamentals of Heat and Mass Transfer, Wiley, New York (1990). (Book—not attached).
F. A. Duck, "Optical Properties of Tissue Including Ultraviolet and Infrared Radiation," pp. 43-71 in *Physical Properties of Tissue* (1990).
Orr et al., "Overview of Bioheat Transfer," pp. 367-384 in Optical-Thermal Response of Laser-Irradiated Tissue, A. J. Welch and M. J. C. van Gemert, eds., Plenum, New York (1995).
Campbell et al, "Thermal Imaging in Surgery," p. 19-3, in *Medical Infrared Imaging*, N. A. Diakides and J. D. Bronzino, Eds. (2008).
U.S. Appl. No. 29/402,697, filed Sep. 26, 2011.
U.S. Appl. No. 29/402,699, filed Sep. 26, 2011.
U.S. Appl. No. 29/402,700, filed Sep. 26, 2011.
U.S. Appl. No. 29/402,701, filed Sep. 26, 2011.
U.S. Appl. No. 29/404,676, filed Oct. 24, 2011.
U.S. Appl. No. 13/452,386, filed Apr. 20, 2012.
European Search Report for 12187105.7, dated May 23, 2013 (10 pages).
U.S. Appl. No. 14/136,836, filed Dec. 20, 2013.
Gerhard, Glen C., "Surgical Electrotechnology: Quo Vadis?," Biomedical Engineering, IEEE Transactions on , vol. BME-31, No. 12, pp. 787, 792, Dec. 1984.
Fowler, K.R., "A programmable, arbitrary waveform electrosurgical device," Engineering in Medicine and Biology Society, 1988. Proceedings of the Annual International Conference of the IEEE, vol., no., pp. 1324, 1325 vol. 3, Nov. 4-7, 1988.
LaCourse, J.R.; Vogt, M.C.; Miller, W.T., III; Selikowitz, S.M., "Spectral analysis interpretation of electro-surgical generator nerve and muscle stimulation," Biomedical Engineering, IEEE Transactions on , vol. 35, No. 7, pp. 505, 509, Jul. 1988.
International Preliminary Report on Patentability for PCT/US2010/051787, Apr. 11, 2012 (27 pages).
http://www.apicalinstr.com/generators.htm.
http://www.dotmed.com/listing/electrosurical-unit/ethicon/ultracision-g110-/41466724.
http:/www.ethicon.com/gb-en/healthcare-professionals/products/energy-devices/capital//ge . . . .
http://www.4-traders.com/JOHNSON-JOHNSON-4832/news/Johnson-Johnson-Ethicon-E . . . .
http://www.medicalexpo.com/medical-manufacturer/electrosurgical-generator-6951.html.
http://www.megadyne.com/es_generator.php.
http://www.valleylab.com/product/es/generators/index.html.
International Preliminary Report on Patentability for PCT/US2013/036568, Oct. 21, 2014 (10 pages).
International Search Report for PCT/US2013/036568, dated Nov. 11, 2013 (7 pages).
Partial European Search Report for 14194795.2, dated May 26, 2015 (7 pages).

* cited by examiner

SURGICAL GENERATOR FOR ULTRASONIC AND ELECTROSURGICAL DEVICES

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATION

This application is a *reissue of U.S. patent application Ser. No. 13/448,175, entitled SURGICAL GENERATOR FOR ULTRASONIC AND ELECTROSURGICAL DEVICES, filed on Apr. 16, 2012, which issued as U.S. Pat. No. 9,168,054 on Oct. 27, 2015, which is a* continuation-in-part of copending U.S. patent application Ser. No. 13/251,766 entitled [“] SURGICAL GENERATOR FOR ULTRASONIC AND ELECTROSURGICAL DEVICES,[”] filed Oct. 3, 2011, now U.S. Patent Publication No. 2012/0078139, which is a continuation-in-part of copending U.S. patent application Ser. No. 12/896,360 entitled [“] SURGICAL GENERATOR FOR ULTRASONIC AND ELECTROSURGICAL DEVICES,[”] filed Oct. 1, 2010, [now U.S. Patent Publication No. 2011/0087256] *which issued as U.S. Pat. No. 9,060,775 on Jun. 23, 2015*, and which claims the benefit under Title 35, United States Code §119(e), of U.S. Provisional Patent Application Ser. No. 61/250,217, filed Oct. 9, 2009 and entitled A DUAL BIPOLAR AND ULTRASONIC GENERATOR FOR ELECTRO-SURGICAL INSTRUMENTS. Each of the applications is hereby incorporated by reference in its entirety.

The present application also is related to the following U.S. patent applications, concurrently-filed on Oct. 3, 2011, each of which is incorporated herein by reference in its entirety:

(1) U.S. patent application Ser. No. 12/896,351, entitled DEVICES AND TECHNIQUES FOR CUTTING AND COAGULATING TISSUE, now U.S. Patent Publication No. 2011/0082486, (2) U.S. patent application Ser. No. 12/896,479, entitled SURGICAL GENERATOR FOR ULTRASONIC AND ELECTROSURGICAL DEVICES, now U.S. Patent Publication No. 2011/0087216, (3) U.S. patent application Ser. No. 12/896,345, entitled SURGICAL GENERATOR FOR ULTRASONIC AND ELECTROSURGICAL DEVICES, now U.S. Patent Publication No. 2011/0087212, (4) U.S. patent application Ser. No. 12/896,384, entitled SURGICAL GENERATOR FOR ULTRASONIC AND ELECTROSURGICAL DEVICES, now U.S. Patent Publication No. 2011/0087213, (5) U.S. patent application Ser. No. 12/896,467, entitled SURGICAL GENERATOR FOR ULTRASONIC AND ELECTROSURGICAL DEVICES, now U.S. Patent Publication No. 2011/0087215, (6) U.S. patent application Ser. No. 12/896,451, entitled SURGICAL GENERATOR FOR ULTRASONIC AND ELECTROSURGICAL DEVICES, now U.S. Patent Publication No. 2011/0087214, and (7) U.S. patent application Ser. No. 12/896,470, entitled SURGICAL GENERATOR FOR ULTRASONIC AND ELECTROSURGICAL DEVICES, now U.S. Patent Publication No. 2011/0087217.

BACKGROUND

Various embodiments are directed to surgical devices, and generators for supplying energy to surgical devices, for use in open or minimally invasive surgical environments.

Ultrasonic surgical devices, such as ultrasonic scalpels, are finding increasingly widespread applications in surgical procedures by virtue of their unique performance characteristics. Depending upon specific device configurations and operational parameters, ultrasonic surgical devices can provide substantially simultaneous transection of tissue and homeostasis by coagulation, desirably minimizing patient trauma. An ultrasonic surgical device may comprise a handpiece containing an ultrasonic transducer, and an instrument coupled to the ultrasonic transducer having a distally-mounted end effector (e.g., a blade tip) to cut and seal tissue. In some cases, the instrument may be permanently affixed to the handpiece. In other cases, the instrument may be detachable from the handpiece, as in the case of a disposable instrument or an instrument that is interchangeable between different. The end effector transmits ultrasonic energy to tissue brought into contact with the end effector to realize cutting and sealing action. Ultrasonic surgical devices of this nature can be configured for open surgical use, laparoscopic, or endoscopic surgical procedures including robotic-assisted procedures.

Ultrasonic energy cuts and coagulates tissue using temperatures lower than those used in electrosurgical procedures and can be transmitted to the end effector by an ultrasonic generator in communication with the handpiece. Vibrating at high frequencies (e.g., 55,500 times per second), the ultrasonic blade denatures protein in the tissue to form a sticky coagulum. Pressure exerted on tissue by the blade surface collapses blood vessels and allows the coagulum to form a haemostatic seal. A surgeon can control the cutting speed and coagulation by the force applied to the tissue by the end effector, the time over which the force is applied and the selected excursion level of the end effector.

The ultrasonic transducer may be modeled as an equivalent circuit comprising first branch having a static capacitance and a second “motional” branch having a serially connected inductance, resistance and capacitance that define the electromechanical properties of a resonator. Known ultrasonic generators may include a tuning inductor for tuning out the static capacitance at a resonant frequency so that substantially all of generator’s drive signal current flows into the motional branch. Accordingly, by using a tuning inductor, the generator’s drive signal current represents the motional branch current, and the generator is thus able to control its drive signal to maintain the ultrasonic transducer’s resonant frequency. The tuning inductor may also transform the phase impedance plot of the ultrasonic transducer to improve the generator’s frequency lock capabilities. However, the tuning inductor must be matched with the specific static capacitance of an ultrasonic transducer at the operational resonance frequency. In other words, a different ultrasonic transducer having a different static capacitance requires a different tuning inductor.

Additionally, in some ultrasonic generator architectures, the generator’s drive signal exhibits asymmetrical harmonic distortion that complicates impedance magnitude and phase measurements. For example, the accuracy of impedance phase measurements may be reduced due to harmonic distortion in the current and voltage signals.

Moreover, electromagnetic interference in noisy environments decreases the ability of the generator to maintain lock on the ultrasonic transducer's resonant frequency, increasing the likelihood of invalid control algorithm inputs.

Electrosurgical devices for applying electrical energy to tissue in order to treat and/or destroy the tissue are also finding increasingly widespread applications in surgical procedures. An electrosurgical device may comprise a handpiece and an instrument having a distally-mounted end effector (e.g., one or more electrodes). The end effector can be positioned against the tissue such that electrical current is introduced into the tissue. Electrosurgical devices can be configured for bipolar or monopolar operation. During bipolar operation, current is introduced into and returned from the tissue by active and return electrodes, respectively, of the end effector. During monopolar operation, current is introduced into the tissue by an active electrode of the end effector and returned through a return electrode (e.g., a grounding pad) separately located on a patient's body. Heat generated by the current flow through the tissue may form haemostatic seals within the tissue and/or between tissues and thus may be particularly useful for sealing blood vessels, for example. The end effector of an electrosurgical device may also comprise a cutting member that is movable relative to the tissue and the electrodes to transect the tissue.

Electrical energy applied by an electrosurgical device can be transmitted to the instrument by a generator in communication with the handpiece. The electrical energy may be in the form of radio frequency ("RF") energy. RF energy is a form of electrical energy that may be in the frequency range of 300 kHz to 1 MHz. During its operation, an electrosurgical device can transmit low frequency RF energy through tissue, which causes ionic agitation, or friction, in effect resistive heating, thereby increasing the temperature of the tissue. Because a sharp boundary may be created between the affected tissue and the surrounding tissue, surgeons can operate with a high level of precision and control, without sacrificing un-targeted adjacent tissue. The low operating temperatures of RF energy may be useful for removing, shrinking, or sculpting soft tissue while simultaneously sealing blood vessels. RF energy may work particularly well on connective tissue, which is primarily comprised of collagen and shrinks when contacted by heat.

Due to their unique drive signal, sensing and feedback needs, ultrasonic and electrosurgical devices have generally required different generators. Additionally, in cases where the instrument is disposable or interchangeable with a handpiece, ultrasonic and electrosurgical generators are limited in their ability to recognize the particular instrument configuration being used and to optimize control and diagnostic processes accordingly. Moreover, capacitive coupling between the non-isolated and patient-isolated circuits of the generator, especially in cases where higher voltages and frequencies are used, may result in exposure of a patient to unacceptable levels of leakage current.

Furthermore, due to their unique drive signal, sensing and feedback needs, ultrasonic and electrosurgical devices have generally required different user interfaces for the different generators. In such conventional ultrasonic and electrosurgical devices, one user interface is configured for use with an ultrasonic instrument whereas a different user interface may be configured for use with an electrosurgical instrument. Such user interfaces include hand and/or foot activated user interfaces such as hand activated switches and/or foot activated switches. As various embodiments of combined generators for use with both ultrasonic and electrosurgical instruments are contemplated in the subsequent disclosure, additional user interfaces that are configured to operate with both ultrasonic and/or electrosurgical instrument generators also are contemplated.

Additional user interfaces for providing feedback, whether to the user or other machine, are contemplated within the subsequent disclosure to provide feedback indicating an operating mode or status of either an ultrasonic and/or electrosurgical instrument. Providing user and/or machine feedback for operating a combination ultrasonic and/or electrosurgical instrument will require providing sensory feedback to a user and electrical/mechanical/electromechanical feedback to a machine. Feedback devices that incorporate visual feedback devices (e.g., an LCD display screen, LED indicators), audio feedback devices (e.g., a speaker, a buzzer) or tactile feedback devices (e.g., haptic actuators) for use in combined ultrasonic and/or electrosurgical instruments are contemplated in the subsequent disclosure.

SUMMARY

Various embodiments of a generator to communicate a drive signal to a surgical device are disclosed. In accordance with various embodiments, the generator may comprise a power amplifier to receive a time-varying drive signal waveform. The drive signal waveform may be generated by a digital-to-analog conversion of at least a portion of a plurality of drive signal waveform samples. An output of the power amplifier may be for generating a drive signal. The drive signal may comprise one of: a first drive signal to be communicated to an ultrasonic surgical device, a second drive signal to be communicated to an electrosurgical device. The generator may also comprise a sampling circuit to generate samples of current and voltage of the drive signal when the drive signal is communicated to the surgical device. Generation of the samples may be synchronized with the digital-to-analog conversion of the drive signal waveform samples such that, for each digital-to-analog conversion of a drive signal waveform sample, the sampling circuit generates a corresponding set of current and voltage samples. The generator may also comprise at least one device programmed to, for each drive signal waveform sample and corresponding set of current and voltage samples, store the current and voltage samples in a memory of the at least one device to associate the stored samples with the drive signal waveform sample. The at least one device may also be programmed to, when the drive signal comprises the first drive signal: determine a motional branch current sample of the ultrasonic surgical device based on the stored current and voltage samples, compare the motional branch current sample to a target sample selected from a plurality of target samples that define a target waveform, the target sample selected based on the drive signal waveform sample, determine an amplitude error between the target sample and the motional branch current sample, and modify the drive signal waveform sample such that an amplitude error determined between the target sample and a subsequent motional branch current sample based on current and voltage samples associated with the modified drive signal waveform sample is reduced.

In accordance with various embodiments. the generator may comprise a memory and a device coupled to the memory to receive for each of a plurality of drive signal waveform samples used to synthesize the drive signal, a corresponding set of current and voltage samples of the drive signal. For each drive signal waveform sample and corresponding set of current and voltage samples, the device may store the samples in a memory of the device to associate the stored samples with the drive signal waveform sample. Also, for each drive signal waveform sample and corresponding set of current and voltage samples, the device may, when the drive signal comprises a first drive signal to be communicated to an ultrasonic surgical device, determine a motional branch current sample of the ultrasonic surgical device based on the stored samples, compare the motional branch current sample to a target sample selected from a plurality of target samples that define a target waveform, the target sample selected based on the drive signal waveform sample, determine an amplitude error between the target sample and the motional branch current sample, and modify the drive signal waveform sample such that an amplitude error determined between the target sample and a subsequent motional branch current sample based on current and voltage samples associated with the modified drive signal waveform sample is reduced.

In accordance with various embodiments, methods for determining motional branch current in an ultrasonic transducer of an ultrasonic surgical device over multiple frequencies of a transducer drive signal are also disclosed. In one embodiment, the method may comprise, at each of a plurality of frequencies of the transducer drive signal, oversampling a current and voltage of the transducer drive signal, receiving, by a processor, the current and voltage samples, and determining, by the processor, the motional branch current based on the current and voltage samples, a static capacitance of the ultrasonic transducer and the frequency of the transducer drive signal.

In accordance with various embodiments, methods for controlling a waveform shape of a motional branch current in an ultrasonic transducer of a surgical device are also disclosed. In one embodiment, the method may comprise generating a transducer drive signal by selectively recalling, using a direct digital synthesis (DDS) algorithm, drive signal waveform samples stored in a look-up table (LUT), generating samples of current and voltage of the transducer drive signal when the transducer drive signal is communicated to the surgical device, determining samples of the motional branch current based on the current and voltage samples, a static capacitance of the ultrasonic transducer and a frequency of the transducer drive signal, comparing each sample of the motional branch current to a respective target sample of a target waveform to determine an error amplitude, and modifying the drive signal waveform samples stored in the LUT such that an amplitude error between subsequent samples of the motional branch current and respective target samples is reduced.

In accordance with various embodiments, a surgical generator for providing a drive signal to a surgical device may comprise a first transformer and a second transformer. The first transformer may comprise a first primary winding and a first secondary winding. The second transformer may comprise a second primary winding and a second secondary winding. The surgical generator may further comprise a generator circuit to generate the drive signal. The generator circuit may be electrically coupled to the first primary winding to provide the drive signal across the first primary winding. The surgical generator may also comprise a patient-side circuit electrically isolated from the generator circuit. The patient-side circuit may be electrically coupled to the first secondary winding. Further, the patient-side circuit may comprise first and second output lines to provide the drive signal to the surgical device. In addition, the surgical generator may comprise a capacitor. The capacitor and the second secondary winding may be electrically coupled in series between the first output line and ground.

In accordance with various embodiments, a surgical generator for providing a drive signal to a surgical device may comprise a first transformer, a patient-side circuit, and a capacitor. The first transformer may comprise a primary winding, a first secondary winding, and a second secondary winding. A polarity of the first secondary winding relative to the primary winding may be opposite the polarity of the second secondary winding. The generator circuit may generate the drive signal and may be electrically coupled to the first primary winding to provide the drive signal across the first primary winding. The patient-side circuit may be electrically isolated from the generator circuit and may be electrically coupled to the first secondary winding. Also, the patient-side circuit may comprise first and second output lines to provide the drive signal to the surgical device. The capacitor and second secondary winding may be electrically coupled in series between the first output line and ground.

In accordance with various embodiments, a surgical generator for providing a drive signal to a surgical device may comprise a first transformer, a generator circuit, a patient-side circuit and a capacitor. The first transformer may comprise a primary winding and a secondary winding. The generator circuit may generate the drive signal and may be electrically coupled to the first primary winding to provide the drive signal across the first primary winding. The patient-side circuit may be electrically isolated from the generator circuit and may be electrically coupled to the secondary winding. Further, the patient-side circuit may comprise first and second output lines to provide the drive signal to the surgical device. The capacitor may be electrically coupled to the primary winding and to the first output line.

In accordance with various embodiments, a surgical generator for providing a drive signal to a surgical device may comprise a first transformer, a generator circuit, a patient-side circuit, as well as first, second and third capacitors. The first transformer may comprise a primary winding and a secondary winding. The generator circuit may generate the drive signal and may be electrically coupled to the first primary winding to provide the drive signal across the first primary winding. The patient-side circuit may be electrically isolated from the generator circuit and may be electrically coupled to the secondary winding. Further, the patient-side circuit may comprise first and second output lines to provide the drive signal to the surgical device. A first electrode of the first capacitor may be electrically coupled to the primary winding. A first electrode of the second capacitor may be electrically coupled to the first output line and a second electrode of the second capacitor may be electrically coupled to a second electrode of the first capacitor. A first electrode of the third capacitor may be electrically coupled to the second electrode of the first capacitor and the second electrode of the second capacitor. A second electrode of the third capacitor may be electrically coupled to ground.

In accordance with various embodiments, control circuits for surgical devices are also disclosed. In one embodiment, the control circuit may comprise a first circuit portion comprising at least one first switch. The first circuit portion may communicate with a surgical generator over a conductor pair. The control circuit may also comprise a second circuit portion comprising a data circuit element. The data circuit element may be disposed in an instrument of the surgical device and transmit or receive data. The data circuit element may implement data communications with the surgical generator over at least one conductor of the conductor pair.

In accordance with various embodiments, the control circuit may comprise a first circuit portion comprising at least one first switch. The first circuit portion may communicate with a surgical generator over a conductor pair. The control circuit may also comprise a second circuit portion comprising a data circuit element. The data circuit element may be disposed in an instrument of the surgical device and transmit or receive data. The data circuit element may implement data communications with the surgical generator over at least one conductor of the conductor pair. The first circuit portion may receive a first interrogation signal transmitted from the surgical generator in a first frequency band. The data circuit element may communicate with the surgical generator using an amplitude-modulated communication protocol transmitted in a second frequency band. The second frequency band may be higher than the first frequency band.

In accordance with various embodiments, the control circuit may comprise a first circuit portion comprising at least one first switch. The first circuit portion may receive a first interrogation signal transmitted from a surgical generator over a conductor pair. The control circuit may also comprise a second circuit portion comprising at least one of a resistive element and an inductive element disposed in an instrument of the device. The second circuit portion may receive a second interrogation signal transmitted from the surgical generator over the conductor pair. The second circuit portion may be frequency-band separated from the first circuit portion. A characteristic of the first interrogation signal, when received through the first circuit portion, may be indicative of a state of the at least one first switch. A characteristic of the second interrogation signal, when received through the second circuit portion, may uniquely identify the instrument of the device.

In accordance with various embodiments, the control circuit may comprise a first circuit portion comprising a first switch network and a second switch network. The first switch network may comprise at least one first switch, and the second switch network may comprise at least one second switch. The first circuit portion may communicate with a surgical generator over a conductor pair. The control circuit may also comprise a second circuit portion comprising a data circuit element. The data circuit element may be disposed in an instrument of the surgical device and may transmit or receive data. The data circuit element may be in data communication with the surgical generator over at least one conductor of the conductor pair.

In accordance with various embodiments, a surgical generator for providing a drive signal to a surgical device may comprise a surgical generator body having an aperture. The surgical generator may also comprise a receptacle assembly positioned in the aperture. The receptacle assembly may comprise a receptacle body and a flange having an inner wall and an outer wall. The inner wall may be comprised of at least one curved section and at least one linear section. The inner wall may define a cavity. A central protruding portion may be positioned in the cavity and may comprise a plurality of sockets and a magnet. An outer periphery of the central protruding portion may comprise at least one curved section and at least one linear section.

In accordance with various embodiments, a surgical instrument may comprises an electrical connector assembly. The electrical connector assembly may comprise a flange defining a central cavity and a magnetically compatible pin extending into the central cavity. The electrical connector assembly may comprise a circuit board and a plurality of electrically conductive pins coupled to the circuit board. Each of the plurality of electrically conductive pins may extend into the central cavity. The electrical connector assembly may further comprise a strain relief member and a boot.

In accordance with various embodiments, a surgical instrument system may comprise a surgical generator comprising a receptacle assembly. The receptacle assembly may comprise at least one curved section and at least one linear portion. The surgical instrument system may comprise a surgical instrument comprising a connector assembly and an adapter assembly operatively coupled to the receptacle assembly and the connector assembly. The adapter assembly may comprise a distal portion contacting the receptacle assembly. The distal portion may comprise a flange with the flange having at least one curved section and at least one linear portion. The adapter assembly may comprise a proximal portion contacting the connector assembly. The proximal portion may define a cavity dimensioned to receive at least a portion of the connector assembly. The adapter assembly may further comprise a circuit board.

In accordance with various embodiments, methods may be utilized (e.g., in conjunction with surgical instruments) to accomplish various surgical objectives. For example, methods to control electrical power provided to tissue via first and second electrodes may comprise providing a drive signal to the tissue via the first and second electrodes and modulating a power provided to the tissue via the drive signal based on a sensed tissue impedance according to a first power curve. The first power curve may define, for each of a plurality of potential sensed tissue impedances, a first corresponding power. The methods may also comprise monitoring a total energy provided to the tissue via the first and second electrodes. When the total energy reaches a first energy threshold, the methods may comprise determining whether an impedance of the tissue has reached a first impedance threshold. The methods may further comprise, conditioned upon the impedance of the tissue failing to reach the first impedance threshold, modulating the power provided to the tissue via the drive signal based on the sensed tissue impedance according to a second power curve. The second power curve may define, for each of the plurality of potential sensed tissue impedances, a second corresponding power.

In accordance with various embodiments, methods for controlling electrical power provided to tissue via first and second electrodes may comprise providing a drive signal to the tissue via the first and second electrodes and determining a power to be provided to the tissue. The determining may comprise receiving an indication of a sensed tissue impedance; determining a first corresponding power for the sensed tissue impedance according to a power curve; and multiplying the corresponding power by a multiplier. The power curve may define a corresponding power for each of a plurality of potential sensed tissue impedances. The methods may further comprise modulating the drive signal to provide the determined power to the tissue and, conditioned upon the impedance of the tissue failing to reach a first impedance threshold, increasing the multiplier as a function of the total energy provided to the tissue.

In accordance with various embodiments, methods for controlling electrical power provided to tissue via first and second electrodes may comprise providing a drive signal to the tissue via the first and second electrodes and determining a power to be provided to the tissue. The determining may comprise receiving an indication of a sensed tissue impedance; determining a first corresponding power for the sensed tissue impedance according to a power curve; and multiplying the corresponding power by a first multiplier to find a determined power. The power curve may define a corresponding power for each of a plurality of potential sensed tissue impedances. The methods may further comprise modulating the drive signal to provide the determined power to the tissue and monitoring a total energy provided to the tissue via the first and second electrodes. In addition, the methods may comprise, when the total energy reaches a first energy threshold, determining whether the impedance of the tissue has reached a first impedance threshold; and, conditioned upon the impedance of the tissue not reaching the first impedance threshold, increasing the first multiplier by a first amount.

In accordance with various embodiments, methods for controlling electrical power provided to tissue via a surgical device may comprise providing a drive signal to a surgical device; receiving an indication of an impedance of the tissue; calculating a rate of increase of the impedance of the tissue; and modulating the drive signal to hold the rate of increase of the impedance greater than or equal to a predetermined constant.

In accordance with various embodiments, methods for controlling electrical power provided to tissue via a surgical device may comprise providing a drive signal. A power of the drive signal may be proportional to a power provided to the tissue via the surgical device. The methods may also comprise periodically receiving indications of an impedance of the tissue and applying a first composite power curve to the tissue, wherein applying the first composite power curve to the tissue comprises. Applying the first composite power curve to the tissue may comprise modulating a first predetermined number of first composite power curve pulses on the drive signal; and for each of the first composite power curve pulses, determining a pulse power and a pulse width according to a first function of the impedance of the tissue The methods may also comprise applying a second composite power curve to the tissue. Applying the second composite power curve to the tissue may comprise modulating at least one second composite power curve pulse on the drive signal; and for each of the at least one second composite power curve pulses, determining a pulse power and a pulse width according to a second function of the impedance of the tissue.

In accordance with various embodiments, a generator is provided to generate a drive signal to a surgical device. The generator includes an ultrasonic generator module to generate a first drive signal to drive an ultrasonic device, an electrosurgery/radio frequency (RF) generator module to generate a second drive signal to drive an electrosurgical device, and a foot switch coupled to each of the ultrasonic generator module and the electrosurgery/RF generator module. The foot switch is configured to operate in a first mode when the ultrasonic device is coupled to the ultrasonic generator module and the foot switch is configured to operate in a second mode when the electrosurgical device is coupled to the electrosurgery/RF generator module.

In accordance with various embodiments, a generator is provided that includes a user interface to provide feedback in accordance with the operation of any one of the ultrasonic device and the electrosurgical device in accordance with a predetermined algorithm.

In accordance with various embodiments, a control circuit of a surgical device is provided. The control circuit comprises a first circuit portion coupled to at least one switch operable between an open state and a closed state. The first circuit portion communicates with a surgical generator over a conductor pair to receive a control signal to determine a state of the at least one switch.

In accordance with various embodiments, a control circuit of a surgical device is provided. The control circuit comprises a first circuit portion coupled to at least one switch operable between an open state and a closed state. The first circuit portion communicates with a surgical generator over a conductor pair to receive a control signal from input terminals to determine a state of the at least one switch. The control signal having a positive phase and a negative phase. A first transistor is coupled between the input terminals, a first capacitor, and a first resistor is coupled in series with the first capacitor. During the positive phase of the control signal the first transistor is held in cutoff mode while the first capacitor charges to a predetermined voltage and during an initial portion of the negative phase of the control signal the first transistor transitions from cutoff mode to saturation mode and is held in saturation mode until the first capacitor discharges through the first resistor. During a final portion of the negative phase of the control signal the first transistor transitions from saturation mode to cutoff mode when the first capacitor voltage drops below a predetermined threshold.

In accordance with various embodiments, a method is provided. The method comprises receiving a control signal at a control circuit of a surgical device and determining the state of the at least one switch based on the value of the resistor. The control circuit comprising a first circuit portion coupled to at least one switch operable between an open state and a closed state. The circuit portion to communicate with a surgical generator over a conductor pair to receive the control signal. The first circuit portion comprising at least one resistor coupled to the at least one switch.

FIGURES

The novel features of the various embodiments are set forth with particularity in the appended claims. The described embodiments, however, both as to organization and methods of operation, may be best understood by reference to the following description, taken in conjunction with the accompanying drawings in which:

DESCRIPTION

Figure 1:
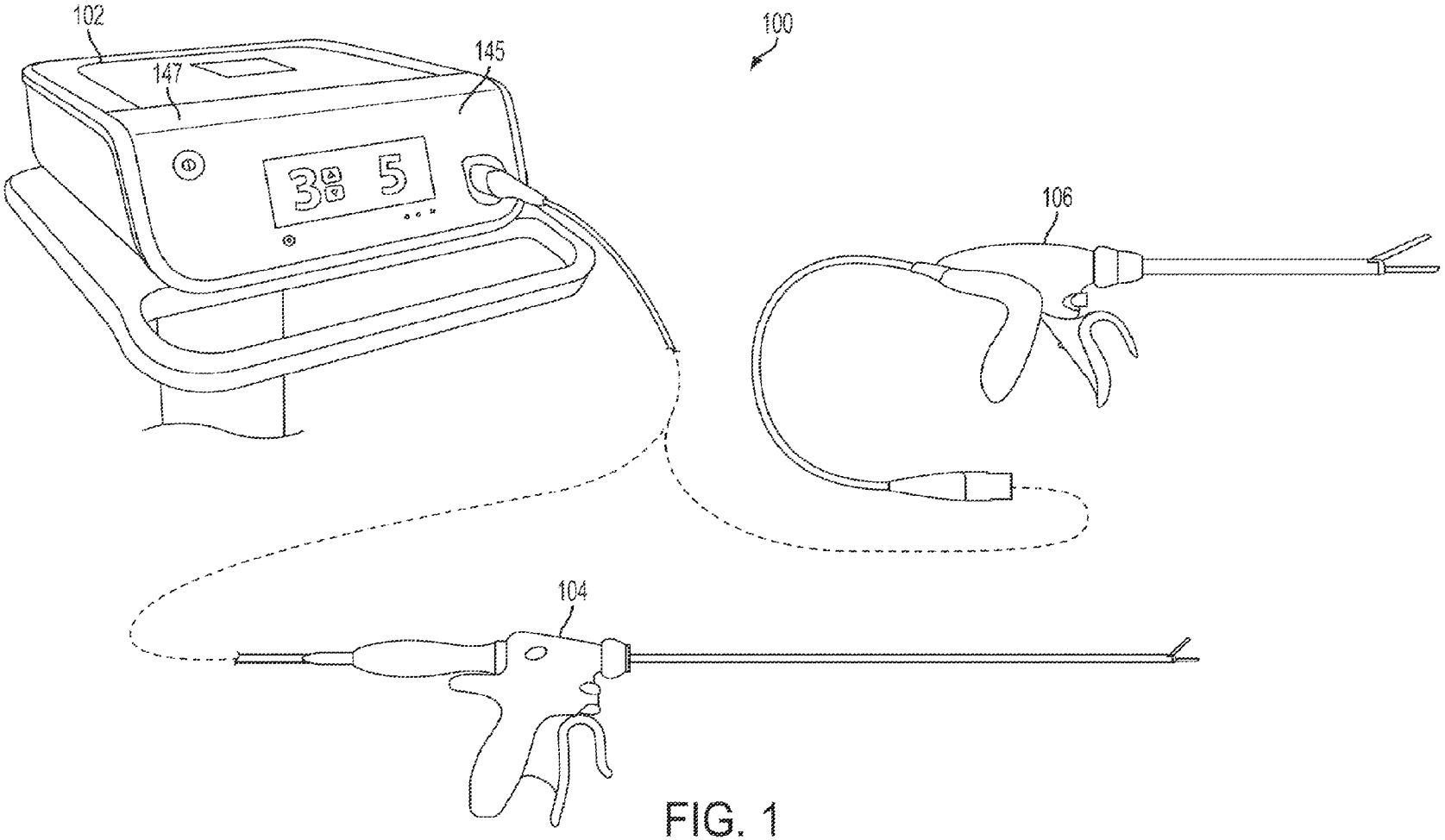
FIG. 1 illustrates one embodiment of a surgical system comprising a generator and various surgical instruments usable therewith.

Before explaining various embodiments of surgical devices and generators in detail, it should be noted that the illustrative embodiments are not limited in application or use to the details of construction and arrangement of parts illustrated in the accompanying drawings and description. The illustrative embodiments may be implemented or incorporated in other embodiments, variations and modifications, and may be practiced or carried out in various ways. Further, unless otherwise indicated, the terms and expressions employed herein have been chosen for the purpose of describing the illustrative embodiments for the convenience of the reader and are not for the purpose of limitation thereof. Also, it will be appreciated that one or more of the following-described embodiments, expressions of embodiments and/or examples, can be combined with any one or more of the other following-described embodiments, expressions of embodiments and/or examples.

Various embodiments are directed to improved ultrasonic surgical devices, electrosurgical devices and generators for use therewith. Embodiments of the ultrasonic surgical devices can be configured for transecting and/or coagulating tissue during surgical procedures, for example. Embodiments of the electrosurgical devices can be configured for transecting, coagulating, scaling, welding and/or desiccating tissue during surgical procedures, for example.

Embodiments of the generator utilize high-speed analog-to-digital sampling (e.g., approximately 200× oversampling, depending on frequency) of the generator drive signal current and voltage, along with digital signal processing, to provide a number of advantages and benefits over known generator architectures. In one embodiment, for example, based on current and voltage feedback data, a value of the ultrasonic transducer static capacitance, and a value of the drive signal frequency, the generator may determine the motional branch current of an ultrasonic transducer. This provides the benefit of a virtually tuned system, and simulates the presence of a system that is tuned or resonant with any value of the static capacitance (e.g., $C_0$ in FIG. 9) at any frequency. Accordingly, control of the motional branch current may be realized by tuning out the effects of the static capacitance without the need for a tuning inductor. Additionally, the elimination of the tuning inductor may not degrade the generator's frequency lock capabilities, as frequency lock can be realized by suitably processing the current and voltage feedback data.

High-speed analog-to-digital sampling of the generator drive signal current and voltage, along with digital signal processing, may also enable precise digital filtering of the samples. For example, embodiments of the generator may utilize a low-pass digital filter (e.g., a finite impulse response (FIR) filter) that rolls off between a fundamental drive signal frequency and a second-order harmonic to reduce the asymmetrical harmonic distortion and EMI-induced noise in current and voltage feedback samples. The filtered current and voltage feedback samples represent substantially the fundamental drive signal frequency, thus enabling a more accurate impedance phase measurement with respect to the fundamental drive signal frequency and an improvement in the generator's ability to maintain resonant frequency lock. The accuracy of the impedance phase measurement may be further enhanced by averaging falling edge and rising edge phase measurements, and by regulating the measured impedance phase to 0°.

Various embodiments of the generator may also utilize the high-speed analog-to-digital sampling of the generator drive signal current and voltage, along with digital signal processing, to determine real power consumption and other quantities with a high degree of precision. This may allow the generator to implement a number of useful algorithms, such as, for example, controlling the amount of power delivered to tissue as the impedance of the tissue changes and controlling the power delivery to maintain a constant rate of tissue impedance increase.

Various embodiments of the generator may have a wide frequency range and increased output power necessary to drive both ultrasonic surgical devices and electrosurgical devices. The lower voltage, higher current demand of electrosurgical devices may be met by a dedicated tap on a wideband power transformer, thereby eliminating the need for a separate power amplifier and output transformer. Moreover, sensing and feedback circuits of the generator may support a large dynamic range that addresses the needs of both ultrasonic and electrosurgical applications with minimal distortion.

Various embodiments may provide a simple, economical means for the generator to read from, and optionally write to, data circuit (e.g., a single-wire bus device, such as a one-wire protocol EEPROM known under the trade name "1-Wire") disposed in an instrument attached to the handpiece using existing multi-conductor generator/handpiece cables. In this way, the generator is able to retrieve and process instrument-specific data from an instrument attached to the handpiece. This may enable the generator to provide better control and improved diagnostics and error detection. Additionally, the ability of the generator to write data to the instrument makes possible new functionality in terms of, for example, tracking instrument usage and capturing operational data. Moreover, the use of frequency band permits the backward compatibility of instruments containing a bus device with existing generators.

Disclosed embodiments of the generator provide active cancellation of leakage current caused by unintended capacitive coupling between non-isolated and patient-isolated circuits of the generator. In addition to reducing patient risk, the reduction of leakage current may also lessen electromagnetic emissions.

These and other benefits of embodiments of the present invention will be apparent from the description to follow.

It will be appreciated that the terms "proximal" and "distal" are used herein with reference to a clinician gripping a handpiece. Thus, an end effector is distal with respect to the more proximal handpiece. It will be further appreciated that, for convenience and clarity, spatial terms such as "top" and "bottom" may also be used herein with respect to the clinician gripping the handpiece. However, surgical devices are used in many orientations and positions, and these terms are not intended to be limiting and absolute.

FIG. 1 illustrates one embodiment of a surgical system 100 comprising a generator 102 configurable for use with surgical devices. According to various embodiments, the generator 102 may be configurable for use with surgical devices of different types, including, for example, the ultrasonic surgical device 104 and electrosurgical or RF surgical device 106. Although in the embodiment of FIG. 1 the generator 102 is shown separate from the surgical devices 104, 106, in certain embodiments the generator 102 may be formed integrally with either of the surgical devices 104, 106 to form a unitary surgical system.

Figure 2:
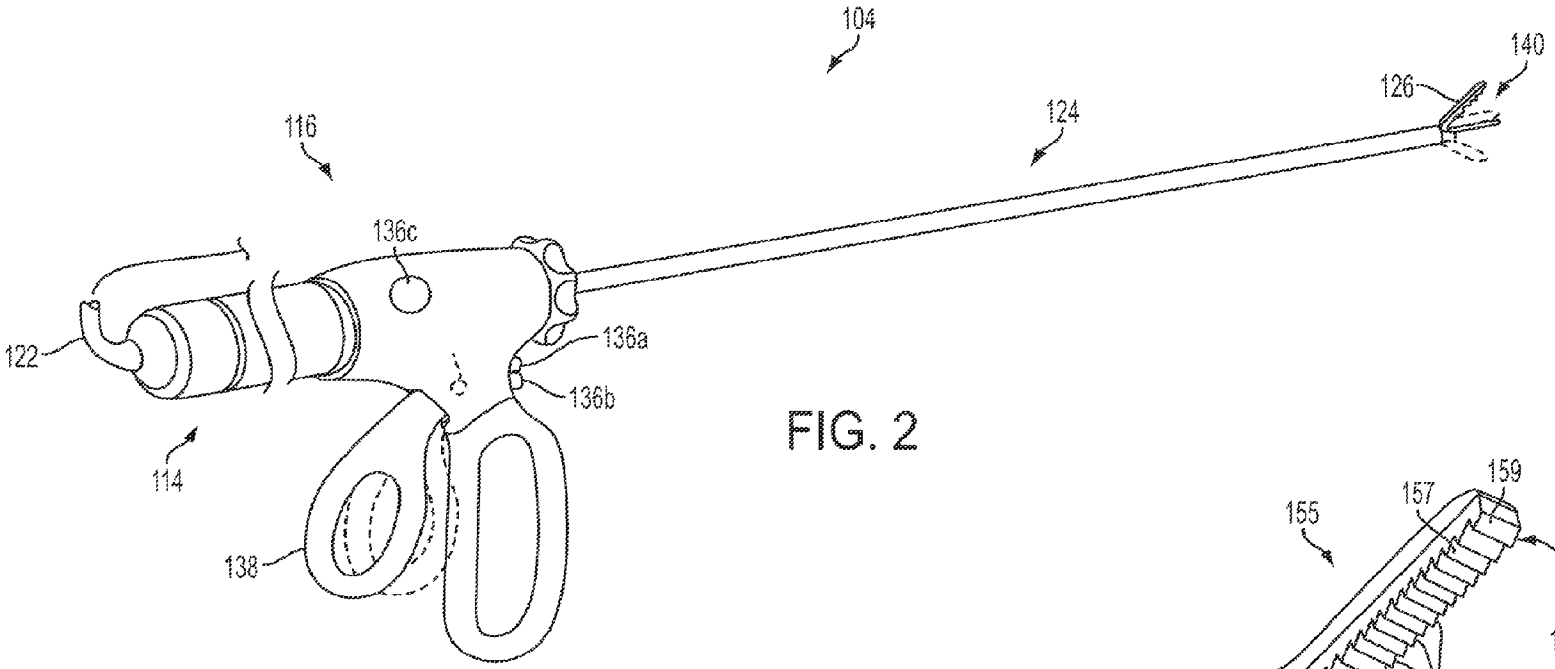
FIG. 2 illustrates one embodiment of an example ultrasonic device that may be used for transection and/or sealing.

FIG. 2 illustrates one embodiment of an example ultrasonic device 104 that may be used for transection and/or sealing. The device 104 may comprise a hand piece 116 which may, in turn, comprise an ultrasonic transducer 114. The transducer 114 may be in electrical communication with the generator 102, for example, via a cable 122 (e.g., a multi-conductor cable). The transducer 114 may comprise piezoceramic elements, or other elements or components suitable for converting the electrical energy of a drive signal into mechanical vibrations. When activated by the generator 102, the ultrasonic transducer 114 may cause longitudinal vibration. The vibration may be transmitted through an instrument portion 124 of the device 104 (e.g., via a waveguide embedded in an outer sheath) to an end effector 126 of the instrument portion 124.

Figure 3:
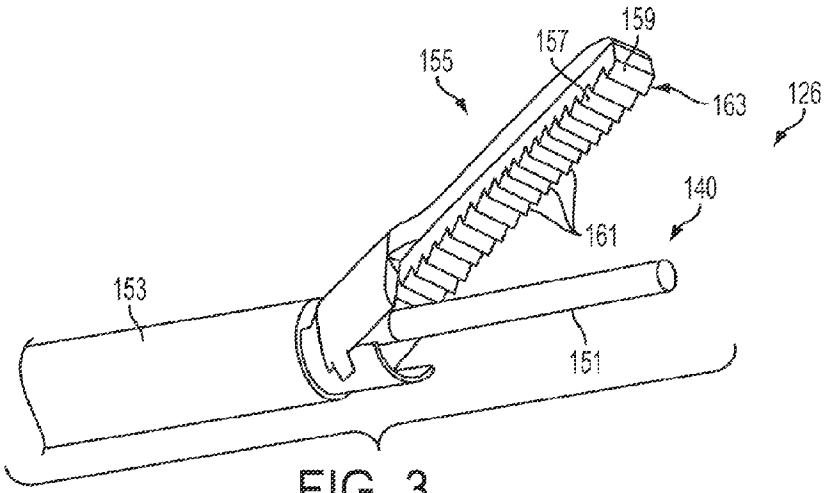
FIG. 3 illustrates one embodiment of the end effector of the example ultrasonic device of FIG. 2.

FIG. 3 illustrates one embodiment of the end effector 126 of the example ultrasonic device 104. The end effector 126 may comprise a blade 151 that may be coupled to the ultrasonic transducer 114 via the wave guide (not shown). When driven by the transducer 114, the blade 151 may vibrate and, when brought into contact with tissue, may cut and/or coagulate the tissue, as described herein. According to various embodiments, and as illustrated in FIG. 3, the end effector 126 may also comprise a clamp arm 155 that may be configured for cooperative action with the blade 151 of the end effector 126. With the blade 151, the clamp arm 155 may comprise a set of jaws 140. The clamp arm 155 may be pivotally connected at a distal end of a shaft 153 of the instrument portion 124. The clamp arm 155 may include a clamp arm tissue pad 163, which may be formed from TEFLON® or other suitable low-friction material. The pad 163 may be mounted for cooperation with the blade 151, with pivotal movement of the clamp arm 155 positioning the clamp pad 163 in substantially parallel relationship to, and in contact with, the blade 151. By this construction, a tissue bite to be clamped may be grasped between the tissue pad 163 and the blade 151. The tissue pad 163 may be provided with a saw-tooth-like configuration including a plurality of axially spaced, proximally extending gripping teeth 161 to enhance the gripping of tissue in cooperation with the blade 151. The clamp arm 155 may transition from the open position shown in FIG. 3 to a closed position (with the clamp arm 155 in contact with or proximity to the blade 151) in any suitable manner. For example, the hand piece 116 may comprise a jaw closure trigger 138. When actuated by a clinician, the jaw closure trigger 138 may pivot the clamp arm 155 in any suitable manner.

Figure 8:
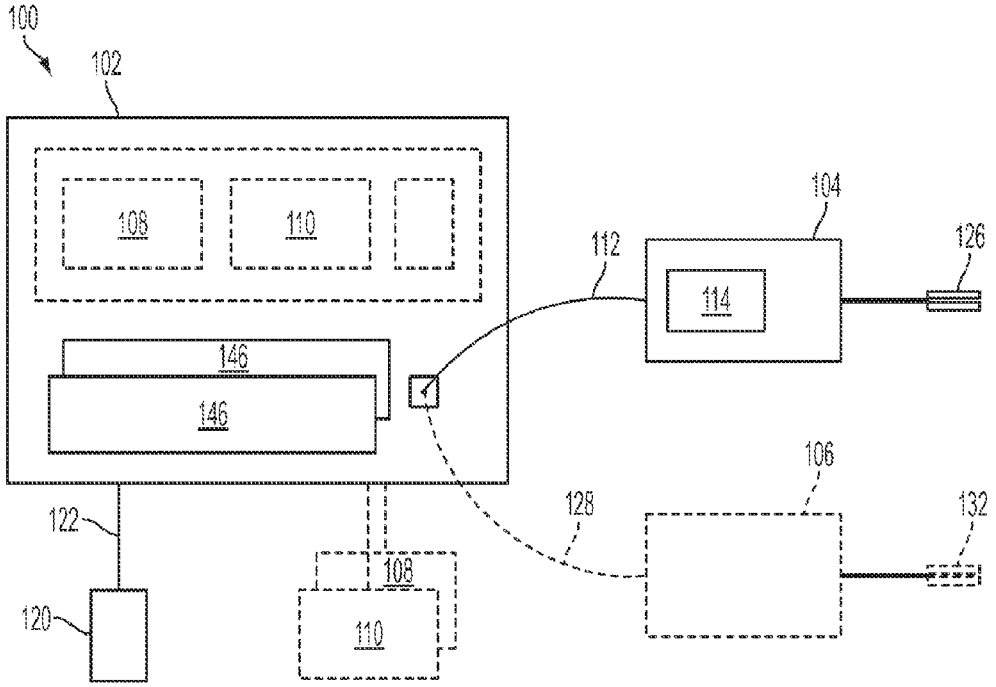
FIG. 8 is a diagram of the surgical system of FIG. 1.

The generator 102 may be activated to provide the drive signal to the transducer 114 in any suitable manner. For example, the generator 102 may comprise a foot switch 120 coupled to the generator 102 via a footswitch cable 122 (FIG. 8). A clinician may activate the transducer 114, and thereby the transducer 114 and blade 151, by depressing the foot switch 120. In addition, or instead of the foot switch 120 some embodiments of the device 104 may utilize one or more switches positioned on the hand piece 116 that, when activated, may cause the generator 102 to activate the transducer 114. In one embodiment, for example, the one or more switches may comprise a pair of toggle buttons 136a, 136b, for example, to determine an operating mode of the device 104. When the toggle button 136a is depressed, for example, the ultrasonic generator 102 may provide a maximum drive signal to the transducer 114, causing it to produce maximum ultrasonic energy output. Depressing toggle button 136b may cause the ultrasonic generator 102 to provide a user-selectable drive signal to the transducer 114, causing it to produce less than the maximum ultrasonic energy output. The device 104 additionally or alternatively may comprise a second switch to, for example, indicate a position of a jaw closure trigger 138 for operating jaws 140 of the end effector 126. Also, in some embodiments, the ultrasonic generator 102 may be activated based on the position of the jaw closure trigger 138, (e.g., as the clinician depresses the jaw closure trigger 138 to close the jaws 140, ultrasonic energy may be applied.

Additionally or alternatively, the one or more switches may comprises a toggle button 136c that, when depressed, causes the generator 102 to provide a pulsed output. The pulses may be provided at any suitable frequency and grouping, for example. In certain embodiments, the power level of the pulses may be the power levels associated with toggle buttons 136a, b (maximum, less than maximum), for example.

It will be appreciated that a device 104 may comprise any combination of the toggle buttons 136a, b, c. For example, the device 104 could be configured to have only two toggle buttons: a toggle button 136a for producing maximum ultrasonic energy output and a toggle button 136c for producing a pulsed output at either the maximum or less than maximum power level per. In this way, the drive signal output configuration of the generator 102 could be 5 continuous signals and 5 or 4 or 3 or 2 or 1 pulsed signals. In certain embodiments, the specific drive signal configuration may be controlled based upon, for example, EEPROM settings in the generator 102 and/or user power level selection(s).

In certain embodiments, a two-position switch may be provided as an alternative to a toggle button 136c. For example, a device 104 may include a toggle button 136a for producing a continuous output at a maximum power level and a two-position toggle button 136b. In a first detented position, toggle button 136b may produce a continuous output at a less than maximum power level, and in a second detented position the toggle button 136b may produce a pulsed output (e.g., at either a maximum or less than maximum power level, depending upon the EEPROM settings).

In some embodiments, the end effector 126 may also comprise a pair of electrodes 159, 157. The electrodes 159, 157 may be in communication with the generator 102, for example, via the cable 122. The electrodes 159, 157 may be used, for example, to measure an impedance of a tissue bite present between the clamp arm 155 and the blade 151. The generator 102 may provide a signal (e.g., a non-therapeutic signal) to the electrodes 159, 157. The impedance of the tissue bite may be found, for example, by monitoring the current, voltage, etc. of the signal.

Figure 4:
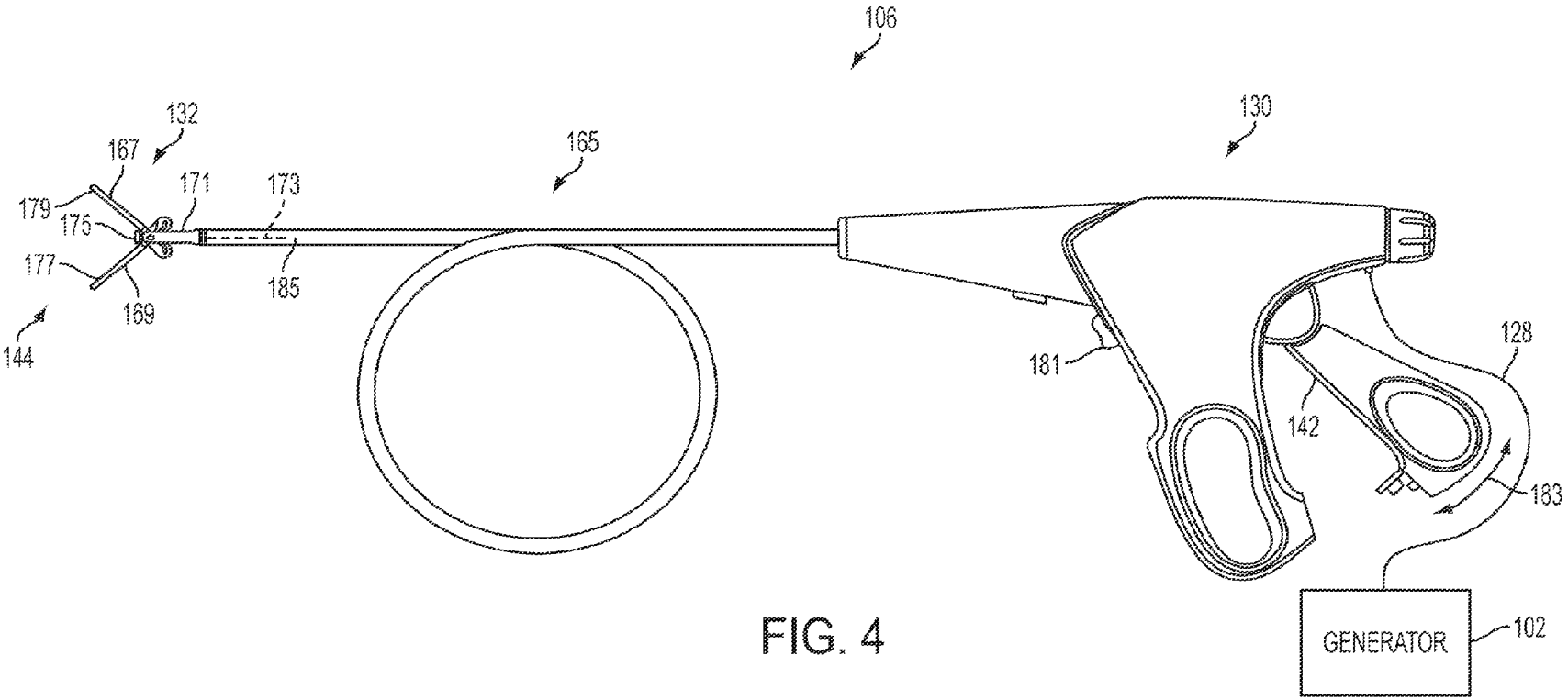
FIG. 4 illustrates one embodiment of an example electrosurgical device that may also be used for transection and sealing.

FIG. 4 illustrates one embodiment of an example electrosurgical device 106 that may also be used for transection and sealing. According to various embodiments, the transection and sealing device 106 may comprise a hand piece assembly 130, a shaft 165 and an end effector 132. The shaft 165 may be rigid (e.g., for laparoscopic and/or open surgical application) or flexible, as shown, (e.g., for endoscopic application). In various embodiments, the shaft 165 may comprise one or more articulation points. The end effector 132 may comprise jaws 144 having a first jaw member 167 and a second jaw member 169. The first jaw member 167 and second jaw member 169 may be connected to a clevis 171, which, in turn, may be coupled to the shaft 165. A translating member 173 may extend within the shaft 165 from the end effector 132 to the hand piece 130. At the hand piece 130, the shaft 165 may be directly or indirectly coupled to a jaw closure trigger 142 (FIG. 4).

The jaw members 167, 169 of the end effector 132 may comprise respective electrodes 177, 179. The electrodes 177, 179 may be connected to the generator 102 via electrical leads 187a, 187b (FIG. 5) extending from the end effector 132 through the shaft 165 and handpiece 130 and ultimately to the generator 102 (e.g., by a multiconductor cable 128). The generator 102 may provide a drive signal to the electrodes 177, 179 to bring about a therapeutic effect to tissue present within the jaw members 167, 169. The electrodes 177, 179 may comprise an active electrode and a return electrode, wherein the active electrode and the return electrode can be positioned against, or adjacent to, the tissue to be treated such that current can flow from the active electrode to the return electrode through the tissue. As illustrated in FIG. 4, the end effector 132 is shown with the jaw members 167, 169 in an open position. A reciprocating blade 175 is illustrated between the jaw members 167, 169.

Figure 5:
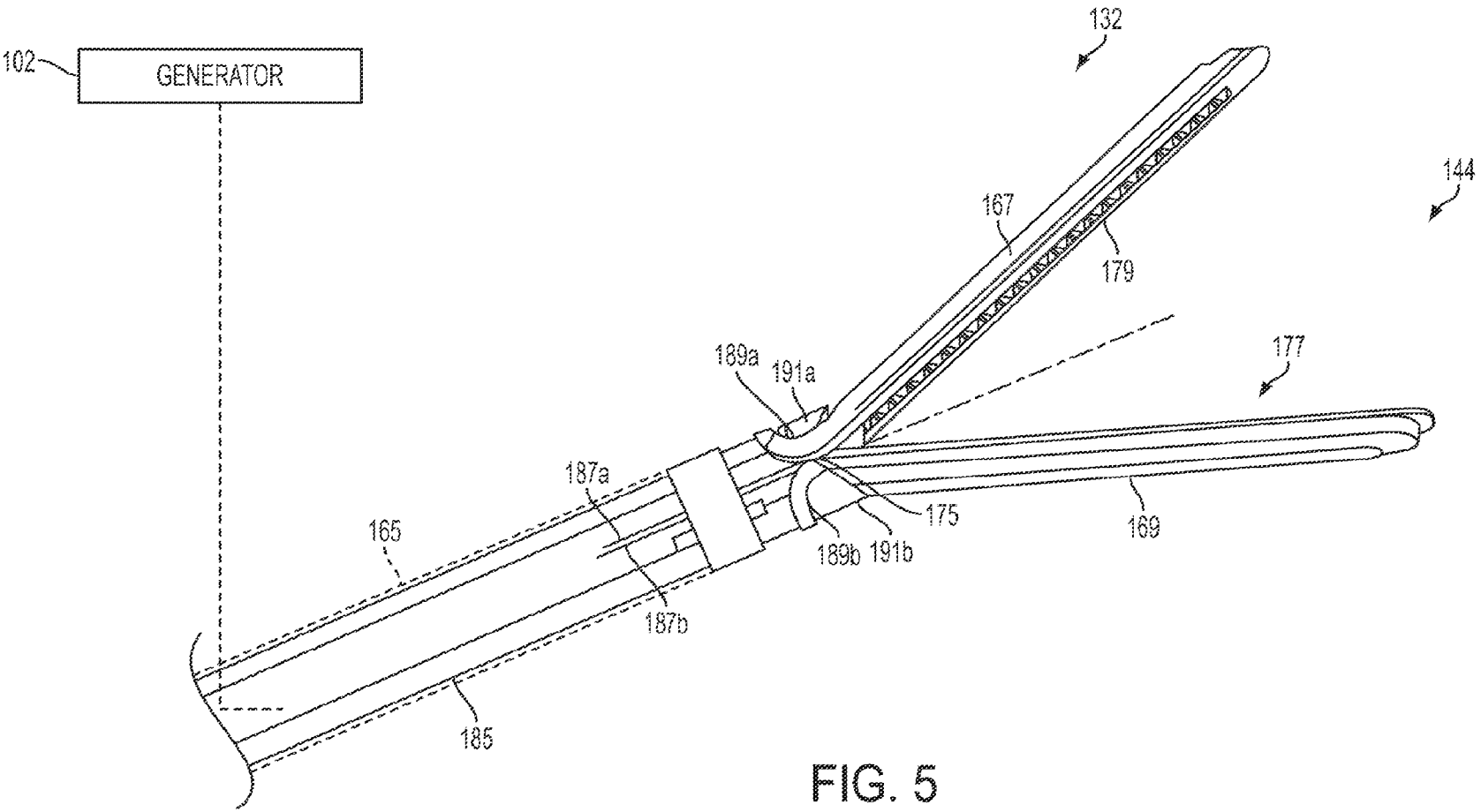
FIGS. 5, 6 and 7 illustrate one embodiment of the end effector shown in FIG. 4.
Figure 6:
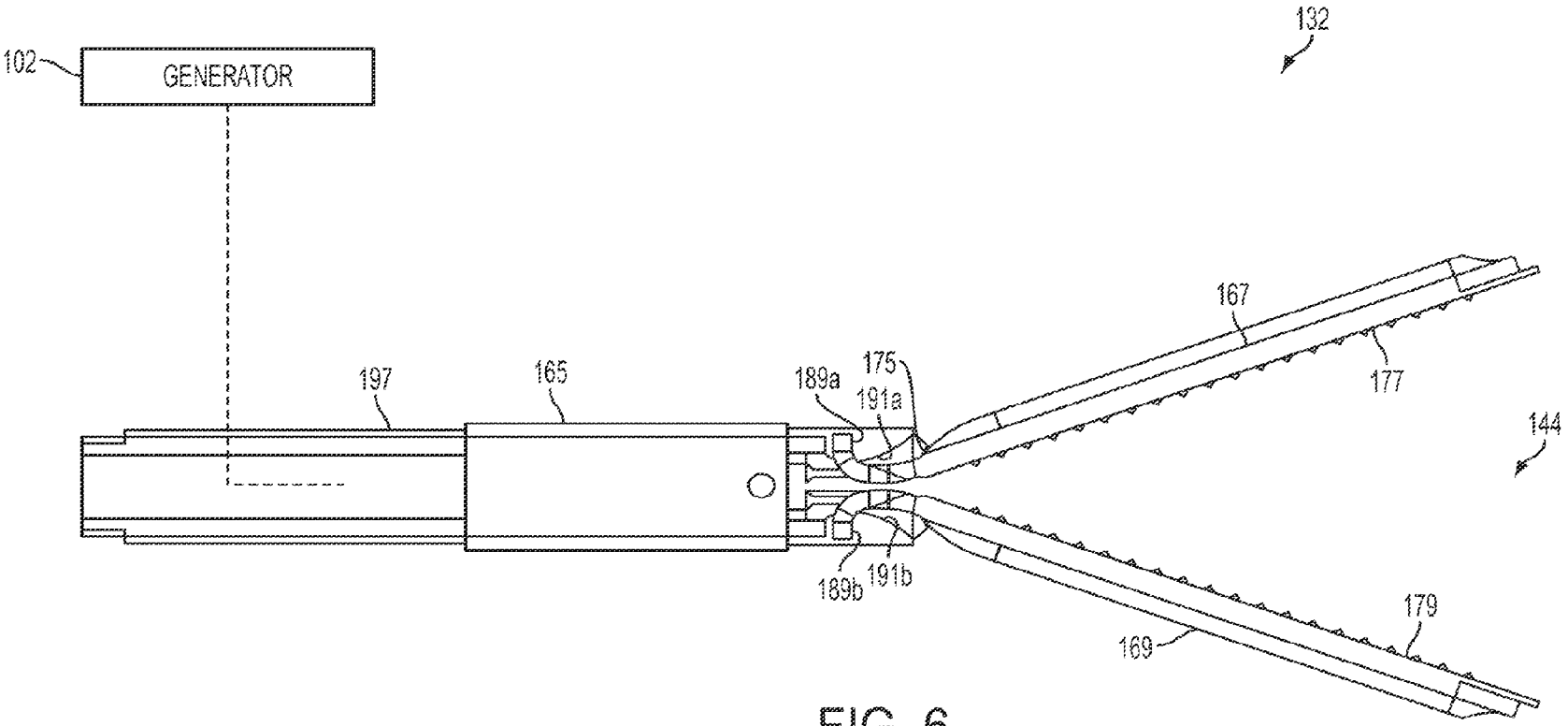
Figure 7:
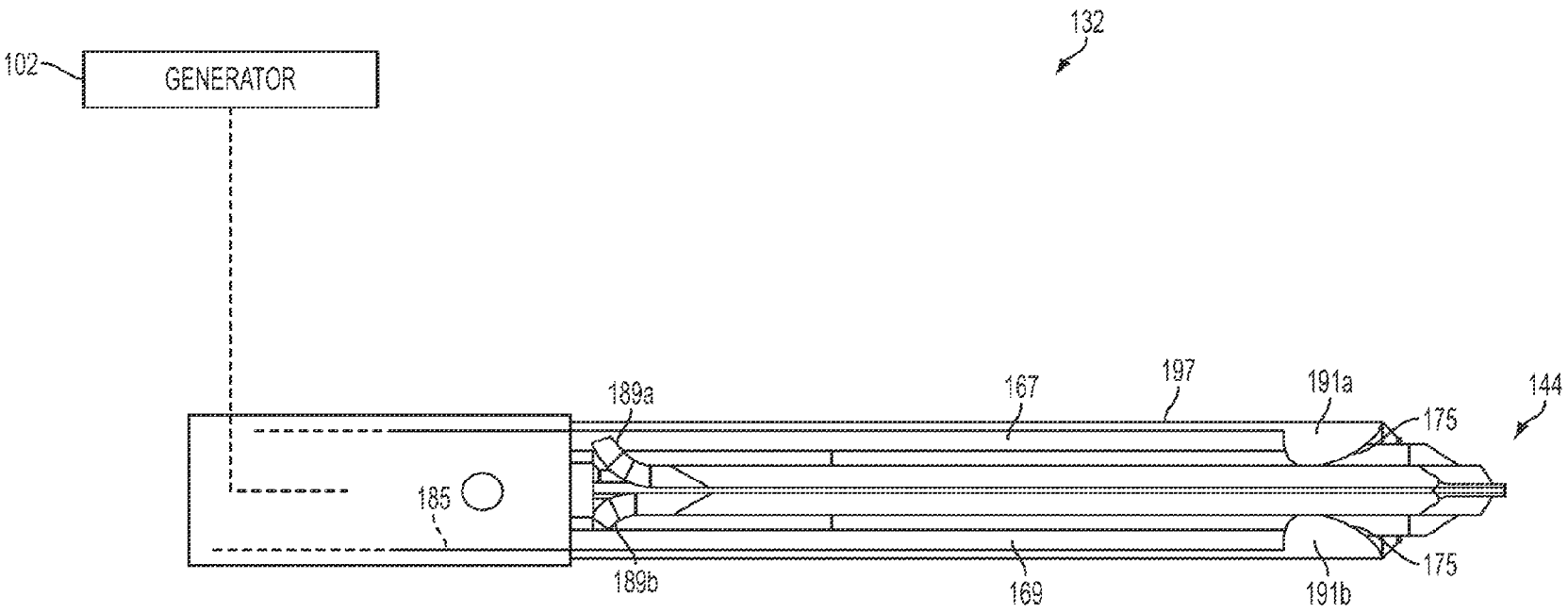

FIGS. 5, 6 and 7 illustrate one embodiment of the end effector 132 shown in FIG. 4. To close the jaws 144 of the end effector 132, a clinician may cause the jaw closure trigger 142 to pivot along arrow 183 from a first position to a second position. This may cause the jaws 144 to open and close according to any suitable method. For example, motion of the jaw closure trigger 142 may, in turn, cause the translating member 173 to translate within a bore 185 of the shaft 165. A distal portion of the translating member 173 may be coupled to a reciprocating member 197 such that distal and proximal motion of the translating member 173 causes corresponding distal and proximal motion of the reciprocating member. The reciprocating member 197 may have shoulder portions 191a, 191b, while the jaw members 167, 169 may have corresponding cam surfaces 189a, 189b. As the reciprocating member 197 is translated distally from the position shown in FIG. 6 to the position shown in FIG. 7, the shoulder portions 191a, 191b may contact the cam surfaces 189a, 189b, causing the jaw members 167, 169 to transition to the closed position. Also, in various embodiments, the blade 175 may be positioned at a distal end of the reciprocating member 197. As the reciprocating member extends to the fully distal position shown in FIG. 7, the blade 175 may be pushed through any tissue present between the jaw members 167, 169, in the process, severing it. In use, a clinician may place the end effector 132 and close the jaws 144 around a tissue bite to be acted upon, for example, by pivoting the jaw closure trigger 142 along arrow 183 as described. Once the tissue bite is secure between the jaws 144, the clinician may initiate the provision of RF or other electro-surgical energy by the generator 102 and through the electrodes 177, 179. The provision of RF energy may be accomplished in any suitable way. For example, the clinician may activate the foot switch 120 (FIG. 8) of the generator 102 to initiate the provision of RF energy. Also, for example, the hand piece 130 may comprise one or more switches 181 that may be actuated by the clinician to cause the generator 102 to begin providing RF energy. Additionally, in some embodiments, RF energy may be provided based on the position of the jaw closure trigger 142. For example, when the trigger 142 is fully depressed (indicating that the jaws 144 are closed), RF energy may be provided. Also, according to various embodiments, the blade 175 may be advanced during closure of the jaws 144 or may be separately advanced by the clinician after closure of the jaws 144 (e.g., after a RF energy has been applied to the tissue).

FIG. 8 is a diagram of the surgical system 100 of FIG. 1. In various embodiments, the generator 102 may comprise several separate functional elements, such as modules and/or blocks. Different functional elements or modules may be configured for driving the different kinds of surgical devices 104, 106. For example an ultrasonic generator module 108 may drive an ultrasonic device, such as the ultrasonic device 104. An electrosurgery/RF generator module 110 may drive the electrosurgical device 106. For example, the respective modules 108, 110 may generate respective drive signals for driving the surgical devices 104, 106. In various embodiments, the ultrasonic generator module 108 and/or the electrosurgery/RF generator module 110 each may be formed integrally with the generator 102. Alternatively, one or more of the modules 108, 110 may be provided as a separate circuit module electrically coupled to the generator 102. (The modules 108 and 110 are shown in phantom to illustrate this option.) Also, in some embodiments, the electrosurgery/RF generator module 110 may be formed integrally with the ultrasonic generator module 108, or vice versa.

In accordance with the described embodiments, the ultrasonic generator module 108 may produce a drive signal or signals of particular voltages, currents, and frequencies, e.g. 55,500 cycles per second (Hz). The drive signal or signals may be provided to the ultrasonic device 104, and specifically to the transducer 114, which may operate, for example, as described above. In one embodiment, the generator 102 may be configured to produce a drive signal of a particular voltage, current, and/or frequency output signal that can be stepped with high resolution, accuracy, and repeatability.

In accordance with the described embodiments, the electrosurgery/RF generator module 110 may generate a drive signal or signals with output power sufficient to perform bipolar electrosurgery using radio frequency (RF) energy. In bipolar electrosurgery applications. The drive signal may be provided, for example, to the electrodes 177, 179 of the electrosurgical device 106, for example, as described above. Accordingly, the generator 102 may be configured for therapeutic purposes by applying electrical energy to the tissue sufficient for treating the tissue (e.g., coagulation, cauterization, tissue welding, etc.).

The generator 102 may comprise an input device 145 (FIG. 1) located, for example, on a front panel of the generator 102 console. The input device 145 may comprise any suitable device that generates signals suitable for programming the operation of the generator 102. In operation, the user can program or otherwise control operation of the generator 102 using the input device 145. The input device 145 may comprise any suitable device that generates signals that can be used by the generator (e.g., by one or more processors contained in the generator) to control the operation of the generator 102 (e.g., operation of the ultrasonic generator module 108 and/or electrosurgery/RF generator module 110). In various embodiments, the input device 145 includes one or more of buttons, switches, thumbwheels, keyboard, keypad, touch screen monitor, pointing device, remote connection to a general purpose or dedicated computer. In other embodiments, the input device 145 may comprise a suitable user interface, such as one or more user interface screens displayed on a touch screen monitor, for example. Accordingly, by way of the input device 145, the user can set or program various operating parameters of the generator, such as, for example, current (I), voltage (V), frequency (f), and/or period (T) of a drive signal or signals generated by the ultrasonic generator module 108 and/or electrosurgery/RF generator module 110.

The generator 102 may also comprise an output device 147 (FIG. 1) located, for example, on a front panel of the generator 102 console. The output device 147 includes one or more devices for providing a sensory feedback to a user. Such devices may comprise, for example, visual feedback devices (e.g., an LCD display screen, LED indicators), audio feedback devices (e.g., a speaker, a buzzer) or tactile feedback devices (e.g., haptic actuators).

Although certain modules and/or blocks of the generator 102 may be described by way of example, it can be appreciated that a greater or lesser number of modules and/or blocks may be used and still fall within the scope of the embodiments. Further, although various embodiments may be described in terms of modules and/or blocks to facilitate description, such modules and/or blocks may be implemented by one or more hardware components, e.g., processors, Digital Signal Processors (DSPs), Programmable Logic Devices (PLDs), Application Specific Integrated Circuits (ASICs), circuits, registers and/or software components, e.g., programs, subroutines, logic and/or combinations of hardware and software components.

In one embodiment, the ultrasonic generator drive module 108 and electrosurgery/RF drive module 110 may comprise one or more embedded applications implemented as firmware, software, hardware, or any combination thereof. The modules 108, 110 may comprise various executable modules such as software, programs, data, drivers. application program interfaces (APIs), and so forth. The firmware may be stored in nonvolatile memory (NVM), such as in bit-masked read-only memory (ROM) or flash memory. In various implementations, storing the firmware in ROM may preserve flash memory. The NVM may comprise other types of memory including, for example, programmable ROM (PROM), erasable programmable ROM (EPROM), electrically erasable programmable ROM (EEPROM), or battery backed random-access memory (RAM) such as dynamic RAM (DRAM), Double-Data-Rate DRAM (DDRAM), and/or synchronous DRAM (SDRAM).

In one embodiment, the modules 108, 110 comprise a hardware component implemented as a processor for executing program instructions for monitoring various measurable characteristics of the devices 104, 106 and generating a corresponding output drive signal or signals for operating the devices 104, 106. In embodiments in which the generator 102 is used in conjunction with the device 104, the drive signal may drive the ultrasonic transducer 114 in cutting and/or coagulation operating modes. Electrical characteristics of the device 104 and/or tissue may be measured and used to control operational aspects of the generator 102 and/or provided as feedback to the user. In embodiments in which the generator 102 is used in conjunction with the device 106, the drive signal may supply electrical energy (e.g., RF energy) to the end effector 132 in cutting, coagulation and/or desiccation modes. Electrical characteristics of the device 106 and/or tissue may be measured and used to control operational aspects of the generator 102 and/or provided as feedback to the user. In various embodiments, as previously discussed, the hardware components may be implemented as DSP, PLD, ASIC, circuits, and/or registers. In one embodiment, the processor may be configured to store and execute computer software program instructions to generate the step function output signals for driving various components of the devices 104, 106, such as the ultrasonic transducer 114 and the end effectors 126, 132.

Figure 9:
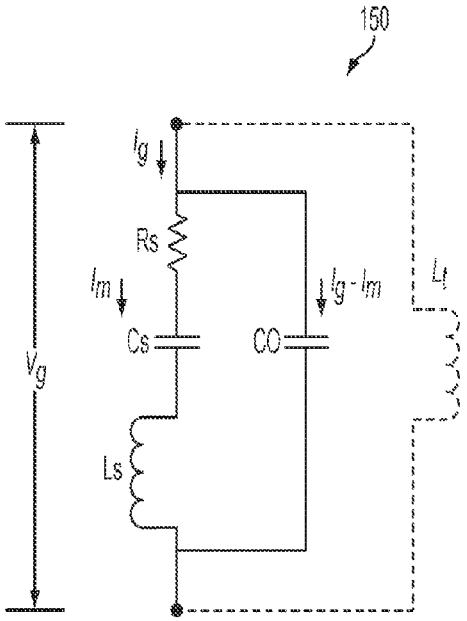
FIG. 9 is a model illustrating motional branch current in 30 one embodiment.

FIG. 9 illustrates an equivalent circuit 150 of an ultrasonic transducer, such as the ultrasonic transducer 114, according to one embodiment. The circuit 150 comprises a first "motional" branch having a serially connected inductance $L_s$, resistance $R_s$ and capacitance $C_s$ that define the electromechanical properties of the resonator, and a second capacitive branch having a static capacitance $C_0$. Drive current $I_g$ may be received from a generator at a drive voltage $V_g$, with motional current $I_m$ flowing through the first branch and current $I_g-I_m$ flowing through the capacitive branch. Control of the electromechanical properties of the ultrasonic transducer may be achieved by suitably controlling $I_g$ and $V_g$. As explained above, known generator architectures may include a tuning inductor $L_t$ (shown in phantom in FIG. 9) for tuning out in a parallel resonance circuit the static capacitance $C_0$ at a resonant frequency so that substantially all of generator's current output $I_g$ flows through the motional branch. In this way, control of the motional branch current $I_m$ is achieved by controlling the generator current output $I_g$. The tuning inductor $L_t$ is specific to the static capacitance $C_0$ of an ultrasonic transducer, however, and a different ultrasonic transducer having a different static capacitance requires a different tuning inductor $L_t$. Moreover, because the tuning inductor $L_t$ is matched to the nominal value of the static capacitance $C_0$ at a single resonant frequency, accurate control of the motional branch current $I_m$ is assured only at that frequency, and as frequency shifts down with transducer temperature, accurate control of the motional branch current is compromised.

Various embodiments of the generator 102 may not rely on a tuning inductor $L_t$ to monitor the motional branch current $I_m$. Instead, the generator 102 may use the measured value of the static capacitance $C_0$ in between applications of power for a specific ultrasonic surgical device 104 (along with drive signal voltage and current feedback data) to determine values of the motional branch current $I_m$ on a dynamic and ongoing basis (e.g., in real-time). Such embodiments of the generator 102 are therefore able to provide virtual tuning to simulate a system that is tuned or resonant with any value of static capacitance $C_0$ at any frequency, and not just at a single resonant frequency dictated by a nominal value of the static capacitance $C_0$.

Figure 10:
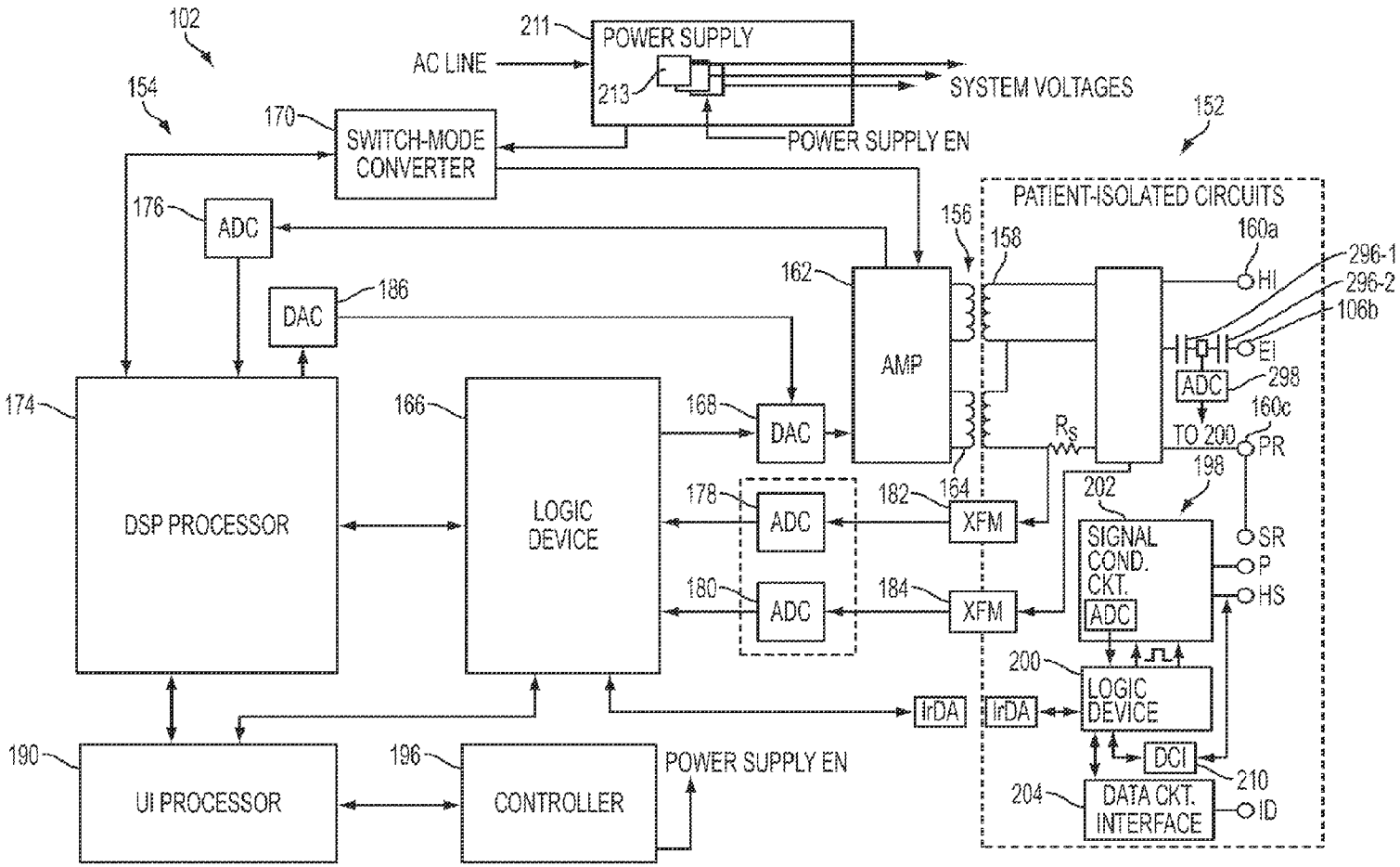
FIG. 10 is a structural view of a generator architecture in one embodiment.
Figure 11A:
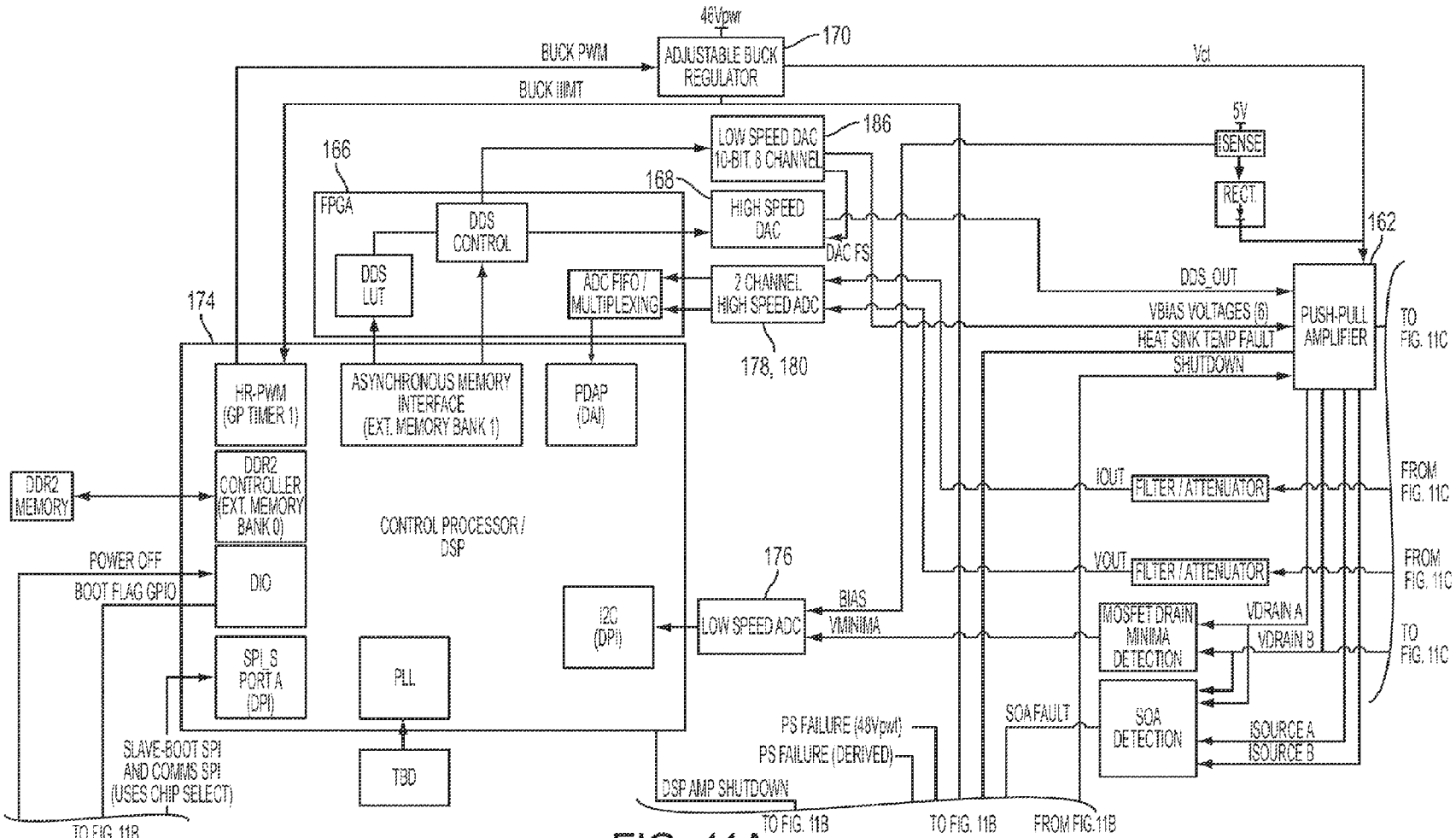
FIGS. 11A-11C are functional views of a generator architecture in one embodiment.
Figure 11B:
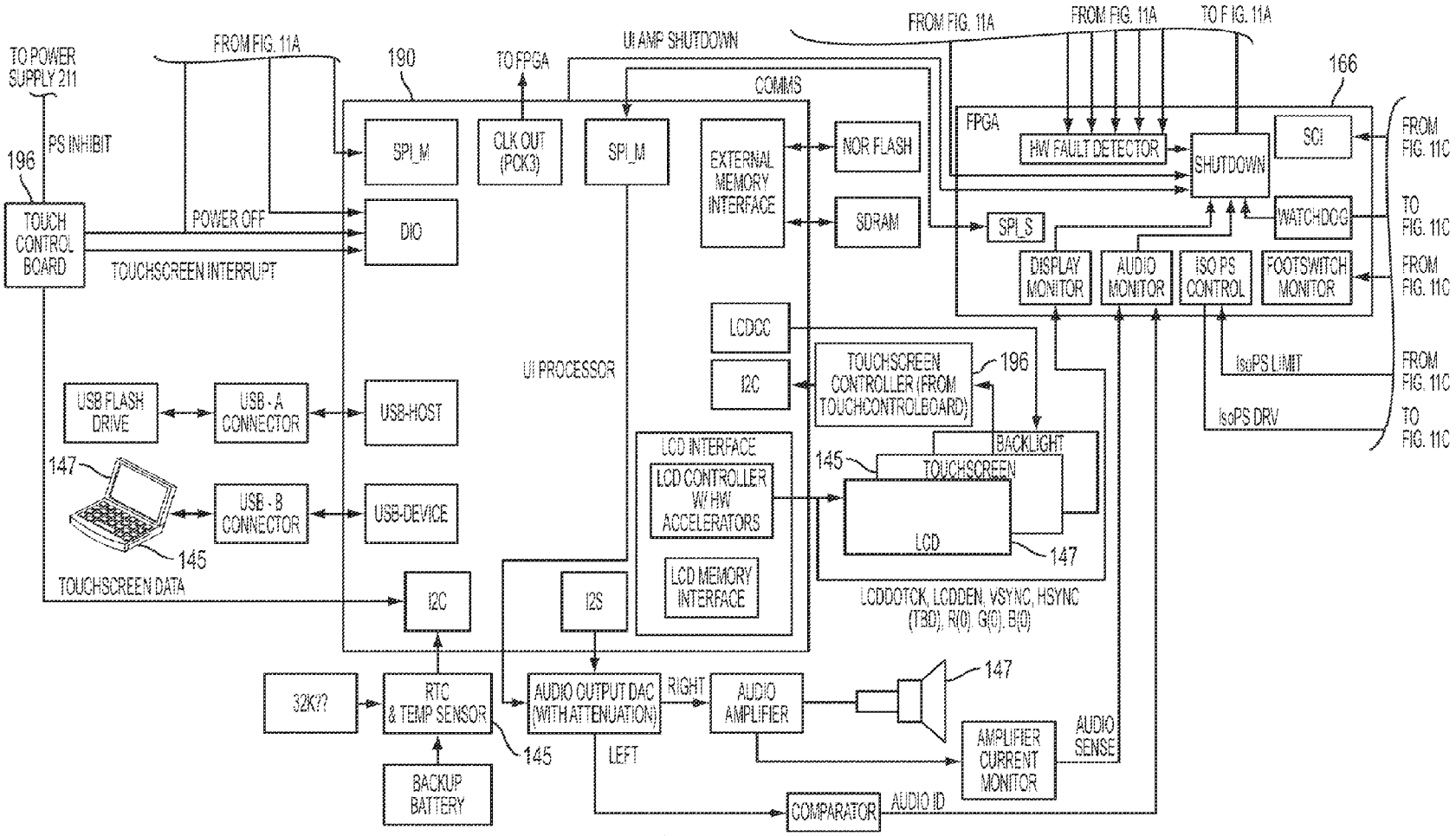
Figure 11C:
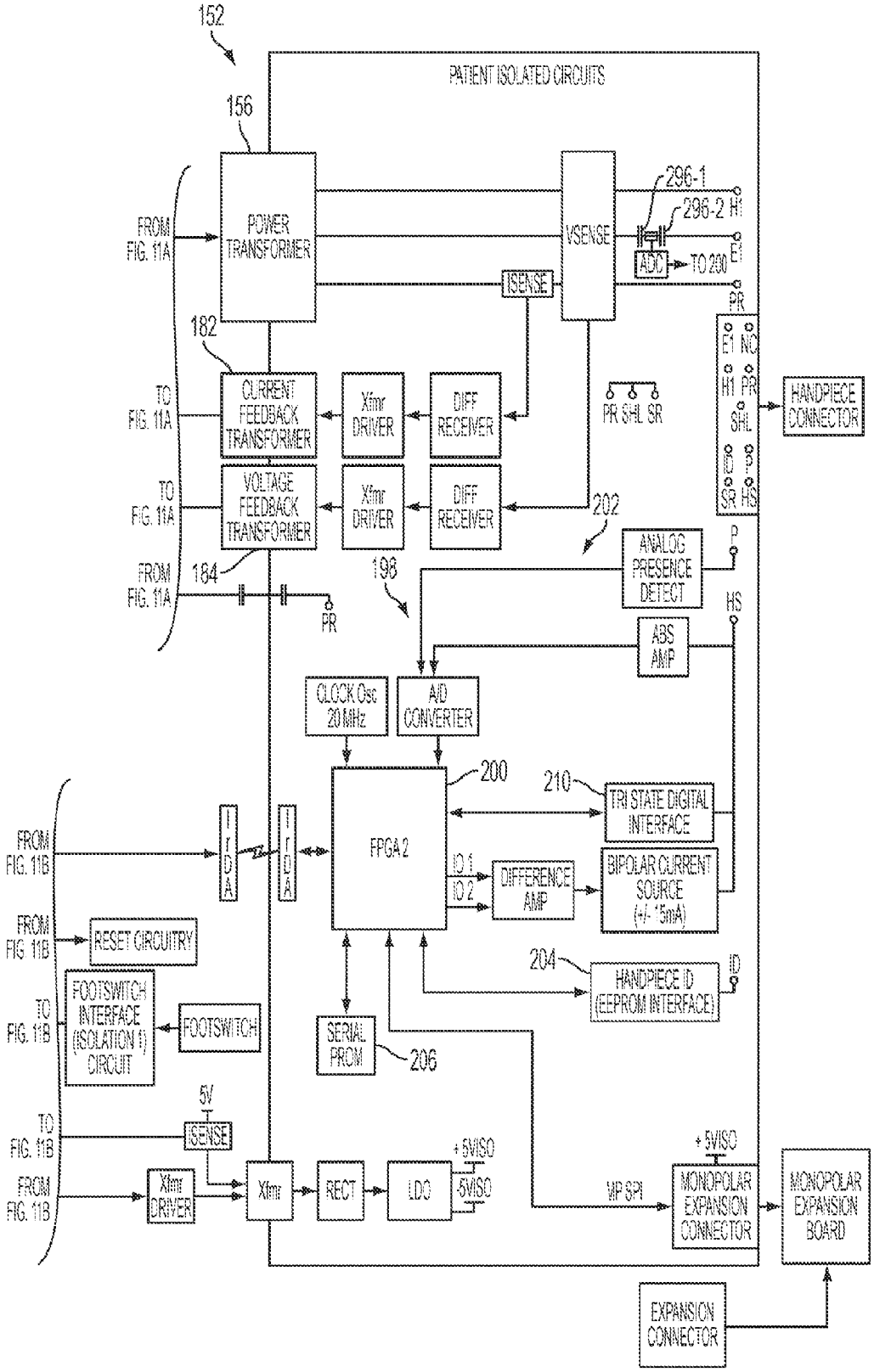
Figure 12:
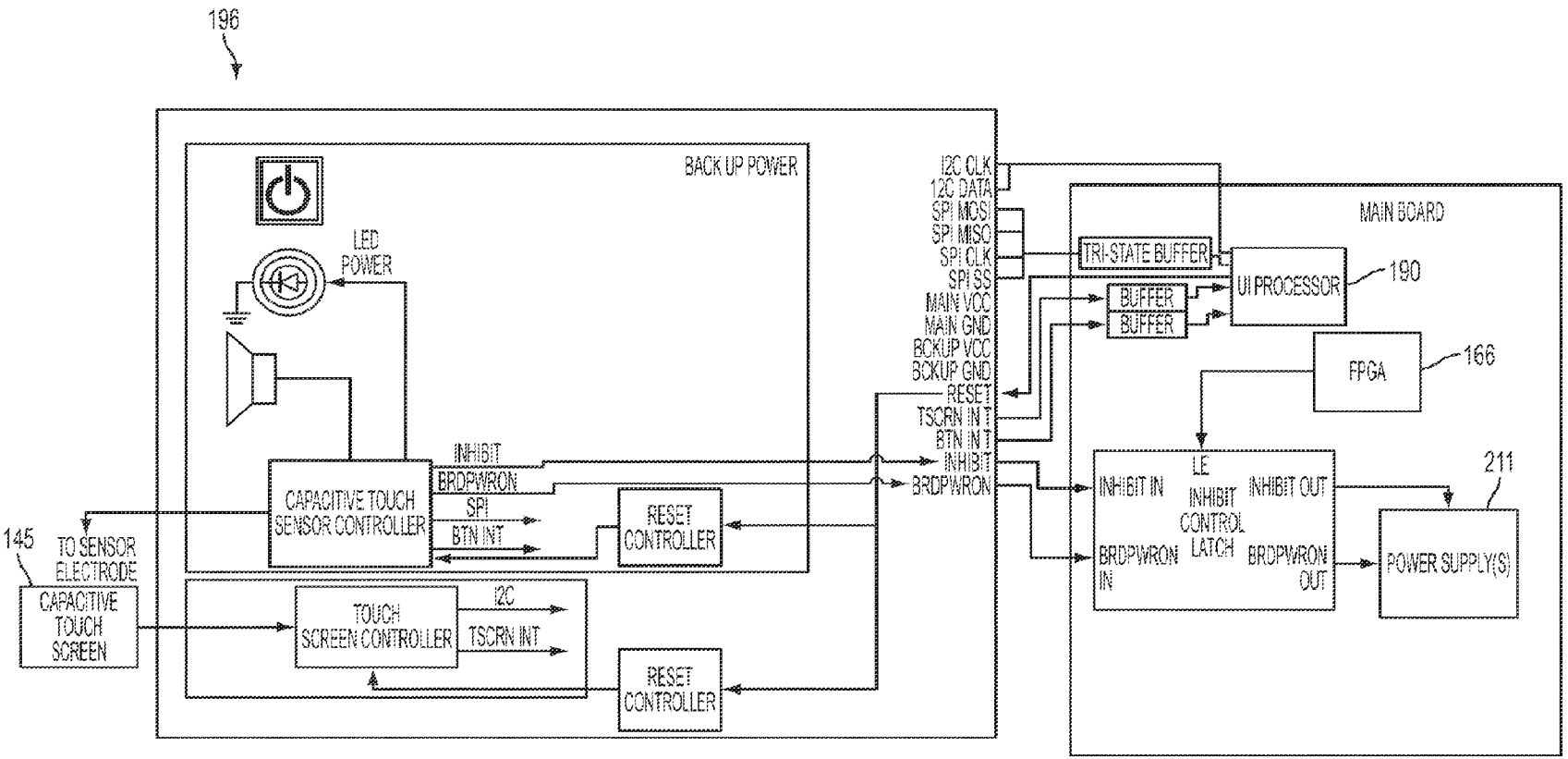
FIG. 12 illustrates a controller for monitoring input devices and controlling output devices in one embodiment.

FIG. 10 is a simplified block diagram of one embodiment of the generator 102 for proving inductorless tuning as described above, among other benefits. FIGS. 11A-11C illustrate an architecture of the generator 102 of FIG. 10 according to one embodiment. With reference to FIG. 10, the generator 102 may comprise a patient isolated stage 152 in communication with a non-isolated stage 154 via a power transformer 156. A secondary winding 158 of the power transformer 156 is contained in the isolated stage 152 and may comprise a tapped configuration (e.g., a center-tapped or non-center tapped configuration) to define drive signal outputs 160a, 160b, 160c for outputting drive signals to different surgical devices, such as, for example, an ultrasonic surgical device 104 and an electrosurgical device 106. In particular, drive signal outputs 160a, 160c may output a drive signal (e.g., a 420V RMS drive signal) to an ultrasonic surgical device 104, and drive signal outputs 160b, 160c may output a drive signal (e.g., a 100V RMS drive signal) to an electrosurgical device 106, with output 160b corresponding to the center tap of the power transformer 156. The non-isolated stage 154 may comprise a power amplifier 162 having an output connected to a primary winding 164 of the power transformer 156. In certain embodiments the power amplifier 162 may comprise a push-pull amplifier, for example. The non-isolated stage 154 may further comprise a programmable logic device 166 for supplying a digital output to a digital-to-analog converter (DAC) 168, which in turn supplies a corresponding analog signal to an input of the power amplifier 162. In certain embodiments the programmable logic device 166 may comprise a field-programmable gate array (FPGA), for example. The programmable logic device 166, by virtue of controlling the power amplifier's 162 input via the DAC 168, may therefore control any of a number of parameters (e.g., frequency, waveform shape, waveform amplitude) of drive signals appearing at the drive signal outputs 160a, 160b, 160c. In certain embodiments and as discussed below, the programmable logic device 166, in conjunction with a processor (e.g., processor 174 discussed below), may implement a number of digital signal processing (DSP)-based and/or other control algorithms to control parameters of the drive signals output by the generator 102.

Power may be supplied to a power rail of the power amplifier 162 by a switch-mode regulator 170. In certain embodiments the switch-mode regulator 170 may comprise an adjustable buck regulator, for example. The non-isolated stage 154 may further comprise a processor 174. which in one embodiment may comprise a DSP processor such as an Analog Devices ADSP-21469 SHARC DSP, available from Analog Devices, Norwood, Mass., for example. In certain embodiments the processor 174 may control operation of the switch-mode power converter 170 responsive to voltage feedback data received from the power amplifier 162 by the processor 174 via an analog-to-digital converter (ADC) 176. In one embodiment, for example, the processor 174 may receive as input, via the ADC 176, the waveform envelope of a signal (e.g., an RF signal) being amplified by the power amplifier 162. The processor 174 may then control the switch-mode regulator 170 (e.g., via a pulse-width modulated (PWM) output) such that the rail voltage supplied to the power amplifier 162 tracks the waveform envelope of the amplified signal. By dynamically modulating the rail voltage of the power amplifier 162 based on the waveform envelope, the efficiency of the power amplifier 162 may be significantly improved relative to a fixed rail voltage amplifier schemes.

In certain embodiments and as discussed in further detail in connection with FIGS. 13A-13B, the programmable logic device 166, in conjunction with the processor 174, may implement a direct digital synthesizer (DDS) control scheme to control the waveform shape, frequency and/or amplitude of drive signals output by the generator 102. In one embodiment, for example, the programmable logic device 166 may implement a DDS control algorithm 268 by recalling waveform samples stored in a dynamically-updated look-up table (LUT), such as a RAM LUT which may be embedded in an FPGA. This control algorithm is particularly useful for ultrasonic applications in which an ultrasonic transducer, such as the ultrasonic transducer 114, may be driven by a clean sinusoidal current at its resonant frequency. Because other frequencies may excite parasitic resonances, minimizing or reducing the total distortion of the motional branch current may correspondingly minimize or reduce undesirable resonance effects. Because the waveform shape of a drive signal output by the generator 102 is impacted by various sources of distortion present in the output drive circuit (e.g., the power transformer 156, the power amplifier 162), voltage and current feedback data based on the drive signal may be input into an algorithm, such as an error control algorithm implemented by the processor 174, which compensates for distortion by suitably pre-distorting or modifying the waveform samples stored in the LUT on a dynamic, ongoing basis (e.g., in real-time). In one embodiment, the amount or degree of pre-distortion applied to the LUT samples may be based on the error between a computed motional branch current and a desired current waveform shape, with the error being determined on a sample-by sample basis. In this way, the pre-distorted LUT samples, when processed through the drive circuit, may result in a motional branch drive signal having the desired waveform shape (e.g., sinusoidal) for optimally driving the ultrasonic transducer. In such embodiments, the LUT waveform samples will therefore not represent the desired waveform shape of the drive signal, but rather the waveform shape that is required to ultimately produce the desired waveform shape of the motional branch drive signal when distortion effects are taken into account.

The non-isolated stage 154 may further comprise an ADC 178 and an ADC 180 coupled to the output of the power transformer 156 via respective isolation transformers 182, 184 for respectively sampling the voltage and current of drive signals output by the generator 102. In certain embodiments, the ADCs 178, 180 may be configured to sample at high speeds (e.g., 80 Msps) to enable oversampling of the drive signals. In one embodiment, for example, the sampling speed of the ADCs 178, 180 may enable approximately 200× (depending on drive frequency) oversampling of the drive signals. In certain embodiments, the sampling operations of the ADCs 178, 180 may be performed by a single ADC receiving input voltage and current signals via a two-way multiplexer. The use of high-speed sampling in embodiments of the generator 102 may enable, among other things, calculation of the complex current flowing through the motional branch (which may be used in certain embodiments to implement DDS-based waveform shape control described above), accurate digital filtering of the sampled signals, and calculation of real power consumption with a high degree of precision. Voltage and current feedback data output by the ADCs 178, 180 may be received and processed (e.g., FIFO buffering, multiplexing) by the programmable logic device 166 and stored in data memory for subsequent retrieval by, for example, the processor 174. As noted above, voltage and current feedback data may be used as input to an algorithm for pre-distorting or modifying LUT waveform samples on a dynamic and ongoing basis. In certain embodiments, this may require each stored voltage and current feedback data pair to be indexed based on, or otherwise associated with, a corresponding LUT sample that was output by the programmable logic device 166 when the voltage and current feedback data pair was acquired. Synchronization of the LUT samples and the voltage and current feedback data in this manner contributes to the correct timing and stability of the pre-distortion algorithm.

In certain embodiments, the voltage and current feedback data may be used to control the frequency and/or amplitude (e.g., current amplitude) of the drive signals. In one embodiment, for example, voltage and current feedback data may be used to determine impedance phase. The frequency of the drive signal may then be controlled to minimize or reduce the difference between the determined impedance phase and an impedance phase setpoint (e.g., 0°), thereby minimizing or reducing the effects of harmonic distortion and correspondingly enhancing impedance phase measurement accuracy. The determination of phase impedance and a frequency control signal may be implemented in the processor 174, for example, with the frequency control signal being supplied as input to a DDS control algorithm implemented by the programmable logic device 166.

In another embodiment, for example, the current feedback data may be monitored in order to maintain the current amplitude of the drive signal at a current amplitude setpoint. The current amplitude setpoint may be specified directly or determined indirectly based on specified voltage amplitude and power setpoints. In certain embodiments, control of the current amplitude may be implemented by control algorithm, such as, for example, a proportional-integral-derivative (PID) control algorithm, in the processor 174. Variables controlled by the control algorithm to suitably control the current amplitude of the drive signal may include, for example, the scaling of the LUT waveform samples stored in the programmable logic device 166 and/or the full-scale output voltage of the DAC 168 (which supplies the input to the power amplifier 162) via a DAC 186.

The non-isolated stage 154 may further comprise a processor 190 for providing, among other things user interface (UI) functionality. In one embodiment, the processor 190 may comprise an Atmel AT91 SAM9263 processor having an ARM 926EJ-S core, available from Atmel Corporation, San Jose, Calif., for example. Examples of UI functionality supported by the processor 190 may include audible and visual user feedback, communication with peripheral devices (e.g., via a Universal Serial Bus (USB) interface), communication with the footswitch 120, communication with an input device 112 (e.g., a touch screen display) and communication with an output device 147 (e.g., a speaker). The processor 190 may communicate with the processor 174 and the programmable logic device (e.g., via serial peripheral interface (SPI) buses). Although the processor 190 may primarily support UI functionality, it may also coordinate with the processor 174 to implement hazard mitigation in certain embodiments. For example, the processor 190 may be programmed to monitor various aspects of user input and/or other inputs (e.g., touch screen inputs, footswitch 120 inputs, temperature sensor inputs) and may disable the drive output of the generator 102 when an erroneous condition is detected.

In certain embodiments, both the processor 174 and the processor 190 may determine and monitor the operating state of the generator 102. For the processor 174, the operating state of the generator 102 may dictate, for example, which control and/or diagnostic processes are implemented by the processor 174. For the processor 190, the operating state of the generator 102 may dictate, for example, which elements of a user interface (e.g., display screens, sounds) are presented to a user. The processors 174, 190 may independently maintain the current operating state of the generator 102 and recognize and evaluate possible transitions out of the current operating state. The processor 174 may function as the master in this relationship and determine when transitions between operating states are to occur. The processor 190 may be aware of valid transitions between operating states and may confirm if a particular transition is appropriate. For example, when the processor 174 instructs the processor 190 to transition to a specific state, the processor 190 may verify that requested transition is valid. In the event that a requested transition between states is determined to be invalid by the processor 190, the processor 190 may cause the generator 102 to enter a failure mode.

The non-isolated stage 154 may further comprise a controller 196 for monitoring input devices 145 (e.g., a capacitive touch sensor used for turning the generator 102 on and off, a capacitive touch screen). In certain embodiments, the controller 196 may comprise at least one processor and/or other controller device in communication with the processor 190. In one embodiment, for example, the controller 196 may comprise a processor (e.g., a Mega168 8-bit controller available from Atmel) configured to monitor user input provided via one or more capacitive touch sensors. In one embodiment, the controller 196 may comprise a touch screen controller (e.g., a QT5480 touch screen controller available from Atmel) to control and manage the acquisition of touch data from a capacitive touch screen.

In certain embodiments, when the generator 102 is in a "power off" state, the controller 196 may continue to receive operating power (e.g., via a line from a power supply of the generator 102, such as the power supply 211 discussed below). In this way, the controller 196 may continue to monitor an input device 145 (e.g., a capacitive touch sensor located on a front panel of the generator 102) for turning the generator 102 on and off. When the generator 102 is in the power off state, the controller 196 may wake the power supply (e.g., enable operation of one or more DC/DC voltage converters 213 of the power supply 211) if activation of the "on/off" input device 145 by a user is detected. The controller 196 may therefore initiate a sequence for transitioning the generator 102 to a "power on" state. Conversely, the controller 196 may initiate a sequence for transitioning the generator 102 to the power off state if activation of the "on/off" input device 145 is detected when the generator 102 is in the power on state. In certain embodiments, for example, the controller 196 may report activation of the "on/off" input device 145 to the processor 190, which in turn implements the necessary process sequence for transitioning the generator 102 to the power off state. In such embodiments, the controller 196 may have no independent ability for causing the removal of power from the generator 102 after its power on state has been established.

In certain embodiments, the controller 196 may cause the generator 102 to provide audible or other sensory feedback for alerting the user that a power on or power off sequence has been initiated. Such an alert may be provided at the beginning of a power on or power off sequence and prior to the commencement of other processes associated with the sequence.

In certain embodiments, the isolated stage 152 may comprise an instrument interface circuit 198 to, for example, provide a communication interface between a control circuit of a surgical device (e.g., a control circuit comprising handpiece switches) and components of the non-isolated stage 154, such as, for example, the programmable logic device 166, the processor 174 and/or the processor 190. The instrument interface circuit 198 may exchange information with components of the non-isolated stage 154 via a communication link that maintains a suitable degree of electrical isolation between the stages 152, 154, such as, for example, an infrared (IR)-based communication link. Power may be supplied to the instrument interface circuit 198 using, for example, a low-dropout voltage regulator powered by an isolation transformer driven from the non-isolated stage 154.

In one embodiment, the instrument interface circuit 198 may comprise a programmable logic device 200 (e.g., an FPGA) in communication with a signal conditioning circuit 202. The signal conditioning circuit 202 may be configured to receive a periodic signal from the programmable logic device 200 (e.g., a 2 kHz square wave) to generate a bipolar interrogation signal having an identical frequency. The interrogation signal may be generated, for example, using a bipolar current source fed by a differential amplifier. The interrogation signal may be communicated to a surgical device control circuit (e.g., by using a conductive pair in a cable that connects the generator 102 to the surgical device) and monitored to determine a state or configuration of the control circuit. As discussed below in connection with FIGS. 16-32, for example, the control circuit may comprise a number of switches, resistors and/or diodes to modify one or more characteristics (e.g., amplitude, rectification) of the interrogation signal such that a state or configuration of the control circuit is uniquely discernable based on the one or more characteristics. In one embodiment, for example, the signal conditioning circuit 202 may comprise an ADC for generating samples of a voltage signal appearing across inputs of the control circuit resulting from passage of interrogation signal therethrough. The programmable logic device 200 (or a component of the non-isolated stage 154) may then determine the state or configuration of the control circuit based on the ADC samples.

In one embodiment, the instrument interface circuit 198 may comprise a first data circuit interface 204 to enable information exchange between the programmable logic device 200 (or other element of the instrument interface circuit 198) and a first data circuit disposed in or otherwise associated with a surgical device. In certain embodiments and with reference to FIGS. 33E-33G, for example, a first data circuit 206 may be disposed in a cable integrally attached to a surgical device handpiece, or in an adaptor for interfacing a specific surgical device type or model with the generator 102. In certain embodiments, the first data circuit may comprise a non-volatile storage device, such as an electrically erasable programmable read-only memory (EEPROM) device. In certain embodiments and referring again to FIG. 10, the first data circuit interface 204 may be implemented separately from the programmable logic device 200 and comprise suitable circuitry (e.g., discrete logic devices, a processor) to enable communication between the programmable logic device 200 and the first data circuit. In other embodiments, the first data circuit interface 204 may be integral with the programmable logic device 200.

In certain embodiments, the first data circuit 206 may store information pertaining to the particular surgical device with which it is associated. Such information may include, for example, a model number, a serial number, a number of operations in which the surgical device has been used, and/or any other type of information. This information may be read by the instrument interface circuit 198 (e.g., by the programmable logic device 200), transferred to a component of the non-isolated stage 154 (e.g., to programmable logic device 166, processor 174 and/or processor 190) for presentation to a user via an output device 147 and/or for controlling a function or operation of the generator 102. Additionally, any type of information may be communicated to first data circuit 206 for storage therein via the first data circuit interface 204 (e.g., using the programmable logic device 200). Such information may comprise, for example, an updated number of operations in which the surgical device has been used and/or dates and/or times of its usage.

As discussed previously, a surgical instrument may be detachable from a handpiece (e.g., instrument 124 may be detachable from handpiece 116) to promote instrument interchangeability and/or disposability. In such cases, known generators may be limited in their ability to recognize particular instrument configurations being used and to optimize control and diagnostic processes accordingly. The addition of readable data circuits to surgical device instruments to address this issue is problematic from a compatibility standpoint, however. For example, designing a surgical device to remain backwardly compatible with generators that lack the requisite data reading functionality may be impractical due to, for example, differing signal schemes, design complexity and cost. Embodiments of instruments discussed below in connection with FIGS. 16-32 address these concerns by using data circuits that may be implemented in existing surgical instruments economically and with minimal design changes to preserve compatibility of the surgical devices with current generator platforms.

Additionally, embodiments of the generator 102 may enable communication with instrument-based data circuits, such as those described below in connection with FIGS. 16-32 and FIGS. 33A-33C. For example, the generator 102 may be configured to communicate with a second data circuit (e.g., data circuit 284 of FIG. 16) contained in an instrument (e.g., instrument 124 or 134) of a surgical device. The instrument interface circuit 198 may comprise a second data circuit interface 210 to enable this communication. In one embodiment, the second data circuit interface 210 may comprise a tri-state digital interface, although other interfaces may also be used. In certain embodiments, the second data circuit may generally be any circuit for transmitting and/or receiving data. In one embodiment, for example, the second data circuit may store information pertaining to the particular surgical instrument with which it is associated. Such information may include, for example, a model number, a serial number, a number of operations in which the surgical instrument has been used, and/or any other type of information. Additionally or alternatively, any type of information may be communicated to second data circuit for storage therein via the second data circuit interface 210 (e.g., using the programmable logic device 200). Such information may comprise, for example, an updated number of operations in which the instrument has been used and/or dates and/or times of its usage. In certain embodiments, the second data circuit may transmit data acquired by one or more sensors (e.g., an instrument-based temperature sensor). In certain embodiments, the second data circuit may receive data from the generator 102 and provide an indication to a user (e.g., an LED indication or other visible indication) based on the received data.

In certain embodiments, the second data circuit and the second data circuit interface 210 may be configured such that communication between the programmable logic device 200 and the second data circuit can be effected without the need to provide additional conductors for this purpose (e.g., dedicated conductors of a cable connecting a handpiece to the generator 102). In one embodiment, for example, information may be communicated to and from the second data circuit using a one-wire bus communication scheme implemented on existing cabling, such as one of the conductors used transmit interrogation signals from the signal conditioning circuit 202 to a control circuit in a handpiece. In this way, design changes or modifications to the surgical device that might otherwise be necessary are minimized or reduced. Moreover, as discussed in further detail below in connection with FIGS. 16-32 and FIGS. 33A-33C, because different types of communications can be implemented over a common physical channel (either with or without frequency-band separation), the presence of a second data circuit may be "invisible" to generators that do not have the requisite data reading functionality, thus enabling backward compatibility of the surgical device instrument.

In certain embodiments, the isolated stage 152 may comprise at least one blocking capacitor 296-1 connected to the drive signal output 160b to prevent passage of DC current to a patient. A single blocking capacitor may be required to comply with medical regulations or standards, for example. While failure in single-capacitor designs is relatively uncommon, such failure may nonetheless have negative consequences. In one embodiment, a second blocking capacitor 296-2 may be provided in series with the blocking capacitor 296-1, with current leakage from a point between the blocking capacitors 296-1, 296-2 being monitored by, for example, an ADC 298 for sampling a voltage induced by leakage current. The samples may be received by the programmable logic device 200, for example. Based on changes in the leakage current (as indicated by the voltage samples in the embodiment of FIG. 10), the generator 102 may determine when at least one of the blocking capacitors 296-1, 296-2 has failed. Accordingly, the embodiment of FIG. 10 may provide a benefit over single-capacitor designs having a single point of failure.

In certain embodiments, the non-isolated stage 154 may comprise a power supply 211 for outputting DC power at a suitable voltage and current. The power supply may comprise, for example, a 400 W power supply for outputting a 48 VDC system voltage. The power supply 211 may further comprise one or more DC/DC voltage converters 213 for receiving the output of the power supply to generate DC outputs at the voltages and currents required by the various components of the generator 102. As discussed above in connection with the controller 196, one or more of the DC/DC voltage converters 213 may receive an input from the controller 196 when activation of the "on/off" input device 145 by a user is detected by the controller 196 to enable operation of, or wake, the DC/DC voltage converters 213.

Figure 13A:
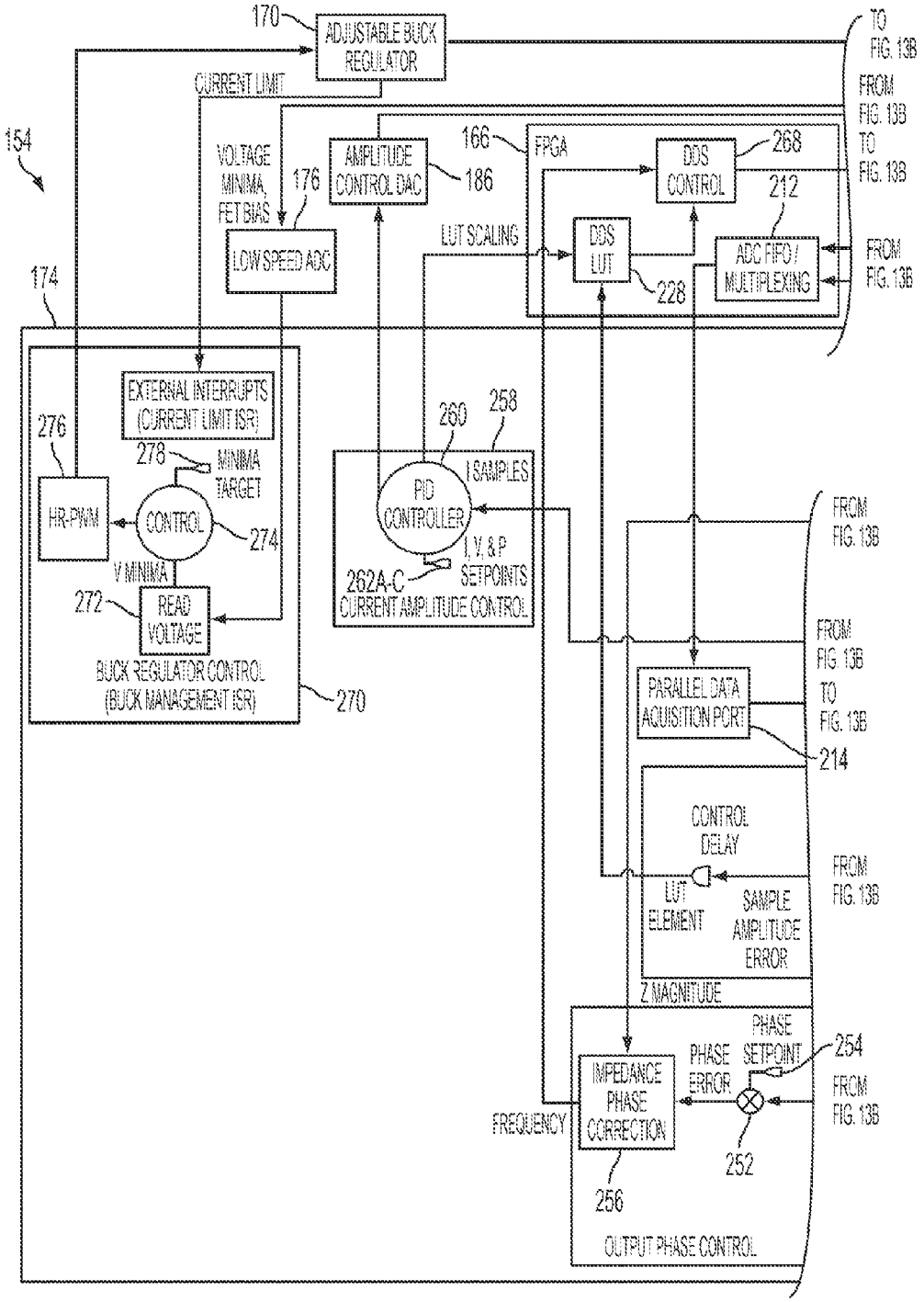
FIGS. 13A-13B illustrate structural and functional aspects of one embodiment of the generator.
Figure 13B:
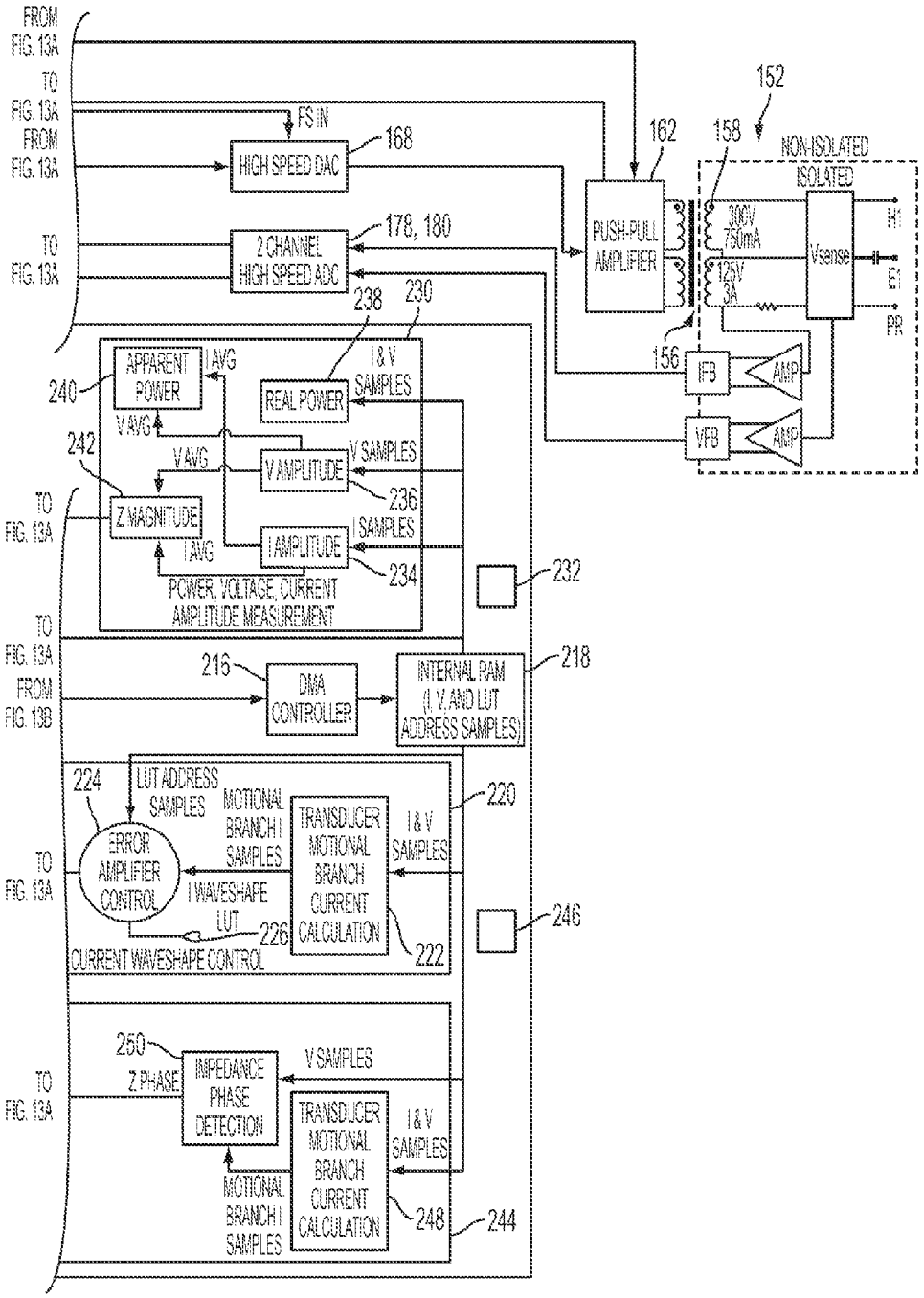

FIGS. 13A-13B illustrate certain functional and structural aspects of one embodiment of the generator 102. Feedback indicating current and voltage output from the secondary winding 158 of the power transformer 156 is received by the ADCs 178, 180, respectively. As shown, the ADCs 178, 180 may be implemented as a 2-channel ADC and may sample the feedback signals at a high speed (e.g., 80 Msps) to enable oversampling (e.g., approximately 200× oversampling) of the drive signals. The current and voltage feedback signals may be suitably conditioned in the analog domain (e.g., amplified, filtered) prior to processing by the ADCs 178, 180. Current and voltage feedback samples from the ADCs 178, 180 may be individually buffered and subsequently multiplexed or interleaved into a single data stream within block 212 of the programmable logic device 166. In the embodiment of FIGS. 13A-13B, the programmable logic device 166 comprises an FPGA.

The multiplexed current and voltage feedback samples may be received by a parallel data acquisition port (PDAP) implemented within block 214 of the processor 174. The PDAP may comprise a packing unit for implementing any of a number of methodologies for correlating the multiplexed feedback samples with a memory address. In one embodiment, for example, feedback samples corresponding to a particular LUT sample output by the programmable logic device 166 may be stored at one or more memory addresses that are correlated or indexed with the LUT address of the LUT sample. In another embodiment, feedback samples corresponding to a particular LUT sample output by the programmable logic device 166 may be stored, along with the LUT address of the LUT sample, at a common memory location. In any event, the feedback samples may be stored such that the address of an LUT sample from which a particular set of feedback samples originated may be subsequently ascertained. As discussed above, synchronization of the LUT sample addresses and the feedback samples in this way contributes to the correct timing and stability of the pre-distortion algorithm. A direct memory access (DMA) controller implemented at block 216 of the processor 174 may store the feedback samples (and any LUT sample address data, where applicable) at a designated memory location 218 of the processor 174 (e.g., internal RAM).

Block 220 of the processor 174 may implement a pre-distortion algorithm for pre-distorting or modifying the LUT samples stored in the programmable logic device 166 on a dynamic, ongoing basis. As discussed above, pre-distortion of the LUT samples may compensate for various sources of distortion present in the output drive circuit of the generator 102. The pre-distorted LUT samples, when processed through the drive circuit, will therefore result in a drive signal having the desired waveform shape (e.g., sinusoidal) for optimally driving the ultrasonic transducer.

At block 222 of the pre-distortion algorithm, the current through the motional branch of the ultrasonic transducer is determined. The motional branch current may be determined using Kirchoff's Current Law based on, for example, the current and voltage feedback samples stored at memory location 218 (which, when suitably scaled, may be representative of $I_g$ and $V_g$ in the model of FIG. 9 discussed above), a value of the ultrasonic transducer static capacitance $C_0$ (measured or known a priori) and a known value of the drive frequency. A motional branch current sample for each set of stored current and voltage feedback samples associated with a LUT sample may be determined.

At block 224 of the pre-distortion algorithm, each motional branch current sample determined at block 222 is compared to a sample of a desired current waveform shape to determine a difference, or sample amplitude error, between the compared samples. For this determination, the sample of the desired current waveform shape may be supplied, for example, from a waveform shape LUT 226 containing amplitude samples for one cycle of a desired current waveform shape. The particular sample of the desired current waveform shape from the LUT 226 used for the comparison may be dictated by the LUT sample address associated with the motional branch current sample used in the comparison. Accordingly, the input of the motional branch current to block 224 may be synchronized with the input of its associated LUT sample address to block 224. The LUT samples stored in the programmable logic device 166 and the LUT samples stored in the waveform shape LUT 226 may therefore be equal in number. In certain embodiments, the desired current waveform shape represented by the LUT samples stored in the waveform shape LUT 226 may be a fundamental sine wave. Other waveform shapes may be desirable. For example, it is contemplated that a fundamental sine wave for driving main longitudinal motion of an ultrasonic transducer superimposed with one or more other drive signals at other frequencies, such as a third order harmonic for driving at least two mechanical resonances for beneficial vibrations of transverse or other modes, could be used.

Each value of the sample amplitude error determined at block 224 may be transmitted to the LUT of the programmable logic device 166 (shown at block 228 in FIG. 13A) along with an indication of its associated LUT address. Based on the value of the sample amplitude error and its associated address (and, optionally, values of sample amplitude error for the same LUT address previously received), the LUT 228 (or other control block of the programmable logic device 166) may pre-distort or modify the value of the LUT sample stored at the LUT address such that the sample amplitude error is reduced or minimized. It will be appreciated that such pre-distortion or modification of each LUT sample in an iterative manner across the entire range of LUT addresses will cause the waveform shape of the generator's output current to match or conform to the desired current waveform shape represented by the samples of the waveform shape LUT 226.

Current and voltage amplitude measurements, power measurements and impedance measurements may be determined at block 230 of the processor 174 based on the current and voltage feedback samples stored at memory location 218. Prior to the determination of these quantities, the feedback samples may be suitably scaled and, in certain embodiments, processed through a suitable filter 232 to remove noise resulting from, for example, the data acquisition process and induced harmonic components. The filtered voltage and current samples may therefore substantially represent the fundamental frequency of the generator's drive output signal. In certain embodiments, the filter 232 may be a finite impulse response (FIR) filter applied in the frequency domain. Such embodiments may use the fast Fourier transform (FFT) of the output drive signal current and voltage signals. In certain embodiments, the resulting frequency spectrum may be used to provide additional generator functionality. In one embodiment, for example, the ratio of the second and/or third order harmonic component relative to the fundamental frequency component may be used as a diagnostic indicator.

At block 234, a root mean square (RMS) calculation may be applied to a sample size of the current feedback samples representing an integral number of cycles of the drive signal to generate a measurement $I_{rms}$ representing the drive signal output current.

At block 236, a root mean square (RMS) calculation may be applied to a sample size of the voltage feedback samples representing an integral number of cycles of the drive signal to determine a measurement $V_{rms}$ representing the drive signal output voltage.

At block 238, the current and voltage feedback samples may be multiplied point by point, and a mean calculation is applied to samples representing an integral number of cycles of the drive signal to determine a measurement $P_r$ of the generator's real output power.

At block 240, measurement $P_a$ of the generator's apparent output power may be determined as the product $V_{rms} \cdot I_{rms}$.

At block 242, measurement $Z_m$ of the load impedance magnitude may be determined as the quotient $V_{rms}/I_{rms}$. In certain embodiments, the quantities $I_{rms}$, $V_{rms}$, $P_r$, $P_a$ and $Z_m$ determined at blocks 234, 236, 238, 240 and 242 may be used by the generator 102 to implement any of number of control and/or diagnostic processes. In certain embodiments, any of these quantities may be communicated to a user via, for example, an output device 147 integral with the generator 102 or an output device 147 connected to the generator 102 through a suitable communication interface (e.g., a USB interface). Various diagnostic processes may include, without limitation, handpiece integrity, instrument integrity, instrument attachment integrity, instrument overload, approaching instrument overload, frequency lock failure, over-voltage, over-current, over-power, voltage sense failure, current sense failure, audio indication failure, visual indication failure, short circuit, power delivery failure, blocking capacitor failure, for example.

Block 244 of the processor 174 may implement a phase control algorithm for determining and controlling the impedance phase of an electrical load (e.g., the ultrasonic transducer) driven by the generator 102. As discussed above, by controlling the frequency of the drive signal to minimize or reduce the difference between the determined impedance phase and an impedance phase setpoint (e.g., 0°), the effects of harmonic distortion may be minimized or reduced, and the accuracy of the phase measurement increased.

The phase control algorithm receives as input the current and voltage feedback samples stored in the memory location 218. Prior to their use in the phase control algorithm, the feedback samples may be suitably scaled and, in certain embodiments, processed through a suitable filter 246 (which may be identical to filter 232) to remove noise resulting from the data acquisition process and induced harmonic components, for example. The filtered voltage and current samples may therefore substantially represent the fundamental frequency of the generator's drive output signal.

At block 248 of the phase control algorithm, the current through the motional branch of the ultrasonic transducer is determined. This determination may be identical to that described above in connection with block 222 of the pre-distortion algorithm. The output of block 248 may thus be, for each set of stored current and voltage feedback samples associated with a LUT sample, a motional branch current sample.

At block 250 of the phase control algorithm, impedance phase is determined based on the synchronized input of motional branch current samples determined at block 248 and corresponding voltage feedback samples. In certain embodiments, the impedance phase is determined as the average of the impedance phase measured at the rising edge of the waveforms and the impedance phase measured at the falling edge of the waveforms.

At block 252 of the of the phase control algorithm, the value of the impedance phase determined at block 222 is compared to phase setpoint 254 to determine a difference, or phase error, between the compared values.

At block 256 of the phase control algorithm, based on a value of phase error determined at block 252 and the impedance magnitude determined at block 242, a frequency output for controlling the frequency of the drive signal is determined. The value of the frequency output may be continuously adjusted by the block 256 and transferred to a DDS control block 268 (discussed below) in order to maintain the impedance phase determined at block 250 at the phase setpoint (e.g., zero phase error). In certain embodiments, the impedance phase may be regulated to a 0° phase setpoint. In this way, any harmonic distortion will be centered about the crest of the voltage waveform, enhancing the accuracy of phase impedance determination.

Block 258 of the processor 174 may implement an algorithm for modulating the current amplitude of the drive signal in order to control the drive signal current, voltage and power in accordance with user specified setpoints, or in accordance with requirements specified by other processes or algorithms implemented by the generator 102. Control of these quantities may be realized, for example, by scaling the LUT samples in the LUT 228 and/or by adjusting the full-scale output voltage of the DAC 168 (which supplies the input to the power amplifier 162) via a DAC 186. Block 260 (which may be implemented as a PID controller in certain embodiments) may receive as input current feedback samples (which may be suitably scaled and filtered) from the memory location 218. The current feedback samples may be compared to a "current demand" $I_d$ value dictated by the controlled variable (e.g., current, voltage or power) to determine if the drive signal is supplying the necessary current. In embodiments in which drive signal current is the control variable, the current demand $I_d$ may be specified directly by a current setpoint 262A ($I_{sp}$). For example, an RMS value of the current feedback data (determined as in block 234) may be compared to user-specified RMS current setpoint $I_{sp}$ to determine the appropriate controller action. If, for example, the current feedback data indicates an RMS value less than the current setpoint $I_{sp}$, LUT scaling and/or the full-scale output voltage of the DAC 168 may be adjusted by the block 260 such that the drive signal current is increased. Conversely, block 260 may adjust LUT scaling and/or the full-scale output voltage of the DAC 168 to decrease the drive signal current when the current feedback data indicates an RMS value greater than the current setpoint $I_{sp}$.

In embodiments in which the drive signal voltage is the control variable, the current demand $I_d$ may be specified indirectly, for example, based on the current required maintain a desired voltage setpoint 262B ($V_{sp}$) given the load impedance magnitude $Z_m$ measured at block 242 (e.g. $I_d=V_{sp}/Z_m$). Similarly, in embodiments in which drive signal power is the control variable, the current demand $I_d$ may be specified indirectly, for example, based on the current required to maintain a desired power setpoint 262C ($P_{sp}$) given the voltage $V_{rms}$ measured at blocks 236 (e.g. $I_d=P_{sp}/V_{rms}$.

Block 268 may implement a DDS control algorithm for controlling the drive signal by recalling LUT samples stored in the LUT 228. In certain embodiments, the DDS control algorithm be a numerically-controlled oscillator (NCO) algorithm for generating samples of a waveform at a fixed clock rate using a point (memory location)-skipping technique. The NCO algorithm may implement a phase accumulator, or frequency-to-phase converter, that functions as an address pointer for recalling LUT samples from the LUT 228. In one embodiment, the phase accumulator may be a D step size, modulo N phase accumulator, where D is a positive integer representing a frequency control value, and N is the number of LUT samples in the LUT 228. A frequency control value of D=1, for example, may cause the phase accumulator to sequentially point to every address of the LUT 228, resulting in a waveform output replicating the waveform stored in the LUT 228. When D>1, the phase accumulator may skip addresses in the LUT 228, resulting in a waveform output having a higher frequency. Accordingly, the frequency of the waveform generated by the DDS control algorithm may therefore be controlled by suitably varying the frequency control value. In certain embodiments, the frequency control value may be determined based on the output of the phase control algorithm implemented at block 244. The output of block 268 may supply the input of DAC 168, which in turn supplies a corresponding analog signal to an input of the power amplifier 162.

Block 270 of the processor 174 may implement a switch-mode converter control algorithm for dynamically modulating the rail voltage of the power amplifier 162 based on the waveform envelope of the signal being amplified, thereby improving the efficiency of the power amplifier 162. In certain embodiments, characteristics of the waveform envelope may be determined by monitoring one or more signals contained in the power amplifier 162. In one embodiment, for example. characteristics of the waveform envelope may be determined by monitoring the minima of a drain voltage (e.g., a MOSFET drain voltage) that is modulated in accordance with the envelope of the amplified signal. A minima voltage signal may be generated, for example, by a voltage minima detector coupled to the drain voltage. The minima voltage signal may be sampled by ADC 176, with the output minima voltage samples being received at block 272 of the switch-mode converter control algorithm. Based on the values of the minima voltage samples, block 274 may control a PWM signal output by a PWM generator 276, which, in turn, controls the rail voltage supplied to the power amplifier 162 by the switch-mode regulator 170. In certain embodiments, as long as the values of the minima voltage samples are less than a minima target 278 input into block 262, the rail voltage may be modulated in accordance with the waveform envelope as characterized by the minima voltage samples. When the minima voltage samples indicate low envelope power levels, for example, block 274 may cause a low rail voltage to be supplied to the power amplifier 162, with the full rail voltage being supplied only when the minima voltage samples indicate maximum envelope power levels. When the minima voltage samples fall below the minima target 278, block 274 may cause the rail voltage to be maintained at a minimum value suitable for ensuring proper operation of the power amplifier 162.

Figure 33A:
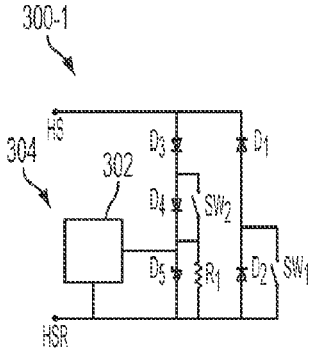
Figure 33B:
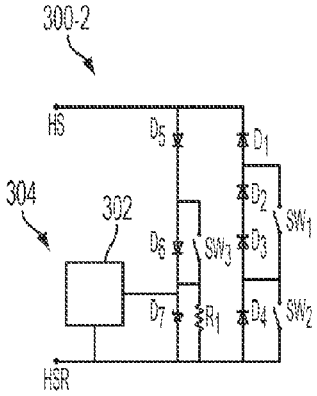
Figure 33C:
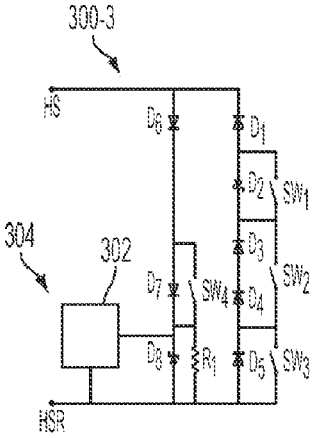
Figure 33D:
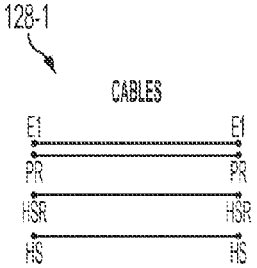
FIG. 33D-33I illustrate embodiments of cabling and adaptor configurations for connecting various generators and various surgical instruments.
Figure 33E:
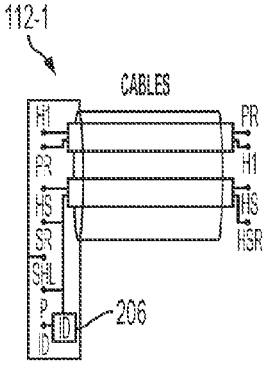
Figure 33F:
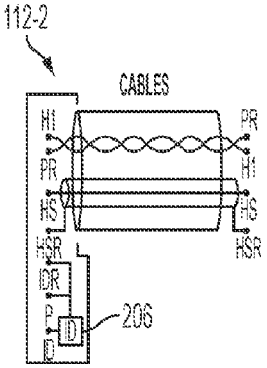
Figure 33G:
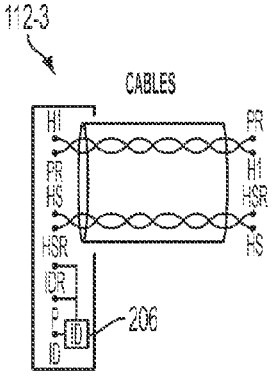

FIGS. 33A-33C illustrate control circuits of surgical devices according to various embodiments. As discussed above in connection with FIG. 10, a control circuit may modify characteristics of an interrogation signal transmitted by the generator 102. The characteristics of the interrogation signal, which may uniquely indicate a state or configuration of the control circuit, can be discerned by the generator 102 and used to control aspects of its operation. The control circuits may be contained in an ultrasonic surgical device (e.g., in the handpiece 116 of the ultrasonic surgical device 104), or in an electrosurgical device (e.g., in the handpiece 130 of the electrosurgical device 106).

Referring to the embodiment of FIG. 33A, a control circuit 300-1 may be connected to the generator 102 to receive an interrogation signal (e.g., a bipolar interrogation signal at 2 kHz) from the signal conditioning circuit 202 (e.g., from generator terminals HS and SR (FIG. 10) via a conductive pair of cable 112 or cable 128). The control circuit 300-1 may comprise a first branch that includes series-connected diodes D1 and D2 and a switch SW1 connected in parallel with D2. The control circuit 300-1 may also comprise a second branch that includes series-connected diodes D3, D4 and D5, a switch SW2 connected in parallel with D4, and a resistor R1 connected in parallel with D5. In certain embodiments and as shown, D5 may be a Zener diode. The control circuit 300-1 may additionally comprise a data storage element 302 that, together with one or more components of the second branch (e.g., D5, R1), define a data circuit 304. In certain embodiments, the data storage element 302, and possibly other components of the data circuit 304, may be contained in the instrument (e.g., instrument 124, instrument 134) of the surgical device, with other components of the control circuit 300-1 (e.g., SW1, SW2, D1, D2, D3, D4) being contained in the handpiece (e.g., handpiece 116, handpiece 130). In certain embodiments, the data storage element 302 may be a single-wire bus device (e.g., a single-wire protocol EEPROM), or other single-wire protocol or local interconnect network (LIN) protocol device. In one embodiment, for example, the data storage element 302 may comprise a Maxim DS28EC20 EEPROM, available from Maxim Integrated Products, Inc., Sunnyvale, Calif., known under the trade name "1-Wire." The data storage element 302 is one example of a circuit element that may be contained in the data circuit 304. The data circuit 304 may additionally or alternatively comprise one or more other circuit elements or components capable of transmitting or receiving data. Such circuit elements or components may be configured to, for example, transmit data acquired by one or more sensors (e.g., an instrument-based temperature sensor) and/or receive data from the generator 102 and provide an indication to a user (e.g., an LED indication or other visible indication) based on the received data.

During operation, an interrogation signal (e.g., a bipolar interrogation signal at 2 kHz) from the signal conditioning circuit 202 may be applied across both branches of the control circuit 300-1. In this way, the voltage appearing across the branches may be uniquely determined by the states of SW1 and SW2. For example, when SW1 is open, the voltage drop across the control circuit 300-1 for negative values of the interrogation signal will be sum of the forward voltage drops across D1 and D2. When SW1 is closed, the voltage drop for negative values of the interrogation signal will be determined by the forward voltage drop of D1 only. Thus, for example, with a forward voltage drop of 0.7 volts for each of D1 and D2, open and closed states of SW1 may correspond to voltage drops of 1.4 volts and 0.7 volts, respectively. In the same way, the voltage drop across the control circuit 300-1 for positive values of the interrogation signal may be uniquely determined by the state of SW2. For example, when SW2 is open, the voltage drop across the control circuit 300-1 will be the sum of the forward voltage drops across D3 and D4 (e.g., 1.4 volts) and the breakdown voltage of D5 (e.g., 3.3 volts). When SW2 is closed, the voltage drop across the control circuit 300-1 will be the sum of the forward voltage drop across D3 and the breakdown voltage of D5. Accordingly, the state or configuration of SW1 and SW2 may be discerned by the generator 102 based on the interrogation signal voltage appearing across the inputs of the control circuit 300-1 (e.g., as measured by an ADC of the signal conditioning circuit 202).

In certain embodiments, the generator 102 may be configured to communicate with the data circuit 304, and, in particular, with the data storage element 302, via the second data circuit interface 210 (FIG. 10) and the conductive pair of cable 112 or cable 128. The frequency band of the communication protocol used to communicate with the data circuit 304 may be higher than the frequency band of the interrogation signal. In certain embodiments, for example, the frequency of the communication protocol for the data storage element 302 may be, for example, 200 kHz or a significantly higher frequency, whereas the frequency of the interrogation signal used to determine the different states of SW1 and SW2 may be, for example, 2 kHz. Diode D5 may limit the voltage supplied to the data storage element 302 to a suitable operating range (e.g., 3.3-5V).

As explained above in connection with FIG. 10, the data circuit 304, and, in particular, the data storage element 302, may store information pertaining to the particular surgical instrument with which it is associated. Such information may be retrieved by the generator 102 and include, for example, a model number, a serial number, a number of operations in which the surgical instrument has been used, and/or any other type of information. Additionally, any type of information may be communicated from the generator 102 to the data circuit 304 for storage in the data storage element 302. Such information may comprise, for example, an updated number of operations in which the instrument has been used and/or dates and/or times of its usage.

As noted above, the data circuit 304 may additionally or alternatively comprise components or elements other than the data storage element 302 for transmitting or receiving data. Such components or elements may be configured to, for example, transmit data acquired by one or more sensors (e.g., an instrument-based temperature sensor) and/or receive data from the generator 102 and provide an indication to a user (e.g., an LED indication or other visible indication) based on the received data.

Embodiments of the control circuit may comprise additional switches. With reference to the embodiment of FIG. 33B, for example, control circuit 300-2 may comprise a first branch having a first switch SW1 and a second switch SW2 (for a total of three switches), with each combination of SW1 and SW2 states corresponding to a unique voltage drop across the control circuit 300-2 for negative values of the interrogation signal. For example, the open and closed states of SW1 add or remove, respectively, the forward voltage drops of D2 and D3, and the open and closed states of SW2 add or remove, respectively, the forward voltage drop of D4. In the embodiment of FIG. 33C, the first branch of control circuit 300-3 comprises three switches (for a total of four switches), with the breakdown voltage of Zener diode D2 being used to distinguish changes in the voltage drop resulting from the operation of SW1 from voltage changes resulting from the operation of SW2 and SW3.

Figure 14:
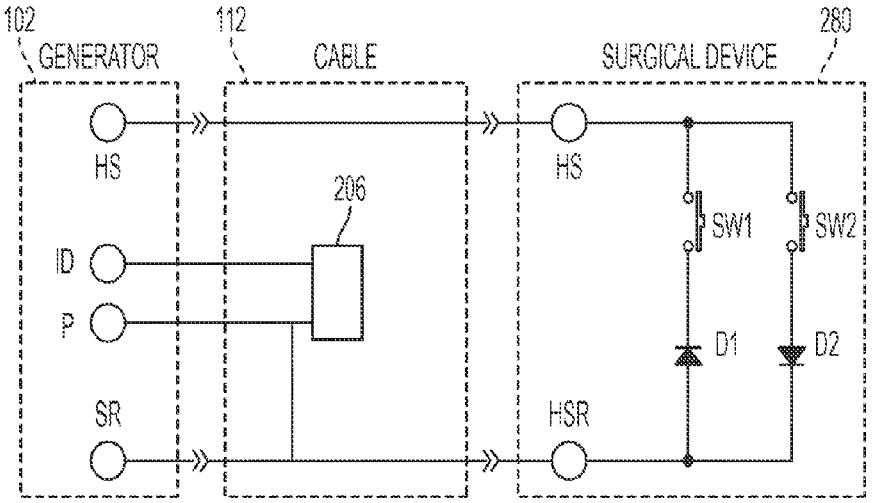
FIGS. 14-32 and 33A-33C illustrate embodiments of control circuits.
Figure 15:
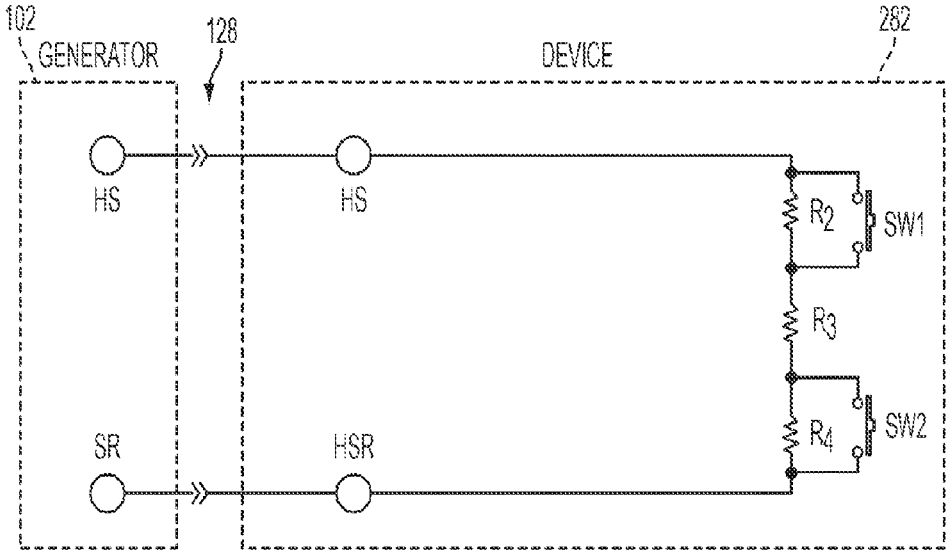

FIGS. 14 and 15 illustrate control circuits of surgical devices according to various embodiments. As discussed above in connection with FIG. 10, a control circuit may modify characteristics of an interrogation signal transmitted by the generator 102. The characteristics of the interrogation signal, which may uniquely indicate the state or configuration of the control circuit, can be discerned by the generator 102 and used to control aspects of its operation. The control circuit 280 of FIG. 14 may be contained in an ultrasonic surgical device (e.g., in handpiece 116 of ultrasonic surgical device 104), and the control circuit 282 of FIG. 15 may be contained in an electrosurgical device (e.g., in handpiece 130 of electrosurgical device 106).

Referring to FIG. 14, control circuit 280 may be connected to the generator 102 to receive an interrogation signal (e.g., a bipolar interrogation signal at 2 kHz) from the signal conditioning circuit 202 (e.g., from generator terminals HS and SR (FIG. 10) via a conductive pair of cable 112). The control circuit 280 may comprise a first switch SW1 in series with a first diode D1 to define a first branch, and a second switch SW2 in series with a second diode D2 to define a second branch. The first and second branches may be connected in parallel such that the forward conduction direction of D2 is opposite that of D1. The interrogation signal may be applied across both branches. When both SW1 and SW2 are open, the control circuit 280 may define an open circuit. When SW1 is closed and SW2 is open, the interrogation signal may undergo half-wave rectification in a first direction (e.g., positive half of interrogation signal blocked). When SW1 is open and SW2 is closed, the interrogation signal may undergo half-wave rectification in a second direction (e.g., negative half of interrogation signal blocked). When both SW1 and SW2 are closed, no rectification may occur. Accordingly, based on the different characteristics of the interrogation signal corresponding to the different states of SW1 and SW2, the state or configuration of the control circuit 280 may be discerned by the generator 102 based on a voltage signal appearing across the inputs of the control circuit 280 (e.g., as measured by an ADC of the signal conditioning circuit 202).

In certain embodiments and as shown in FIG. 14, the cable 112 may comprise a data circuit 206. The data circuit 206 may comprise, for example, a non-volatile storage device, such as an EEPROM device. The generator 102 may exchange information with the data circuit 206 via the first data circuit interface 204 as discussed above in connection with FIG. 10. Such information may be specific to a surgical device integral with, or configured for use with, the cable 112 and may comprise, for example, a model number, a serial number, a number of operations in which the surgical device has been used, and/or any other type of information. Information may also be communicated from the generator 102 to the data circuit 206 for storage therein, as discussed above in connection with FIG. 10. In certain embodiments and with reference to FIGS. 33E-33G, the data circuit 206 may be disposed in an adaptor for interfacing a specific surgical device type or model with the generator 102.

Referring to FIG. 15, control circuit 282 may be connected to the generator 102 to receive an interrogation signal (e.g., a bipolar interrogation signal at 2 kHz) from the signal conditioning circuit 202 (e.g., from generator terminals HS and SR (FIG. 10) via a conductive pair of cable 128). The control circuit 282 may comprise series-connected resistors R2, R3 and R4, with switches SW1 and SW2 connected across R2 and R4, respectively. The interrogation signal may be applied across at least one of the series-connected resistors to generate a voltage drop across the control circuit 282. For example, when both SW1 and SW2 are open, the voltage drop may be determined by R2, R3 and R4. When SW1 is closed and SW2 is open, the voltage drop may be determined by R3 and R4. When SW1 is open and SW2 is closed, the voltage drop may be determined by R2 and R3. When both SW1 and SW2 are closed, the voltage drop may be determined by R3. Accordingly, based on the voltage drop across the control circuit 282 (e.g., as measured by an ADC of the signal conditioning circuit 202), the state or configuration of the control circuit 282 may be discerned by the generator 102.

Figure 16:
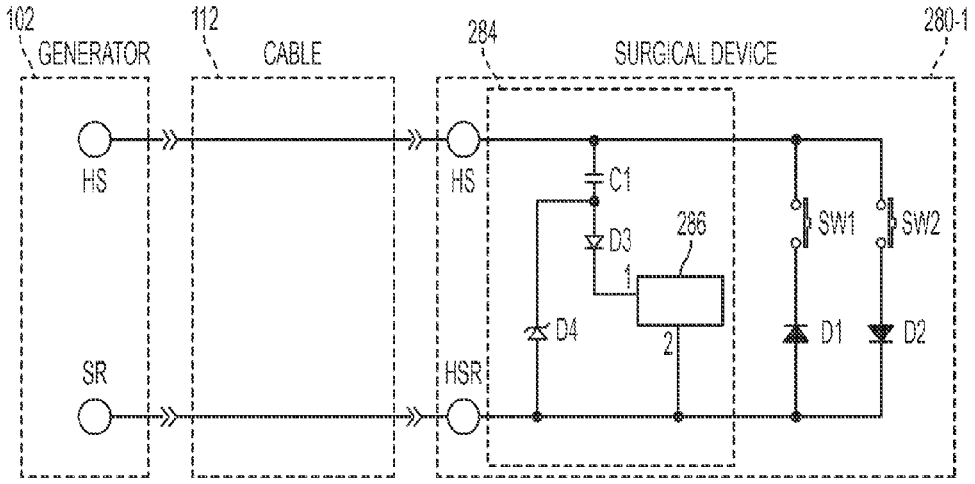

FIG. 16 illustrates one embodiment of a control circuit 280-1 of an ultrasonic surgical device, such as the ultrasonic surgical device 104. The control circuit 280-1, in addition to comprising components of the control circuit 280 of FIG. 14, may comprise a data circuit 284 having a data storage element 286. In certain embodiments, the data storage element 286, and possibly other components of the data circuit 284, may be contained in the instrument (e.g., instrument 124) of the ultrasonic surgical device, with other components of the control circuit 280-1 (e.g., SW1, SW2, D1, D2, D3, D4, C1) being contained in the handpiece (e.g., handpiece 116). In certain embodiments, the data storage element 286 may be a single-wire bus device (e.g., a single-wire protocol EEPROM), or other single-wire protocol or local interconnect network (LIN) protocol device. In one embodiment, for example, the data storage element 286 may comprise a Maxim DS28EC20 one-wire EEPROM, available from Maxim Integrated Products, Inc., Sunnyvale, Calif., known under the trade name "1-Wire."

In certain embodiments, the generator 102 may be configured to communicate with the data circuit 284, and, in particular, with the data storage element 286, via the second data circuit interface 210 (FIG. 10) and the conductive pair of the cable 112. In particular, the frequency band of the communication protocol used to communicate with the data circuit 284 may be higher than the frequency band of the interrogation signal. In certain embodiments, for example, the frequency of the communication protocol for the data storage element 286 may be, for example, 200 kHz or a significantly higher frequency, whereas the frequency of the interrogation signal used to determine the different states of SW1 and SW2 may be, for example, 2 kHz. Accordingly, the value of capacitor C1 of the data circuit 284 may be selected such that the data storage element 286 is "hidden" from the relatively low frequency of the interrogation signal while allowing the generator 102 to communicate with the data storage element 286 at the higher frequency of the communication protocol. A series diode D3 may protect the data storage element 286 from negative cycles of the interrogation signal, and a parallel Zener diode D4 may limit the voltage supplied to the data storage element 286 to a suitable operating range (e.g., 3.3-5V). When in the forward conduction mode, D4 may also clamp negative cycles of the interrogation signal to ground.

As explained above in connection with FIG. 10, the data circuit 284, and, in particular, the data storage element 286, may store information pertaining to the particular surgical instrument with which it is associated. Such information may be retrieved by the generator 102 and include, for example, a model number, a serial number, a number of operations in which the surgical instrument has been used, and/or any other type of information. Additionally, any type of information may be communicated from the generator 102 to the data circuit 284 for storage in the data storage element 286. Such information may comprise, for example, an updated number of operations in which the instrument has been used and/or dates and/or times of its usage. Moreover, because the different types of communications between the generator 102 and the surgical device may be frequency-band separated, the presence of the data storage element 286 may be "invisible" to generators that do not have the requisite data reading functionality, thus enabling backward compatibility of the surgical device.

Figure 17:
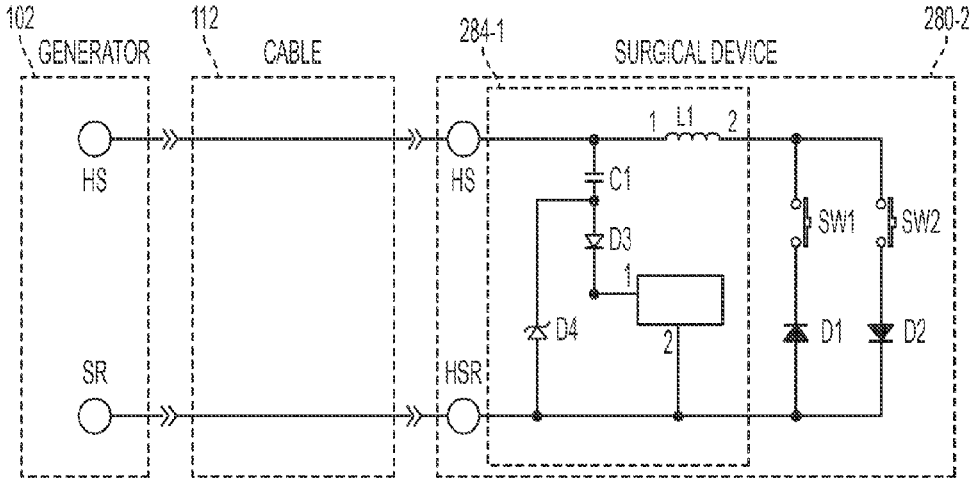
Figure 18:
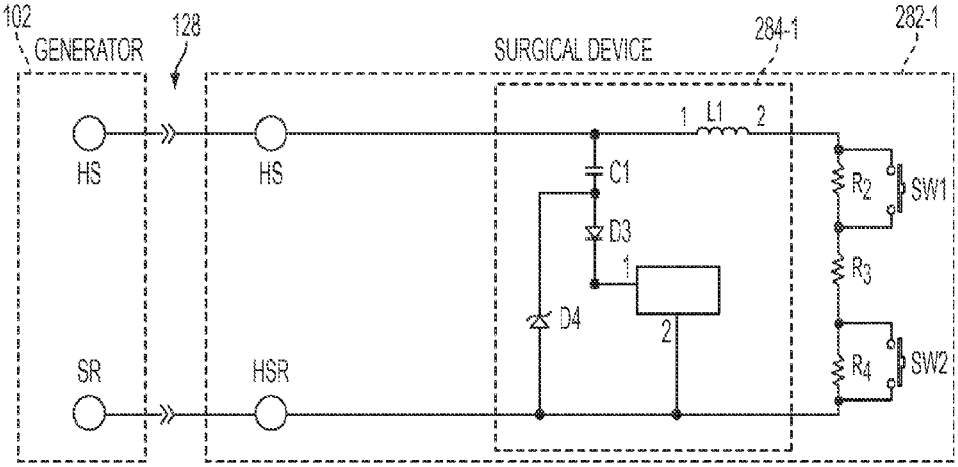

In certain embodiments and as shown in FIG. 17, the data circuit 284-1 may comprise an inductor L1 to provide isolation of the data storage element 286 from the states of SW1 and SW2. The addition of L1 may additionally enable use of the data circuit 284-1 in electrosurgical devices. FIG. 18, for example, illustrates one embodiment of a control circuit 282-1 that combines the control circuit 282 of FIG. 15 with the data circuit 284-1 of FIG. 17.

Figure 19:
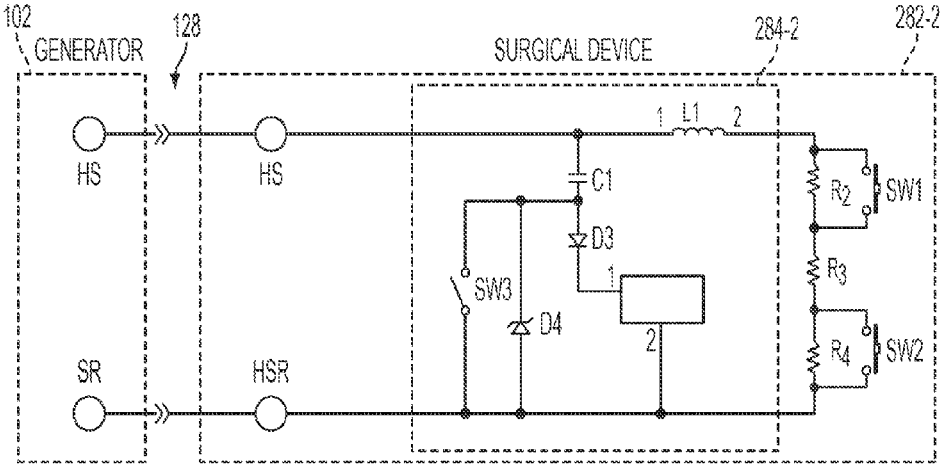

In certain embodiments, a data circuit may comprise one or more switches to modify one or more characteristics (e.g., amplitude, rectification) of an interrogation signal received by the data circuit such that a state or configuration of the one or more switches is uniquely discernable based on the one or more characteristics. FIG. 19, for example, illustrates one embodiment of a control circuit 282-2 in which the data circuit 284-2 comprises a switch SW3 connected in parallel with D4. An interrogation signal may be communicated from the generator 102 (e.g., from the signal conditioning circuit 202 of FIG. 10) at a frequency sufficient for the interrogation signal to be received by the data circuit 284-2 via C1 but blocked from other portions of the control circuit 282-2 by L1. In this way, one or more characteristics of a first interrogation signal (e.g., a bipolar interrogation signal at 25 kHz) may be used to discern the state of SW3, and one or more characteristics of a second interrogation signal at a lower frequency (e.g., a bipolar interrogation signal at 2 kHz) may be used to discern the states of SW1 and SW2. Although the addition of SW3 is illustrated in connection with the control circuit 282-2 in an electrosurgical device, it will be appreciated that SW3 may be added to a control circuit of an ultrasonic surgical device, such as, for example, the control circuit 280-2 of FIG. 17.

Figure 20:
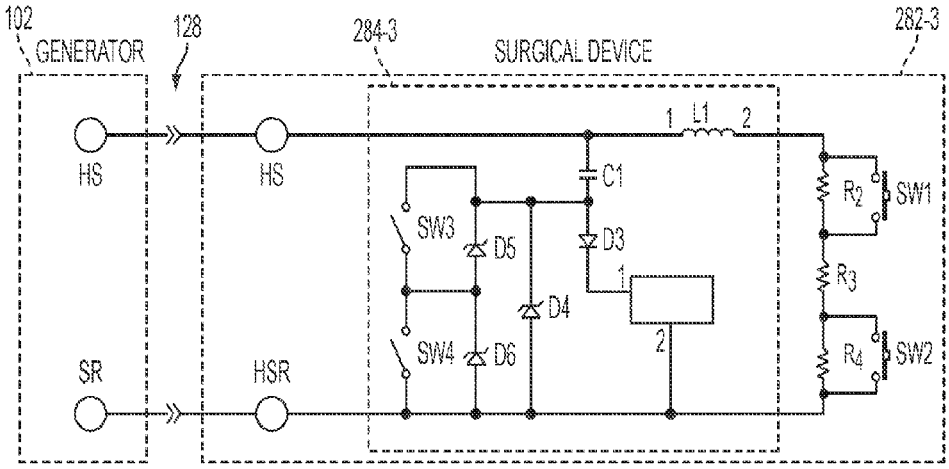
Figure 21:
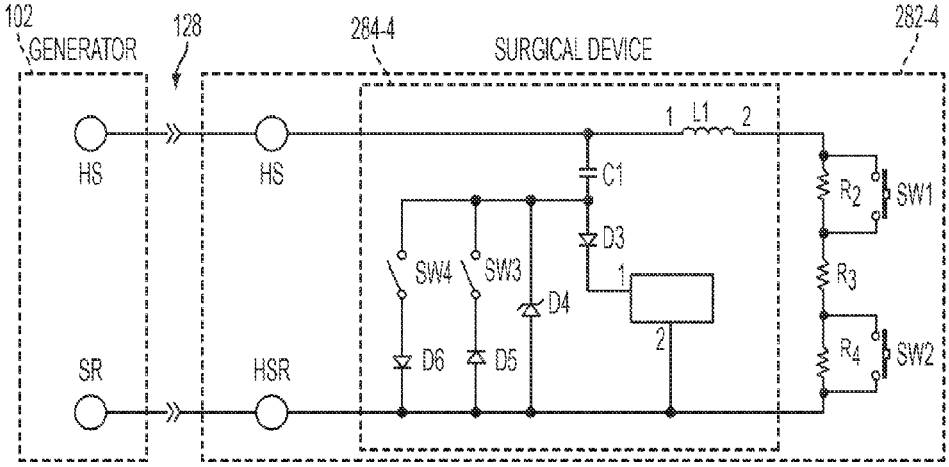

Additionally, it will be appreciated that switches in addition to SW3 may be added to a data circuit. As shown in FIGS. 20 and 21, for example, embodiments of the data circuit 284-3 and 284-4, respectively, may comprise a second switch SW4. In FIG. 20, voltage values of Zener diodes D5 and D6 may be selected such that their voltage values sufficiently differ to allow reliable discrimination of the interrogation signal in the presence of noise. The sum of the voltages values of D5 and D6 may be equal to or less than the voltage value of D4. In certain embodiments, depending upon the voltages values of D5 and D6, it may be possible to eliminate D4 from the embodiment of the data circuit 284-3 illustrated in FIG. 20.

Figure 22:
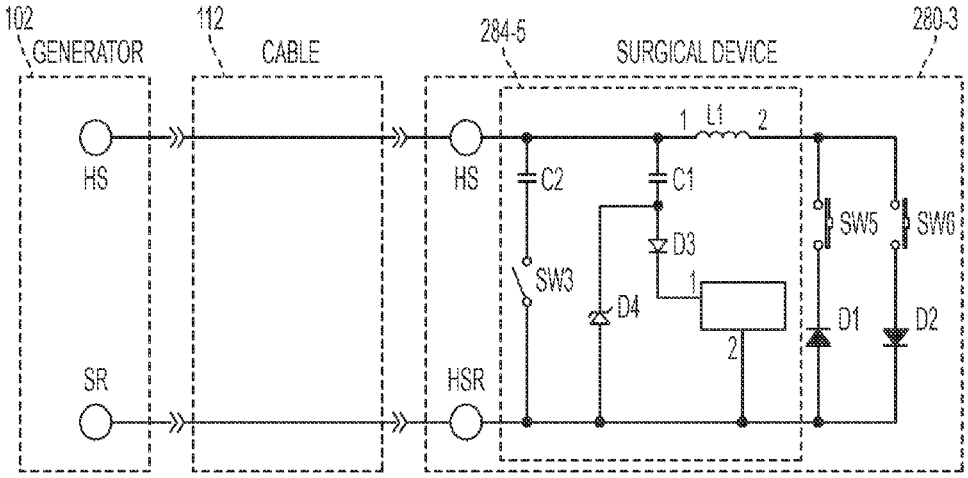
Figure 23:
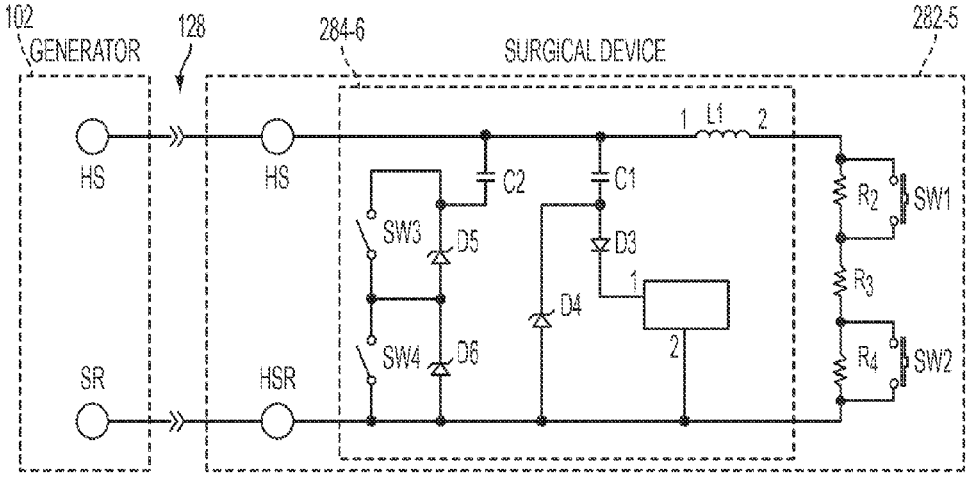
Figure 24:
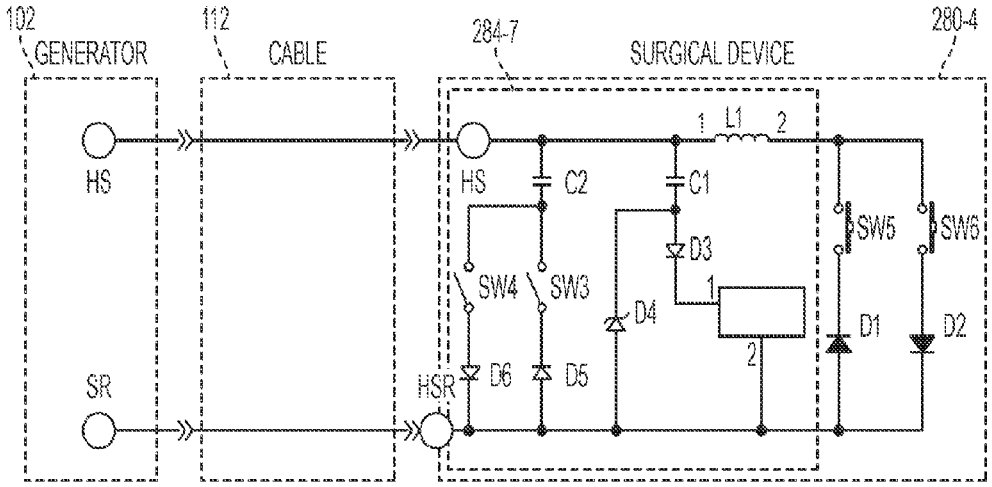

In certain cases, the switches (e.g., SW1-SW4) may impede the ability of the generator 102 to communicate with the data storage element 286. In one embodiment, this issue may be addressed by declaring an error if the states of the switches are such that they will interfere with communication between the generator 102 and the data storage element 286. In another embodiment, the generator 102 may only permit communication with the data storage element 286 when determined by the generator 102 that the states of the switches will not interfere with the communication. Because the states of the switches may be unpredictable to an extent, the generator 102 may make this determination on a recurring basis. The addition of L1 in certain embodiments may prevent interference caused by switches external to the data circuit (e.g., SW1 and SW2). For switches contained within the data circuit (e.g., SW3 and SW4), isolation of the switches by frequency band separation may be realized by the addition of a capacitor C2 having a capacitance value significantly smaller than C1 (e.g., C2<<C1). Embodiments of data circuits 284-5, 284-6, 284-7 comprising C2 are shown in FIGS. 22-24, respectively.

In any of the embodiments of FIGS. 16-24, depending on the frequency response characteristics of D4, it may be desirable or necessary to add a fast diode in parallel with D4 and pointing in the same direction.

Figure 25:
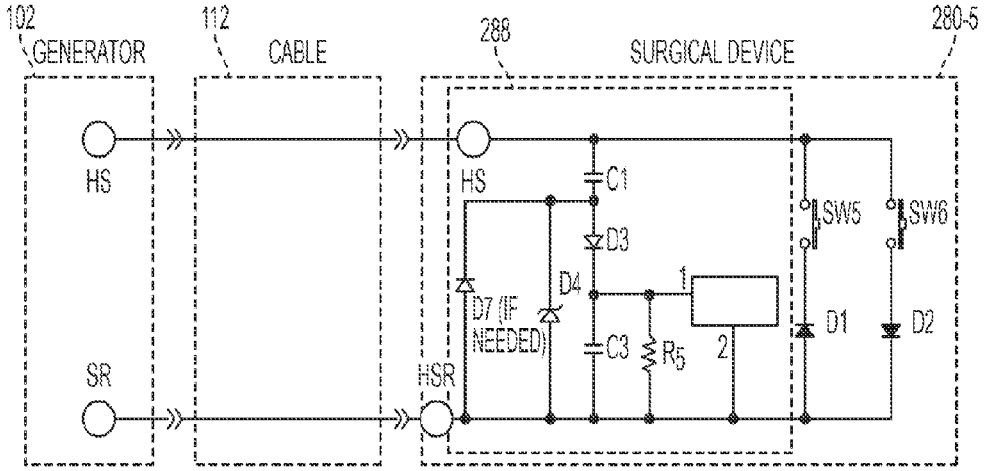

FIG. 25 illustrates one embodiment of a control circuit 280-5 in which communication between the generator 102 and a data storage element is implemented using an amplitude-modulated communication protocol (e.g., amplitude-modulated one-wire protocol [known under the trade name "1-Wire"] amplitude-modulated LIN protocol). Amplitude modulation of the communication protocol on a high-frequency carrier (e.g., 8 MHz or higher) substantially increases frequency band separation between low frequency interrogation signals (e.g., interrogation signals at 2 kHz) and the native "baseband" frequency of the communication protocol used in the embodiments of FIGS. 16-24. The control circuit 280-5 may be similar to the control circuit 280-1 of FIG. 16, with the data circuit 288 comprising an additional capacitor C3 and resistor R5, which, in conjunction with D3, demodulate the amplitude-modulated communication protocol for receipt by the data storage element 286. As in the embodiment of FIG. 16, D3 may protect the data storage element 286 from negative cycles of the interrogation signal, and D4 may limit the voltage supplied to the data storage element 286 to a suitable operating range (e.g., 3.3-5V) and clamp negative cycles of the interrogation signal to ground when in the forward conduction mode. The increased frequency separation may allow C1 to be somewhat small relative to the embodiments of FIGS. 16-24. Additionally, the higher frequency of the carrier signal may also improve noise immunity of communications with the data storage element because it is further removed from the frequency range of electrical noise that may be generated by other surgical devices used in the same operating room environment. In certain embodiments, the relatively high frequency of the carrier in combination with the frequency response characteristics of D4 may make it desirable or necessary to add a fast diode in parallel with D4 and pointing in the same direction.

Figure 26:
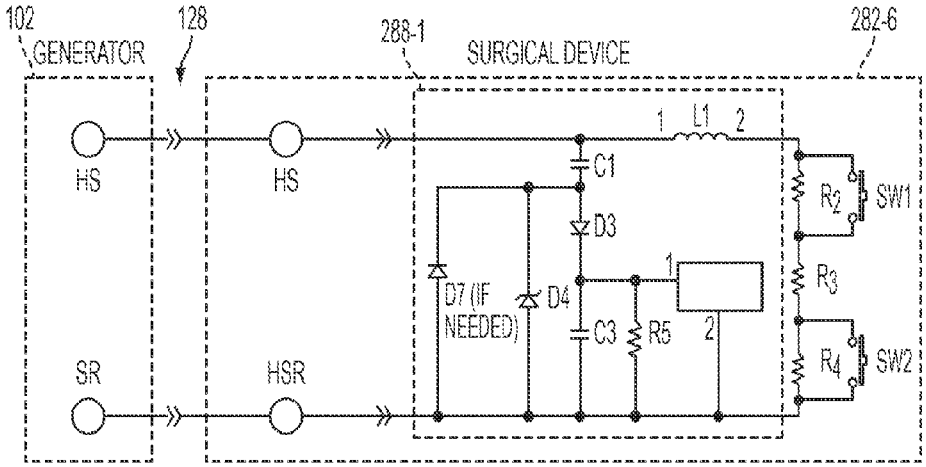

With the addition of an inductor L1 to prevent interference with data storage element 286 communications caused by switches external to the data circuit 288 (e.g., SW1 and SW2), the data circuit 288 may be used in control circuits of electrosurgical instruments, as shown in the embodiment of the data circuit 288-1 of FIG. 26.

With the exception of C2 and R3, and the more likely need for D7, the embodiments of FIGS. 25 and 26 are similar to the "baseband" embodiments of FIGS. 16-24. For example, the manner in which switches may be added to the data circuits of FIGS. 19-21 is directly applicable to the embodiments of FIGS. 25 and 26 (including the possibility of eliminating D4 from the modulated-carrier equivalent of the FIG. 20). Modulated-carrier equivalents of the data circuits embodied in FIGS. 22-24 may simply require the addition of an appropriately-sized inductor L2 in series with C2 in order to isolate the interrogation frequency for the additional switches (e.g., SW3, SW4) to an intermediate frequency band between the carrier frequency and the lower interrogation frequency for switches external to the data circuit. An embodiment of one such data circuit 282-7 is shown in FIG. 27.

Figure 27:
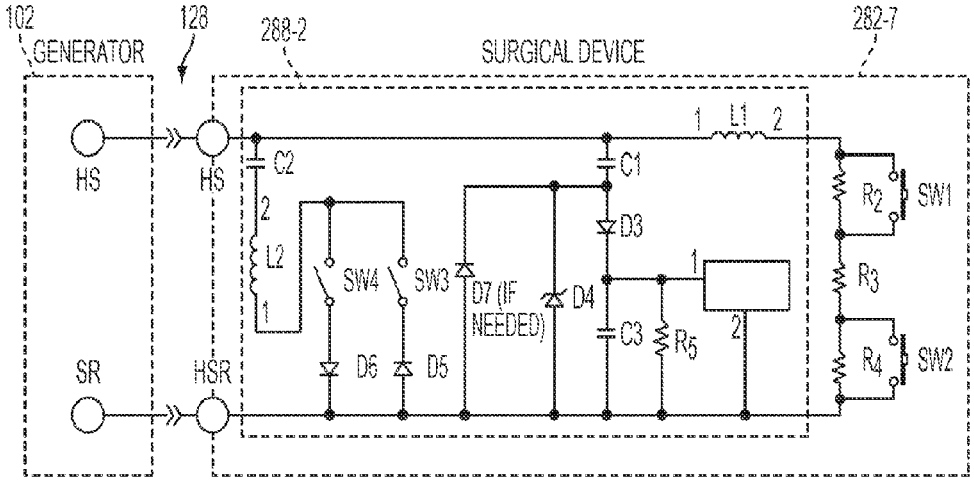

In the embodiment of FIG. 27, any interference with the generator's ability to communicate with the data storage element 286 caused by states of SW1 and SW2 may be addressed as described above in connection with the embodiments of FIGS. 19-24. For example, the generator 102 may declare an error if switch states will prevent communication, or the generator 102 may only permit communication when determined by the generator 102 that the switch states will not cause interference.

In certain embodiments, the data circuit may not comprise a data storage element 286 (e.g., an EEPROM device) to store information. FIGS. 28-32 illustrate embodiments of control circuits that utilize resistive and/or inductive elements to modify one or more characteristics of an interrogation signal (e.g., amplitude, phase) such that a state or configuration of the control circuit may be uniquely discerned based on the one or more characteristics.

Figure 28:
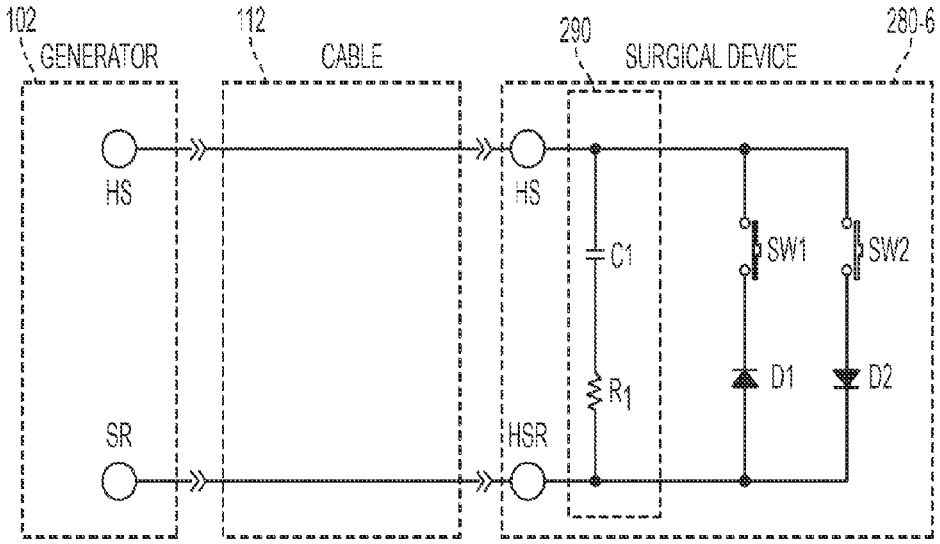
Figure 29:
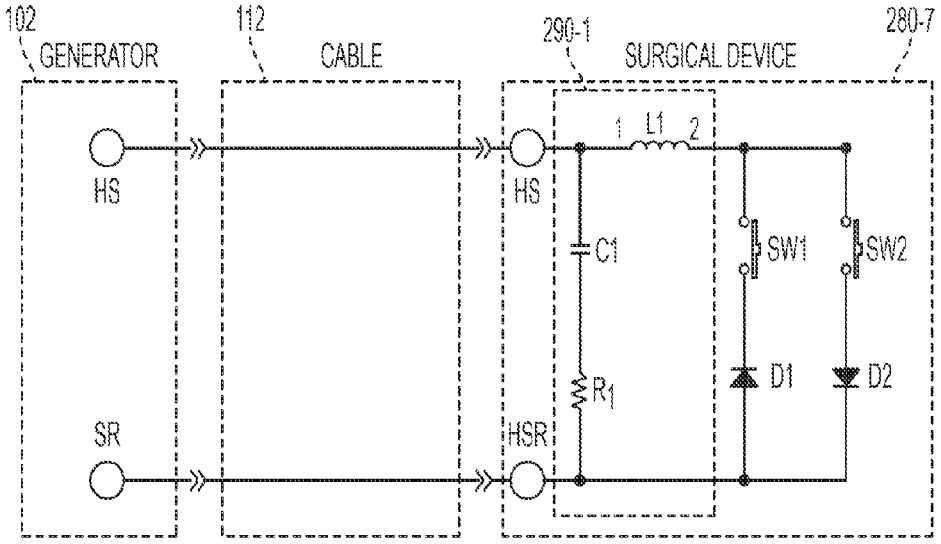
Figure 30:
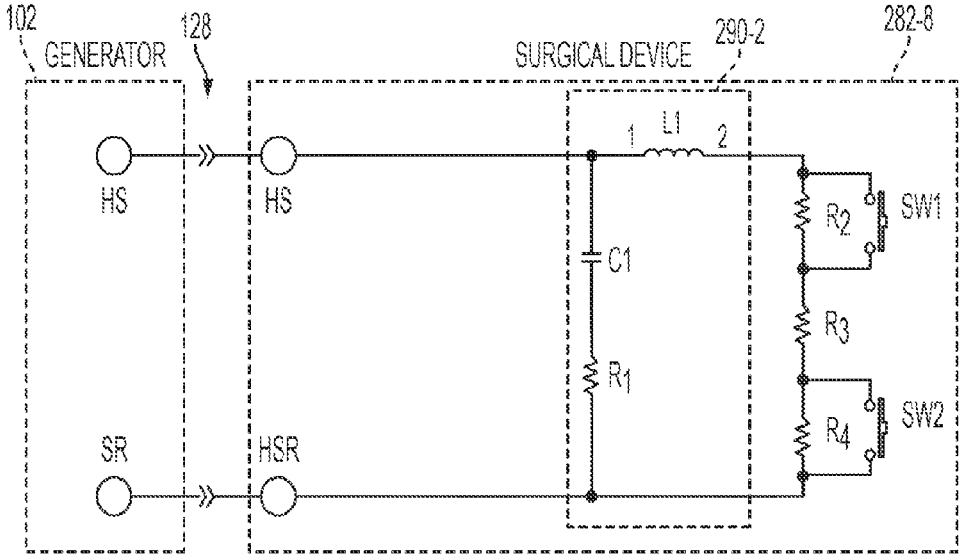
Figure 31:
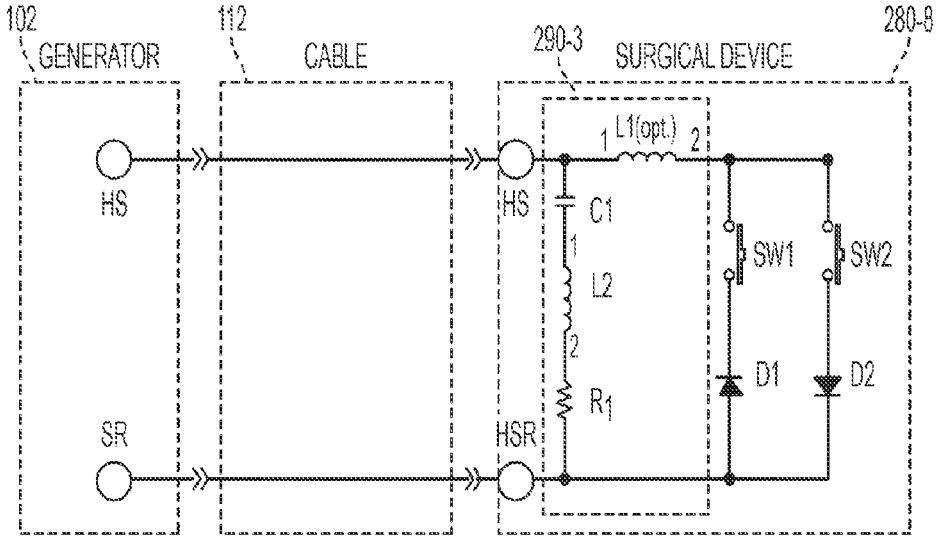

In FIG. 28, for example, the data circuit 290 may comprise an identification resistor R1, with the value of C1 selected such that R1 is "hidden" from a first low frequency interrogation signal (e.g., an interrogation signal at 2 kHz) for determining the states of SW1 and SW2. By measuring the voltage and/or current (e.g., amplitude, phase) at the inputs of the control circuit 280-6 resulting from a second interrogation signal within a substantially higher frequency band, the generator 102 may measure the value of R1 through C1 in order to determine which of a plurality of identification resistors is contained in the instrument. Such information may be used by the generator 102 to identify the instrument, or a particular characteristic of the instrument, so that control and diagnostic processes may be optimized. Any interference with the generator's ability to measure R1 caused by states of SW1 and SW2 may be addressed by declaring an error if switch states will prevent measurement, or by maintaining the voltage of the second higher-frequency interrogation signal below the turn-on voltages of D1 and D2. Such interference may also be addressed by adding an inductor in series with the switch circuitry (L1 in FIG. 29) to block the second higher-frequency interrogation signal while passing the first, lower-frequency interrogation signal. The addition of an inductor in this manner may also enable the use of the data circuit 290 in control circuits of electrosurgical instruments, as shown in the embodiment of the data circuit 290-2 of FIG. 30.

In certain embodiments, multiple capacitors C1 for allowing interrogation at multiple frequencies could be used to differentiate between a larger number of distinct R1 values for a given signal-to-noise ratio, or for a given set of component tolerances. In one such embodiment, inductors may be placed in series with all but the lowest value of C1 to create specific pass bands for different interrogation frequencies, as shown in the embodiment of the data circuit 290-3 in FIG. 31.

Figure 32:
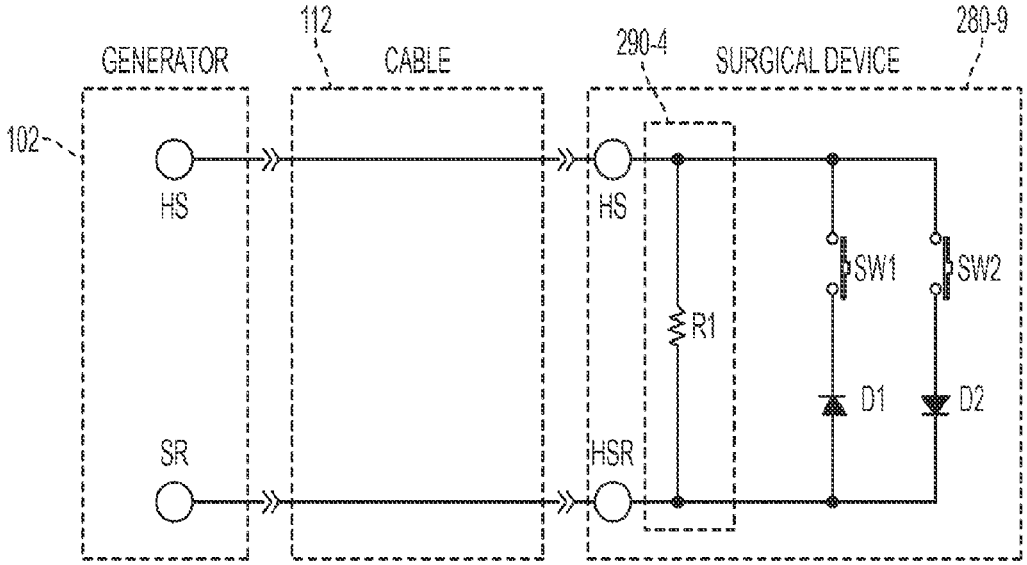

In embodiments of control circuits based on the control circuit 280 of FIG. 14, identification resistors may be measured without the need for frequency band separation. FIG. 32 illustrates one such embodiment, with R1 selected to have a relatively high value.

Figure 33H:
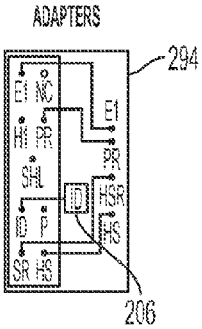
Figure 33I:
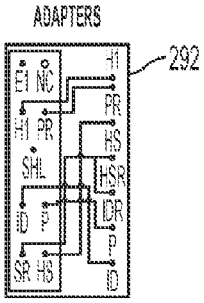

FIGS. 33D-33I illustrate embodiments of multi-conductor cables and adaptors that may be used to establish electrical communication between the generator 102 and a handpiece of a surgical device. In particular, the cables may transmit the generator drive signal to surgical device and enable control-based communications between the generator 102 and a control circuit of the surgical device. In certain embodiments, the cables may be integrally formed with the surgical device or configured for removable engagement by a suitable connector of the surgical device. Cables 112-1, 112-2 and 112-3 (FIGS. 33E-33G, respectively) may be configured for use with an ultrasonic surgical device (e.g., ultrasonic surgical device 104), and cable 128-1 (FIG. 33D) may be configured for use with an electrosurgical device (e.g., electrosurgical device 106). One or more of the cables may be configured to connect directly with the generator 102, such as cable 112-1, for example. In such embodiments, the cable may comprise a data circuit (e.g., data circuit 206) for storing information pertaining to the particular surgical device with which it is associated (e.g., a model number, a serial number, a number of operations in which the surgical device has been used, and/or any other type of information). In certain embodiments, one or more of the cables may connect to the generator 102 via an adaptor. For example, cables 112-2 and 112-3 may connect to the generator 102 via a first adaptor 292 (FIG. 33I), and cable 128-1 may connect to the generator 102 via a second adaptor 294 (FIG. 33H). In such embodiments, a data circuit (e.g., data circuit 206) may be disposed in the cable (e.g., cables 112-2 and 112-3) or in the adaptor (e.g., second adaptor 294).

In various embodiments, the generator 102 may be electrically isolated from the surgical devices 104, 106 in order to prevent undesired and potentially harmful currents in the patient. For example, if the generator 102 and the surgical devices 104, 106 were not electrically isolated, voltage provided to the devices 104, 106 via the drive signal could potentially change the electrical potential of patent tissue being acted upon by the device or devices 104, 106 and, thereby, result in undesired currents in the patient. It will be appreciated that such concerns may be more acute when using an ultrasonic surgical device 104 that is not intended to pass any current though tissue. Accordingly, the remainder of the description of active cancellation of leakage current is described in terms of an ultrasonic surgical device 104. It will be appreciated, however, that the systems and methods described herein may be applicable to electrosurgical devices 106 as well.

According to various embodiments, an isolation transformer, such as the isolation transformer 156, may be used to provide electrical isolation between the generator 102 and the surgical device 104. For example, the transformer 156 may provide isolation between the non-isolated stage 154 and the isolated stage 152 described above. The isolated stage 154 may be in communication with the surgical device 104. The drive signal may be provided by the generator 102 (e.g., the generator module 108) to the primary winding 164 of the isolation transformer 156 and provided to the surgical device 104 from the secondary winding 158 of the isolation transformer. Considering the non-idealities of real transformers, however, this arrangement may not provide complete electrical isolation. For example, a real transformer may have stray capacitance between the primary and secondary windings. The stray capacitance may prevent complete electrical isolation and allow electrical potential present on the primary winding to affect the potential of the secondary winding. This may result in leakage currents within the patient.

Contemporary industry standards, such as the International Electrotechnical Commission (IEC) 60601-1 standard limit allowable patient leakage current to 10 μA or less. Leakage current may be passively reduced by providing a leakage capacitor between the secondary winding of the isolation transformer and ground (e.g., earth ground). The leakage capacitor may operate to smooth changes in patient-side potential coupled from the non-isolated side via the stray capacitance of the isolation transformer and thereby reduce leakage current. As the voltage, current, power and/or frequency of the drive signal provided by the generator 102 increase, however, the leakage current may also increase. In various embodiments, induced leakage current may increase beyond the capability of a passive leakage capacitor to keep it below 10 μA and/or other leakage current standards.

Figure 34:
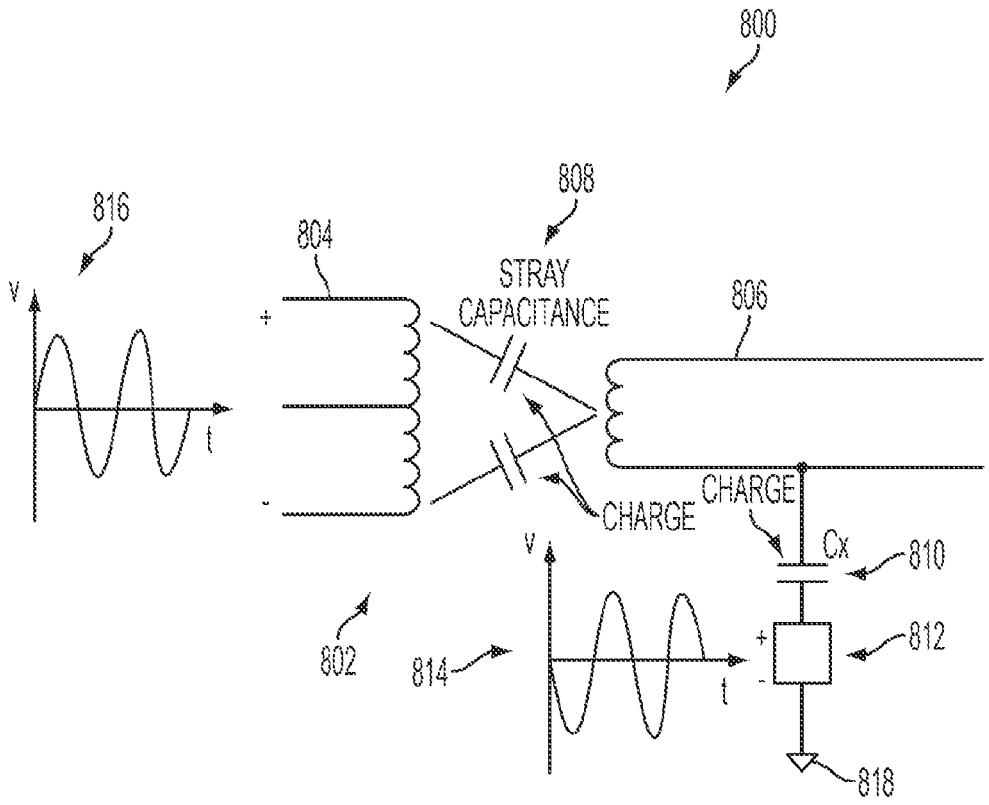
FIG. 34 illustrates one embodiment of a circuit 300 for active cancellation of leakage current.

Accordingly, various embodiments are directed to systems and methods for actively cancelling leakage current. FIG. 34 illustrates one embodiment of a circuit 800 for active cancellation of leakage current. The circuit 800 may be implemented as a part of or in conjunction with the generator 102. The circuit may comprise an isolation transformer 802 having a primary winding 804 and a secondary winding 806. The drive signal 816 may be provided across the primary winding 804, generating an isolated drive signal across the secondary winding 806. In addition to the isolated drive signal, stray capacitance 808 of the isolation transformer 802 may couple some component of the potential of the drive signal relative to ground 818 to the secondary winding 806 on the patient side.

A leakage capacitor 810 and active cancellation circuit 812 may be provided, as shown, connected between the secondary winding 806 and ground 818. The active cancellation circuit 812 may generate an inverse drive signal 814 that may be about 180° out of phase with the drive signal 816. The active cancellation circuit 812 may be electrically coupled to the leakage capacitor 810 to drive the leakage capacitor to a potential that, relative to ground 818, is about 180° out of phase with the drive signal 816. Accordingly, electrical charge on the patient-side secondary winding 806 may reach ground 818 via the leakage capacitor 810 instead of through the patient, reducing leakage current. According to various embodiments, the leakage capacitor 810 may be designed to meet adequate, industry, government and/or design standards for robustness. For example, the leakage capacitor 810 may be a Y-type capacitor complying with the IEC 60384-14 standard and/or may comprise multiple physical capacitors in series.

Figure 35:
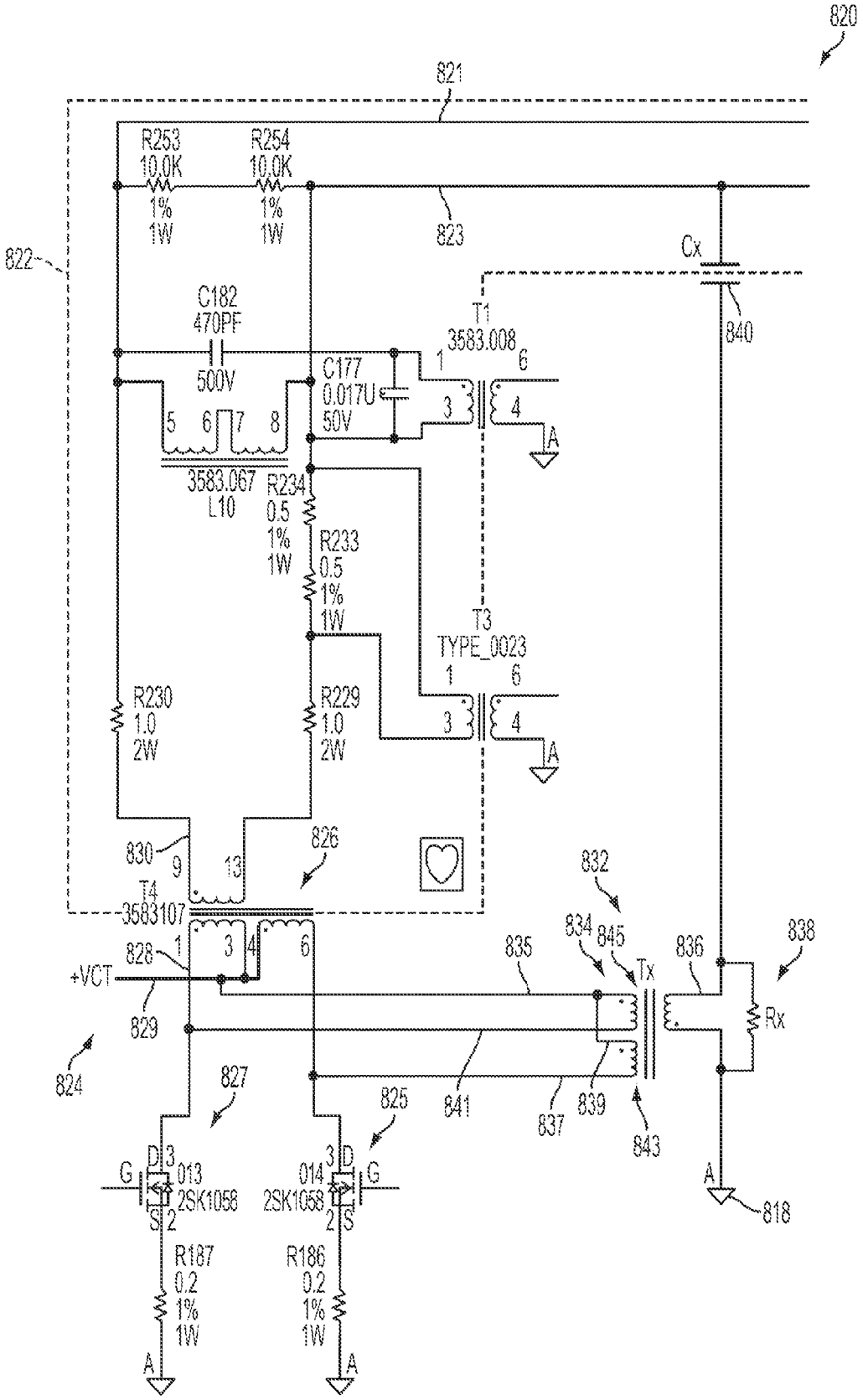
FIG. 35 illustrates one embodiment of a circuit that may be implemented by the generator of FIG. 1 to provide active cancellation of leakage current.

FIG. 35 illustrates one embodiment of a circuit 820 that may be implemented by the generator 102 to provide active cancellation of leakage current. The circuit 820 may comprise a generator circuit 824 and a patient-side circuit 822. The generator circuit 824 may generate and/or modulate the drive signal, as described herein. For example, in some embodiments, the generator circuit 824 may operate similar to the non-isolated stage 154 described above. Also, for example, the patient-side circuit 822 may operate similar to the isolated state 152 described above.

Electrical isolation between the generator circuit 824 and the patient-side circuit 822 may be provided by an isolation transformer 826. The primary winding 828 of the isolation transformer 826 may be coupled to the generator circuit 824. For example, the generator circuit 824 may generate the drive signal across the primary winding 828. The drive signal may be generated across the primary winding 828 according to any suitable method. For example, according to various embodiments, the primary winding 828 may comprise a center tap 829 that may be held to a DC voltage (e.g., 48 volts). The generator circuit 824 may comprise output stages 825, 827 that are, respectively, coupled to the other ends of the primary winding 828. Output stages 825, 827 may cause currents corresponding to the drive signal to flow in the primary winding 828. For example, positive portions of the drive signal may be realized when the output stage 827 pulls its output voltage lower than the center tap voltage, causing the output stage 827 to sink current from across the primary winding 828. A corresponding current may be induced in the secondary winding 830. Likewise, negative portions of the drive signal may be implemented when the output state 827 pulls its output voltage lower than the center tap voltage, causing the output stage 825 to sink an opposite current across the primary winding 828. This may induce a corresponding, opposite current in the secondary winding 830. The patient-side circuit 822 may perform various signal conditioning and/or other processing to the isolated drive signal, which may be provided to a device 104 via output lines 821, 823.

An active cancellation transformer 832 may have a primary winding 834 and a secondary winding 836. The primary winding 834 may be electrically coupled to the primary winding 828 of the isolation transformer 826 such that the drive signal is provided across the winding 834. For example, the primary winding 834 may comprise two windings 843, 845. A first end 835 of the first winding 845 and a first end 839 of the second winding 843 may be electrically coupled to the center tap 829 of the winding 828. A second end 841 of the first winding 845 may be electrically coupled to the output stage 827, while a second end 837 of the second winding 843 may be electrically coupled to the output state 825. The secondary winding 836 of the cancellation transformer 832 may be coupled to ground 818 and to a first electrode of a cancellation capacitor 840. The other electrode of the cancellation capacitor 840 may be coupled to the output line 823. An optional load resistor 838 may also be electrically coupled in parallel across the secondary winding 836.

According to various embodiments, the secondary winding 836 of the active cancellation transformer may be wound and/or wired to the other components 840, 838, 818, such that its polarity is opposite the polarity of the primary winding 834. For example, an inverse drive signal may be induced across the secondary winding 836. Relative to ground 818, the inverse drive signal may be 180° out of phase with the drive signal provided across the primary winding 834 of the active cancellation transform 832. In conjunction with the load resistor 838, the secondary winding 836 may provide the inverse drive signal at the cancellation capacitor 840. Accordingly, charge causing leakage potential appearing at the patient-side circuit 822 due to the drive signal may be drawn to the cancellation capacitor 840. In this way, the capacitor 840, secondary winding 836 and load resistor 838 may sink potential leakage current to ground 818, minimizing patient leakage current.

According to various embodiments, the parameters of the components 832, 838, 840 may be selected to maximize leakage current cancellation and, in various embodiments, to lessen electromagnetic emissions. For example, the active cancellation transformer 832 may be made from materials and according to a construction that allows it to match the frequency, temperature, humidity and other characteristics of the isolation transformer 826. Other parameters of the active transformer 832 (e.g., number of turns, turn ratios, etc.) may be selected to achieve a balance between minimizing output-induced current, electromagnetic (EM) emissions and leakage current due to applied external voltage. For example, the circuit 820 may be configured to meet the IEC 60601 or other suitable industry or government standards. The value of the load resistor 838 may be similarly chosen. In addition, the parameters of the cancellation capacitor 840 (e.g., capacitance, etc.) may be selected to match, as well as possible, the characteristics of the stray capacitances responsible for the inducing leakage current.

Figure 36:
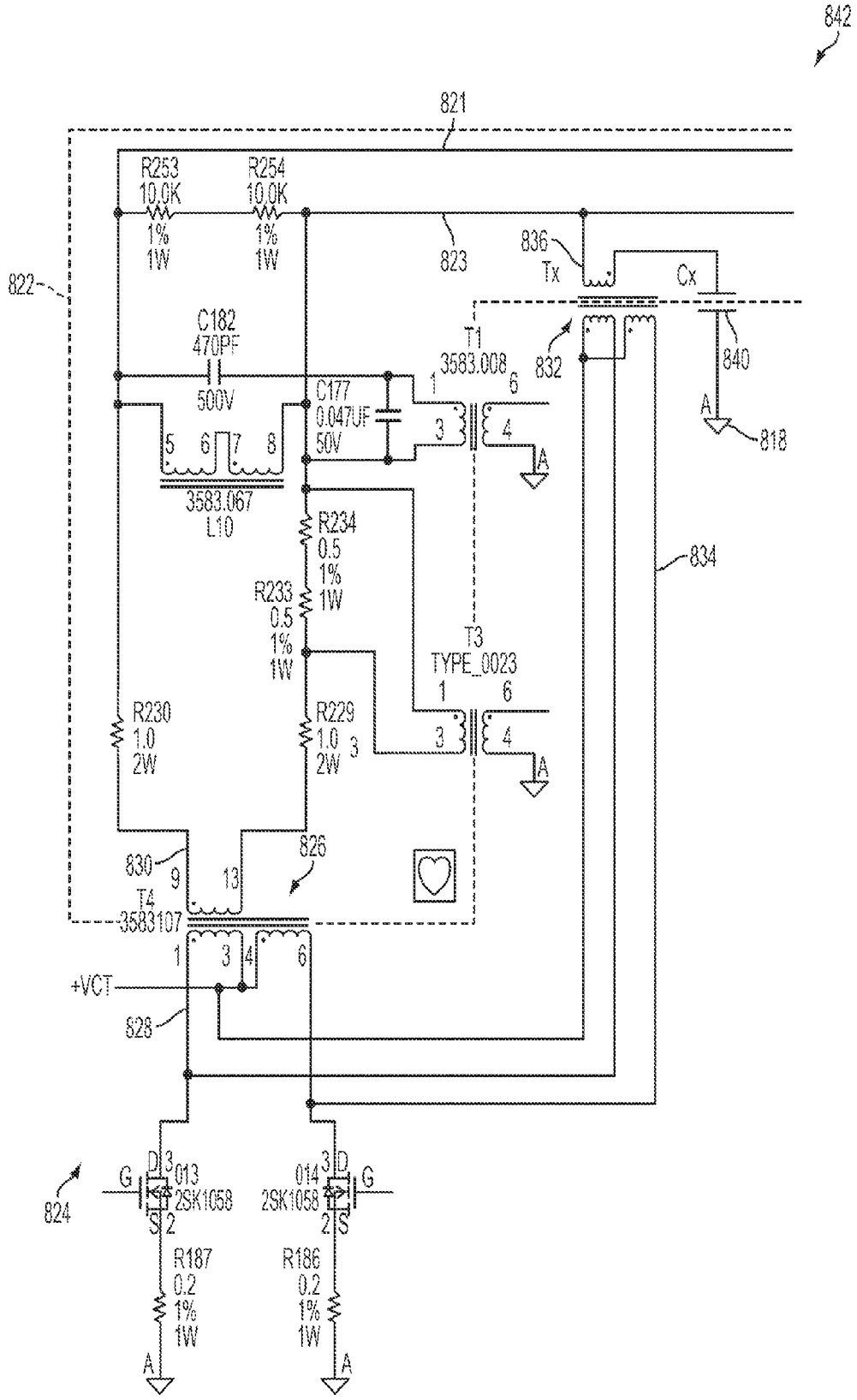
FIG. 36 illustrates an alternative embodiment of a circuit that may be implemented by the generator of FIG. 1 to provide active cancellation of leakage current.

FIG. 36 illustrates an alternate embodiment of a circuit 842 that may be implemented by the generator 102 to provide active cancellation of leakage current. The circuit 842 may be similar to the circuit 820, however, the secondary winding 836 of the active cancellation transformation 832 may be electrically coupled to the output line 823. The cancellation capacitor 823 may be connected in series between the secondary winding 836 and ground 818. The circuit 842 may operate in a manner similar to that of the circuit 820. According to various embodiments, (e.g., when the active cancellation transformer 832 is a step-up transformer), the total working voltage, for example, as defined in IEC 60601-1, may be minimized.

Figure 37:
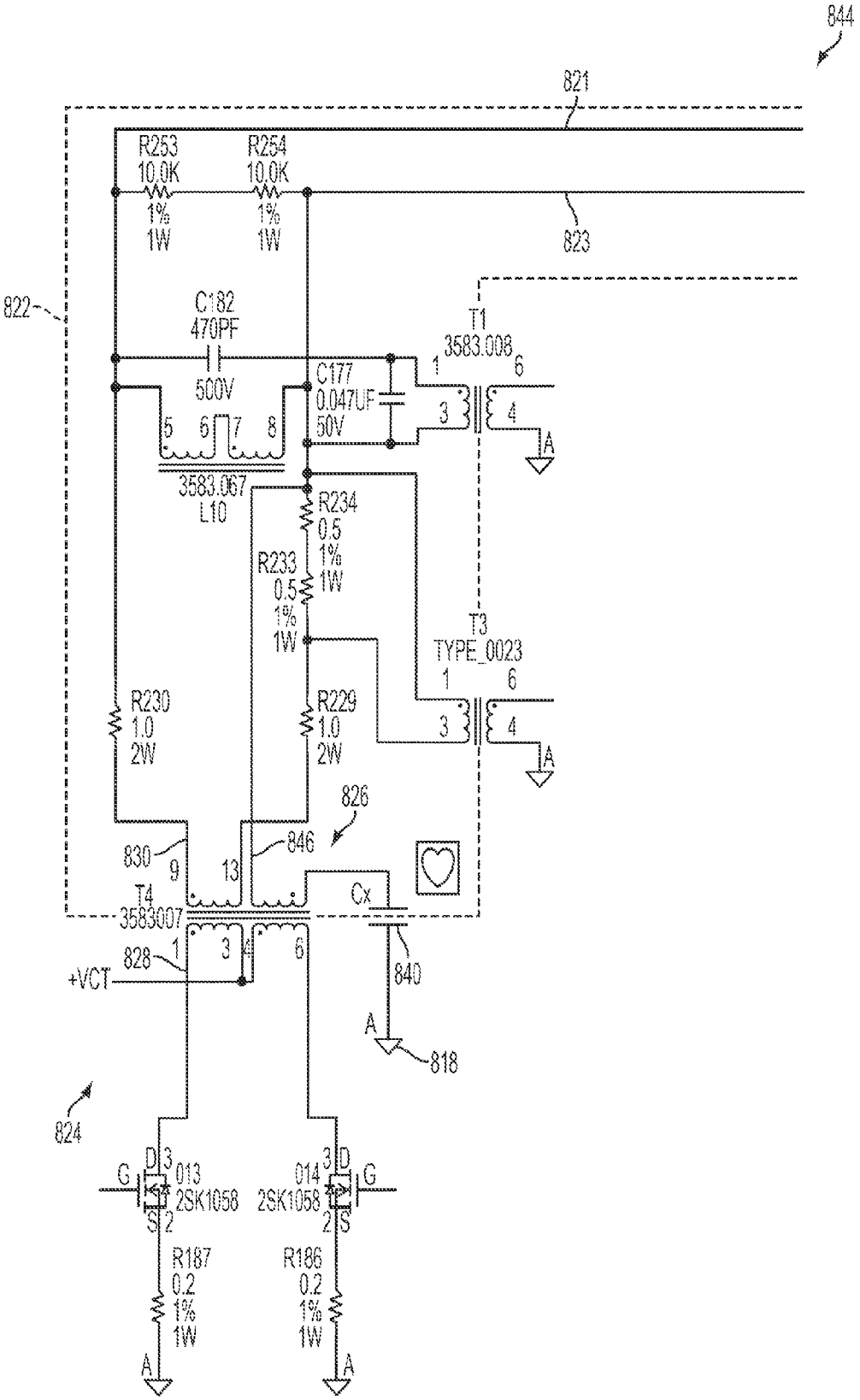
FIG. 37 illustrates an alternative embodiment of a circuit that may be implemented by the generator of FIG. 1 to provide active cancellation of leakage current.

FIG. 37 illustrates an alternate embodiment of a circuit 844 that may be implemented by the generator 102 to provide active cancellation of leakage current. The circuit 844 may omit the active cancellation transformer 832 and replace it with a second secondary winding 846 of the isolation transformer 826. The second secondary winding 846 may be connected to the output line 823. The cancellation capacitor 840 may be connected in series between the second secondary winding 846 and ground. The second secondary winding may be wound and or wired with a polarity opposite that of the primary winding 828 and the secondary winding 830. Accordingly, when the drive signal is present across the primary winding 828, the inverse drive signal, as described above, may be present across the secondary winding 846. Accordingly, the circuit 844 may cancel leakage current in a manner similar to that described above with respect to the circuits 820 and 842. Omitting the active cancellation transformer 832, as shown in circuit 844, may reduce part count, cost and complexity.

Figure 38:
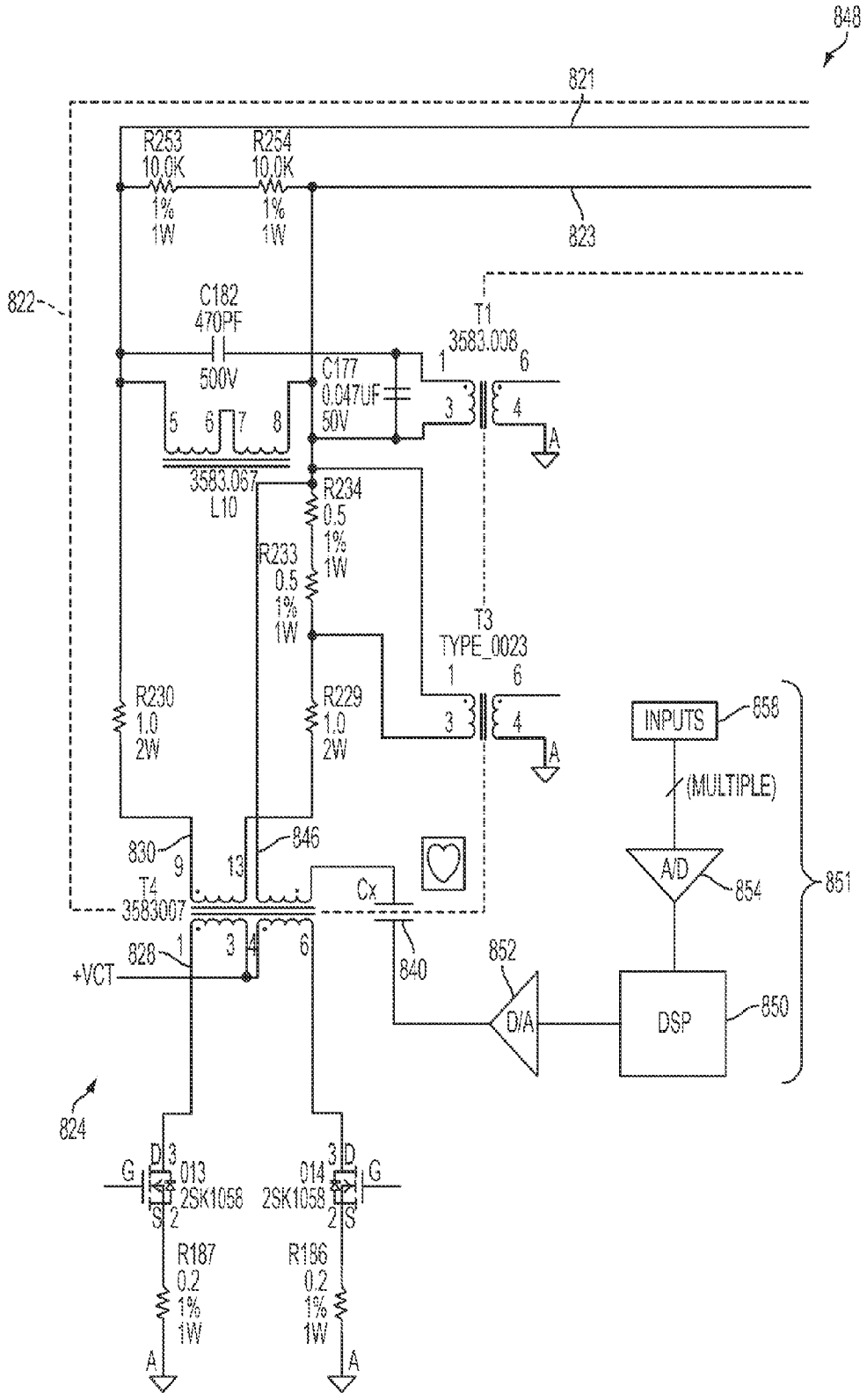
FIG. 38 illustrates yet another embodiment of a circuit that may be implemented by the generator of FIG. 1 to provide active cancellation of leakage current.

FIG. 38 illustrates yet another embodiment of a circuit 848 that may be implemented by the generator 102 to provide active cancellation of leakage current. The circuit 848 may be configured to cancel extraneous currents in the patient side circuit 822 due to capacitive coupling, as described above, as well as other external effects such as, for example, frequency-specific effects (e.g., 60 Hz or other frequency noise from power supplies), path effects, load effects, etc. Instead of being electrically coupled to ground 818, the cancellation capacitor 840, as shown in the circuit 848, may be coupled to an correction control circuit 851. The circuit 851 may comprise a digital signal processor (DSP) 850 or other processor. The DSP 850 may receive inputs 858 (e.g., via an analog-to-digital converter). The inputs 858 may be values tending to indicate external effects that may cause additional leakage current. Examples of such inputs may be, for example, power supply parameters, load data such as impedance, impedance or other values describing the path from the circuit 848 to the device 104, etc. Based on the inputs 858, the DSP 85 may derive a cancellation potential that, when provided to the cancellation capacitor 840, may cancel patient-side currents due to the external effects. The cancellation potential may be provided, digitally, to digital-to-analog converter 852, which may provide an analog version of the cancellation potential to the cancellation capacitor 840. Accordingly, the voltage drop across the cancellation capacitor 840 may be a function of the inverse drive signal, present across the second secondary winding 846 and the cancellation potential found by the circuit 851.

The circuit 848 is shown with the active cancellation transformer 832 omitted and the capacitor 840 and second secondary winding 846 in the configuration of the circuit 844. It will be appreciated, however, that the correction control circuit 851 may be utilized in any of the configurations described herein (e.g., 820, 842, 844, etc.). For example, the correction control circuit 851 may be substituted for ground 818 in any of the circuits 820, 842, 844.

Figure 39:
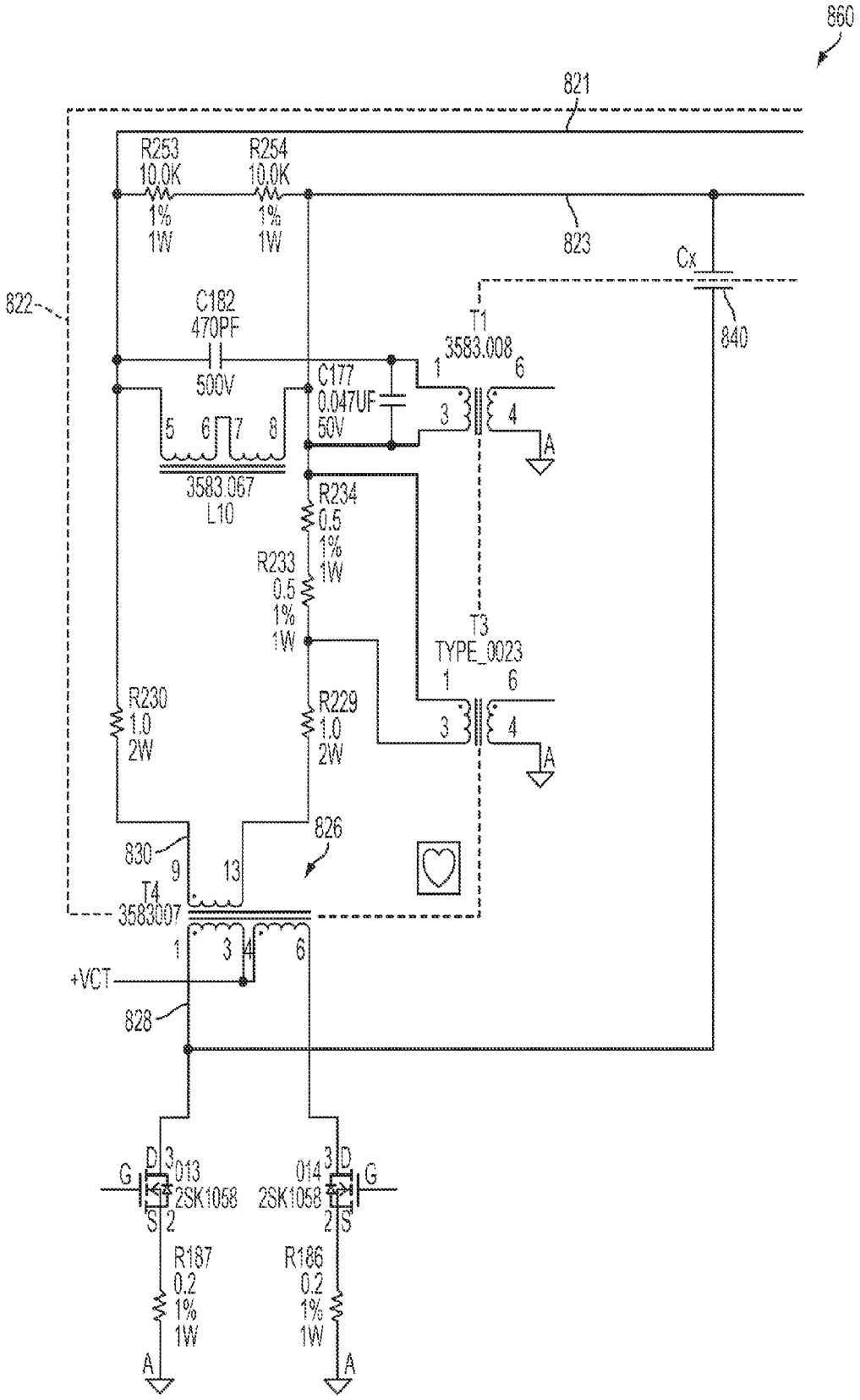
FIG. 39 illustrates an embodiment of a circuit that may be implemented by the generator of FIG. 1 to provide cancellation of leakage current.

FIG. 39 illustrated an embodiment of a circuit 860 that may be implemented by the generator 102 to provide cancellation of leakage current. According to the circuit 860, the cancellation capacitor 840 may be connected between the primary winding 828 of the isolation transformer 826 and the output line 823 (e.g., the common output line). In this way, the inverse of the drive signal may appear across the cancellation capacitor 840, bringing about a similar leakage current cancellation effect to those described above.

Figure 40:
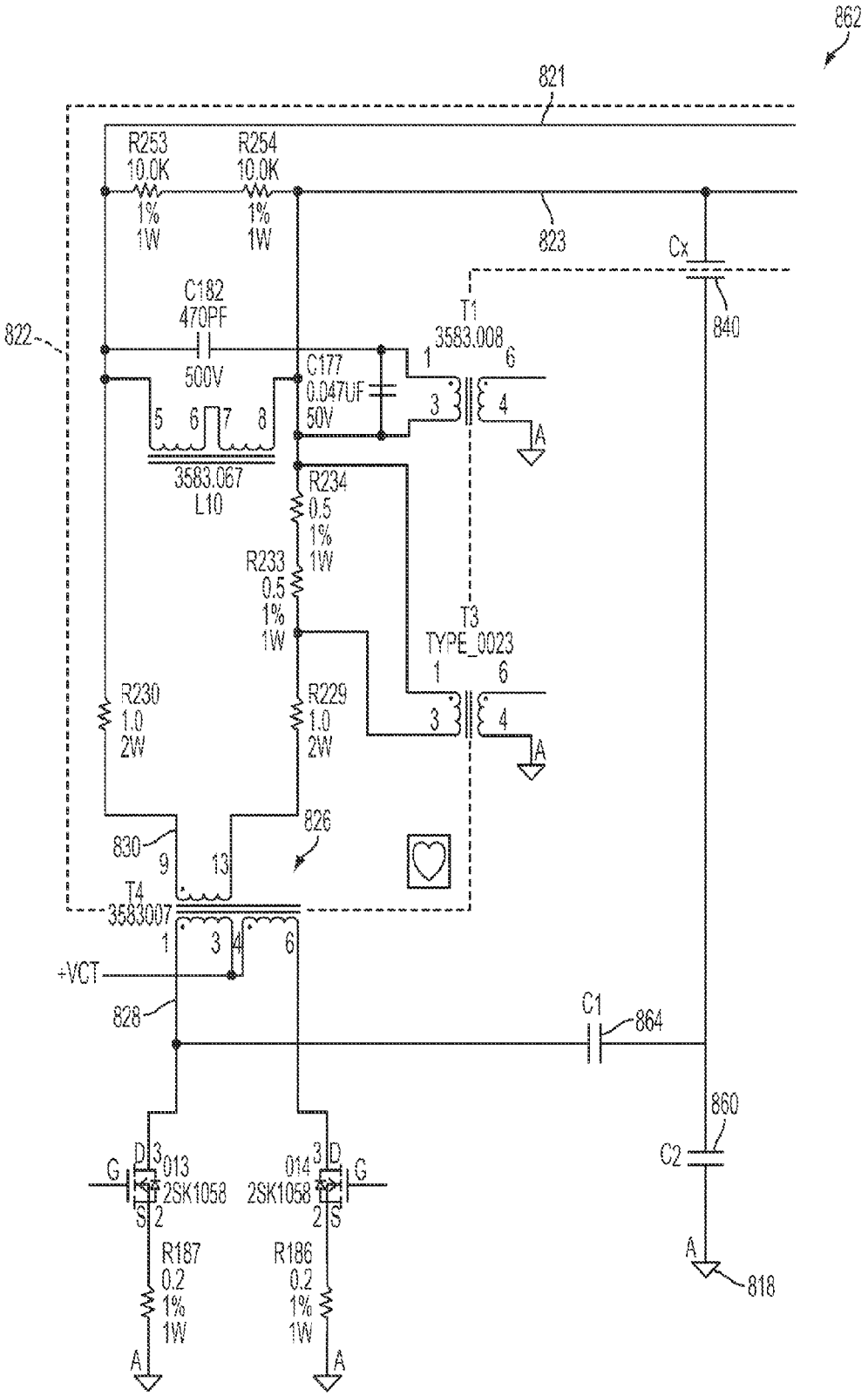
FIG. 40 illustrates another embodiment of a circuit that may be implemented by the generator of FIG. 1 to provide cancellation of leakage current.

FIG. 40 illustrates another embodiment of a circuit 862 that may be implemented by the generator 102 to provide cancellation of leakage current. The circuit 862 may be similar to the circuit 860 with the exception that the cancellation capacitor may be connected between the output line 823 (e.g., the common output line) and two additional capacitors 864, 866. Capacitor 864 may be connected between the cancellation capacitor 840 and the primary winding 828 of the isolation transformer 826. Capacitor 866 maybe connected between the cancellation capacitor 840 and ground 818. The combination of the capacitors 864, 866 may provide a radio frequency (RF) path to ground that may enhance the RF performance of the generator 102 (e.g., by decreasing electromagnetic emissions).

Figure 41:
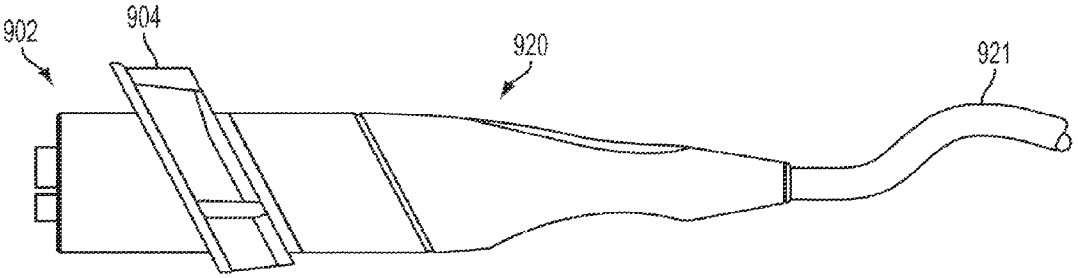
FIG. 41 illustrates a receptacle and connector interface in one embodiment.
Figure 59:
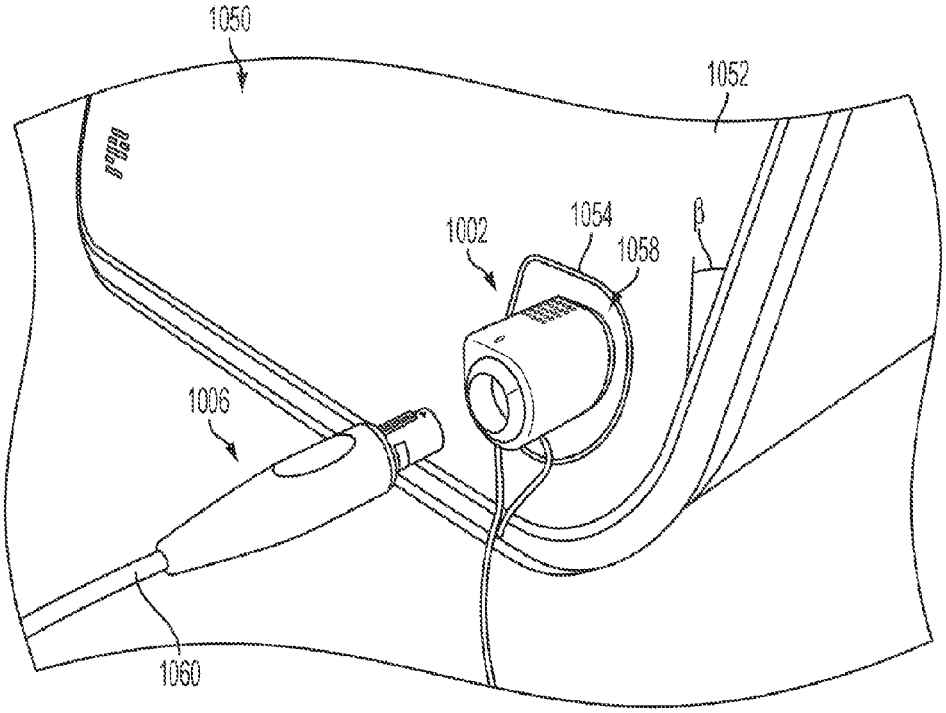
FIG. 59 illustrates a surgical generator in one embodiment.

A surgical generator, such as the generator 102 schematically illustrated in FIG. 10, for example, may be electrically coupled to a variety of surgical instruments. The surgical instruments may include, for example, both RF-based instruments and ultrasonic-based devices. FIG. 41 illustrates a receptacle and connector interface 900 in accordance with one non-limiting embodiment. In one embodiment, the interface 900 comprises a receptacle assembly 902 and a connector assembly 920. The connector assembly 920 may be electrically coupled to the distal end of a cable 921 that is ultimately connected to a handheld surgical instrument, for example. FIG. 59 illustrates a surgical generator 1050 in accordance with one non-limiting embodiment. The surgical generator 1050 may comprise a surgical generator body 1052 that generally includes the outer shell of the generator. The surgical body 1052 may define an aperture 1054 for receiving a receptacle assembly, such as the receptacle assembly 1058 illustrated in FIG. 59. Referring now to FIGS. 41 and 59, the receptacle assembly 902 may comprise a seal 906 to generally prevent fluid ingress into the surgical generator 1050 by was of the aperture 1054. In one embodiment, the seal 906 is an epoxy seal.

Figure 42:
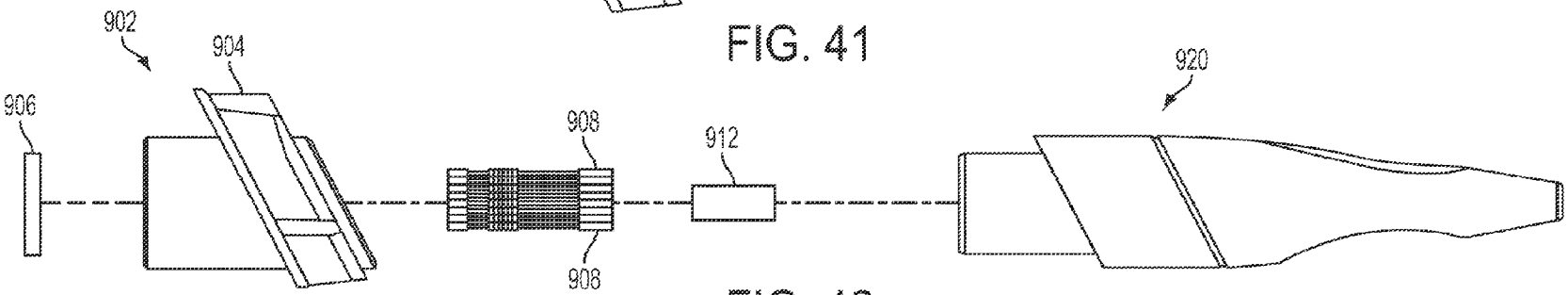
FIG. 42 is an exploded side view of the receptacle assembly in one embodiment.
Figure 48:
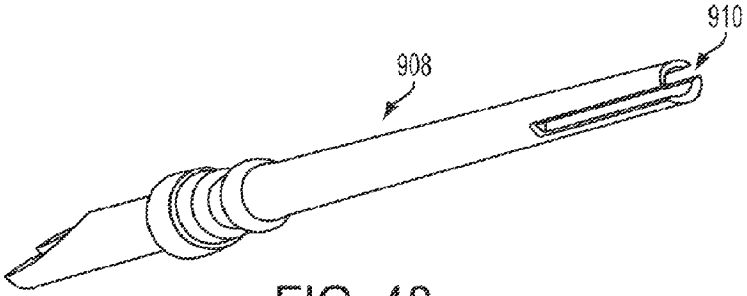
FIG. 48 is an enlarged view of a socket in one embodiment.

FIG. 42 is an exploded side view of the receptacle assembly 902 in accordance with one non-limiting embodiment. The receptacle assembly 902 may include a variety of components, such as a magnet 212, for example. The receptacle assembly 902 may also comprise a plurality of sockets 908 that may be arranged in a generally circular formation, or any other suitable formation. FIG. 48 is an enlarged view of a socket 908 in accordance with one non-limiting embodiment. In one embodiment, the socket 908 is bifurcated and the receptacle assembly 902 includes nine bifurcated sockets 908, while greater or few sockets may be utilized in other embodiments. Each of the sockets 908 may define an inner cavity 910 for receiving electrically conductive pins, as discussed in more detail below. In some embodiments, various sockets 908 will be mounted within the receptacle assembly 902 at different elevations such that certain sockets are contacted prior to other sockets when a connector assembly is inserted into the receptacle assembly.

Figure 43:
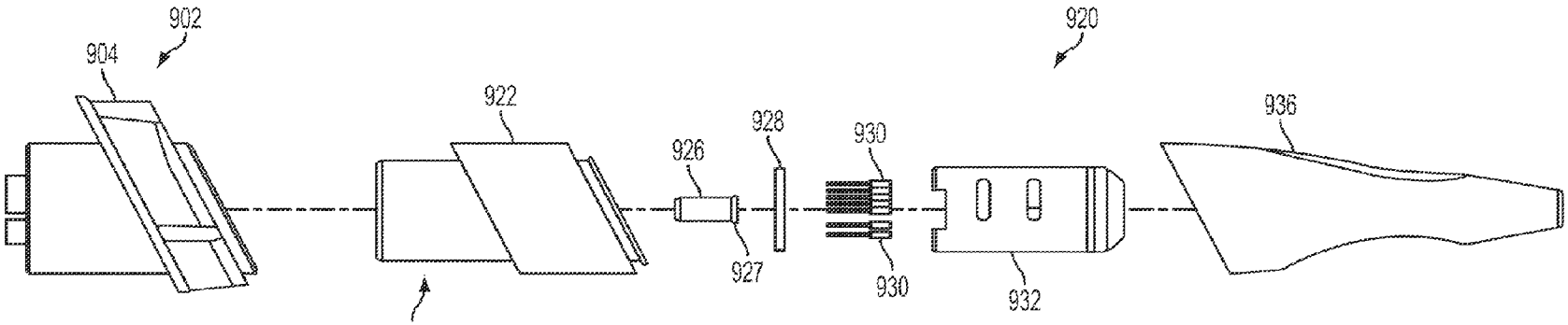
FIG. 43 is an exploded side view of the connector assembly in one embodiment.
Figure 55:
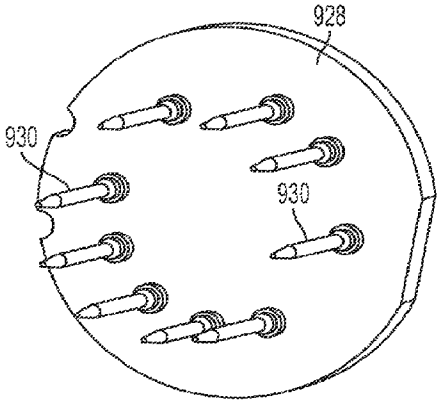
FIG. 55 illustrates electrically conductive pins and a circuit board in one embodiment.
Figure 54:
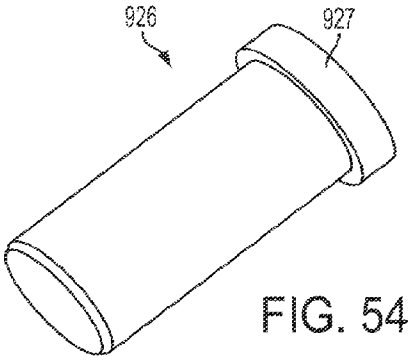
FIG. 54 illustrates a ferrous pin in one embodiment.

FIG. 43 is an exploded side view of the connector assembly 920 in accordance with one non-limiting embodiment. The connector assembly 920 may comprise, for example, a connector body 922 that includes an insertion portion 924 that is sized to be received by the receptacle assembly 902, as described in more detail below. The connector assembly 920 may comprise a variety of other components, such as a ferrous pin 926, a circuit board 928, and a plurality of electrically conductive pins 930. As shown in FIG. 54, the ferrous pin 926 may be cylindrical. In other embodiments, the ferrous pin 926 may be other shapes, such as rectangular, for example. The ferrous pin 926 may be steel, iron, or any other magnetically compatible material that is attracted to magnetic fields or that may be magnetizable. The ferrous pin 926 may also have a shoulder 927, or other type of laterally extending feature. Referring now to FIG. 55, the electrical conductive pins 930 may be affixed to and extend from the circuit board 928. The circuit board 928 may also include device identification circuitry, such as the circuits illustrated in FIGS. 33E-33G, for example. Thus, in various embodiments, the circuit board 928 may carry EEPROM, resistors, or any other electrical components. In some embodiments, portions of the circuit board 928 may be potted, or otherwise encapsulated, to improve the sterility of the surgical device and assist in water resistance.

Figure 57:
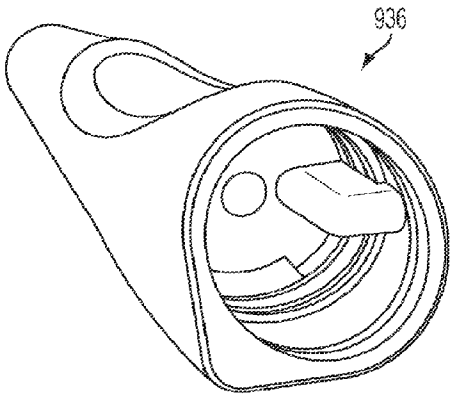
FIG. 57 illustrates a boot in one embodiment.
Figure 56:
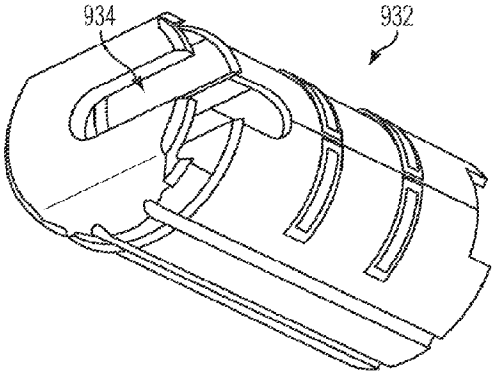
FIG. 56 illustrates a strain relief member in one embodiment.

Referring again to FIG. 43, the connector assembly 920 may also include a strain relief member 932. As shown in FIG. 56, the strain relief member 932 generally accepts cable loading to prevent that loading from being applied to the circuit board 928 and/or the sockets 908. In some embodiments, the strain relief member 932 may include an alignment notch 934 to aid in assembly. Referring again to FIG. 43, the connector assembly 920 may also include a boot 936 that is coupled to the connector body 922. FIG. 57 illustrates the boot 936 in accordance with one non-limiting embodiment. The boot 936 may generally serve as bend relief for an associated cable and assist in sealing the connector assembly 920. In some embodiments, the boot 936 may snap onto the connector body 922. For autoclave applications, the boot 936 may be an overmolded component. In other embodiments, other attachment techniques may be used, such as adhesives or spin welding, for example.

Figure 44:
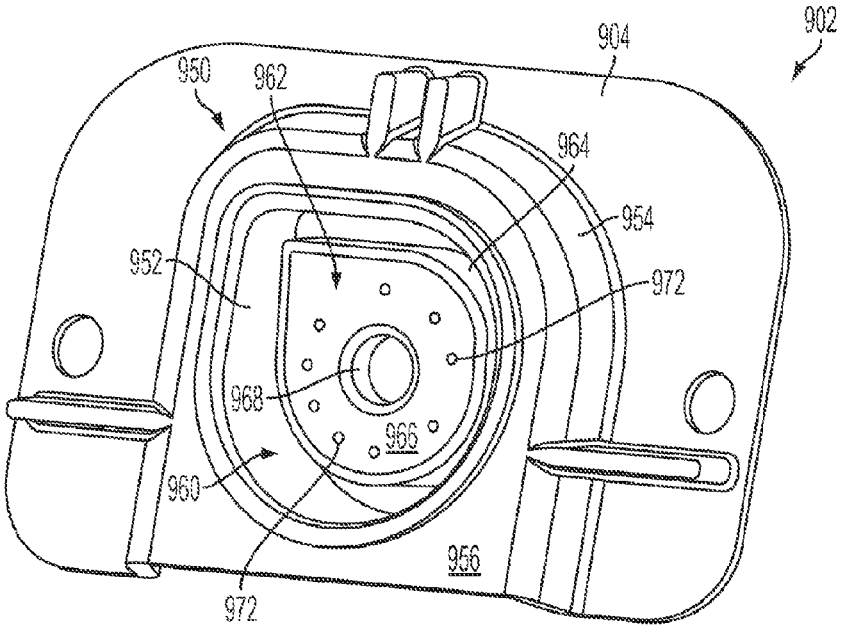
FIG. 44 is a perspective view of the receptacle assembly shown in FIG. 41.
Figure 45:
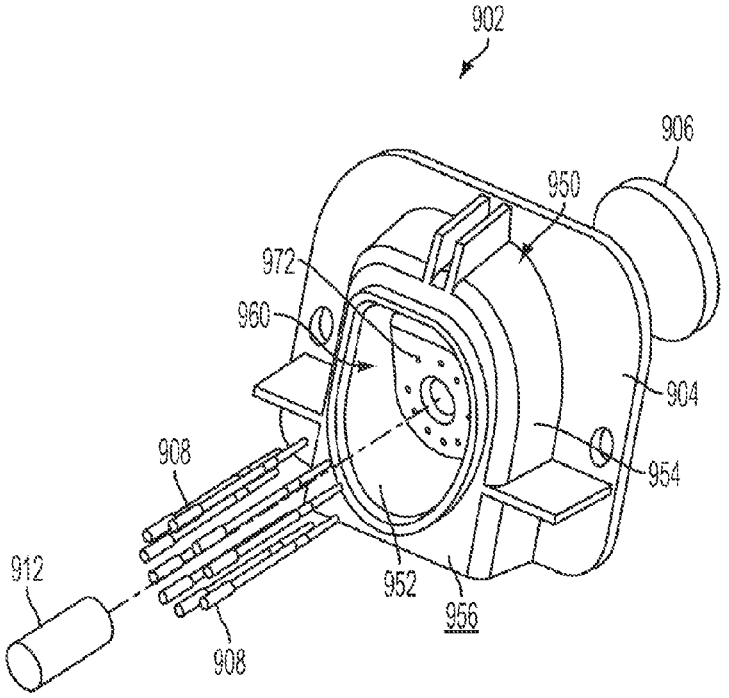
FIG. 45 is a exploded perspective view of the receptacle assembly in one embodiment.
Figure 47:
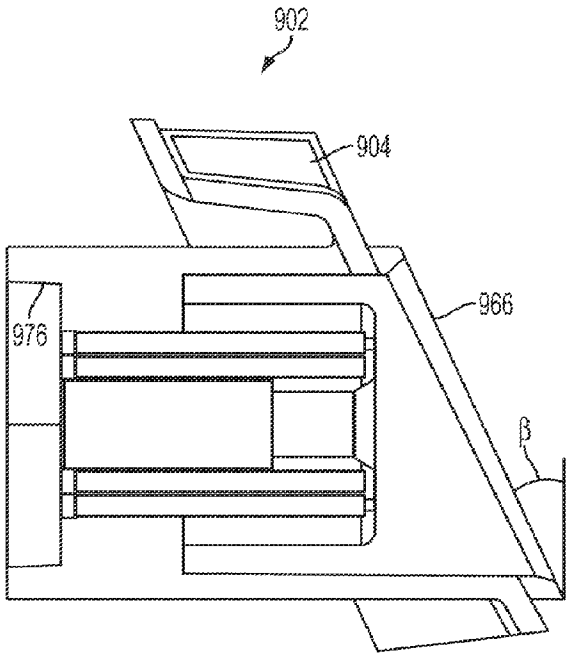
FIG. 47 is a side elevation view of the receptacle assembly in one embodiment.
Figure 46:
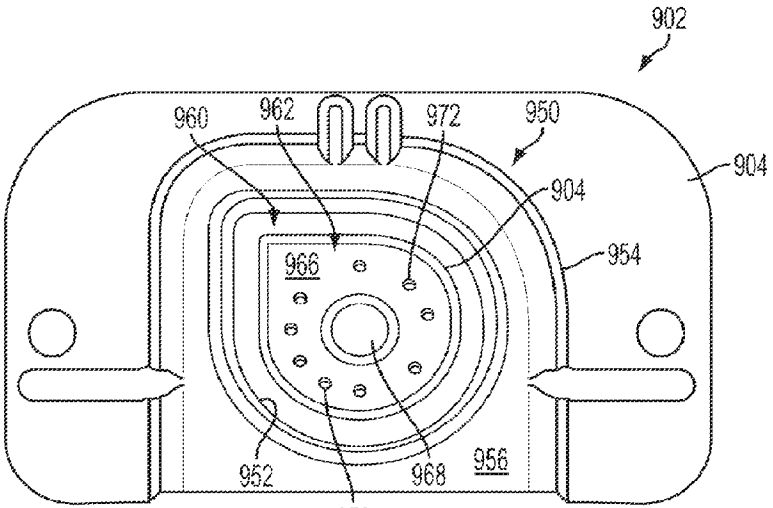
FIG. 46 is a front elevation view of the receptacle assembly in one embodiment.
Figure 61:
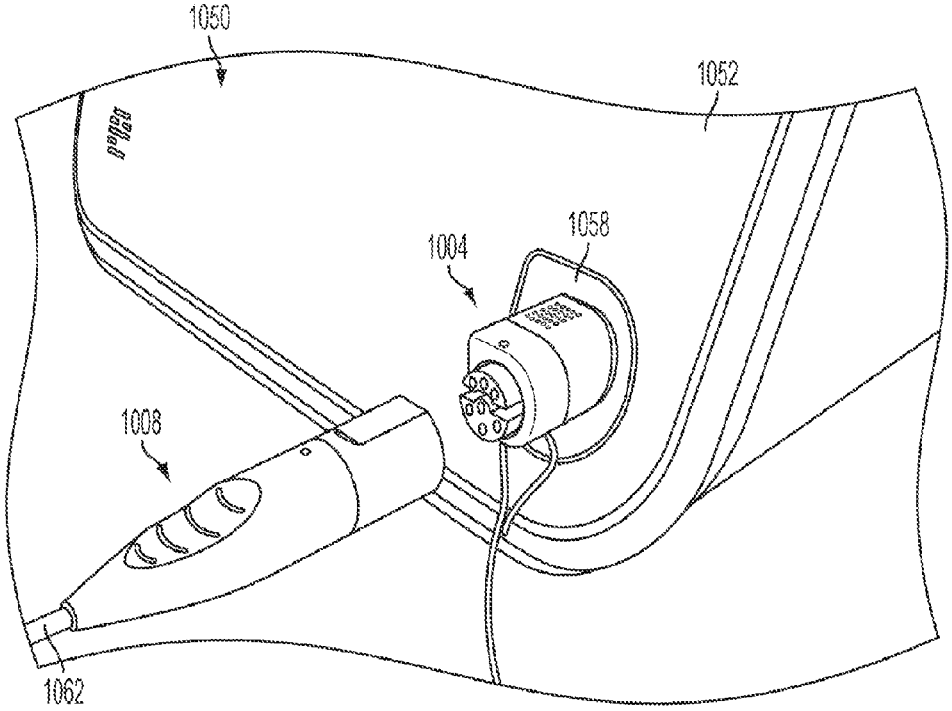
FIG. 61 illustrates an adaptor assembly inserted into a receptacle assembly of a surgical generator in one embodiment.

FIG. 44 is a perspective view of the receptacle assembly 902 shown in FIG. 41. FIG. 45 is an exploded perspective view of the receptacle assembly 902. FIG. 46 is a front elevation view of the receptacle assembly 902. FIG. 47 is a side elevation view of the receptacle assembly 902. Referring to FIGS. 44-47, the receptacle assembly 902 may comprise a flange 950. The flange 950 may have an inner wall 952 and an outer wall 954. Spanning the inner wall 952 and the outer wall 954 is a flange surface 956. The inner wall 952 may include at least one curved portion and at least one linear portion. The inner wall 952 of the flange 950 defines a cavity 960 having a unique geometry. In one embodiment, the cavity 960 is defined by about 270 degrees of a circle and two linear segments that are tangential to the circle and intersect to form an angle $\Theta$. In one embodiment, angle $\Theta$ is about 90 degrees. In one embodiment, a central protruding portion 962 having an outer periphery 964 is positioned in the cavity 960. The central protruding portion 962 may have a central surface 966 that defines a recess 968. The magnet 912 (FIG. 42) may be positioned proximate the recess 968. As illustrated, the sockets 908 may be positioned through apertures 972 defined by the central surface 966 of the central protruding portion 962. In embodiments utilizing a circular arrangement of sockets 908, the magnet 912 may be positioned internal to the circle defined by the sockets. The receptacle body 904 may also define a rear recess 976 (FIG. 47). The rear recess 976 may be sized to receive the seal 906. The flange face 966 may be slanted at an angle $\beta$ (FIG. 47). As illustrated in FIG. 61, a face of the body 1052 of the surgical generator 1050 also may be slanted at the angle $\beta$ as well.

Figure 49:
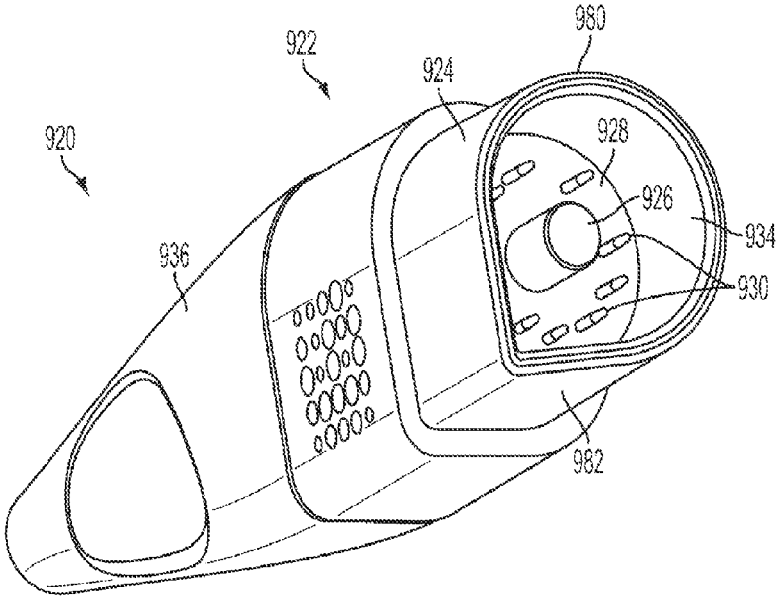
FIG. 49 is a perspective view of the connector assembly in one embodiment.
Figure 50:
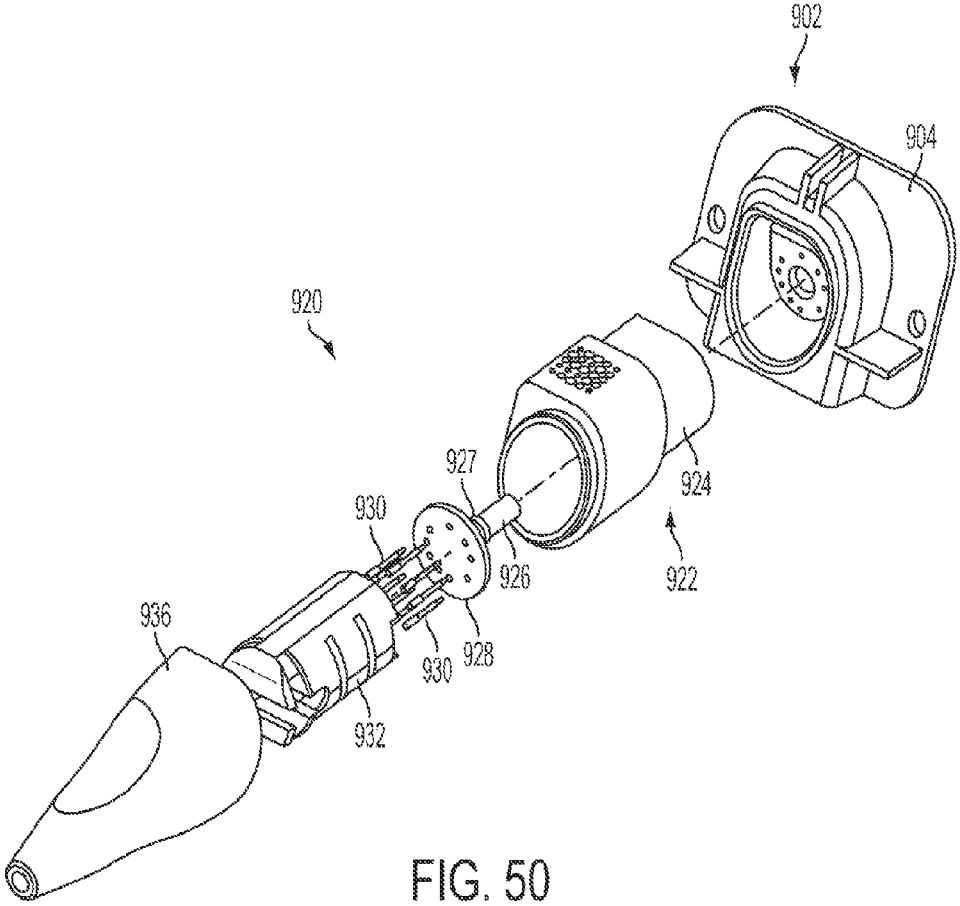
FIG. 50 is an exploded perspective view of the connector assembly in one embodiment.
Figure 52:
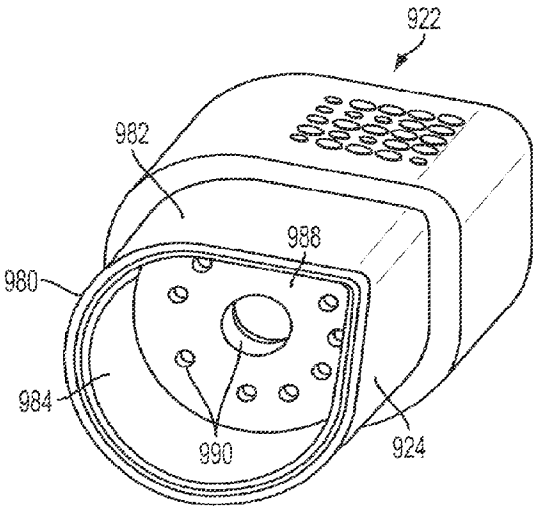
FIG. 52 is perspective view of the distal end of a connector body in one embodiment.
Figure 53:
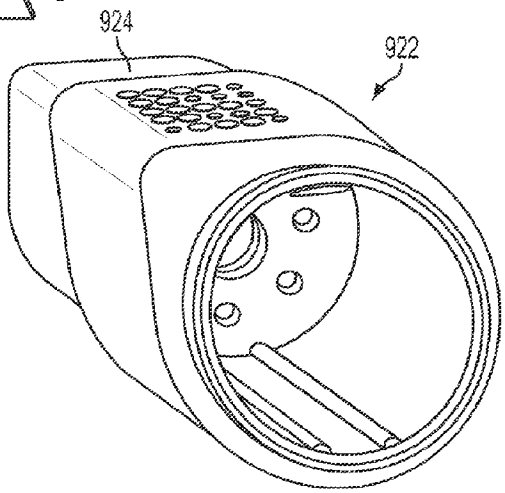
FIG. 53 is perspective view of the proximal end of a connector body in one embodiment.
Figure 51:
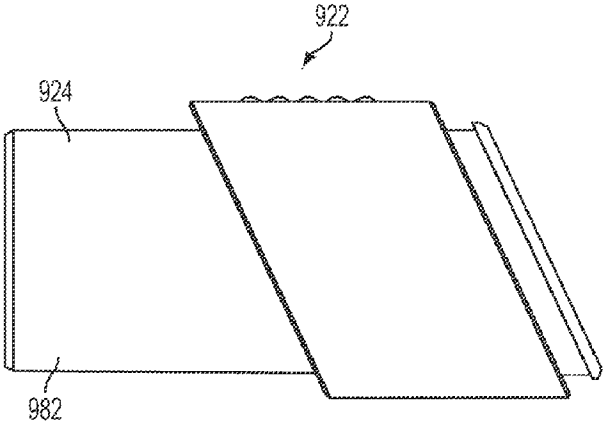
FIG. 51 is a side elevation view of a connector body in one embodiment.

FIG. 49 is a perspective view of the connector assembly 920 and FIG. 50 is an exploded perspective view of the connector assembly 920. FIG. 51 is a side elevation view of the connector body 922 with FIGS. 52 and 53 illustrating perspective views of the distal and proximal ends, respectively, of the connector body 922. Referring now to FIGS. 49-53, connector body 922 may have a flange 980. The flange 980 may comprise at least one curved portion and at least one linear portion.

The adapter assemblies 1002 and 1004 may comprise substantially the similar components that are contained by the connector body 922 (FIG. 50). For example, the adapter assemblies 1002 and 1004 may each house a circuit board with device identification circuitry. The adapter assemblies 1002 and 1004 may also each house one of a ferrous pin and a magnet to aid in the connection with the surgical generator. An outer wall 982 of the flange 980 may generally be shaped similarly to the inner wall 952 of the receptacle assembly 902 (FIG. 46). An inner wall 984 of the flange 980 may be shaped similarly to the outer periphery 964 of the central protruding portion 962. The connector body 922 may also have a wall 988 that includes a plurality of apertures 990. The apertures 990 may be sized to receive the electrically conductive pins 930 and the ferrous pin 926. In one embodiment, the shoulder 927 of the ferrous pin 926 is sized so that it can not pass through the aperture 990. In some embodiments, the ferrous pin 926 may be able to translate with respect to the wall 988. When assembled, the shoulder 927 of the ferrous pin 926 may be positioned intermediate the wall 988 and the circuit board 928. The ferrous pin 926 may be positioned such that it encounters the magnetic field of the magnet 912 when the connector assembly 920 is inserted into the receptacle assembly 902. In some embodiments, a proper connection will be denoted by an audible click when the ferrous pin 926 translates to the wall 988 and strikes the magnet 912. As is to be appreciated, various components may be positioned intermediate the ferrous pin 926 and the magnet 912, such as a washer, for example, to reduce incidental wear to the interfacing components. Additionally, in some embodiments the magnet 912 may be coupled to the connector assembly 920 and the ferrous pin 926 may be coupled to the receptacle assembly 902.

Figure 58:
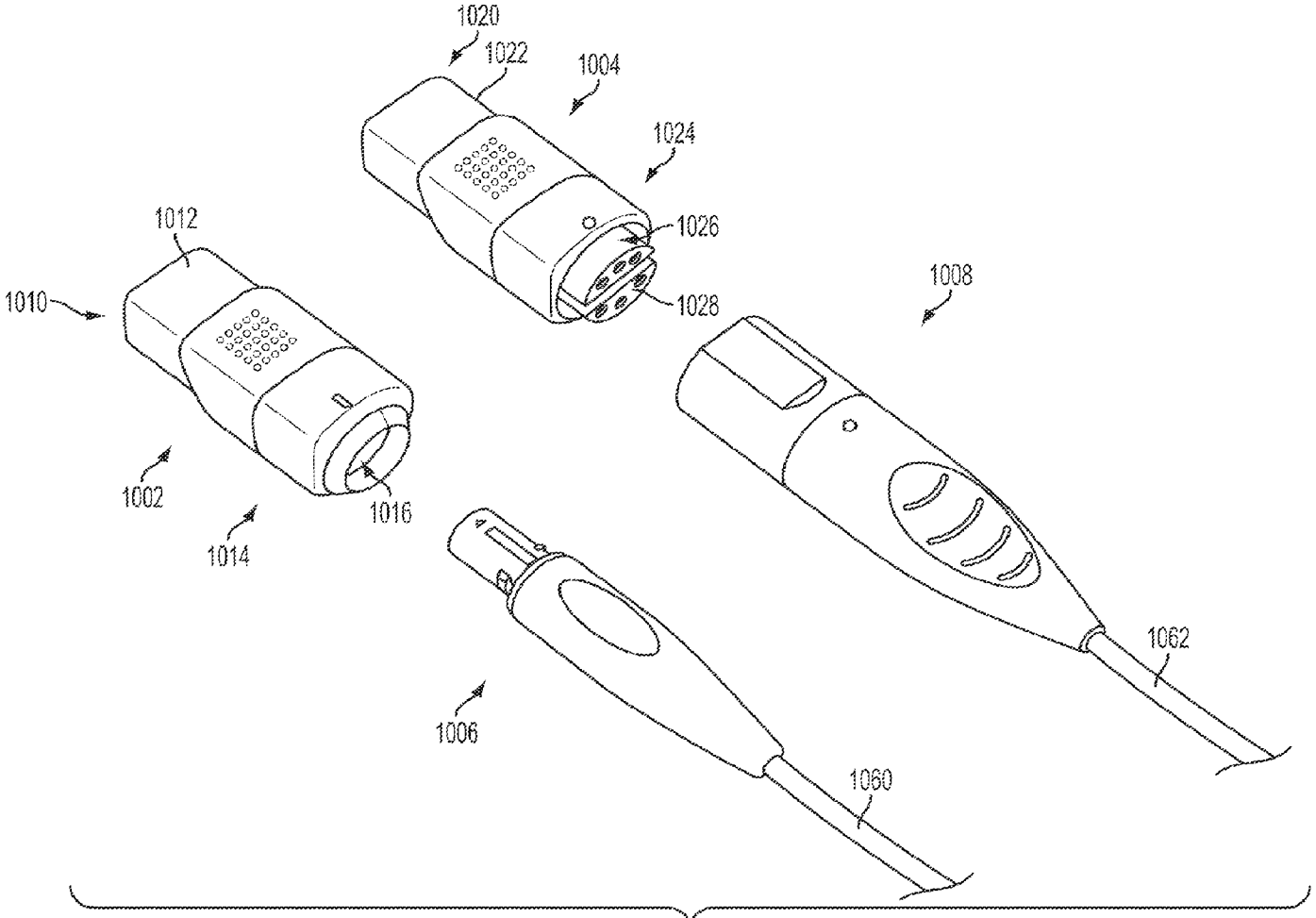
FIG. 58 illustrates two adaptor assemblies in accordance with various non-limiting embodiments.
Figure 60:
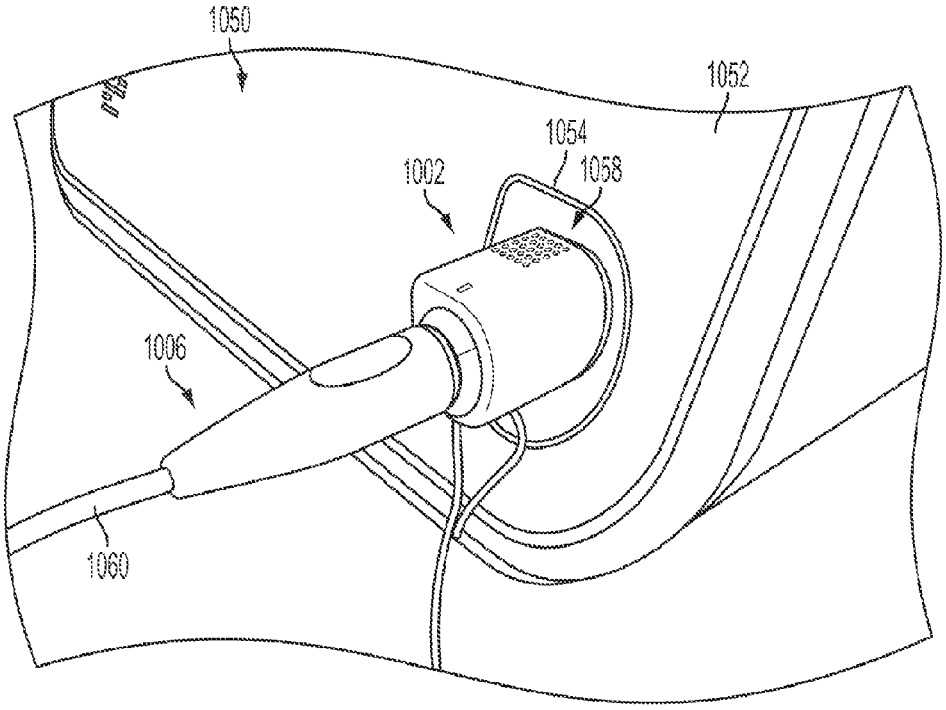
FIG. 60 illustrates a connector assembly connected to an adaptor assembly in one embodiment.
Figure 62:
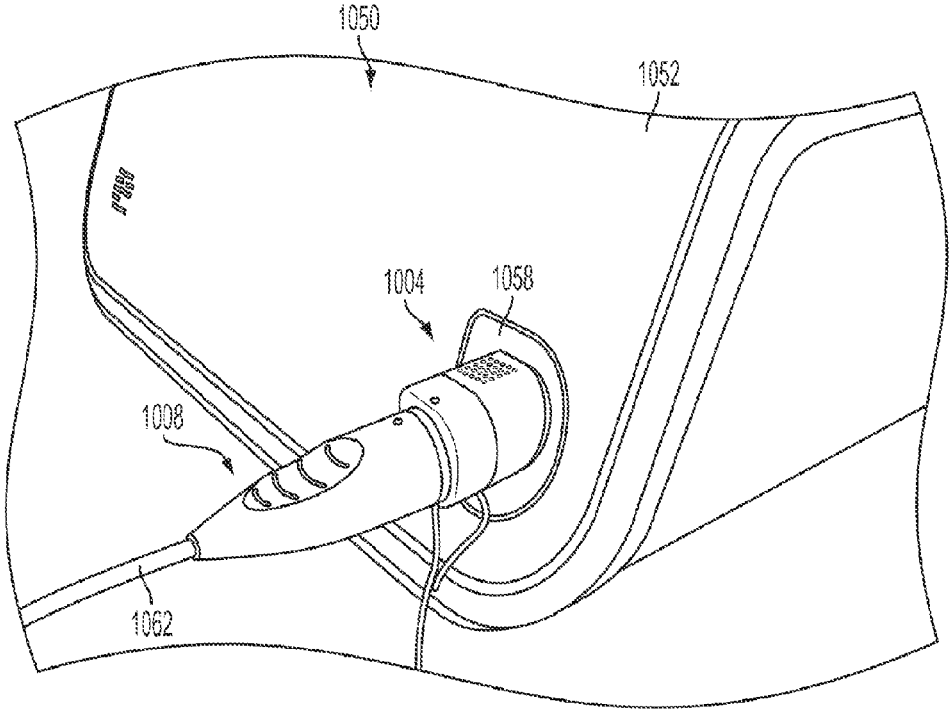
FIG. 62 illustrates a connector assembly connected to an adaptor assembly in one embodiment.

FIG. 58 illustrates two adaptor assemblies 1002 and 1004 in accordance with various non-limiting embodiments. The adaptor assemblies 1002 and 1004 allow of connector assemblies having various geometries to be electrically coupled to a receptacle assembly of a surgical generator. Adaptor assembly 1002 is configured to accommodate a surgical instrument having connector assembly 1006 and adaptor assembly 1004 is configured to accommodate a surgical instrument having a connector assembly 1008. In one embodiment, the connector assembly 1006 is associated with an RF-based surgical device via a cable 1060 and the connector assembly 1008 is associated with an ultrasonic-based device via a cable 1062. As is to be appreciated, other embodiments of adaptor assemblies may accommodate surgical instruments have connector assemblies different than those illustrated in FIG. 58. FIG. 59 illustrates the adaptor assembly 1002 after being inserting into the receptacle assembly 1058 of a surgical generator 1050 in accordance with one non-limiting embodiment. FIG. 60 illustrates the connector assembly 1006 after being inserted into the adaptor assembly 1002 and therefore electrically coupled to the surgical generator 1050. Similarly, FIG. 61 illustrates the adaptor assembly 1004 after being inserted into the receptacle assembly 1058 of a surgical generator 1050 in accordance with one non-limiting embodiment. FIG. 62 illustrates the connector assembly 1008 after being inserted into the adaptor assembly 1004. Accordingly, while connector assemblies 1006 and 1008 each having different geometries, both may be used with the surgical generator 1050.

Referring to FIGS. 58-62, in one embodiment, the adaptor assembly 1002 has a distal portion 1010 that comprises a flange 1012. The flange 1012 is configured to be inserted into the receptacle assembly 1058 of the surgical instrument 1050 and may be similar to the flange 980 illustrated in FIG. 52, for example. Any number of electrically conductive pins, or other connection components, may be positioned in the distal portion to engage the receptacle assembly 1058. In one embodiment, the adaptor assembly 1002 also has a proximal portion 1014 that defines a cavity 1016. The cavity 1016 may be configured to accept a particular connector assembly, such as connector assembly 1006. As is to be appreciated, the proximal portion 1014 may be configured appropriately based on the type of connector assembly with which it will be used. In one embodiment, the adaptor assembly 1006 has a distal portion 1020 that comprises a flange 1022. The flange 1022 is configured to be inserted into the receptacle assembly 1058 of the surgical instrument 1050 and may be similar to the flange 980 illustrated in FIG. 52, for example. The adaptor assembly 1004 also has a proximal portion 1024 that defines a cavity 1026. In the illustrated embodiment, the central portion 1028 is positioned in the cavity 1026 and is configured to accept the connector assembly 1008.

Figure 63:
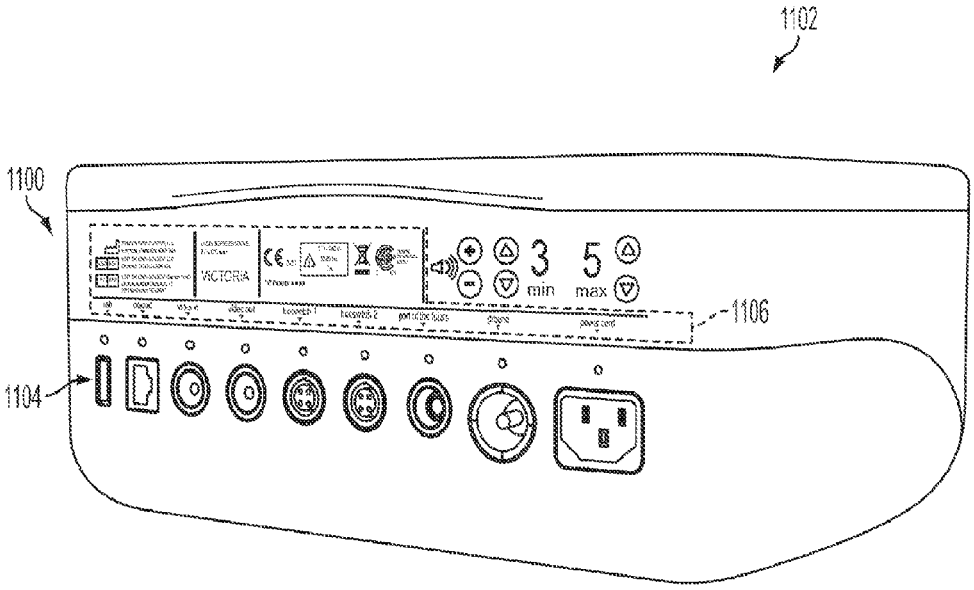
FIG. 63 illustrates a perspective view of a back panel of a generator in one embodiment.

FIG. 63 illustrates a perspective view of a back panel 1100 of a generator 1102 in accordance with one non-limiting embodiment. The generator 1102 may be similar to generator 102 illustrated in FIG. 10, for example. The back panel 1100 may comprise various input and/or output ports 1104. The back panel 1110 may also comprise an electronic paper display device 1106. The electronic paper display device 1106 may be based on electrophoresis in which an electromagnetic field is applied to a conductive material such that the conductive material has mobility. Micro particles having conductivity are distributed between thin-type flexible substrates, and positions of the micro particles (or toner particles) are changed due to the change of the polarities of an electromagnetic field, whereby data is displayed. The technical approach to realize the electronic paper may be accomplished using any suitable technique, such as liquid crystals, organic electro luminescence (EL), reflective film reflection-type display, electrophoresis, twist balls, or mechanical reflection-type display, for example.

Generally, electrophoresis is a phenomenon in which, when particles are suspended in a medium (i.e., a dispersion medium), the particles are electrically charged, and, when an electric field is applied to the charged particles, the particles move to an electrode having opposite charge through the dispersion medium. Further discussion regarding electronic paper display devices may be found in U.S. Pat. No. 7,751,115 entitled ELECTRONIC PAPER DISPLAY DEVICE, MANUFACTURING METHOD AND DRIVING METHOD THEREOF, the entirety of which is incorporated by reference.

Figure 64:
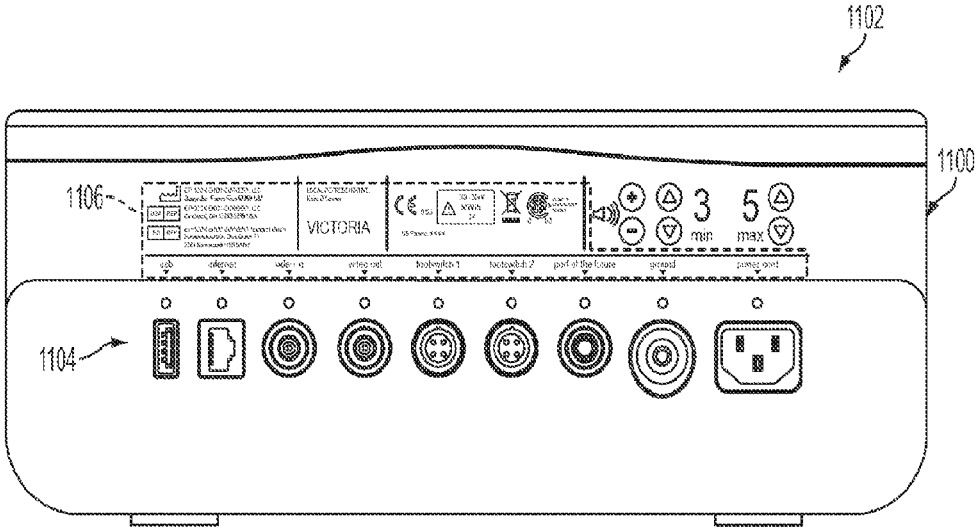
FIG. 64 illustrates a back panel of a generator in one embodiment.
Figure 65:
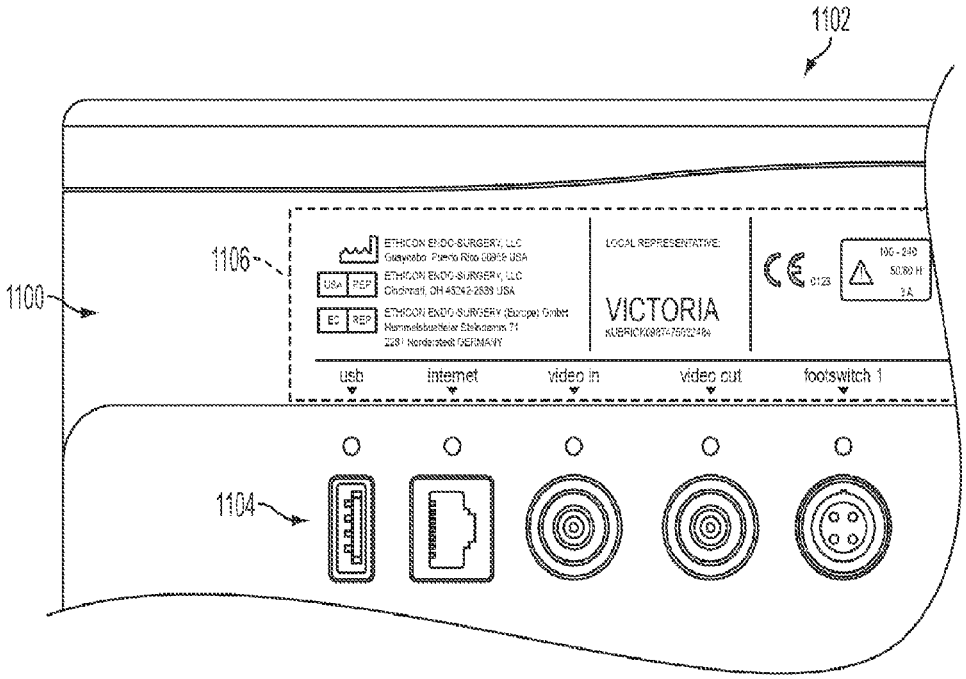
FIGS. 65 and 66 illustrate different portions of a back panel of a generator in one embodiment.
Figure 66:
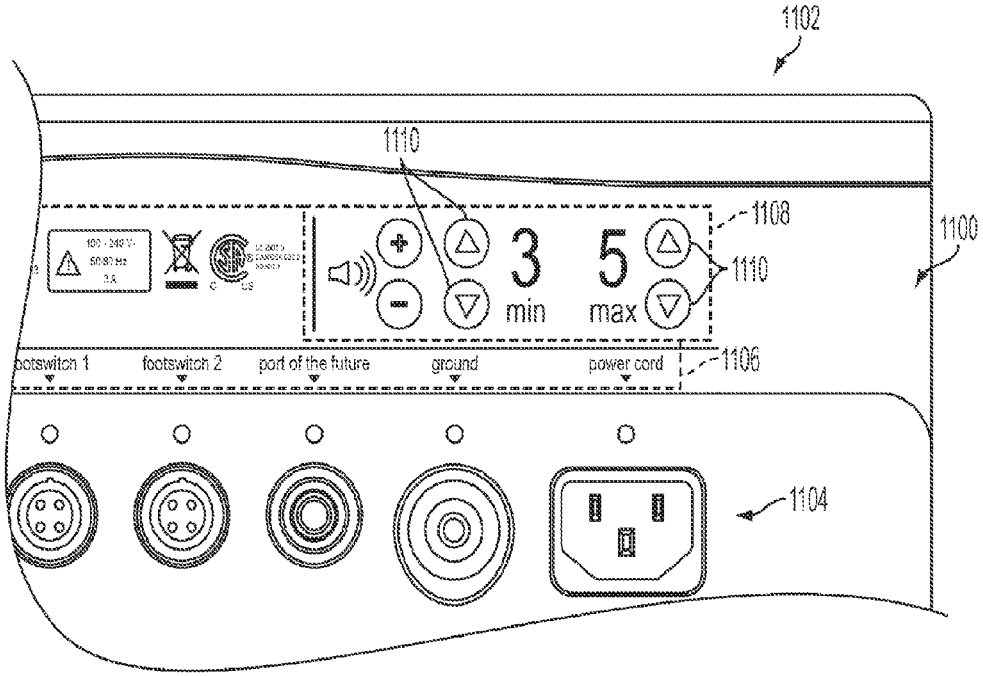

FIG. 64 illustrates the back panel 1110 illustrated in FIG. 63. FIGS. 65 and 66 provide enlarged views of the back panel 1110. Referring to FIGS. 64-66, the electronic paper display device 1106 may display a variety of information, such a serial number, apart number, patent numbers, warning labels, port identifiers, instructions, vendor information, service information, manufacturer information, operational information, or any other type of information. In one embodiment, the information displayed on the electronic paper display device 1106 may be changed or updated through connecting a computing device to a communication port (e.g., a USB port) of the generator 1102.

As shown in FIG. 66, in some embodiments. the back panel 1100 may comprise an interactive portion 1108. In one embodiment, the interactive portion 1108 allows a user to input information to the generator 1102 using input devices, such as buttons 1110. The interactive portion 1108 may also display information that is simultaneously displayed on a front panel (not shown) of the generator 1102.

In a surgical procedure utilizing an ultrasonic surgical device, such as the ultrasonic surgical device 104, the end effector 126 transmits ultrasonic energy to tissue brought into contact with the end effector 126 to realize cutting and sealing action. The application of ultrasonic energy in this manner may cause localized heating of the tissue. Monitoring and controlling such heating may be desirable to minimize unintended tissue damage and/or to optimize the effectiveness of the cutting and sealing action. Direct measurement of ultrasonic heating requires temperature sensing devices in or near the end effector 126. Although sensor-based measurements of ultrasonic heating is technically feasible, design complexity and other considerations may make direct measurement impractical. Various embodiments of the generator 102 may address this problem by generating an estimate of temperature or heating resulting from an application of ultrasonic energy.

In particular, one embodiment of the generator 102 may implement an artificial neural network to estimate ultrasonic heating based on a number of input variables 1218. Artificial neural networks are mathematical models that learn complex, nonlinear relationships between inputs and outputs based on exposure to known input and output patterns, a process commonly referred to as "training." An artificial neural network may comprise a network of simple processing units, or nodes, connected together to perform data processing tasks. The structure of an artificial neural network may be somewhat analogous to the structure of biological neural networks in the brain. When an artificial neural network is presented with an input data pattern, it produces an output pattern. An artificial neural network may be trained for a specific processing task by presentation of large amounts of training data. In this way, the artificial neural network may modify its structure by changing the "strength" of communication between nodes to improve its performance on the training data.

Figure 67:
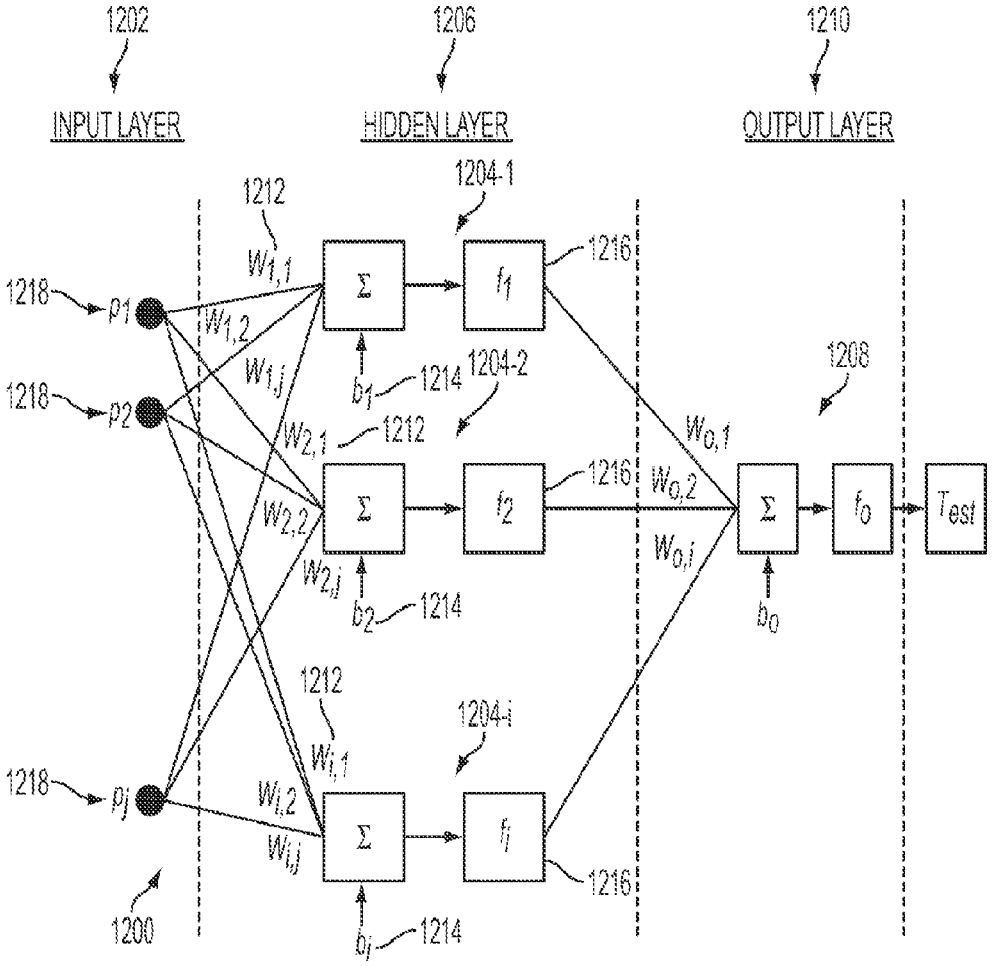
FIG. 67 illustrates a neural network for controlling a generator in one embodiment.

FIG. 67 illustrates one embodiment of an artificial neural network 1200 for generating an estimated temperature $T_{est}$ resulting from an application of ultrasonic energy using an ultrasonic surgical device, such as the ultrasonic surgical device 104. In certain embodiments, the neural network may be implemented in the processor 174 and/or the programmable logic device 166 of the generator 102. The neural network 1200 may comprise an input layer 1202, one or more nodes 1204 defining a hidden layer 1206, and one or more nodes 1208 defining an output layer 1210. For the sake of clarity, only one hidden layer 1206 is shown. In certain embodiments, the neural network 1200 may comprise one or more additional hidden layers in a cascaded arrangement, with each additional hidden layer having a number of nodes 1204 that may be equal to or different from the number of nodes 1204 in the hidden layer 1206.

Each node 1204, 1208 in the layers 1202, 1210 may include one or more weight values w 1212, a bias value b 1214, and a transform function f 1216. In FIG. 67, the use of different subscripts for these values and functions is intended to illustrate that each of these values and functions may be different from the other values and functions. The input layer 1202 comprises one or more input variables p 1218, with each node 1204 of the hidden layer 1206 receiving as input at least one of the input variables p 1218. As shown in FIG. 67, for example, each node 1204 may receive all of the input variables p 1218. In other embodiments, less than all of the input variables p 1218 may be received by a node 1204. Each input variable p 1218 received by a particular node 1204 is weighted by a corresponding weight value w 1212, then added to any other similarly weighted input variables p 1218, and to the bias value b 1214. The transform function f 1216 of the node 1204 is then applied to the resulting sum to generate the node's output. In FIG.

67, for example, the output of node 1204-1 may be given as $f_1(n_1)$, where $n_1=(w_{1,1}\cdot p_1+w_{1,2}\cdot p_2+ \ldots w_{1,j}\cdot p_j)+b_1$.

A particular node 1208 of the output layer 1210 may receive an output from one or more of the nodes 1204 of the hidden layer 1206 (e.g., each node 1208 receives outputs $f_1(\bullet)$, $f_2(\bullet)$, . . . , $f_i(\bullet)$ from respective nodes 1204-1, 1204-2, . . . , 1204-i in FIG. 67), with each received output being weighted by a corresponding weight value w 1212 and subsequently added to any other similarly weighted received outputs, and to a bias value b 1214. The transform function f 1216 of the node 1208 is then applied to the resulting sum to generate the node's output, which corresponds to an output of the neural network 1200 (e.g., the estimated temperature $T_{est}$ in the embodiment of FIG. 67). Although the embodiment of the neural network 1200 in FIG. 67 comprises only one node 1208 in the output layer 1210, in other embodiments the neural network 1200 may comprise more than one output, in which case the output layer 1210 may comprise multiple nodes 1208.

In certain embodiments, the transform function f 1216 of a node 1204, 1208 may be a nonlinear transfer function. In one embodiment, for example, one or more of the transform functions f 1216 may be a sigmoid function. In other embodiments, the transform functions f 1216 may include a tangent sigmoid, a hyperbolic tangent sigmoid, a logarithmic sigmoid, a linear transfer function, a saturated linear transfer function, a radial basis transfer function, or some other type of transfer function. The transform function f 1216 of a particular node 1204, 1208 may be the same as, or different from, a transform function f 1216 in another node 1204, 1208.

In certain embodiments, the input variables p 1218 received by the nodes 1204 of the hidden layer 1206 may represent, for example, signals and/or other quantities or conditions known or believed to have an effect on the temperature or heating resulting from an application of ultrasonic energy. Such variables may comprise, for example, one or more of: drive voltage output by the generator 102, drive current output by the generator 102, drive frequency of the generator output 102, drive power output by the generator 102, drive energy output by the generator 102, impedance of the ultrasonic transducer 114, and time duration over which ultrasonic energy is applied. Additionally, one or more of the input variables p 1218 may be unrelated to outputs of the generator 102 and may comprise, for example, characteristics of the end effector 126 (e.g., blade tip size, geometry, and/or material) and a particular type of tissue targeted by the ultrasonic energy.

The neural network 1200 may be trained (e.g., by changing or varying the weight values w 1212, the bias values b 1214, and the transform functions f 1216) such that its output (e.g., estimated temperature $T_{est}$ in the embodiment of FIG. 67) suitably approximates a measured dependency of the output for known values of the input variables p 1218. Training may be performed, for example, by supplying known sets of input variables p 1218, comparing output of the neural network 1200 to measured outputs corresponding to the known sets of input variables p 1218, and modifying the weight values w 1212, the bias values b 1214, and/or the transform functions f 1216 until the error between the outputs of the neural network 1200 and the corresponding measured outputs is below a predetermined error level. For example, the neural network 1200 may be trained until the mean square error is below a predetermined error threshold. In certain embodiments, aspects of the training process may be implemented by the neural network 1200 (e.g., by propagating errors back through the network 1200 to adaptively adjust the weight values w 1212 and/or the bias values b 1214).

Figure 68:
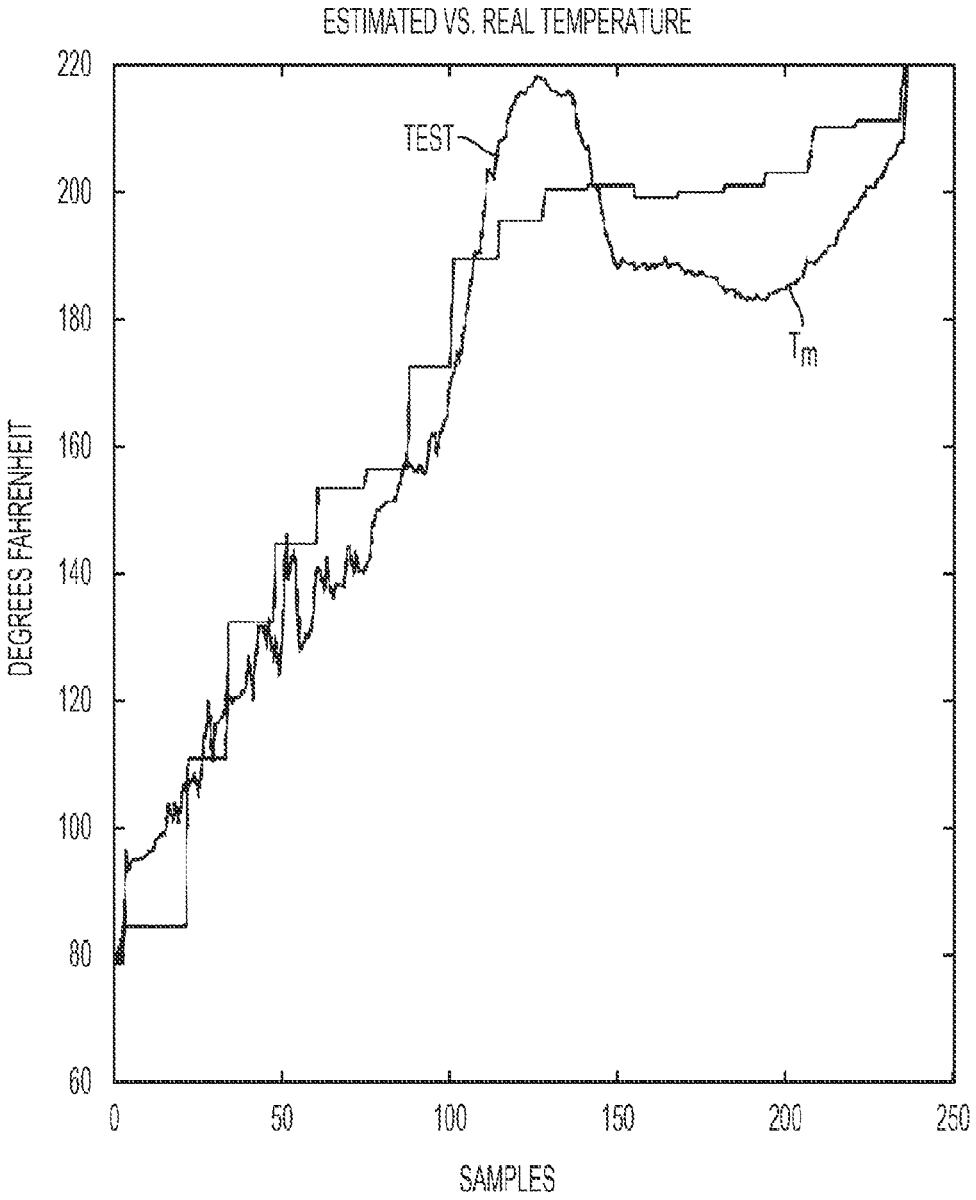
FIG. 68 illustrates measured temperature versus estimated temperature output by a surgical instrument controlled by a generator in one embodiment.

FIG. 68 illustrates a comparison between estimated temperature values $T_{est}$ and measured temperature values $T_m$ for an implementation of one embodiment of the neural network 1200. The neural network 1200 used to generate $T_{est}$ in FIG. 68 comprised six input variables p 1218: drive voltage, drive current, drive frequency, drive power, impedance of the ultrasonic transducer, and time duration over which ultrasonic energy was applied. The hidden layer 1206 comprised 25 nodes, and the output layer 1210 comprised a single node 1208. Training data was generated based on 13 applications of ultrasonic energy to carotid vessels. Actual temperature ($T_m$) was determined based on IR measurements over a 250-sample range for varying values of the input variables p 1218, with estimated temperatures $T_{est}$ being generated by the neural network 1200 based on corresponding values of the input variables p 1218. The data shown in FIG. 68 was generated on a run that was excluded from the training data. The estimated temperatures $T_{est}$ demonstrate a reasonably accurate approximation of the measured temperatures $T_m$ in the region of 110-190° F. It is believed that inconsistencies in estimated temperatures $T_{est}$ appearing in certain regions, such as the region following 110° F., may be minimized or reduced by implementing additional neural networks specific to those regions. Additionally, inconsistencies in the data that may skew the trained output of the neural network 1200 may be identified and programmed in as special cases to further improve performance.

In certain embodiments, when the estimated temperature exceeds a user-defined temperature threshold $T_{th}$, the generator 102 may be configured to control the application of ultrasonic energy such that the estimated temperature $T_{est}$ is maintained at or below the temperature threshold $T_{th}$. For example, in embodiments in which the drive current is an input variable p 1218 to the neural network 1200, the drive current may be treated as a control variable and modulated to minimize or reduce the difference between $T_{est}$ and $T_{th}$. Such embodiments may be implemented using a feedback control algorithm (e.g., a PID control algorithm), with $T_{th}$ being input to the control algorithm as a setpoint, $T_{est}$ being input to the algorithm as process variable feedback, and drive current corresponding to the controlled output of the algorithm. In cases where the drive current serves as the control variable, suitable variations in drive current value should be represented in the sets of input variables p 1218 used to train the neural network 1200. In particular, the effectiveness of drive current as a control variable may be reduced if the training data reflects constant drive current values, as the neural network 1200 may reduce the weight values w 1212 associated with drive current due to its apparent lack of effect on temperature. It will be appreciated that input variables p 1218 other than drive current (e.g., drive voltage) may be used to minimize or reduce the difference between $T_{est}$ and $T_{th}$.

According to various embodiments, the generator 102 may provide power to a tissue bite according to one or more power curves. A power curve may define a relationship between power delivered to the tissue and the impedance of the tissue. For example as the impedance of the tissue changes (e.g., increases) during coagulation, the power provided by the generator 102 may also change (e.g., decrease) according to the applied power curve.

Different power curves may be particularly suited, or ill-suited, to different types and/or sizes of tissue bites. Aggressive power curves (e.g., power curves calling for high power levels) may be suited for large tissue bites. When applied to smaller tissue bites, such as small vessels, more aggressive power curves may lead to exterior searing. Exterior searing may reduce the coagulation/weld quality at the exterior and can also prevent complete coagulation of interior portions of the tissue. Similarly, less aggressive power curves may fail to achieve hemostasis when applied to larger tissue bites (e.g., larger bundles).

Figure 69:
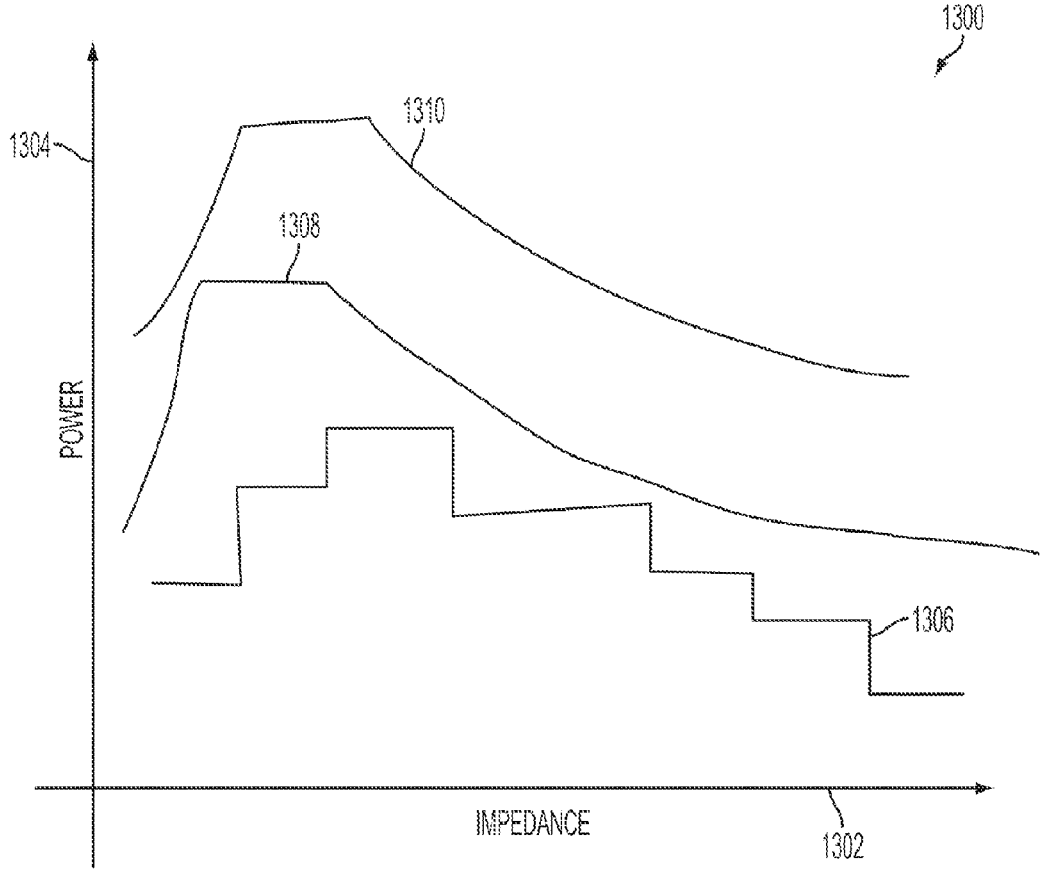
FIG. 69 illustrates one embodiment of a chart showing example power curves.

FIG. 69 illustrates one embodiment of a chart 1300 showing example power curves 1306, 1308, 1310. The chart 1300 comprises an impedance axis 1302 illustrating increasing potential tissue impedances from left to right. A power axis 1304 illustrates increasing power from down to up. Each of the power curves 1306, 1308, 1310 may define a set of power levels, on the power axis 1304, corresponding to a plurality of potential sensed tissue impedances, in the impedance axis 1302. In general, power curves may take different shapes, and this is illustrated in FIG. 69. Power curve 1306 is shown with a step-wise shape, while power curves 1308, 1310 are shown with curved shapes. It will be appreciated that power curves utilized by various embodiments may take any usable continuous or non-continuous shape. The rate of power delivery or aggressiveness of a power curve may be indicated by its position on the chart 1300. For example, power curves that deliver higher power for a given tissue impedance may be considered more aggressive. Accordingly, between two power curves, the curve positioned highest on the power axis 1304 may be the more aggressive. It will be appreciated that some power curves may overlap.

The aggressiveness of two power curves may be compared according to any suitable method. For example, a first power curve may be considered more aggressive than a second power curve over a given range of potential tissue impedances if the first power curve has a higher delivered power corresponding to at least half of the range of potential tissue impedances. Also, for example, a first power curve may be considered more aggressive than a second power curve over a given range of potential tissue impedances if the area under the first curve over the range is larger than the area under the second curve over the range. Equivalently, when power curves are expressed discretely, a first power curve may be considered more aggressive than a second power curve over a given set of potential tissue impedances if the sum of the power values for the first power curve over the set of potential tissue impedances is greater than the sum of the power values for the second power curve over the set of potential tissue impedances.

According to various embodiments, the power curve shifting algorithms described herein may be used with any kind of surgical device (e.g., ultrasonic device 104, electrosurgical device 106). In embodiments utilizing a ultrasonic device 104, tissue impedance readings may be taken utilizing electrodes 157, 159. With an electrosurgical device, such as 106, tissue impedance readings may be taken utilizing first and second electrodes 177, 179.

In some embodiments, an electrosurgical device 104 may comprise a positive temperature coefficient (PTC) material positioned between one or both of the electrodes 177, 179 and the tissue bite. The PTC material may have an impedance profile that remains relatively low and relatively constant until it reaches a threshold or trigger temperature, at which point the impedance of the PTC material may increase. In use, the PTC material may be placed in contact with the tissue while power is applied. The trigger temperature of the PTC material may be selected such that it corresponds to a tissue temperature indicating the completion of welding or coagulation. Accordingly, as a welding or coagulation process is completed, the impedance of the PTC material may increase, bringing about a corresponding decrease in power actually provided to the tissue.

It will be appreciated that during the coagulation or welding process, tissue impedance may generally increase. In some embodiments, tissue impedance may display a sudden impedance increase indicating successful coagulation. The increase may be due to physiological changes in the tissue, a PTC material reaching its trigger threshold, etc., and may occur at any point in the coagulation process. The amount of energy that may be required to bring about the sudden impedance increase may be related to the thermal mass of the tissue being acted upon. The thermal mass of any given tissue bite, in turn, may be related to the type and amount of tissue in the bite.

Various embodiments may utilize this sudden increase in tissue impedance to select an appropriate power curve for a given tissue bite. For example, the generator 102 may select and apply successively more aggressive power curves until the tissue impedance reaches an impedance threshold indicating that the sudden increase has occurred. For example, reaching the impedance threshold may indicate that coagulation is progressing appropriately with the currently applied power curve. The impedance threshold may be a tissue impedance value, a rate of change of tissue impedance, and/or a combination of impedance and rate of change. For example, the impedance threshold may be met when a certain impedance value and/or rate of change are observed. According to various embodiments, different power curves may have different impedance thresholds, as described herein.

Figure 70:
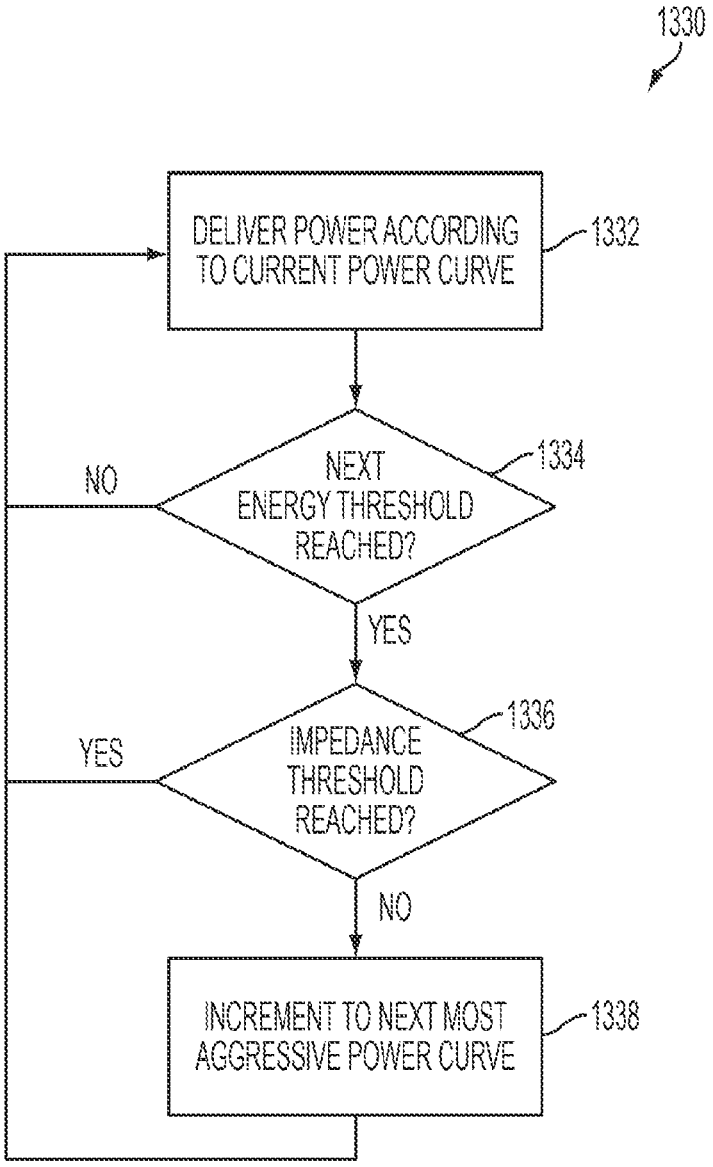
FIG. 70 illustrates one embodiment of a process flow for applying one or more power curves to a tissue bite.

FIG. 70 illustrates one embodiment of a process flow 1330 for applying one or more power curves to a tissue bite. Any suitable number of power curves may be used. The power curves may be successively applied in order of aggressiveness until one of the power curves drives the tissue to the impedance threshold. At 1332, the generator 102 may apply a first power curve. According to various embodiments, the first power curve may be selected to deliver power at a relatively low rate. For example, the first power curve may be selected to avoid tissue searing with the smallest and most vulnerable expected tissue bites.

The first power curve may be applied to the tissue in any suitable manner. For example, the generator 102 may generate a drive signal implementing the first power curve. The power curve may be implemented by modulating the power of the drive signal. The power of the drive signal may be modulated in any suitable manner. For example, the voltage and/or current of the signal may be modulated. Also, in various embodiments, the drive signal may be pulsed. For example, the generator 102 may modulate the average power by changing the pulse width, duty cycle, etc. of the drive signal. The drive signal may be provided to the first and second electrodes 177, 179 of the electrosurgical device 106. Also, in some embodiments the drive signal implementing the first power curve may be provided to an ultrasonic generator 114 of the ultrasonic device 104 described above.

While applying the first power curve, the generator 102 may monitor the total energy provided to the tissue. The impedance of the tissue may be compared to the impedance threshold at one or more energy thresholds. There may be any suitable number of energy thresholds, which may be selected according to any suitable methodology. For example, the energy thresholds may be selected to correspond to known points where different tissue types achieve the impedance threshold. At 1334, the generator 102 may determine whether the total energy delivered to the tissue has met or exceeded a first energy threshold. If the total energy has not yet reached the first energy threshold, the generator 102 may continue to apply the first power curve at 1332.

If the total energy has reached the first energy threshold, the generator 102 may determine whether the impedance threshold has been reached (1336). As described above, the impedance threshold may be a predetermined rate of impedance change (e.g., increase) a predetermined impedance, or combination of the two. If the impedance threshold is reached, the generator 102 may continue to apply the first power curve at 1332. For example, reaching the impedance threshold in the first power curve may indicate that the aggressiveness of the first power curve is sufficient to bring about suitable coagulation or welding.

In the event that the impedance threshold is not reached at 1336, the generator 102 may increment to the next most aggressive power curve at 1338 and apply the power curve as the current power curve at 1332. When the next energy threshold is reached at 1334, the generator 102 again may determine whether the impedance threshold is reached at 1336. If it is to not reached, the generator 102 may again increment to the next most aggressive power curve at 1338 and deliver that power curve at 1332.

The process flow 1330 may continue until terminated. For example, the process flow 1330 may be terminated when the impedance threshold is reached at 1336. Upon reaching the impedance threshold, the generator 102 may apply the then-current power curve until coagulation or welding is complete. Also, for example, the process flow 1330 may terminate upon the exhaustion of all available power curves. Any suitable number of power curves may be used. If the most aggressive power curve fails to drive the tissue to the impedance threshold, the generator 102 may continue to apply the most aggressive power curve until the process is otherwise terminated (e.g., by a clinician or upon reaching a final energy threshold).

According to various embodiments, the process flow 1330 may continue until the occurrence of a termination threshold. The termination threshold may indicate that coagulation and/or welding is complete. For example, the termination threshold may be based on one or more of tissue impedance, tissue temperature, tissue capacitance, tissue inductance, elapsed time, etc. These may be a single termination threshold or, in various embodiments, different power curves may have different termination thresholds. According to various embodiments, different power curves may utilize different impedance thresholds. For example, the process flow 1330 may transition from a first to a second power curve if the first power curve has failed to drive the tissue to a first tissue impedance threshold and may, subsequently, shift from the second to a third power curve if the second power curve has failed to drive the tissue to a second impedance threshold.

Figure 71:
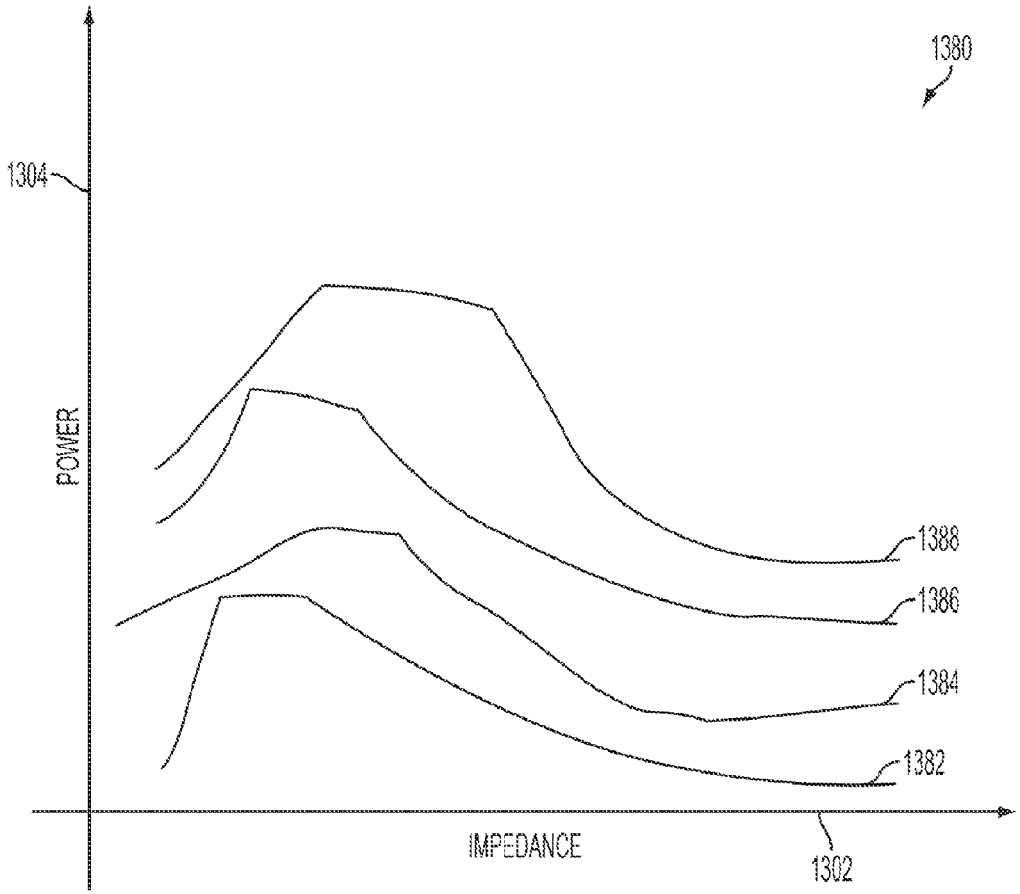
FIG. 71 illustrates one embodiment of a chart showing example power curves that may be used in conjunction with the process flow of FIG. 70.

FIG. 71 illustrates one embodiment of a chart 1380 showing example power curves 1382, 1384, 1386, 1388 that may be used in conjunction with the process flow 1330. Although four power curves 1382, 1384, 1386, 1388 are shown, it will be appreciated that any suitable number of power curves may be utilized. Power curve 1382 may represent the least aggressive power curve and may be applied first. If the impedance threshold is not reached at the first energy threshold, then the generator 102 may provide the second power curve 1384. The other power curves 1386, 1388 may be utilized, as needed, for example in the manner described above.

Figure 72:
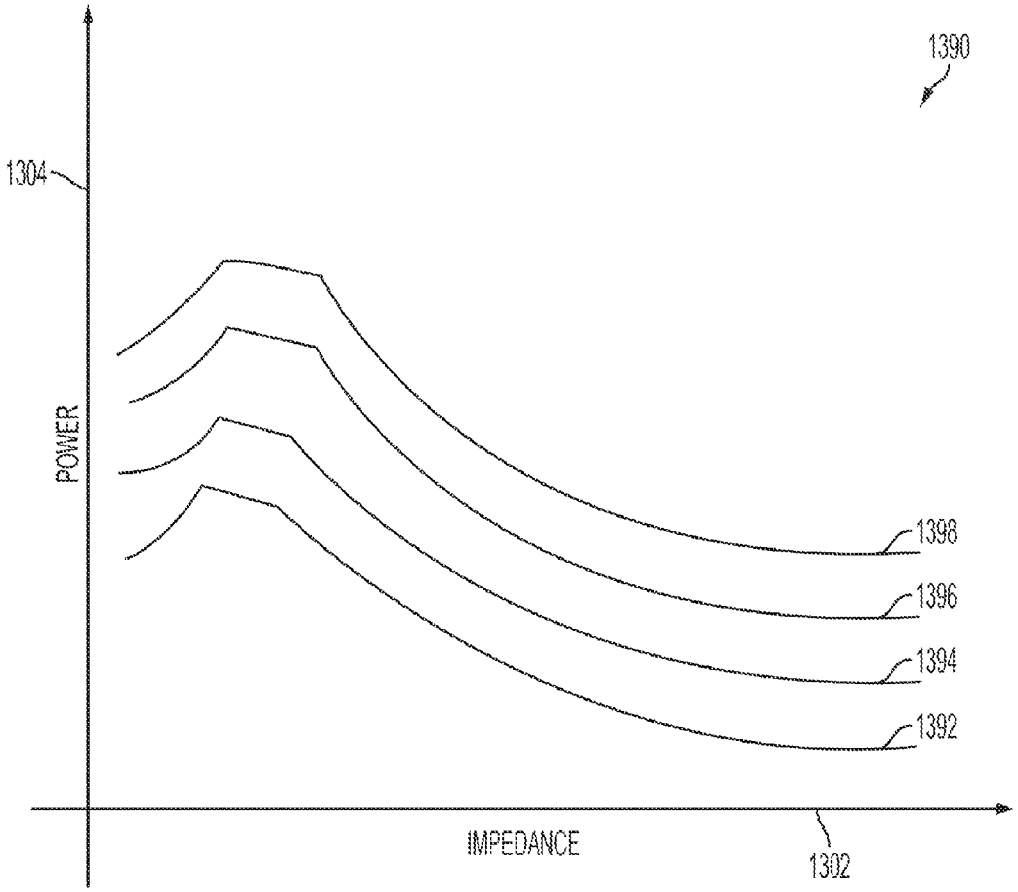
FIG. 72 illustrates one embodiment of a chart showing example common shape power curves that may be used in conjunction with the process flow of FIG. 70.

As illustrated in FIG. 71, the power curves 1382, 1384, 1386, 1388 are of different shapes. It will be appreciated, however, that some or all of a set of power curves implemented by the process flow 1330 may be of the same shape. FIG. 72 illustrates one embodiment of a chart showing example common shape power curves 1392, 1394, 1396, 1398 that may be used in conjunction with the process flow of FIG. 70. According to various embodiments, common shape power curves, such as 1392, 1394, 1396, 1398 may be constant multiples of one another. Accordingly, the generator 102 may implement the common shape power curves 1392, 1394, 1396, 1398 by applying different multiples to a single power curve. For example, the curve 1394 may be implemented by multiplying the curve 1392 by a first constant multiplier. The curve 1396 may be generated by multiplying the curve 1392 by a second constant multiplier. Likewise, the curve 1398 may be generated by multiplying the curve 1392 by a third constant multiplier. Accordingly, in various embodiments, the generator 102 may increment to a next most aggressive power curve at 1338 by changing the constant multiplier.

Figure 73A:
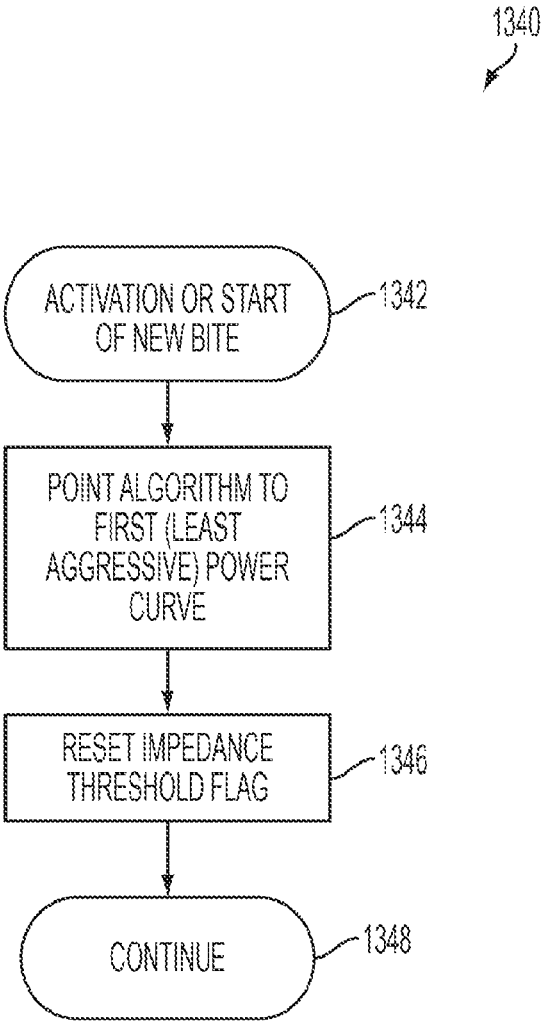
FIG. 73A illustrates one embodiment of a routine that may be performed by a digital device of the generator of FIG. 1 to act upon a new tissue bite.
Figure 73B:
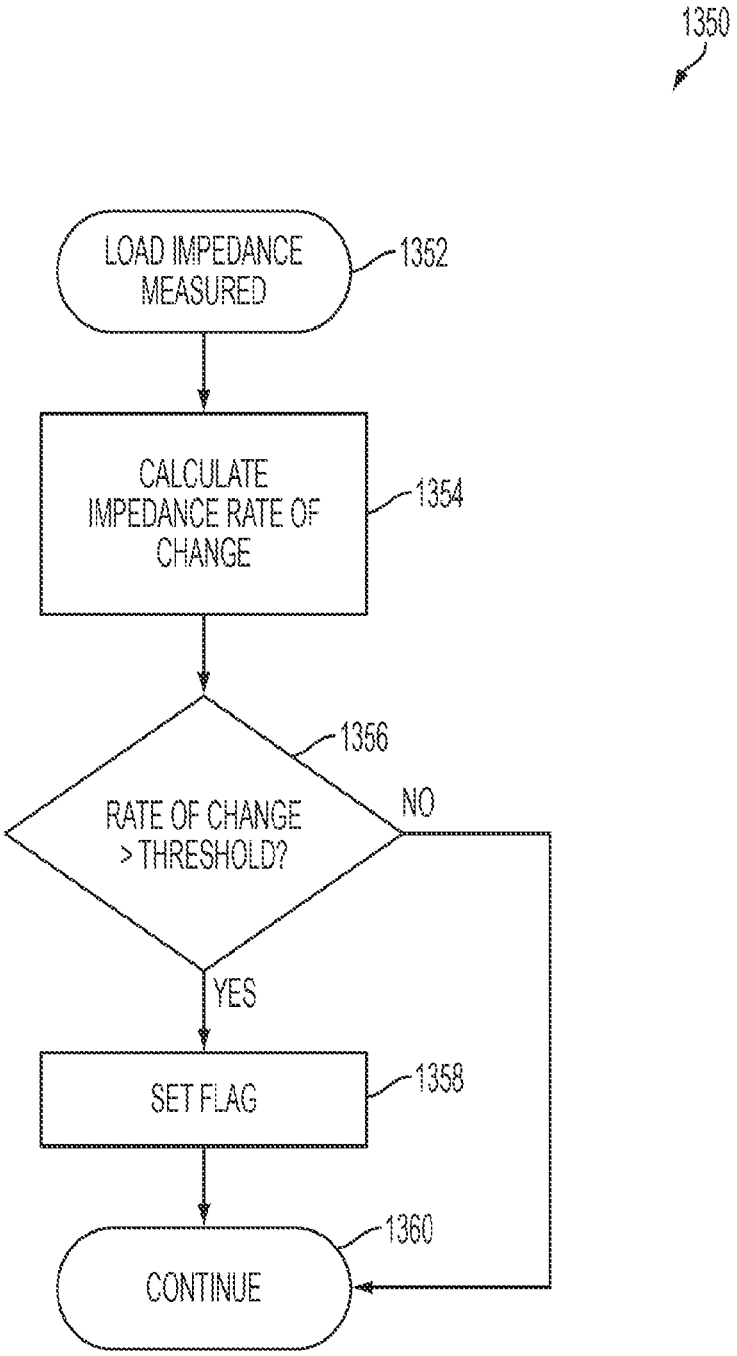
FIG. 73B illustrates one embodiment of a routine that may be performed by a digital device of the generator of FIG. 1 to monitor tissue impedance.
Figure 73C:
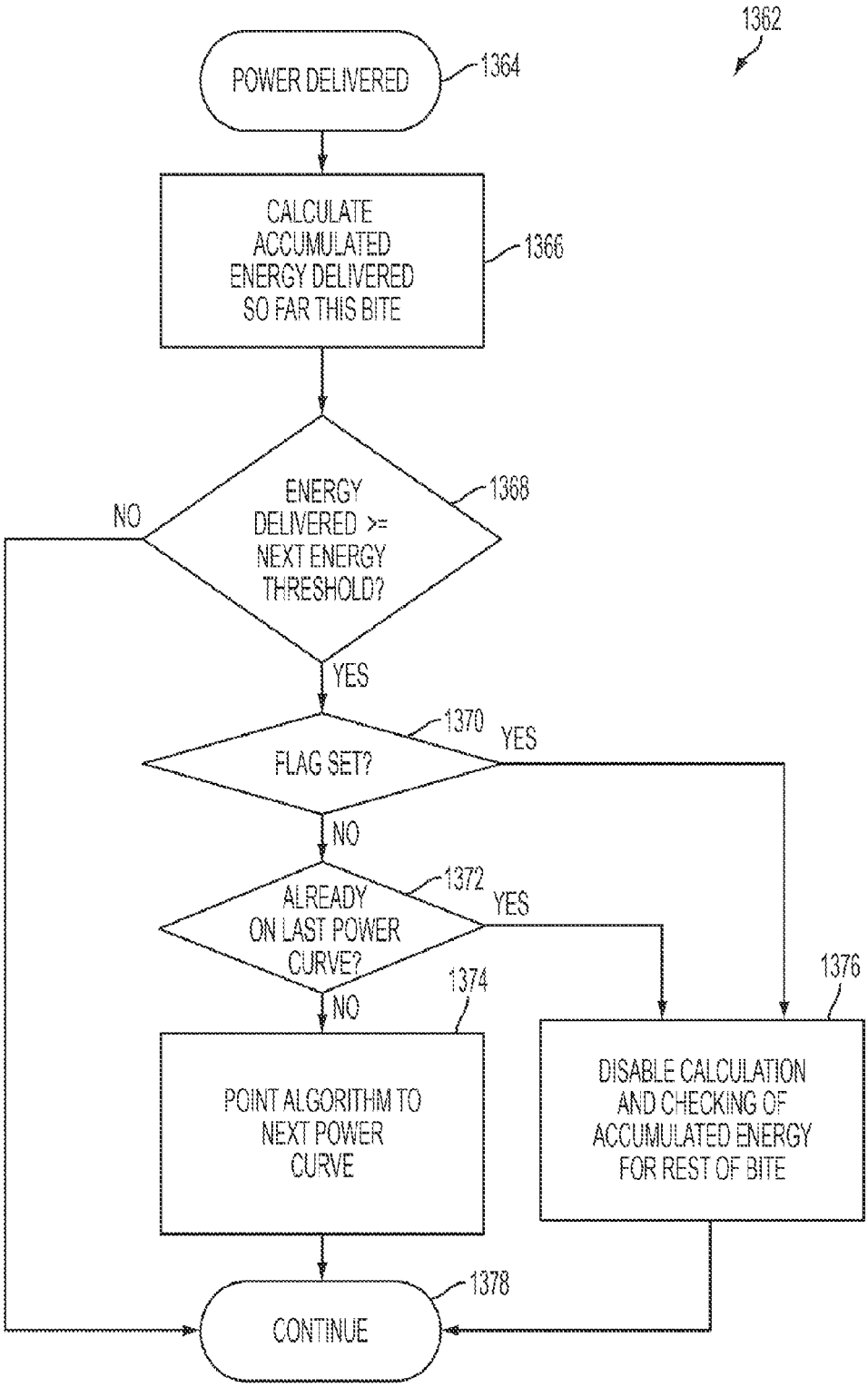
FIG. 73C illustrates one embodiment of a routine that may be performed by a digital device of the generator of FIG. 1 to provide one or more power curves to a tissue bite.

According to various embodiments, the process flow 1330 may be implemented by a digital device (e.g., a processor, digital signal processor, field programmable gate array (FPGA), etc.) of the generator 102. Examples of such digital devices include, for example, processor 174, programmable logic device 166, processor 190, etc.). FIGS. 73A-73C illustrate process flows describing routines that may be executed by a digital device of the generator 102 to generally implement the process flow 1330 described above. FIG. 73A illustrates one embodiment of a routine 1340 for preparing the generator 102 to act upon a new tissue bite. The activation or start of the new tissue bite may be initiated at 1342. At 1344, the digital device may point to a first power curve. The first power curve, as described above, may be the least aggressive power curve to be implemented as a part of the process flow 1330. Pointing to the first power curve may comprise pointing to a deterministic formula indicating the first power curve, pointing to a look-up table representing the first power curve, pointing to a first power curve multiplier, etc.

At 1346, the digital device may reset an impedance threshold flag. As described below, setting the impedance threshold flag may indicate that the impedance threshold has been met. Accordingly, resetting the flag may indicate that the impedance threshold has not been met, as may be appropriate at the outset of the process flow 1330. At 1348, the digital device may continue to the next routine 1350.

FIG. 73B illustrates one embodiment of a routine 1350 that may be performed by the digital device to monitor tissue impedance. At 1352, load or tissue impedance may be measured. Tissue impedance may be measured according to any suitable method and utilizing any suitable hardware. For example, according to various embodiments, tissue impedance may be calculated according to Ohm's law utilizing the current and voltage provided to the tissue. At 1354, the digital device may calculate a rate of change of the impedance. The impedance rate of change may likewise be calculated according to any suitable manner. For example, the digital device may maintain prior values of tissue impedance and calculate a rate of change by comparing a current tissue impedance value or values with the prior values. Also, it will be appreciated that the routine 1350 assumes that the impedance threshold is a rate of change. In embodiments where the impedance threshold is a value, 1354 may be omitted. If the tissue impedance rate of change (or impedance itself) is greater than the threshold (1356), then the impedance threshold flag may be set. The digital device may continue to the next routing at 1360.

FIG. 73C illustrates one embodiment of a routine 1362 that may be performed by the digital device to provide one or more power curves to a tissue bite. At 1364, power may be delivered to the tissue, for example, as described above with respect to 1334 of FIG. 70. The digital device may direct the delivery of the power curve, for example, by applying the power curve to find a corresponding power for each sensed tissue impedance, modulating the corresponding power onto a drive signal provided to the first and second electrodes A20, A22, the transducer 114, etc.

At 1366, the digital device may calculate the total accumulated energy delivered to the tissue. For example, the digital device may monitor the total time of power curve delivery and the power delivered at each time. Total energy may be calculated from these values. At 1368, the digital device may determine whether the total energy is greater than or equal to a next energy threshold, for example, similar to the manner described above with respect to 1334 of FIG. 70. If the next energy threshold is not met, the current power curve may continue to be applied at 1378 and 1364.

If the next energy threshold is met at 1368, then at 1370, the digital device may determine whether the impedance threshold flag is set. The state of the impedance threshold flag may indicate whether the impedance threshold has been met. For example, the impedance threshold flag may have been set by the routine 1350 if the impedance threshold has been met. If the impedance flag is not set (e.g., the impedance threshold is not met), then the digital device may determine, at 1372, whether any more aggressive power curves remain to be implemented. If so, the digital device may point the routine 1362 to the next, more aggressive power curve at 1374. The routine 1362 may continue (1378) to deliver power according to the new power curve at 1364. If all available power curves have been applied, then the digital device may disable calculating and checking of accumulated energy for the remainder of the tissue operation at 1376.

If the impedance flag is set at 1370 (e.g., the impedance threshold has been met), then the digital device may disable calculating and checking of accumulated energy for the remainder of the tissue operation at 1376. It will be appreciated that, in some embodiments, accumulated energy calculation may be continued, while 1370, 1372, 1374, and 1376 may be discontinued. For example, the generator 102 and/or digital device may implement an automated shut-off when accumulated energy reaches a predetermined value.

Figure 74:
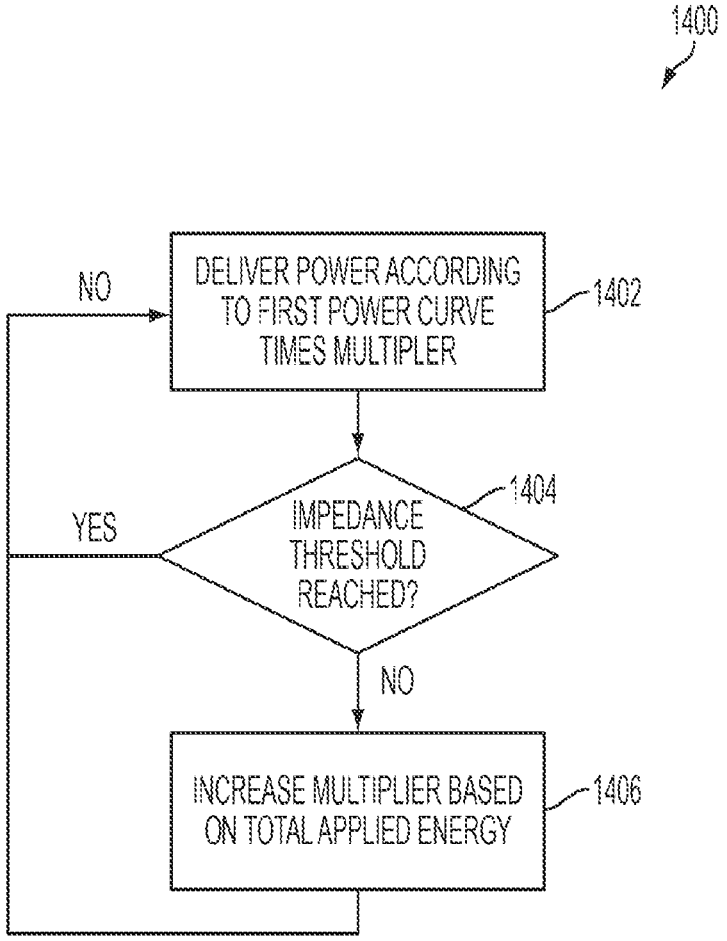
FIG. 74 illustrates one embodiment of a process flow for applying one or more power curves to a tissue bite.

FIG. 74 illustrates one embodiment of a process flow 1400 for applying one or more power curves to a tissue bite. For example, the process flow 1400 may be implemented by the generator 102 (e.g., the digital device of the generator 102). At 1402, the generator 102 may deliver a power curve to the tissue. The power curve may be derived by applying a multiplier to a first power curve. At 1404, the generator 102 may determine if the impedance threshold has been met. If the impedance threshold has not been met, the generator 102 may increase the multiplier as a function of the total applied energy. This may have the effect of increasing the aggressiveness of the applied power curve. It will be appreciated that the multiplier may be increased periodically or continuously. For example, the generator 102 may check the impedance threshold (1404) and increase the multiplier (1406) at a predetermined periodic interval. In various embodiments, the generator 102 may continuously check the impedance threshold (1404) and increase the multiplier (1406). Increasing the multiplier as a function of total applied energy may be accomplished in any suitable manner. For example, the generator 102 may apply a deterministic equation that receives total received energy as input and provides a corresponding multiplier value as output. Also, for example, the generator 102 may store a look-up table that comprises a list of potential values for total applied energy and corresponding multiplier values. According to various embodiments, the generator 102 may provide a pulsed drive signal to tissue (e.g., via one of the surgical devices 104, 106). According to various embodiments, when the impedance threshold is met, the multiplier may be held constant. The generator 102 may continue to apply power, for example, until a termination threshold is reached. The termination threshold may be constant, or may depend on the final value of the multiplier.

In some embodiments utilizing a pulsed drive signal, the generator 102 may apply one or more composite load curves to the drive signal, and ultimately to the tissue. Composite load curves, like other power curves described herein, may define a level of power to be delivered to the tissue as a function of a measured tissue property or properties (e.g., impedance). Composite load curves may, additionally, define pulse characteristics, such as pulse width, in terms of the measured tissue properties.

Figure 75:
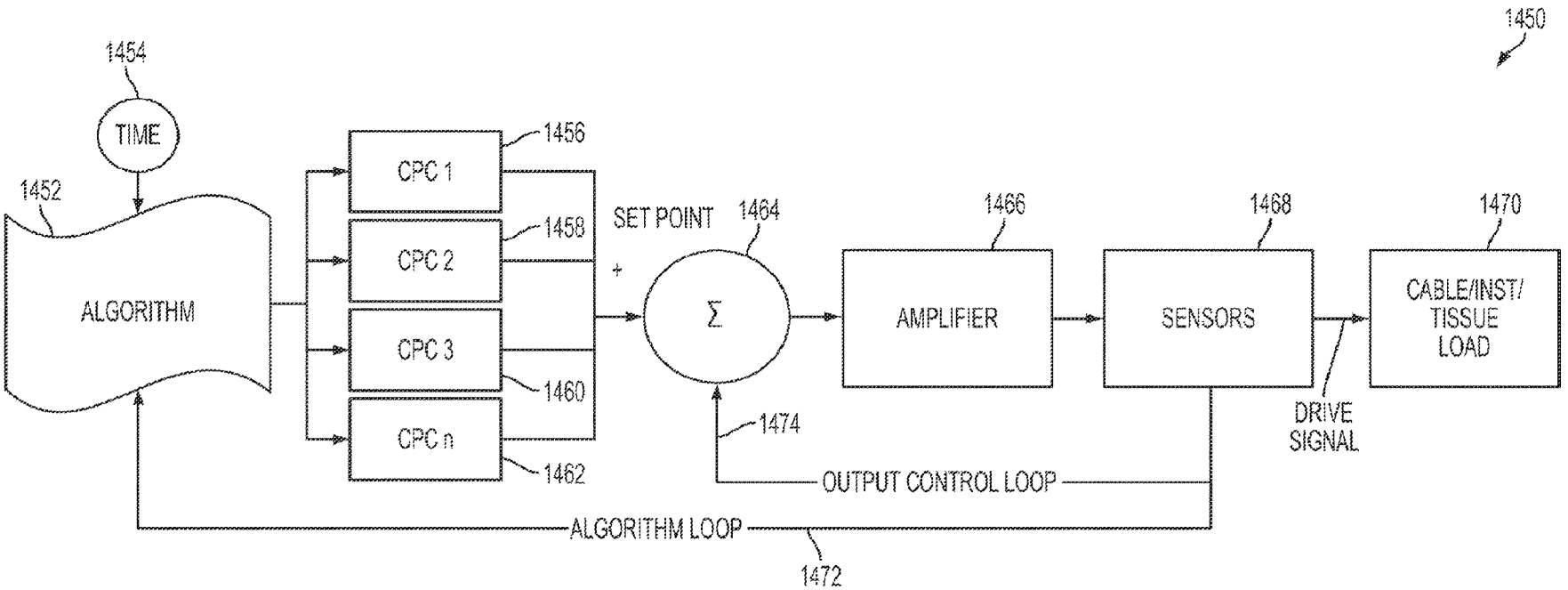
FIG. 75 illustrates one embodiment of a block diagram describing the selection and application of composite load curves by the generator of FIG. 1.

FIG. 75 illustrates one embodiment of a block diagram 1450 describing the selection and application of composite load curves by the generator 102. It will be appreciated that the block diagram 1450 may be implemented with any suitable type of generator or surgical device. According to various embodiments, the block diagram 1450 may be implemented utilizing an electrosurgical device, such as the device 106 described above with respect to FIGS. 4-7. Also, in various embodiments, the block diagram 1450 may be implemented with a ultrasonic surgical device, such as the surgical device 104 described above with respect to FIGS. 2-3. In some embodiments, the block diagram 1450 may be utilized with a surgical device having cutting as well as coagulating capabilities. For example, an RF surgical device, such as the device 106, may comprise a cutting edge, such as the blade 175 for severing tissue either before or during coagulation.

Referring back to FIG. 75, an algorithm 1452 may be executed, for example by a digital device of the generator 102 to select and apply composite load curves 1456, 1458, 1460, 1462. The algorithm 1452 may receive a time input from a clock 1454 and may also receive loop input 1472 from sensors 1468. The loop input 1472 may represent properties or characteristics of the tissue that may be utilized in the algorithm 1452 to select and/or apply a composite load curve. Examples of such characteristics may comprise, for example, current, voltage, temperature, reflectivity, force applied to the tissue, resonant frequency, rate of change of resonant frequency, etc. The sensors 1468 may be dedicated sensors (e.g., thermometers, pressure sensors, etc.) or may be software implemented sensors for deriving tissue characteristics based on other system values (e.g., for observing and/or calculating voltage, current, tissue temperature, etc., based on the drive signal). The algorithm 1452 may select one of the composite load curves 1456, 1458, 1460, 1462 to apply, for example based on the loop input 1472 and/or the time input from the clock 1454. Although four composite load curves are shown, it will be appreciated that any suitable number of composite load curves may be used.

The algorithm 1452 may apply a selected composite load curve in any suitable manner. For example, the algorithm 1452 may use the selected composite load curve to calculate a power level and one or more pulse characteristics based on tissue impedance (e.g., currently measured tissue impedance may be a part of, or may be derived from, the loop input) or resonant frequency characteristics of a ultrasonic device 104. Examples of pulse characteristics that may be determined based on tissue impedance according to a composite load curve may include pulse width, ramp time, and off time.

At set point 1464, the derived power and pulse characteristics may be applied to the drive signal. In various embodiments, a feedback loop 1474 may be implemented to allow for more accurate modulation of the drive signal. At the output of the set point 1464, the drive signal may be provided to an amplifier 1466, which may provide suitable amplification. The amplified drive signal may be provided to a load 1470 (e.g., via sensors 1468). The load 1470 may comprise the tissue, the surgical device 104, 106, and/or any cable electrically coupling the generator 102 with the surgical device 104, 106 (e.g., cables 112, 128).

Figure 76:
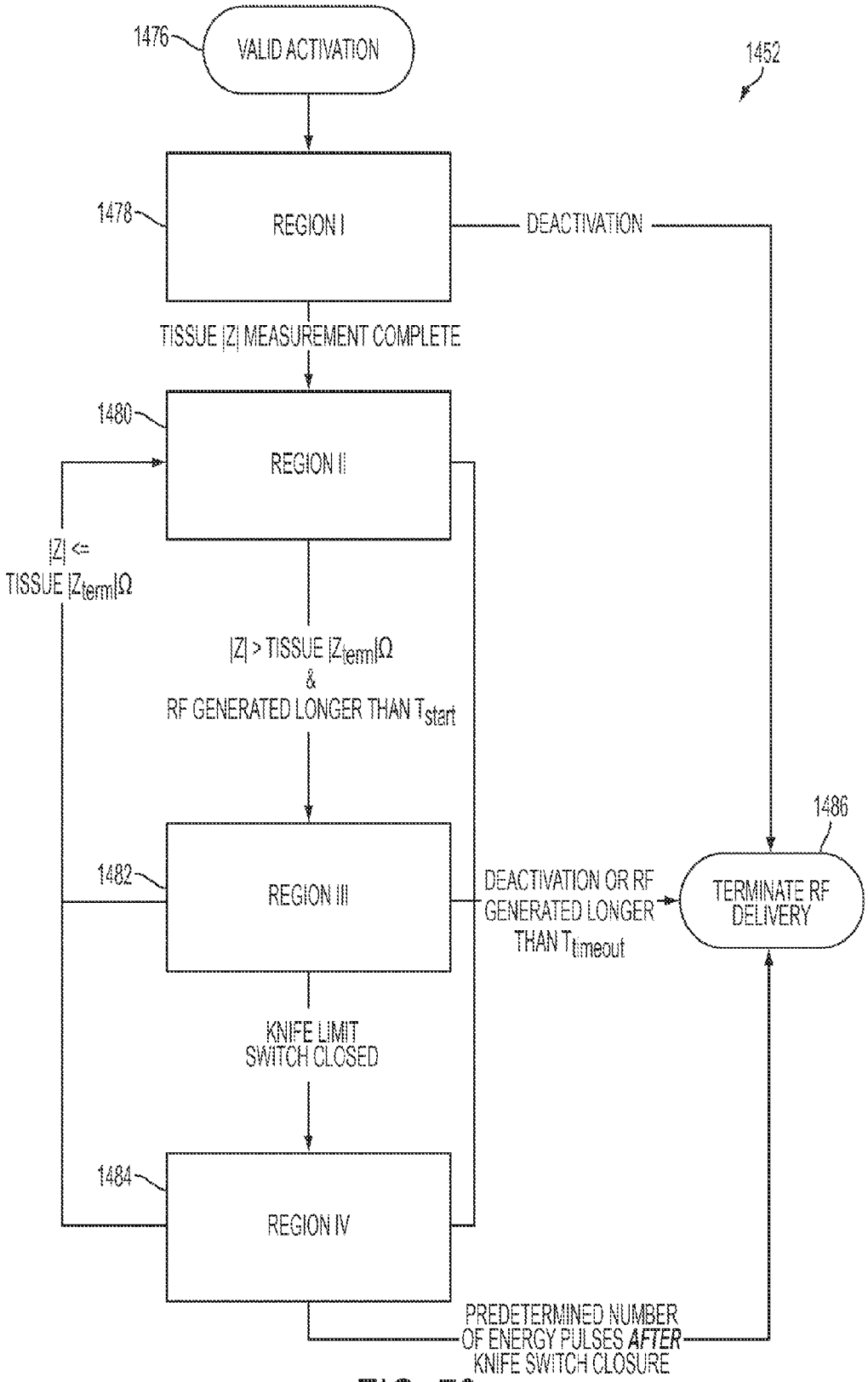
FIG. 76 illustrates shows a process flow illustrating one embodiment of the algorithm of FIG. 75, as implemented by the generator of FIG. 1.

FIG. 76 illustrates shows a process flow illustrating one embodiment of the algorithm 1452, as implemented by the generator 102 (e.g., by a digital device of the generator 102). The algorithm 1452 may be activated at 1476. It will be appreciated that the algorithm 1452 may be activated in any suitable manner. For example, the algorithm 1452 may be activated by a clinician upon actuation of the surgical device 104, 106 (e.g., by pulling or otherwise actuating a jaw closure trigger 138, 142, switch, handle, etc.).

According to various embodiments, the algorithm 1452 may comprise a plurality of regions 1478, 1480, 1482, 1484. Each region may represent a different stage of the cutting and coagulation of a tissue bite. For example, in the first region 1478, the generator 102 may perform an analysis of initial tissue conditions (e.g., impedance). In the second region 1480, the generator 102 may apply energy to the tissue in order to prepare the tissue for cutting. In the third or cut region 1482, the generator 102 may continue to apply energy while the surgical device 104, 106 cuts the tissue (e.g., with the electrosurgical device 106, cutting may be performed by advancing the blade A18). In the fourth or completion region 1484, the generator 102 may apply energy post-cut to complete coagulation.

Referring now to the first region 1478, the generator 102 may measure any suitable tissue condition or conditions including, for example, current, voltage, temperature, reflectivity, force applied to the tissue, etc. In various embodiments, an initial impedance of the tissue may be measured according to any suitable manner. For example, the generator 102 may modulate the drive signal to provide a known voltage or currency to the tissue. Impedance may be derived from the known voltage and the measured current or vice versa. It will be appreciated that tissue impedance may alternately or additionally be measured in any other suitable manner. According to the algorithm 1452, the generator 102 may proceed from the first region 1478 to the second region 1480. In various embodiments, the clinician may end the algorithm 1452 in the first region 1478, for example, by deactivating the generator 102 and/or the surgical device 104, 106. If the clinician terminates the algorithm 1542, RF (and/or ultrasonic) delivery may also be terminated at 1486.

In the second region 1480, the generator 102 may begin to apply energy to the tissue via the drive signal to prepare the tissue for cutting. Energy may be applied according to the composite load curves 1456, 1458, 1460, 1462, as described below. Applying energy according to the second region 1480 may comprise modulating pulses onto the drive signal according to some or all of the composite load curves 1456, 1458, 1460, 1462. In various embodiments, the composite load curves 1456, 1458, 1460, 1462 may be successively applied in order of aggressiveness (e.g., to accommodate various types of tissue-volume clamped in the instrument jaws).

The first composite load curve 1456 may be applied first. The generator 102 may apply the first composite load curve 1456 by modulating one or more first composite load curve pulses onto the drive signal. Each first composite load curve pulse may have a power and pulse characteristics determined according to the first composite load curve and considering measured tissue impedance. Measured tissue impedance for the first pulse may be the impedance measured at the first region 1478. In various embodiments, the generator 102 may utilize all or a portion of the first composite load curve pulses to take additional measurements of tissue impedance or resonant frequency. The additional measurements may be used to determine the power and other pulse characteristics of a subsequent pulse or pulses.

Figure 77:
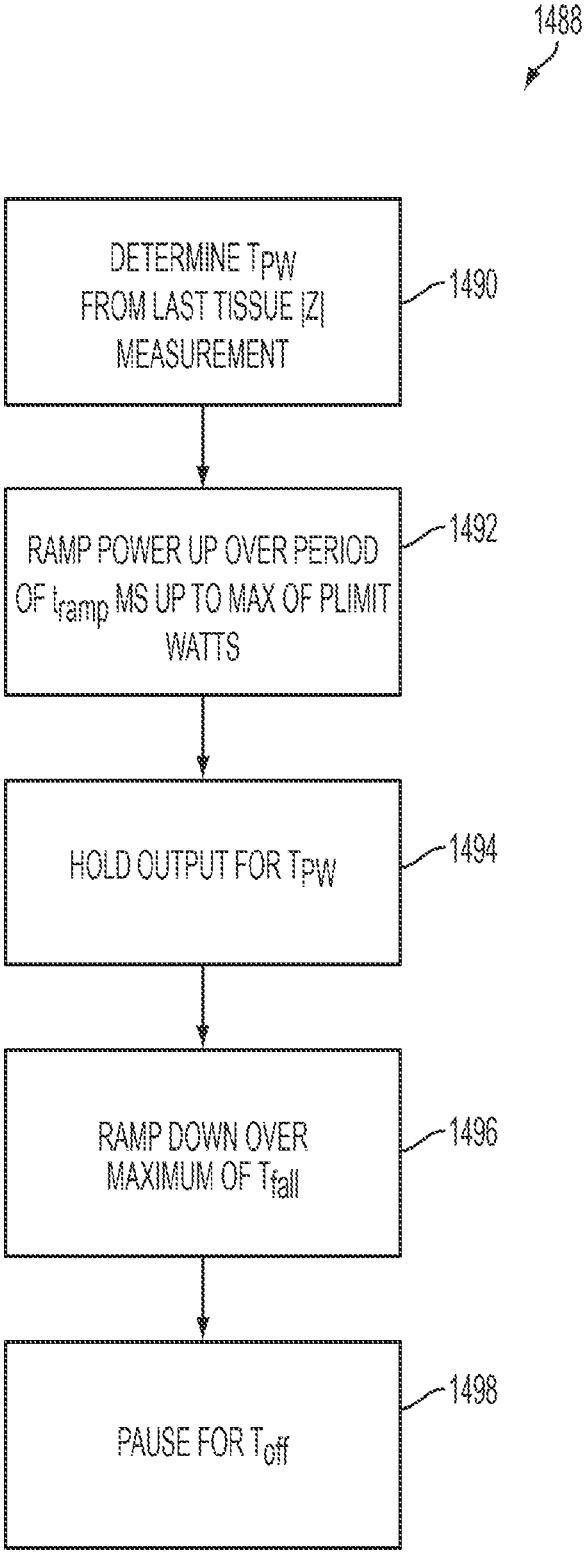
FIG. 77 illustrates one embodiment of a process flow for generating a first composite load curve pulse.

FIG. 77 illustrates one embodiment of a process flow 1488 for generating a first composite load curve pulse. The process flow 1488 may be executed by the generator 102 (e.g., by a digital device of the generator 102), for example, as a part of the algorithm 1452. At 1490, the generator 102 may calculate a pulse width ($T_{pw}$). The pulse width may be determined considering the most recent measured tissue impedance (Z) and according to the first composite load curve 1456.

At 1492, the generator 102 may ramp the power of the drive signal up to a pulse power ($P_{Limit}$) over a ramp time ($t_{ramp}$), thereby applying the pulse to the tissue. The pulse power may be determined, again, considering the most recent measured tissue impedance (Z) and according to the first composite load curve 1456. The ramp time may be determined according to the composite load curve considering tissue impedance or may be constant (e.g., constant for all first composite load curve pulses, constant for all pulses, etc.). The generator 102 may apply the pulse power to the drive signal in any suitable manner including, for example, modulating a current and/or voltage provided by the drive signal. According to various embodiments, the drive signal may be an alternating current (A/C) signal, and therefore the pulse itself may comprise multiple cycles of the drive signal.

The drive signal may be held at the pulse power for the pulse width at 1494. At the conclusion of the pulse, the drive signal may be ramped down, at 1496, over a fall time ($T_{fall}$). The fall time may be determined according to the first composite load curve considering tissue impedance, or may be constant (e.g., constant for all first composite load curve pulses, constant for all pulses, etc.). It will be appreciated that, depending on the embodiment, the ramp time and fall time may or may not be considered part of the pulse width. At 1498, the generator 102 may pause for an off time ($T_{,off}$). Like the ramp time and fall time, the off time may be determined according to the first composite load curve considering tissue impedance, or may be constant (e.g., constant for all first composite load curve pulses, constant for all pulses, etc.).

At the completion of the off time, the generator 102 may repeat the process flow 1488 as long as the first composite load curve 1456 is applied. According to various embodiments, the generator 102 may apply the first composite load curve 1456 for a predetermined amount of time. Accordingly, the process flow 1488 may be repeated until the predetermined amount of time has elapsed (e.g., as determined based on the time input received from the clock 1454). Also, in various embodiments, the first composite load curve may be applied for a predetermined number of pulses. Because the applied pulse width varies according to measured tissue impedance, the total time that the first composite load curve is applied may also vary with measured tissue impedance. According to various embodiments, the first composite load curve 1456 (as well as the other composite load curves 1458, 1460, 1462) may specify decreasing pulse widths as tissue impedance increases. Therefore, a higher initial tissue impedance may lead to less time spent in the first composite load curve.

Upon completion of the first composite load curve 1456, the generator 102 may successively apply the remaining consolidated load curves 1458, 1460, 1462 throughout the application of the second region 1480. Each load curve 1458, 1460, 1462 may be applied in a manner similar to that of the load curve 1456 described above. For example, pulses according to a current load curve may be generated until the completion of that load curve (e.g., the expiration of a predetermined amount of time or a predetermined number of pulses). The predetermined number of pulses may be the same for each composite load curve 1456, 1458, 1460, 1462 or may be different. According to various embodiments, pulses according to the load curves 1458, 1460, 1462 may be generated in a manner similar to process flow 1488, except that pulse power, pulse width and, in some embodiments, ramp time, fall time, and off time, may be derived according to the current composite load curve.

The second region 1480 may be terminated upon the occurrence of various events. For example, if the total RF application time has exceeded a timeout time, then the generator 102 may end the tissue operation by terminating RF (and/or ultrasonic) delivery at 1486. Also, various events may cause the generator 102 to transition from the second region 1480 to the third region 1482. For example, the generator 102 may transition to the third region 1482 when the tissue impedance (Z) exceeds a threshold tissue impedance ($Z_{term}$) and RF energy has been delivered for at least more than a minimum time ($T_{start}$). The threshold tissue impedance may be an impedance and/or an impedance rate of change indicating that the tissue bite is adequately prepared for cutting by the blade 175.

According to various embodiments, if the final load curve 1462 is completed in the second region 1480 before completion of the second region 1480, then the final power curve 1462 may be continuously applied, for example, until the tissue impedance threshold is met, the maximum second region time is reached and/or the timeout time is reached. Also, it will be appreciated that, with some tissue cuts, the second region 1480 may be completed before all available consolidated load curves 1456, 1458, 1460, 1462 are executed.

At the third region 1482, the generator 102 may continue to modulate pulses onto the drive signal. Generally, third region pulses may be modulated onto the drive signal according to any suitable manner including, for example, that described above with reference to the process flow 1488. The power and pulse characteristics of the third region pulses may be determined according to any suitable method and, in various embodiments, may be determined based on the composite load curve that was being executed at the completion of the second region 1480 (the current load curve). According to various embodiments, the current load curve may be utilized to determine the pulse power of third region pulses, while the pulse characteristics (e.g., pulse width, ramp time, fall time, off time, etc.) may be constant regardless of composite load curve. In some embodiments, the third region 1482 may utilize a third-region-specific composite load curve that may be one of the load curves 1456, 1458, 1460, 1462 utilized in the second region 1480, or may be a different composite load curve (not shown).

The generator 102 may continue to execute the third region 1482 until receiving an indication that the tissue cut is complete. In embodiments utilizing surgical implements having a blade, such as 175, the indication may be received when the blade 175 reaches its distal-most position, as shown in FIG. 6. This may trip a knife limit sensor (not shown) indicating that the blade 175 has reached the end of its throw. Upon receiving the indication that the tissue cut is complete, the generator 102 may continue to the fourth region 1484. It will also be appreciated that, in some embodiments, the generator 102 may transition from the third region 1482 directly to RF (and/or ultrasonic) termination at 1486, for example, if the timeout time has been reached.

In the fourth region 1484, the generator 102 may provide an energy profile designed to complete coagulation of the now-cut tissue. For example, according to various embodiments, the generator 102 may provide a predetermined number of pulses. The pulses may be provided in a manner similar to that described above with respect to the process flow 1488. The power and pulse characteristics of the pulses may be determined according to any suitable manner. For example, power and pulse characteristics of the fourth region pulses may be determined based on the current composite load curve, the third-region-specific load curve, or a fourth-region-specific composite load curve. In some embodiments, power may be determined based on the current composite load curve, while pulse characteristics may be fourth region-specific. Also, according to various embodiments, the power and pulse characteristics of fourth region pulses may be determined independent of the current composite load curve.

Figure 78:
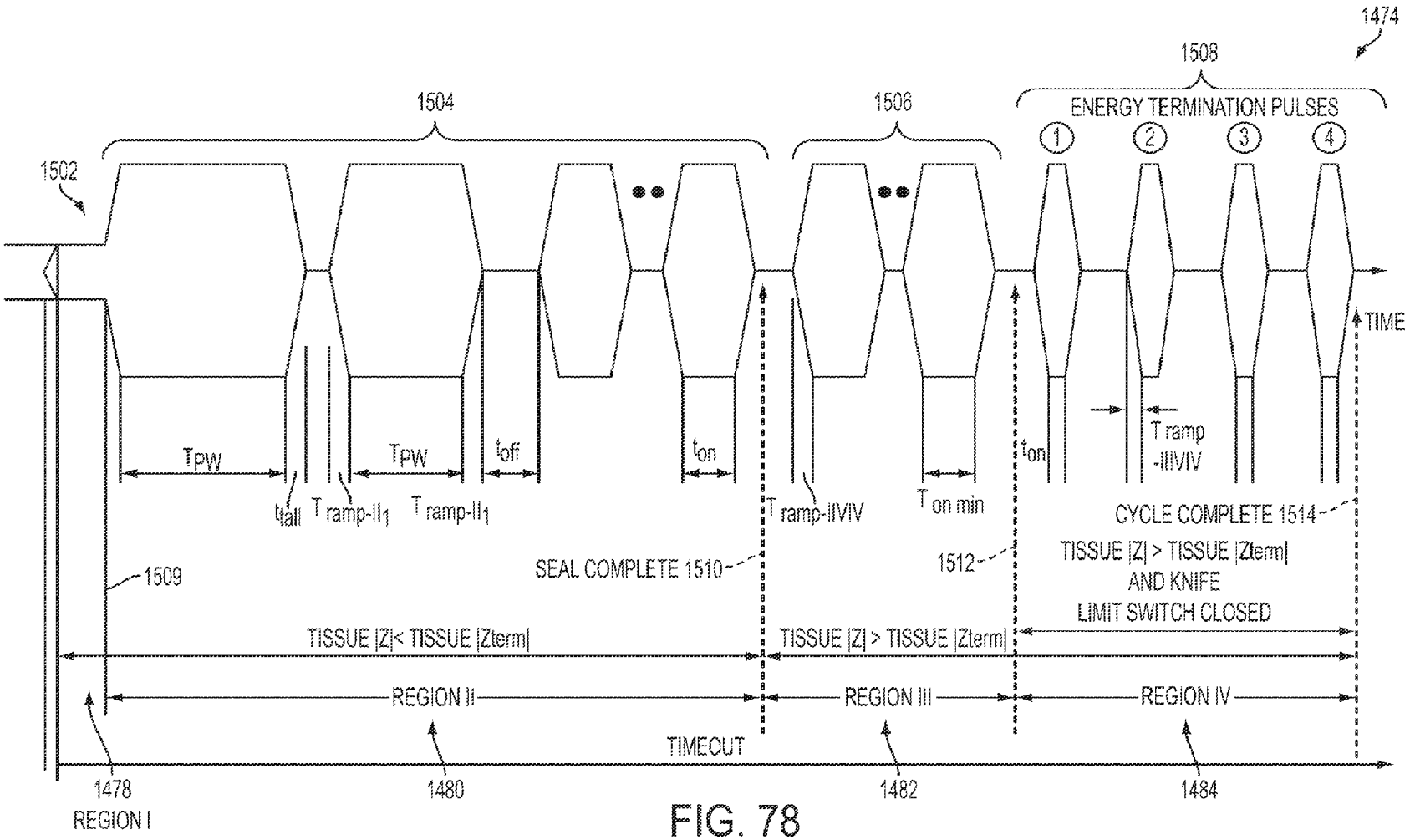
FIG. 78 illustrates one embodiment of a pulse timing diagram illustrating an example application of the algorithm of FIG. 76 by the generator of FIG. 1.

FIG. 78 illustrates one embodiment of a pulse timing diagram 1474 illustrating an example application of the algorithm 1452 by the generator 102 (e.g., by a digital device of the generator 102). A first region pulse 1502 is shown in the first region 1478. The first region pulse 1502 may be utilized, as described, to measure an initial tissue impedance. At the completion of the first region pulse (1509), second region 1480 may begin with second region pulses 1504 applied. The second region pulses 1504 may be applied according to the various composite load curves 1456, 1458, 1460, 1462, for example, as described herein. In the example diagram 1474, the second region 1480 concludes at 1510 when the tissue reaches the threshold impedance ($Z_{term}$). The third region 1482 is then implemented, with third region pulses 1506, as described above, applied until a knife limit signal is received at 1512. At that point, the fourth region 1484 may commence, with fourth region pulses 1508, as described above, applied until cycle completion at 1514.

According to various embodiments, the generator 102 may implement a user interface in conjunction with the algorithm 1452. For example, the user interface may indicate the current region of the algorithm. The user interface may be implemented visually and/or audibly. For example, the generator 102 may comprise a speaker for generating audible tones or other audible indication. At least one audible indication may correspond to the second region 1480. The third and fourth regions 1482, 1484 may also have region-specific audible indications. According to various embodiments, the first region 1478 may have a region-specific audible indication as well. According to various embodiments, the audible indications may comprise pulsed tones generated by the generator 102. The frequency of the tones and/or the pitch of the tones themselves may indicate the current region. In addition to, or instead of, the audible indications, the generator 102 may also provide a visual indication of the current region (e.g., on output device 147). It will be appreciated that the clinician may utilize the described user interface to properly use the generator 102 and associated surgical devices 104, 106. For example, the indication of the second region 1480 may let the clinician know that tissue treatment has begun. The indication of the third region 1482 may let the clinician know that the tissue is ready for the cutting operation. The indication of the fourth region 1484 may let the clinician know that the cutting operation is complete. The cessation of the indication and/or a final indication may indicate that the total cutting/coagulation operation is complete.

Figure 79:
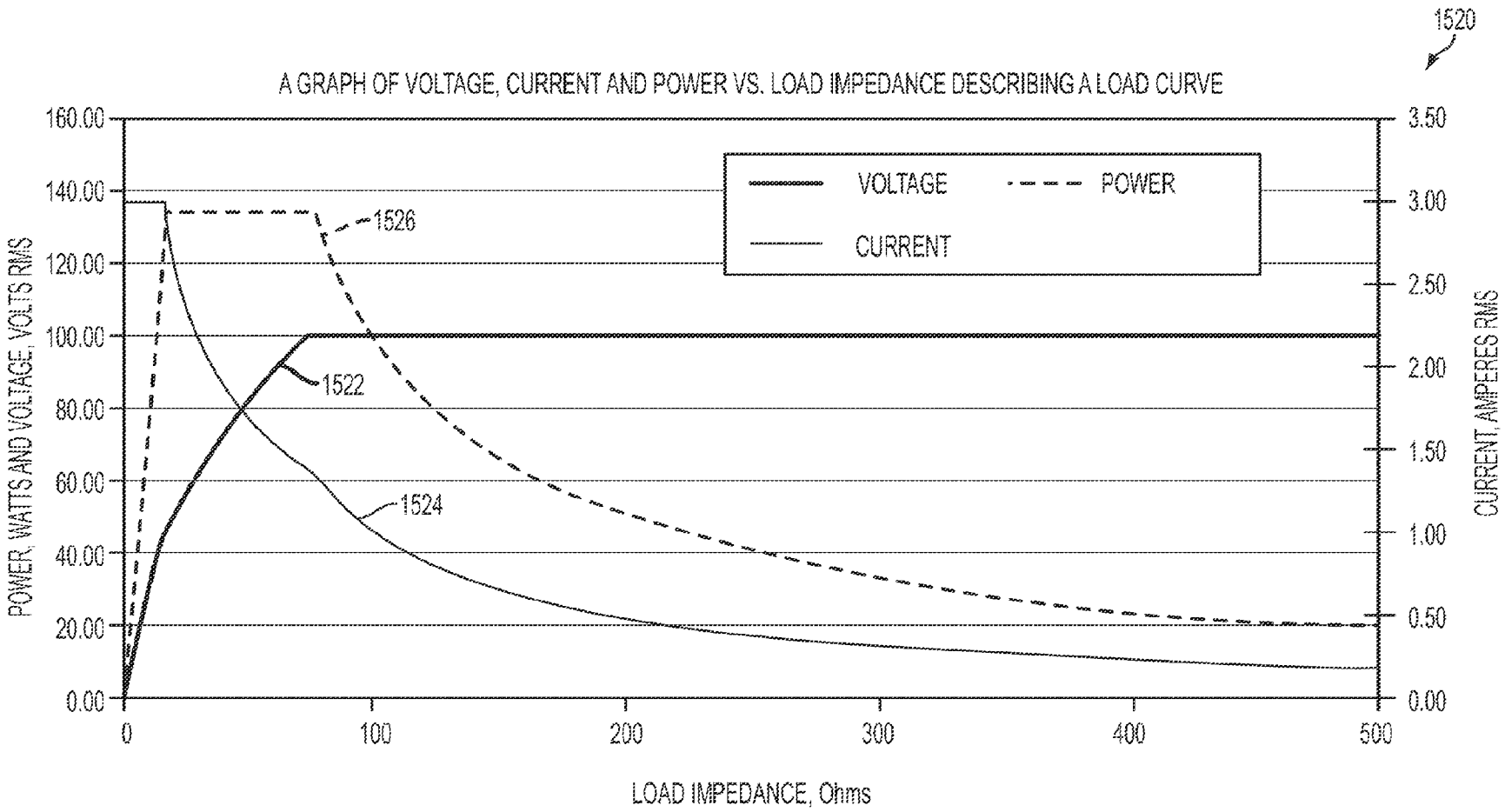
FIG. 79 illustrates a graphical representation of drive signal voltage, current and power according to an example composite load curve.

FIG. 79 illustrates a graphical representation of drive signal voltage, current and power according to an example load curve 1520. In the chart 1520, drive signal voltage is represented by line 1522, drive signal current is represented by line 1524 and drive signal power is represented by line 1526. Pulse width is not indicated in FIG. 79. In various embodiments, the values for voltage 1522, current 1524 and power 1526 indicated by the graph 1520 may represent possible values within a single pulse. Accordingly, the load curve 1520 may be expressed as a composite load curve by adding a curve (not shown) indicating a pulse width as a function of tissue impedance or another tissue condition. As shown for the load curve 1520, the maximum voltage 1522 is 100 Volts Root Mean Square (RMS), the maximum current is 3 Amps RMS and the maximum power is 135 Watts RMS.

FIGS. 79-84 illustrate graphical representations of various example composite load curves 1530, 1532, 1534, 1536, 1538, 1540. Each of the composite load curves 1530, 1532, 1534, 1536, 1538, 1540 may indicate both pulse power and pulse width in terms of measured tissue impedance. The composite load curves 1530, 1532, 1534, 1536 may be implemented either in isolation or as part of a pattern of successively more aggressive composite load curves, as described above with respect to the algorithm 1452.

Figure 80:
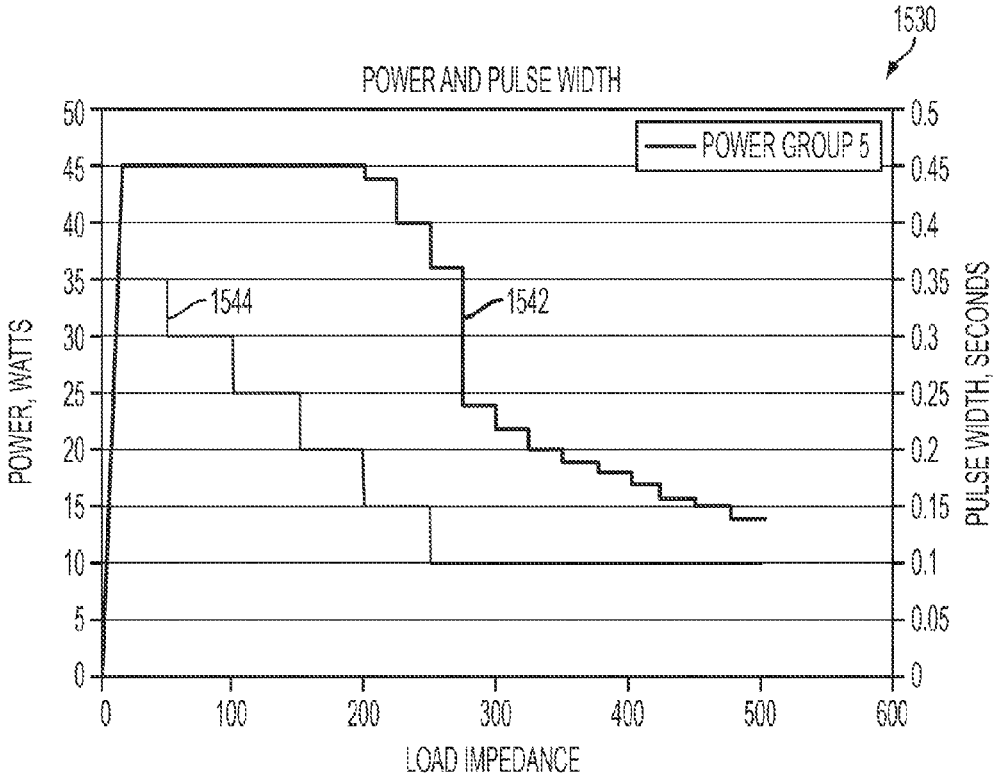
FIGS. 80-85 illustrate a graphical representations of example composite load curves.

FIG. 80 illustrates a graphical representation of a first example composite load curve 1530. The composite load curve 1530 may have a maximum pulse power of 45 Watts RMS and a maximum pulse width of 0.35 seconds. In FIG. 80, the power as a function of tissue impedance is indicated by 1542, while the pulse width as a function of tissue impedance is indicated by 1544. Table 1 below illustrates values for the composite load curve 1530 for tissue impedances from 0Ω to 475Ω.

TABLE 1

| Load, Ohms | V Lim, RMS | I Lim, RMS | P Lim, W | PW, Sec |
|---|---|---|---|---|
| 0-24 | 85 | 1.4 | 45 | 0.35 |
| 25-49 | 85 | 1.4 | 45 | 0.35 |
| 50-74 | 85 | 1.4 | 45 | 0.3 |
| 75-99 | 85 | 1.4 | 45 | 0.3 |
| 100-124 | 85 | 1.4 | 45 | 0.25 |
| 125-149 | 85 | 1.4 | 45 | 0.25 |
| 150-174 | 85 | 1.4 | 45 | 0.2 |
| 175-199 | 85 | 1.4 | 45 | 0.2 |
| 200-224 | 85 | 1.4 | 44 | 0.15 |
| 225-249 | 85 | 1.4 | 40 | 0.15 |
| 250-274 | 85 | 1.4 | 36 | 0.1 |
| 275-299 | 85 | 0.31 | 24 | 0.1 |
| 300-324 | 85 | 0.28 | 22 | 0.1 |

TABLE 1-continued

| Load, Ohms | V Lim, RMS | I Lim, RMS | P Lim, W | PW, Sec |
|---|---|---|---|---|
| 325-349 | 85 | 0.26 | 20 | 0.1 |
| 350-374 | 85 | 0.25 | 19 | 0.1 |
| 375-399 | 85 | 0.22 | 18 | 0.1 |
| 400-424 | 85 | 0.21 | 17 | 0.1 |
| 425-449 | 85 | 0.2 | 16 | 0.1 |
| 450-475 | 85 | 0.19 | 15 | 0.1 |
| 475+ | 85 | 0.15 | 14 | 0.1 |

In various embodiments, the composite load curve 1530 may be suited to smaller surgical devices and/or smaller tissue bites.

Figure 81:
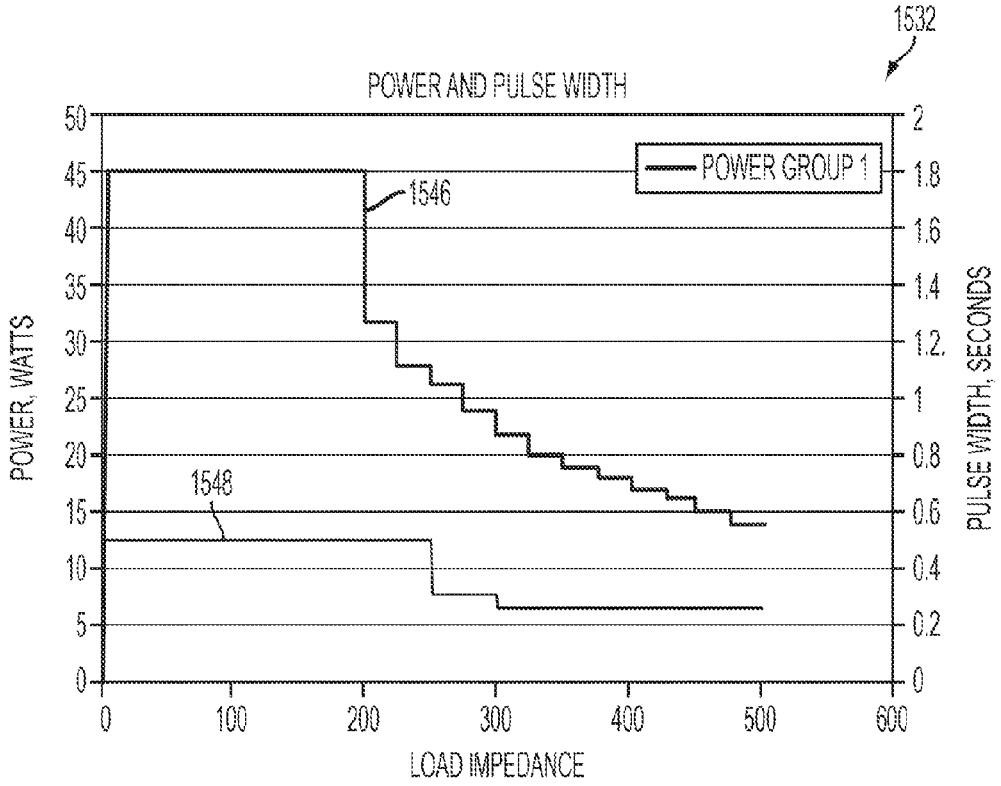

FIG. 81 illustrates a graphical representation of a second example composite load curve 1532. The composite load curve 1532 may have a maximum pulse power of 45 Watts RMS and a maximum pulse width of 0.5 seconds. In FIG. 81, the power as a function of tissue impedance is indicated by 1546, while the pulse width as a function of tissue impedance is indicated by 1548. Table 2 below illustrates values for the composite load curve 1532 for tissue impedances from 0Ω to 475Ω.

TABLE 2

| Load, Ohms | V Lim, RMS | I Lim, RMS | P Lim, W | PW, Sec |
|---|---|---|---|---|
| 0-24 | 85 | 3 | 45 | 0.5 |
| 25-49 | 85 | 2 | 45 | 0.5 |
| 50-74 | 85 | 1.4 | 45 | 0.5 |
| 75-99 | 85 | 1.1 | 45 | 0.5 |
| 100-124 | 85 | 0.9 | 45 | 0.5 |
| 125-149 | 85 | 0.7 | 45 | 0.5 |
| 150-174 | 85 | 0.55 | 45 | 0.5 |
| 175-199 | 85 | 0.48 | 45 | 0.5 |
| 200-224 | 85 | 0.42 | 32 | 0.5 |
| 225-249 | 85 | 0.38 | 28 | 0.5 |
| 250-274 | 85 | 0.33 | 26 | 0.3 |
| 275-299 | 85 | 0.31 | 24 | 0.3 |
| 300-324 | 85 | 0.28 | 22 | 0.25 |
| 325-349 | 85 | 0.26 | 20 | 0.25 |
| 350-374 | 85 | 0.25 | 19 | 0.25 |
| 375-399 | 85 | 0.22 | 18 | 0.25 |
| 400-424 | 85 | 0.21 | 17 | 0.25 |
| 425-449 | 85 | 0.2 | 16 | 0.25 |
| 450-475 | 85 | 0.19 | 15 | 0.25 |
| 475+ | 85 | 0.15 | 14 | 0.25 |

The composite load curve 1532 may be targeted at small, single vessel tissue bites and, according to various embodiments, may be a first composite power curve applied in region two 1480.

Figure 82:
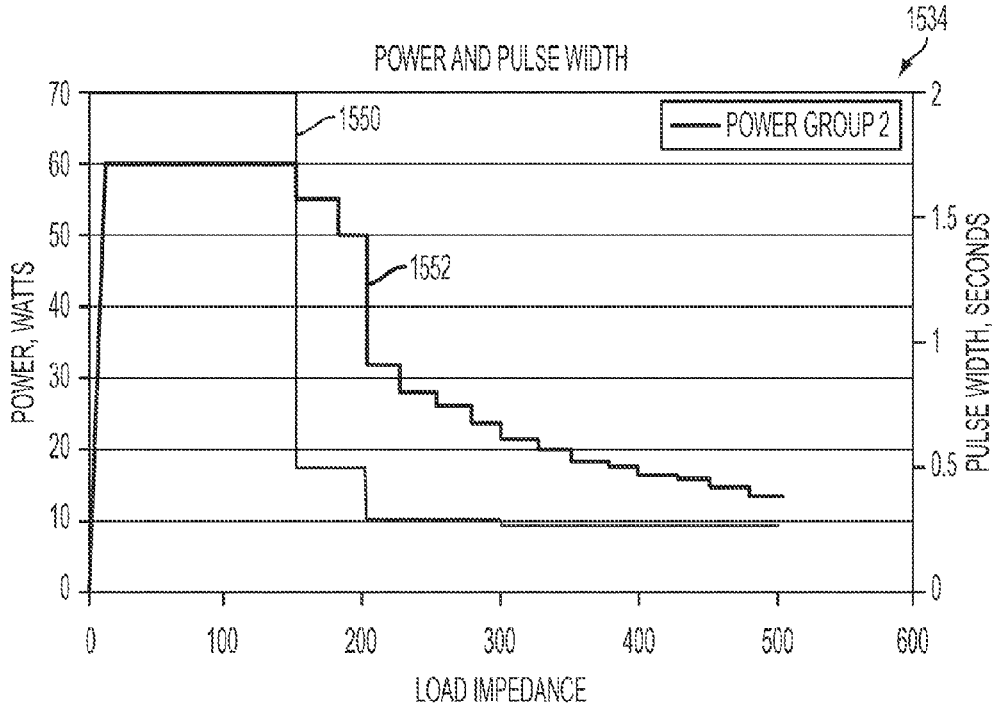

FIG. 82 illustrates a graphical representation of a third example composite load curve 1534. The composite load curve 1534 may have a maximum pulse power of 60 Watts RMS and a maximum pulse width of 2 seconds. In FIG. 82, the power as a function of tissue impedance is indicated by 1550, while the pulse width as a function of tissue impedance is indicated by 1552. Table 3 below illustrates values for the composite load curve 1534 for tissue impedances from 0Ω to 475Ω.

TABLE 3

| Load, Ohms | V Lim, RMS | I Lim, RMS | P Lim, W | PW, Sec |
|---|---|---|---|---|
| 0-24 | 85 | 3 | 60 | 2 |
| 25-49 | 85 | 3 | 60 | 2 |

TABLE 3-continued

| Load, Ohms | V Lim, RMS | I Lim, RMS | P Lim, W | PW, Sec |
|---|---|---|---|---|
| 50-74 | 100 | 3 | 60 | 2 |
| 75-99 | 100 | 3 | 60 | 2 |
| 100-124 | 100 | 3 | 60 | 2 |
| 125-149 | 100 | 3 | 60 | 2 |
| 150-174 | 100 | 3 | 55 | 0.5 |
| 175-199 | 100 | 3 | 50 | 0.5 |
| 200-224 | 85 | 0.42 | 32 | 0.3 |
| 225-249 | 85 | 0.38 | 28 | 0.3 |
| 250-274 | 85 | 0.33 | 26 | 0.3 |
| 275-299 | 85 | 0.31 | 24 | 0.3 |
| 300-324 | 85 | 0.28 | 22 | 0.25 |
| 325-349 | 85 | 0.26 | 20 | 0.25 |
| 350-374 | 85 | 0.25 | 19 | 0.25 |
| 375-399 | 85 | 0.22 | 18 | 0.25 |
| 400-424 | 85 | 0.21 | 17 | 0.25 |
| 425-449 | 85 | 0.2 | 16 | 0.25 |
| 450-475 | 85 | 0.19 | 15 | 0.25 |
| 475+ | 85 | 0.15 | 14 | 0.25 |

The composite load curve 1534 may be more aggressive than the prior curve 1532 by virtue of its generally higher power. The composite load curve 1534 may also, initially, have higher pulse widths than the prior curve 1532, although the pulse widths of the composite load curve 1534 may begin to drop at just 150Ω. According to various embodiments, the composite load curve 1536 may be utilized in the algorithm 1542 as a load curve implemented sequentially after the composite load curve 1532.

Figure 83:
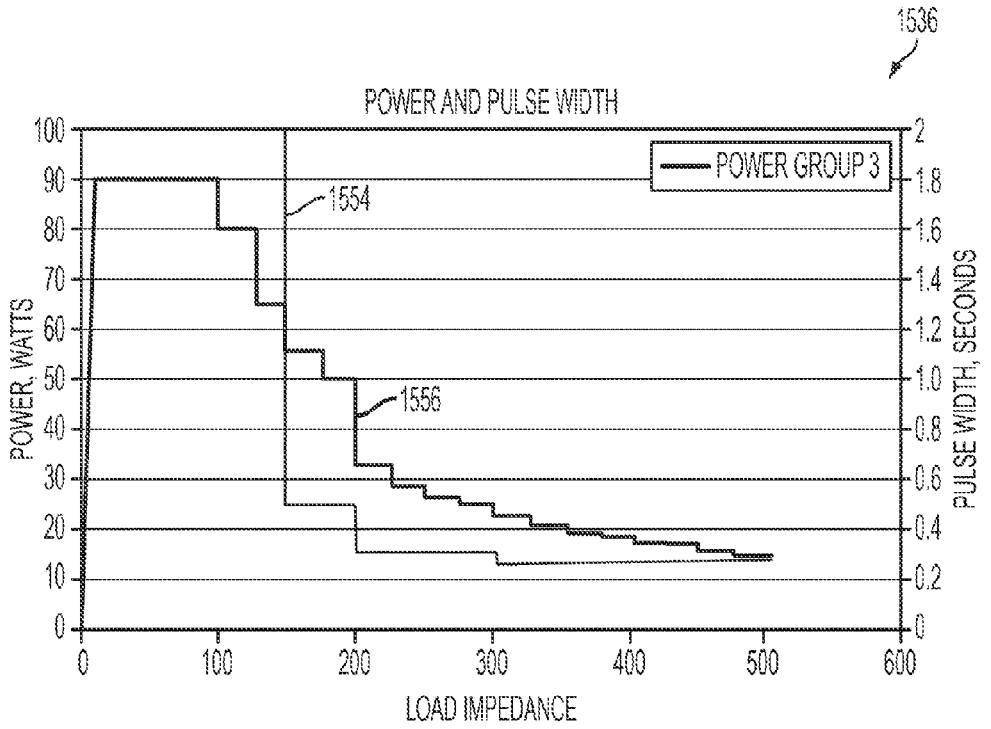

FIG. 83 illustrates a graphical representation of a fourth example composite load curve 1536. The composite load curve 1536 may have a maximum pulse power of 90 Watts RMS and a maximum pulse width of 2 seconds. In FIG. 83, the power as a function of tissue impedance is indicated by 1554, while the pulse width as a function of tissue impedance is indicated by 1556. Table 4 below illustrates values for the composite load curve 1536 for tissue impedances from 0Ω to 475Ω.

TABLE 4

| Load, Ohms | V Lim, RMS | I Lim, RMS | P Lim, W | PW, Sec |
|---|---|---|---|---|
| 0-24 | 85 | 3 | 90 | 2 |
| 25-49 | 85 | 3 | 90 | 2 |
| 50-74 | 100 | 3 | 90 | 2 |
| 75-99 | 100 | 3 | 90 | 2 |
| 100-124 | 100 | 3 | 80 | 2 |
| 125-149 | 100 | 3 | 65 | 2 |
| 150-174 | 100 | 3 | 55 | 0.5 |
| 175-199 | 100 | 3 | 50 | 0.5 |
| 200-224 | 85 | 0.42 | 32 | 0.3 |
| 225-249 | 85 | 0.38 | 28 | 0.3 |
| 250-274 | 85 | 0.33 | 26 | 0.3 |
| 275-299 | 85 | 0.31 | 24 | 0.3 |
| 300-324 | 85 | 0.28 | 22 | 0.25 |
| 325-349 | 85 | 0.26 | 20 | 0.25 |
| 350-374 | 85 | 0.25 | 19 | 0.25 |
| 375-399 | 85 | 0.22 | 18 | 0.25 |
| 400-424 | 85 | 0.21 | 17 | 0.25 |
| 425-449 | 85 | 0.2 | 16 | 0.25 |
| 450-475 | 85 | 0.19 | 15 | 0.25 |
| 475+ | 85 | 0.15 | 14 | 0.25 |

The composite load curve 1536 may, again, be more aggressive than the prior curve 1534 and, therefore, may be implemented sequentially after the curve 1534 in the algorithm 1452. Also, according to various embodiments, the composite load curve 1536 maybe suited to larger tissue bundles.

Figure 84:
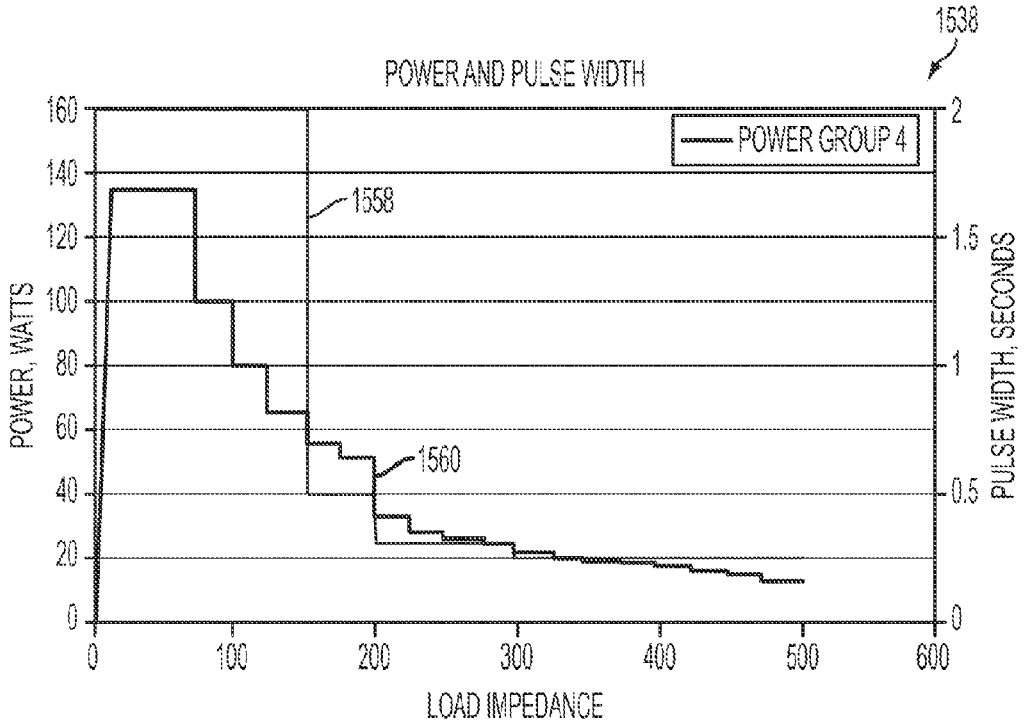

FIG. 84 illustrates a graphical representation of a fifth example composite load curve 1538. The composite load curve 1538 may have a maximum pulse power of 135 Watts RMS and a maximum pulse width of 2 seconds. In FIG. 84, the power as a function of tissue impedance is indicated by 1558, while the pulse width as a function of tissue impedance is indicated by 1560. Table 5 below illustrates values for the composite load curve 1538 for tissue impedances from 0Ω to 475Ω.

TABLE 5

| Load, Ohms | V Lim, RMS | I Lim, RMS | P Lim, W | PW, Sec |
|---|---|---|---|---|
| 0-24 | 85 | 3 | 135 | 2 |
| 25-49 | 85 | 3 | 135 | 2 |
| 50-74 | 100 | 3 | 135 | 2 |
| 75-99 | 100 | 3 | 100 | 2 |
| 100-124 | 100 | 3 | 80 | 2 |
| 125-149 | 100 | 3 | 65 | 2 |
| 150-174 | 100 | 3 | 55 | 0.5 |
| 175-199 | 100 | 3 | 50 | 0.5 |
| 200-224 | 85 | 0.42 | 32 | 0.3 |
| 225-249 | 85 | 0.38 | 28 | 0.3 |
| 250-274 | 85 | 0.33 | 26 | 0.3 |
| 275-299 | 85 | 0.31 | 24 | 0.3 |
| 300-324 | 85 | 0.28 | 22 | 0.25 |
| 325-349 | 85 | 0.26 | 20 | 0.25 |
| 350-374 | 85 | 0.25 | 19 | 0.25 |
| 375-399 | 85 | 0.22 | 18 | 0.25 |
| 400-424 | 85 | 0.21 | 17 | 0.25 |
| 425-449 | 85 | 0.2 | 16 | 0.25 |
| 450-475 | 85 | 0.19 | 15 | 0.25 |
| 475+ | 85 | 0.15 | 14 | 0.25 |

The composite load curve 1538 may be used sequentially after the prior curve 1536 in the algorithm 1452.

Figure 85:
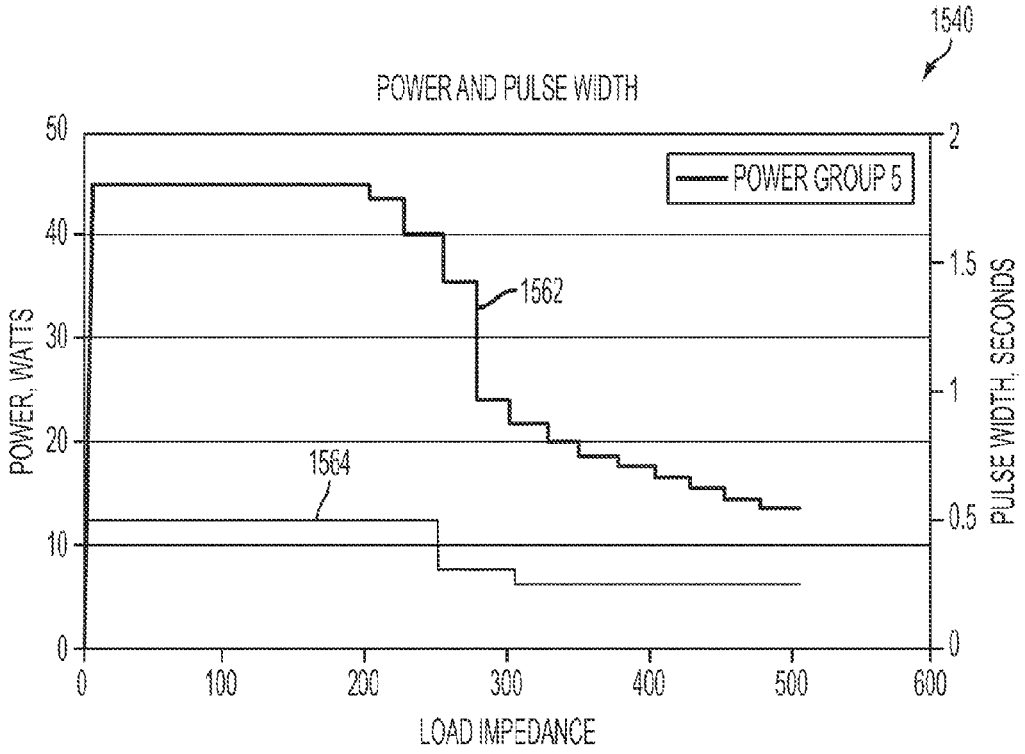

FIG. 85 illustrates a graphical representation of a sixth example composite load curve 1540. The composite load curve 1540 may have a maximum pulse power of 90 Watts RMS and a maximum pulse width of 2 seconds. In FIG. 85, the power as a function of tissue impedance is indicated by 1562, while the pulse width as a function of tissue impedance is indicated by 1564. Table 6 below illustrates values for the composite load curve 1540 for tissue impedances from 0Ω to 475Ω.

TABLE 6

| Load, Ohms | V Lim, RMS | I Lim, RMS | P Lim, W | PW, Sec |
|---|---|---|---|---|
| 0-24 | 85 | 3 | 90 | 2 |
| 25-49 | 85 | 3 | 90 | 2 |
| 50-74 | 100 | 3 | 90 | 2 |
| 75-99 | 100 | 3 | 90 | 2 |
| 100-124 | 100 | 3 | 80 | 2 |
| 125-149 | 100 | 3 | 65 | 2 |
| 150-174 | 100 | 3 | 55 | 0.5 |
| 175-199 | 100 | 3 | 50 | 0.5 |
| 200-224 | 85 | 0.42 | 32 | 0.3 |
| 225-249 | 85 | 0.38 | 28 | 0.3 |
| 250-274 | 85 | 0.33 | 26 | 0.3 |
| 275-299 | 85 | 0.31 | 24 | 0.3 |
| 300-324 | 85 | 0.28 | 22 | 0.25 |
| 325-349 | 85 | 0.26 | 20 | 0.25 |
| 350-374 | 85 | 0.25 | 19 | 0.25 |
| 375-399 | 85 | 0.22 | 18 | 0.25 |
| 400-424 | 85 | 0.21 | 17 | 0.25 |
| 425-449 | 85 | 0.2 | 16 | 0.25 |
| 450-475 | 85 | 0.19 | 15 | 0.25 |
| 475+ | 85 | 0.15 | 14 | 0.25 |

The composite power curve 1540 is less aggressive than the prior power curve 1538. According to various embodiments, the composite power curve 1540 may be implemented in the algorithm 1452 sequentially after the curve 1538. Also, in some embodiments, the composite power curve 1540 may be implemented in the algorithm 1452 as a third or fourth region-specific composite power curve.

As described above, the various composite power curves used in the algorithm 1452 may each be implemented for a predetermined number of pulses. Table 7 below illustrates the number of pulses per composite power curve for an example embodiment utilizing the power curves 1532, 1534, 1536, 1540 sequentially in the algorithm 1452.

TABLE 7

| Composite Load Curve | Number of Pulses |
|---|---|
| 1532 | 4 |
| 1534 | 2 |
| 1536 | 2 |
| 1538 | 8 |
| 1540 | n/a |

The last composite power curve 1540 is shown without a corresponding number of pulses. For example, the composite power curve 1540 may be implemented until the clinician terminates the operation, until the timeout time is reached, until the threshold tissue impedance is reached, etc.

Figure 86:
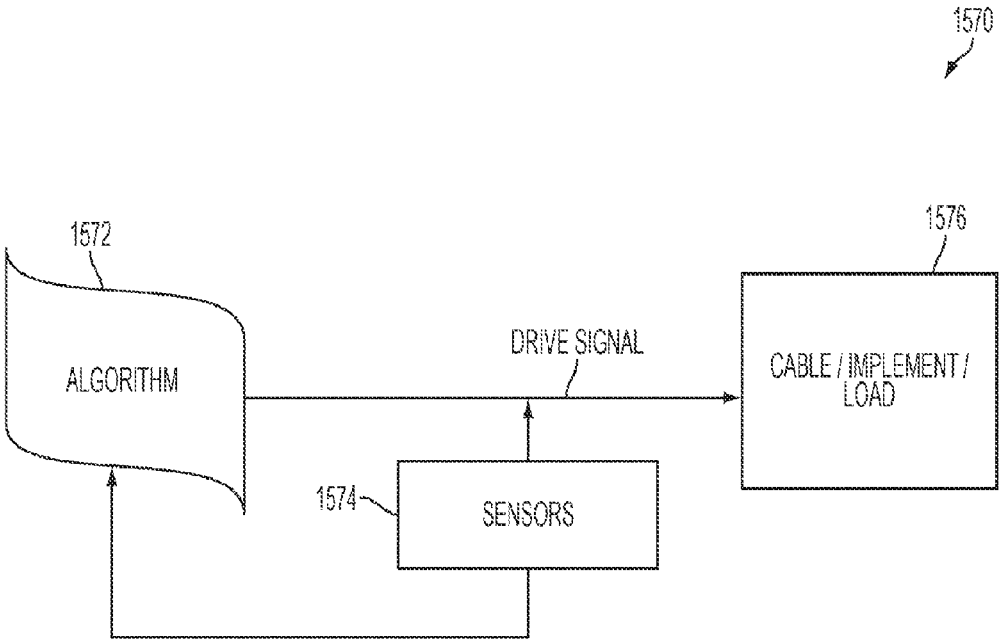
FIG. 86 illustrates one embodiment of a block diagram describing the application of an algorithm for maintaining a constant tissue impedance rate of change

According to various embodiments, the generator 102 may provide power to a tissue bite in a manner that brings about a desired value of other tissue parameters. FIG. 86 illustrates one embodiment of a block diagram 1570 describing the application of an algorithm 1572 for maintaining a constant tissue impedance rate of change. The algorithm 1572 may be implemented by the generator 102 (e.g., by a digital device of the generator 102). For example, the algorithm 1572 may be utilized by the generator 102 to modulate the drive signal. Sensors 1574 may sense a tissue condition, such as tissue impedance and/or a rate of change of tissue impedance. The sensors 1574 may be hardware sensors or, in various embodiments may be software implemented sensors. For example, the sensors 1574 may calculate tissue impedance based on measured drive signal current and voltage. The drive signal may be provided by the generator 102 to the cable/implement/load 1576, which may be the electrical combination of the tissue, the surgical device 104, 106 and a cable 112, 128 electrically coupling the generator 102 to the device 104, 106.

The generator 102, by implementing the algorithm 1572, may monitor the impedance of the tissue or load including, for example, the rate of change of impedance. The generator 102 may modulate one or more of the voltage, current and/or power provided via the drive signal to maintain the rate of change of tissue impedance at a predetermined constant value. Also, according to various embodiments, the generator 102 may maintain the rate of change of the tissue impedance at above a minimum impedance rate of change.

It will be appreciated that the algorithm 1572 may be implemented in conjunction with various other algorithms described herein. For example, according to various embodiments, the generator 102 may sequentially modulate the tissue impedance to different, increasingly aggressive rates similar to the method 1330 described herein with reference to FIG. 70 herein. For example, a first impedance rate of change may be maintained until the total energy delivered to the tissue exceeds a predetermined energy threshold. At the energy threshold, if tissue conditions have not reached a predetermined level (e.g., a predetermined tissue impedance), then the generator 102 may utilize the drive signal to drive the tissue to a second, higher impedance rate of change. Also. in various embodiments, tissue impedance rates of change may be used in a manner similar to that described above with respect to composite load curves. For example, instead of utilizing plurality of composite load curves, the algorithm 1452 of FIG. 75 may call for applying a plurality of rates of tissue impedance change. Each rate of tissue impedance change may be maintained for a predetermined amount of time and/or a predetermined number of pulses. The rates may be successively applied in order of value (e.g., rates may successively increase). In some embodiments, however, the driven rates of tissue impedance change may peak, and then be reduced.

As previously discussed, in one embodiment, the generator 102 may comprise an ultrasonic generator module 108 to drive an ultrasonic device, such as the ultrasonic device 104 be by providing a drive signal to the transducer 114 in any suitable manner. For example, the generator 102 may comprise a foot switch 120 coupled to the generator 102 via a footswitch cable 122 (FIG. 8). Control circuits may be employed to detect the presence of the foot switch 120 and the ultrasonic generator module 108 such that the operation of the foot switch 120 is corresponds with the activation of the ultrasonic generator module 108. Accordingly, a clinician may activate the transducer 114, and thereby the transducer 114 and blade 151, by depressing the foot switch 120. In one embodiment, the foot switch 120 may comprise multiple pedals, where each pedal may be activated to perform a particular function. In one embodiment, the foot switch 120 may comprise a first pedal, for example, to enable and/or control the ultrasonic mode of the generator 120 and a second pedal, for example, to enable and/or control the electrosurgical mode of the generator 120. Accordingly, the generator 102 may configure the foot switch 120 pedals depending upon which drive mode of the generator 102 is active.

As previously discussed, the drive mode of the generator 102 may be determined by the device identification. The characteristics of the interrogation signal may uniquely indicate the state or configuration of a control circuit, which can be discerned by the generator 102 and used to control aspects of its operation. Any of the control circuits 280, 280-1 to 280-9, 282, and 282-1 to 282-8 previously descried in connection with FIGS. 14-32 may be configured to set or indicate the drive mode of the generator 102, for example. Such control circuits may be contained, for example, in an ultrasonic surgical device (e.g., in a handpiece of an ultrasonic surgical device) or may be contained in an electrosurgical device (e.g., in a handpiece of an electrosurgical device).

In one embodiment, the generator 102 may be configured to operate in ultrasonic mode using the ultrasonic generator module 108. Accordingly, the first pedal of the foot switch 120 enables and/or controls the operation of the ultrasonic generator module 108. During ultrasonic mode operation, the first pedal (e.g., the left pedal) may be configured to activate the ultrasonic output of the ultrasonic generator module 108 to generate a drive signal that corresponds to a minimum ($P_{Min}$) ultrasonic power level (e.g., minimum energy setting) and the second pedal (e.g., the right pedal) may be configured to activate the ultrasonic generator module 108 to generate a drive signal that corresponds to a the maximum ($P_{Max}$) ultrasonic power level (e.g., maximum energy setting). It will be appreciated that either the first or second pedal may be configured to activate the ultrasonic generator module 108 to generate a drive signal that corresponds to the minimum ($P_{Min}$) or maximum ($P_{Max}$) ultrasonic power levels, without limitation. Therefore, either the left or right pedal may be assigned as the first pedal, and the other pedal may be assigned as the second pedal. In embodiments where the foot switch 120 comprises more than two pedals, each of the pedals may be assigned a predetermined function. In some embodiments, one or more of the foot pedals may be deactivated or ignored by the generator 102 DSP software or logic (e.g., executable instructions, hardware devices, or combinations thereof).

In one embodiment, the generator 102 is configured in ultrasonic mode and the foot switch 120 comprises two pedals, e.g., first and second or left and right. During ultrasonic foot switch 120 activation mode, when a valid activation of the first pedal (e.g., left pedal) of the foot switch 120 is detected and an ultrasonic surgical device 104 (FIG. 8) is connected to the ultrasonic generator module 108, the generator 102 DSP software is configured to drive the ultrasonic transducer 114 of the ultrasonic surgical device 104 at the maximum power level, for example. For ultrasonic transducers 114, the maximum power ($P_{Max}$) level can be obtained at the maximum drive current ($I_{Max}$). In embodiments where the foot switch 120 comprises more than two pedals, any two of the multiple pedals may be configured in accordance with the above functionality.

In one embodiment, during ultrasonic foot switch 120 activation mode, when a valid activation of the second pedal (e.g., right pedal) of the foot switch 120 is detected and an ultrasonic surgical device 104 (FIG. 8) is connected to the ultrasonic generator module 108, the generator 102 DSP software or logic is configured to drive the ultrasonic transducer 114 of the ultrasonic surgical device 104 at the minimum power level, for example. For ultrasonic transducers 114, the maximum power level can be obtained at the minimum drive current.

In another embodiment, the generator 102 may comprise an electrosurgery/RF generator module 110 to drive the electrosurgical device 106 in any suitable manner. Control circuits may be employed to detect the presence of the foot switch 120 and the electrosurgery/RF generator module 110 such that the operation of the foot switch 120 is corresponds with the activation of the electrosurgery/RF generator module 110. Accordingly, the generator 102 may be configured to operate in electrosurgical mode (e.g., bi-polar RF mode) using the electrosurgery/RF generator module 110 and the foot switch 120 may comprise two pedals, e.g., first and second or left and right. The first pedal of the foot switch 120 enables and/or controls the operation of the electrosurgery/RF generator module 110. During electrosurgical mode operation, the first pedal (e.g., the left pedal) may be configured to activate the bi-polar RF output of the electrosurgery/RF generator module 110 and the second pedal (e.g., the right pedal) switch may be ignored and may be referred to as an inactive switch. It will be appreciated that the inactive switch (e.g., the right pedal) may be used by the user for input to the generator 102 other than power level. For example, tapping the inactive switch pedal may be a way for the user to acknowledge or clear a fault, among other functions, as well as other inputs from the user to the generator by way of the inactive switch pedal. In embodiments where the foot switch 120 comprises more than two pedals, any two of the multiple pedals may be configured in accordance with the above functionality.

In one embodiment, during electrosurgical foot switch 120 activation mode when an electrosurgical or RF surgical device 106 (FIG. 8) is connected to the electrosurgery/RF generator module 110, the generator 102 DSP and user interface (UI) software or logic is configured to ignore the status of the second pedal of the foot switch 120, which is the maximum activation switch. Accordingly, there is no change in power delivery and no change in visual or audible feedback to the user when the second pedal of the foot switch 120 is activated. Therefore, when the electrosurgery/RF generator module 110 transitions from inactive to active of the Max switch-input on the second pedal of the foot switch 120 while all other activation switch inputs are inactive, the electrosurgery/RF generator module 110 ignores the switch input from the second pedal of the foot switch 120 and does not sound or emit a tone.

In one embodiment, during electrosurgical foot switch 120 activation mode when an electrosurgical or RF surgical device 106 (FIG. 8) is connected to the electrosurgery/RF generator module 110, the generator 102 DSP software is configured to drive the electrosurgical or RF device 106 in accordance with a predetermined algorithm specific to the electrosurgical or RF device 106. Various algorithms are discussed in the present disclosure.

As previously discussed, according to various embodiments, the generator 102 may implement a user interface in conjunction with the algorithm 1452 described in connection with FIG. 75. One embodiment of a user interface now will be described with reference to FIGS. 75 and 76 where FIG. 75 illustrates a process flow illustrating one embodiment of the algorithm 1452, as implemented by the generator 102 (e.g., by a digital device of the generator 102) and FIG. 76 illustrates shows a process flow illustrating one embodiment of the algorithm 1452, as implemented by the generator 102 (e.g., by a digital device of the generator 102). The algorithm 1452 may be activated at 1476. It will be appreciated that the algorithm 1452 may be activated in any suitable manner. For example, the algorithm 1452 may be activated by a clinician upon actuation of the surgical device 104, 106 (e.g., by pulling or otherwise actuating a jaw closure trigger 138, 142, switch, handle, etc.).

Accordingly, in one embodiment, the algorithm 1452 may be implemented to control the operation of the electrosurgery/RF generator module 110 to control the electrosurgical or RF surgical device 106 (FIG. 8). Accordingly, in one embodiment of the algorithm 1452, a first activation tone occurs during the activation of the electrosurgical or RF surgical device 106 that transitions to a second activation tone that occurs when the impedance and/or energy conditions/threshold(s) are met and then transitions to a third activation tone that occurs when the impedance and/or energy conditions/threshold(s) and an end effector 132 (e.g., knife) position condition are all met. The tone from the second activation tone to third activation tone is reset upon opening of the jaws as determined by impedance as described with reference to the algorithm 1452 as described and illustrated in connection with FIG. 76 used to drive the electrosurgical or RF surgical device 106.

Accordingly, turning now to FIG. 76, in one embodiment the algorithm 1452 controls the activation of various audible feedback during certain power delivery regions and transitions between regions. In one embodiment, multiple audible feedback is provided based on operational cycle and region of the electrosurgery/RF generator module 110 of the generator 102. In one embodiment, for example, a first audio tone (Audio Tone-I) is emitted when the electrosurgical (RF) power delivery cycle begins. The first audio tone is emitted, for example, whenever the electrosurgery/RF generator module 110 of the generator 102 enters the first region 1478 and continues in the second region 1480.

A second audio tone (Audio Tone-II) is emitted when the tissue impedance threshold is reached. In one embodiment, the second tone is emitted, for example, upon the electrosurgery/RF generator module 110 of the generator 102 entering the third region 1482. In one aspect, the second tone may be latched such that if a transition occurs from the third region 1482 to the second region 1480, the second tone is continued to be emitted.

A third audio tone (Audio Tone-III) is emitted when the electrosurgical (RF) power delivery cycle is complete. In one embodiment, when the generator 102 DSP software and/or logic determines that a "cycle complete" status has been reached, the third tone is emitted upon completion of a fourth energy pulse in the fourth region 1484.

Still with reference to FIG. 76, in one embodiment, the algorithm 1452 may be employed when marching on tissue, which is defined as opening the jaws of the end effector 132 (FIG. 8) without releasing the energy activation, re-grasping on tissue, and then continuing energy activation. To accommodate the marching on tissue functionality, the algorithm 1452 may be implemented as follows. While in the second region 1480 or third region 1482, if the tissue impedance $|Z_{mag}|>|Z_{jaws_open}|$, the algorithm 1452 re-enters the first region 1478 and implements the first region 1478 applicable Power (P), Current (I), Voltage (V) limits. In one embodiment, while re-entering the first region 1478 $T_{timeout}$ is not reset and the $T_{start}$ timer and the energy accumulation parameter is reset. In one embodiment, when re-entering the first region 1478, the algorithm 1452 shall cause the first audio tone (Audio Tone-I) to be emitted and the logic to switch again to the second audio tone (Audio Tone-II) is kept the same as previously discussed.

It will be appreciated that the previously described sequence of tones, first, second, and third audio tones, may be applied to indicate energy delivery to tissue when the generator 102 is configured to operate in ultrasonic mode using the ultrasonic generator module 108. For example, the first audio tone (Audio Tone-I) is emitted when the ultrasonic energy delivery cycle begins, the second audio tone (Audio Tone-II) is emitted when the tissue impedance threshold is reached, and the third audio tone (Audio Tone-III) is emitted when the ultrasonic energy delivery cycle is complete.

FIGS. 87-99 illustrate various additional embodiments of control circuits of surgical devices are provided. In one embodiment, the control circuit may comprise a first circuit portion coupled to at least one switch operable between an open state and a closed state. The first circuit portion communicates with a surgical generator over a conductor pair to receive a control signal to determine a state of the at least one switch. The control circuit also comprises at least one resistor coupled to the at least one switch, where the state of the at least one switch is determinable based on the value of the at least one resistor. In one embodiment, the at least one resistor is coupled in series with the at least one switch. In one embodiment, the at least one resistor is coupled in parallel with the at least one switch. In one embodiment, the control circuit comprises a voltage reference coupled in parallel to the at least one switch. In one embodiment, the control circuit comprises a capacitor coupled to the voltage reference, where the state of the at least one switch is determinable based on a slope of the voltage on the capacitor. In one embodiment, the control circuit comprises an oscillator in communication with the at least one switch, where the state of the at least one switch is determinable based on a frequency of the oscillator, which is determined by the value of the at least one resistor. In one embodiment, the control circuit comprises a one-wire multi-switch input device coupled to the at least one switch and the at least one resistor, wherein the state of the at least one switch is determinable based on the at least one resistor and is communicated to the generator over a one-wire communication protocol. In one embodiment, the control signal is a differential constant current pulse having a positive phase and a negative phase. In one embodiment, the control circuit comprises a second circuit portion comprising a data circuit element coupled to the first circuit portion. In one embodiment, the data circuit element comprises at least one memory device. In one embodiment, the at least one memory device comprises at least one one-wire electrically erasable programmable read only memory (EEPROM).

In various embodiments, a control circuit of a surgical device is provided. In one embodiment, the control circuit comprises a first circuit portion is coupled to at least one switch operable between an open state and a closed state. The first circuit portion communicates with a surgical generator over a conductor pair to receive a control signal from input terminals to determine a state of the at least one switch. The control signal having a first phase and a second phase. A first transistor coupled between the input terminals, a first capacitor, and a first resistor coupled in series with the first capacitor. During the first phase of the control signal the first transistor is held in cutoff mode while the first capacitor charges to a predetermined voltage and during at initial portion of the second phase of the control signal the first transistor transitions from cutoff mode to saturation mode and is held in saturation mode until the first capacitor discharges through the first resistor. During a final portion of the second phase of the control signal the first transistor transitions from saturation mode to cutoff mode when the first capacitor voltage drops below a predetermined threshold. In one embodiment, during the initial portion of the second phase of the control signal while the first transistor is in saturation mode, a first impedance is presented between the input terminals and during the final portion of the second phase of the control signal while the first transistor is in cutoff mode, a second impedance is presented between the input terminals, where the state of the at least one switch is determinable based on the first and second impedance values. In one embodiment, the control circuit comprises at least one second resistor coupled to the at least one switch, where the second impedance is based at least in part on the at least one second resistor when the at least one switch is in the open state. In one embodiment, the control circuit comprises at least one second resistor coupled to the at least one switch, where the second impedance is based at least in part on the at least one second resistor when the at least one switch is in the closed state. In one embodiment, the control circuit comprises a second transistor coupled to the first capacitor to charge the first capacitor during the first phase of the control signal. In one embodiment, the control circuit comprises a second circuit portion comprising a data circuit element coupled to the first circuit portion, wherein the first capacitor voltage is sufficient to supply voltage to the data element. In one embodiment, the control circuit comprises a voltage reference coupled in parallel to the at least one switch. In one embodiment, the control circuit comprises a second capacitor coupled to the voltage reference, where the state of the at least one switch is determinable based on a slope of the voltage on the second capacitor. In one embodiment, the first phase of the control signal is a positive transition of a current pulse and the second phase of the control signal is a negative transition of a current pulse.

In various embodiments, a method is provided. In one embodiment, the method comprises receiving a control signal at a control circuit of a surgical device and determining the state of the at least one switch based on the value of the resistor. The control circuit comprises a first circuit portion coupled to at least one switch operable between an open state and a closed state, the first circuit portion to communicate with a surgical generator over a conductor pair to receive the control signal, the first circuit portion comprising at least one resistor coupled to the at least one switch. In one embodiment, the method comprises presenting a first impedance during a first phase of the control signal and presenting a second impedance during a second phase of the control signal based on the state of the at least one switch, where determining the state of the at least one switch comprises comparing the first impedance to the second impedance. In one embodiment, the method comprises generating a first voltage slope during a first phase of the control signal and generating a second voltage slope during a second phase of the control signal, where determining the state of the at least one switch comprises comparing the first voltage slope to the second voltage slope. In one embodiment, the method comprises generating a first frequency during a first phase of the control signal and generating a second frequency during a second phase of the control signal, where determining the state of the at least one switch comprises comparing the first frequency to the second frequency. In one embodiment, the method comprises reading a value of the least one resistor by a one-wire multi-switch input device coupled to the at least one switch and communicating the value of the at least one resistor to the generator over a one-wire communication protocol.

The control circuits disclosed in connection with FIGS. 87-99 are suitable for use with surgical devices, including, for example. disposable surgical devices. The control circuits can overcome challenges such as cost constraints, non-ideal surgical device usage conditions, and compatibility with existing equipment. In addition, the series resistance in the switch lines may increase over time and usage due to residue buildup from cleaning agents on the surgical device handpiece contacts.

The configuration and detection methodology of each of the control circuits described in connection with FIGS. 87-99, may be configured to operate with any one of, any combination of, or all of, the following requirements: compatibility with constant current sources using voltage level state detection as may be provided in the generator 102; compensation circuits for the cable 112 (e.g., line) impedance (i.e., contaminated handpiece contacts); support functionality for multiple switches provided on the surgical device handpiece (scalable design to support one, two, three, or more switches on the handpiece of the surgical device); provide a circuit presence state; support functionality for multiple simultaneous switch states; support functionality for multiple one-wire memory components (power and communication); low cost for disposable device; maximize use of "off the shelf" components; minimize circuit footprint (e.g., approximately 15 mm×15 mm); provide for mitigation of resultant hazardous conditions due to single point component failure (e.g., open/short circuit); provide electrostatic discharge (ESD) mitigation.

The various embodiments of the control circuits described in connection with FIGS. 87-99 are configured to be located in a handpiece of a surgical instrument. The control circuits receive an interrogation signal transmitted by the generator 102 through a cable 112. As discussed above in connection with FIG. 10, a control circuit may modify the characteristics of an interrogation signal transmitted by the generator 102. The characteristics of the interrogation signal, which may uniquely indicate the state or configuration of the control circuit and/or the handpiece of the surgical device, can be discerned by circuitry located at the generator 102 side and are used to control aspects of its operation. The various embodiments of the control circuits described in connection with FIGS. 87-99 may be contained in an ultrasonic surgical device (e.g., in the handpiece 116 of the ultrasonic surgical device 104), in an electrosurgical device (e.g., in the handpiece 130 of the electrosurgical device 106), or in a combination ultrasonic/electrosurgical device (e.g., in the handpiece of a device that incorporates the functional aspects of the ultrasonic device 104 and the electrosurgical device 106 in a single handpiece), as described herein.

Figure 87:
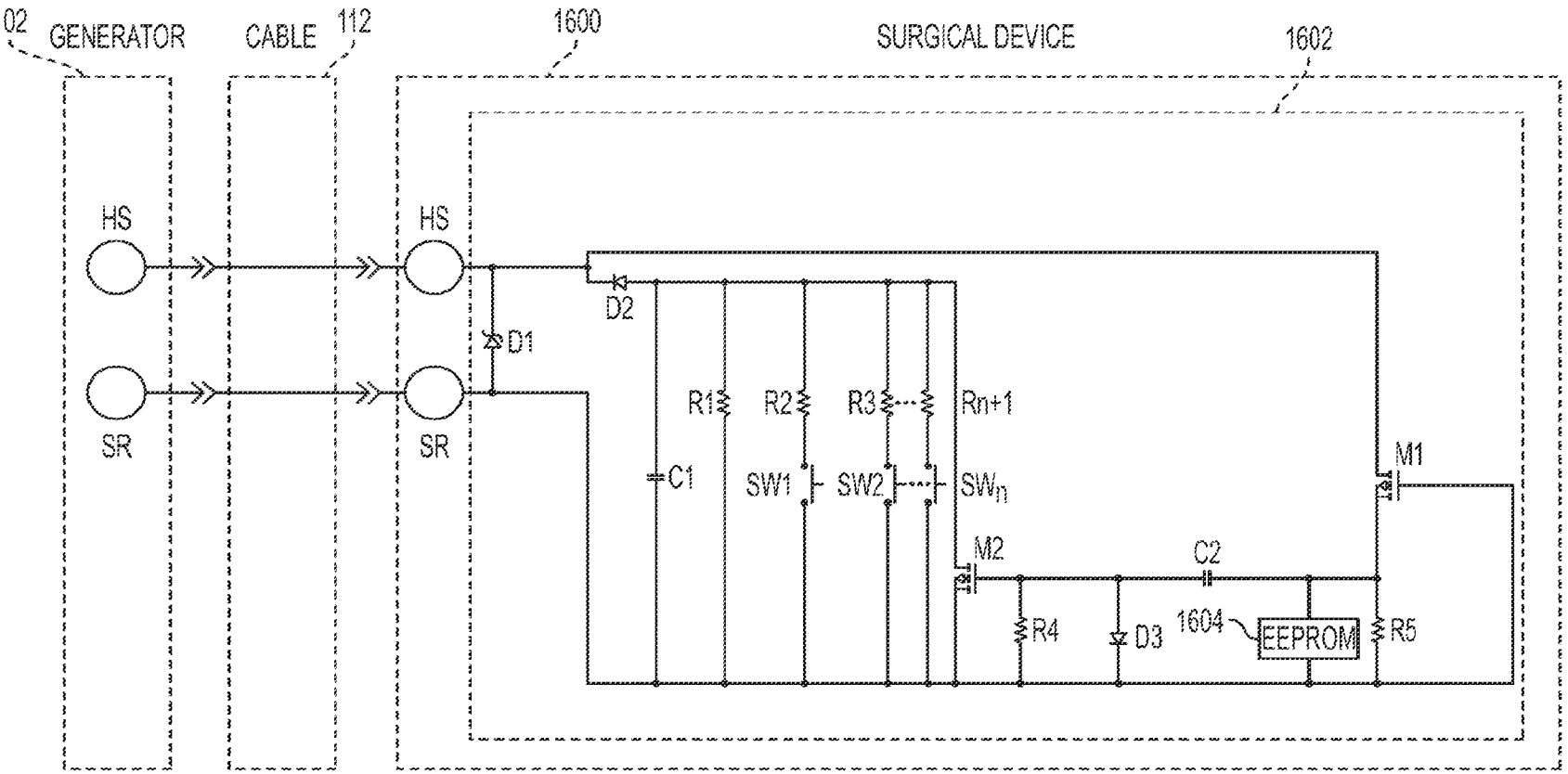
FIG. 87 illustrates one embodiment of a control circuit comprising parallel switched resistance circuit with high speed data communication support and at least one data element comprising at least one memory device.

FIG. 87 illustrates one embodiment of a control circuit 1602 comprising parallel switched resistance circuit with high speed data communication support and at least one data element comprising at least one memory device. In one embodiment, the control circuit 1602 is operable by a control signal in the form of a differential current pulse. As shown in FIG. 87, in one embodiment, the control circuit 1602 may be connected or coupled to the generator 102 via the cable 112 (and/or 128) to receive an interrogation signal (e.g., a bipolar interrogation signal at a predetermined frequency, such as 2 kHz, for example) from a signal conditioning circuit 202 (e.g., from generator terminals HS and SR shown in FIG. 10 via a conductive pair of cable 112 or 128). In one embodiment, the control circuit 1602 comprises multiple parallel switches SW1, SW2, SWn. The embodiment of the control circuit 1602 in FIG. 87 can be employed with any suitable number n of switches in parallel with a fixed resistor R1. Accordingly, any suitable number of switches SWn, where n is an integer greater than zero, may be located in parallel with a predetermined fixed resistance to provide an indication of the configuration and/or operation of a surgical device 1600 (e.g., an ultrasonic device 104, an electrosurgical device 106, or a combined ultrasonic/electrosurgical device 104/106). The number of switches n determines the number of possible states. For example, a single switch SW1 can indicate up to two states, two switches can indicate up to four states, and n switches can indicate up to $2^n$ states. The switches SW1, SW2, SWn may be any type of switch. In one embodiment, the switches SW1, SW2, SWn are pushbutton switches located on the handpiece of the surgical device 1600. The embodiments, however, are not limited in this context.

Depending on the open or closed state of each of the switches SW1, SW2, SWn, for example, the signal conditioning circuit 202 (e.g., from generator terminals HS and SR shown in FIG. 10 via a conductive pair of the cable 112, 128) would see a different impedance (e.g., resistance). For embodiments where n=2 that employ two switches SW1, SW2, for example, four unique switch configurable impedances can be detected by the signal conditional conditioning circuit 202, as described in Table 8, below:

TABLE 8

| SW1 | SW2 | Impedance |
|---|---|---|
| Open | Open | R1 |
| Open | Closed | R1 ‖ R3 |
| Closed | Open | R1 ‖ R2 |
| Closed | Closed | R1 ‖ R2 ‖ R3 |

The interrogation signal may be coupled across the inputs HS/SR of the control circuit 1602 and applied across both branches of switches SW1, SW2. When both SW1 and SW2 are open, the control circuit 280 may define an open circuit corresponding to a first state. When SW1 is open and SW2 is closed, the interrogation signal may define a second state. When SW1 is closed and SW2 is open, the interrogation signal may define a third state. When both SW1 and SW2 are closed, the interrogation signal may define a fourth state. Accordingly, based on the different characteristics of the interrogation signal corresponding to the different states of SW1 and SW2, the state or configuration of the control circuit 280 may be discerned by the generator 102 based on a voltage signal appearing across the inputs of the control circuit 280 (e.g., as measured by an ADC of the signal conditioning 35 circuit 202).

Still referring to FIG. 87, in one embodiment, the control circuit 1602 comprises a diode D1 placed across the HS/RS terminals of the control circuit 1602 to clamp and protect the control circuit 1602 from electro-static discharges (ESD) and/or transients coming from the surgical device 1600 and the generator 102 when the surgical device 1600 is connected and disconnected to the generator 102. In the illustrated embodiment, diode D1 is a bi-directional transient voltage suppressor. Diode D1 may be selected based on a predetermined ESD rating, such as for example 8 kV contact discharge, 5V nominal working voltage, small size, and low capacitance to minimize affecting the pulse waveforms. Any suitable bi-directional transient voltage suppressor may be employed without limitation. In other embodiments, as shown in FIGS. 93-95 and 97, for example, multiple diodes can be placed across the inputs HS/SR to protect the surgical device 1600 and/or the control circuit 1602 from ESD and other transients.

Diode D2 is provided for unidirectional routing of negative current pulses to the resistor network R1, R2, R3, and $R_{n+1}$ configured by the switches SW1, SW2, $SW_n$. In the illustrated embodiment, diode D2 is a single Schottky diode to provide a low voltage drop and minimize impact to the usable voltage range to the ADC of the generator 102. Diode D2 may be provided in discrete form, as part of a multi-diode package, or may be formed as part of a custom integrated circuit (e.g., and ASIC). In other embodiments, other suitable diodes may be employed without limitation. During the positive phase (rising edge) of the current pulse, diode D2 is reverse biased and current flows through transistor M1, which charges gate capacitor C2 through diode D3. During the negative phase (falling edge) of the current pulse, diode D2 is forward biased and the ADC of the generator 102 sees the impedance of the resistor network R1, R2, R3, and $R_{n+1}$ configured by the switches SW1, SW2, $SW_n$. In other embodiments, a pair of diodes may be employed for bidirectional power as shown in connection with FIGS. 92-95 and 97.

Transistor M1 is provided to route a positive current pulse from the generator 102 to gate capacitor C2. In the illustrated embodiment, transistor M1 is a p-channel MOSFET, although in other embodiments, any suitable transistor may be employed, without limitation. In the illustrated embodiment, the drain terminal of transistor M1 is connected to the HS input terminal and to the cathodes of diodes D1, D2 and the gate terminal is connected to the SR input terminal of the surgical device 1600. The source of transistor M1 is connected to the SR input terminal through resistor R5. A positive current pulse, as described in more detail with reference to FIG. 88, received at the HS terminal charges capacitor C2 through M1. Capacitor C2 is coupled to the gate of transistor M2 and when charged can turn on transistor M2 during a negative phase of the current pulse or supply power to the at least one memory device 1604 during a positive phase of the input current pulse. Although shown as a discrete component, transistor M1 may be provided a multi-transistor package or may be formed as part of a custom integrated circuit (e.g., and ASIC). In other embodiments, other suitable transistors may be employed without limitation.

In one embodiment, the at least one memory device 1604 may comprise, for example, one or more one-wire EEPROM(s), known under the trade name "1-Wire." As previously discussed, the one-wire EEPROM is a one-wire memory device 1604. Generally, multiple EEPROMs may be employed in the control circuit 1602. In the illustrated embodiment, up to two EEPROMs may be used in the surgical device 1600. The EEPROM(s) are powered during the positive phase of the current pulse. Transistor M1 also provides low forward voltage drop and minimizes impact to the EEPROM high speed communications. Transistor M1 provides reverse blocking capabilities, which cannot be realized with a simple diode.

Figure 90:
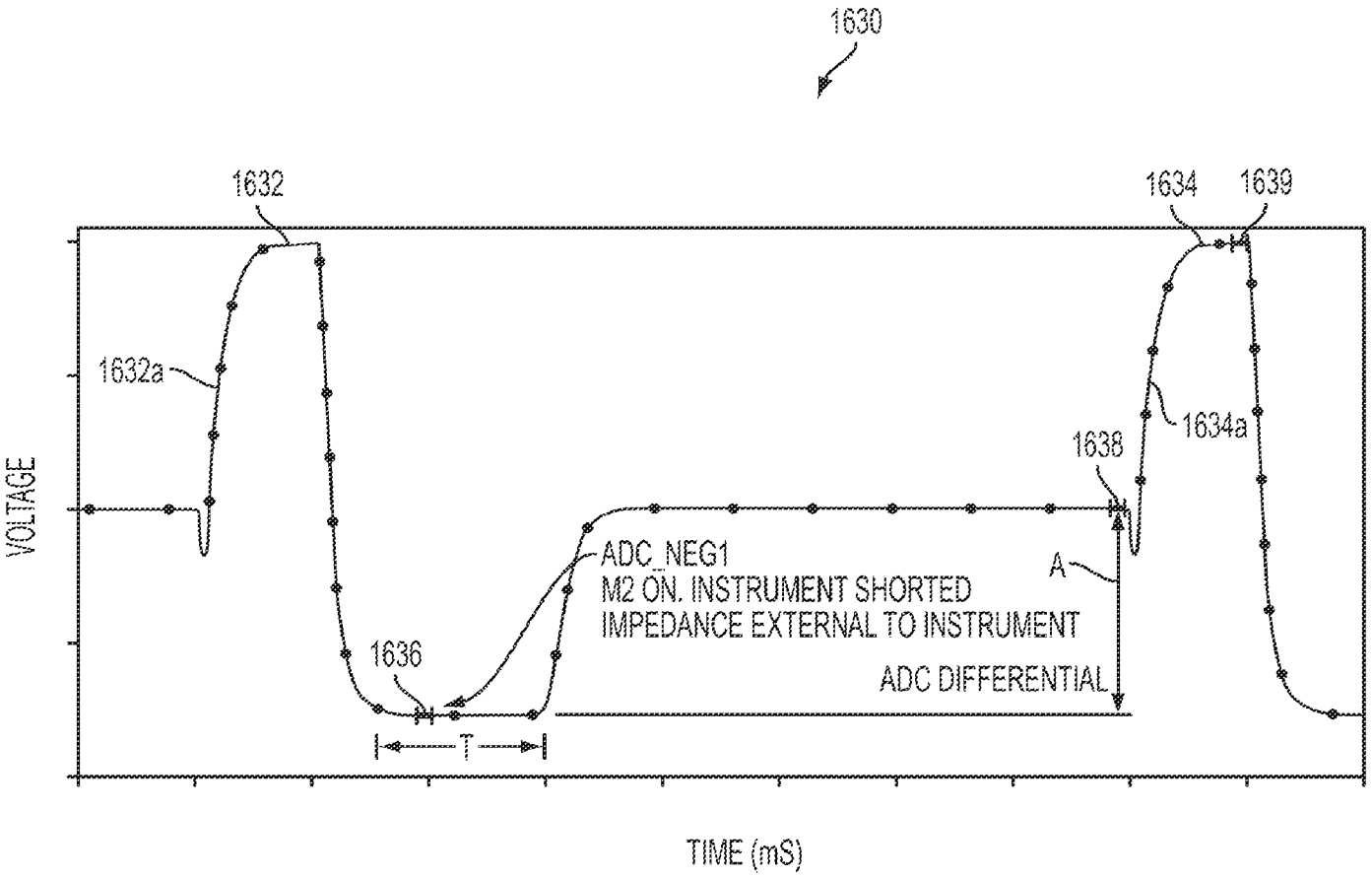
FIG. 90 is a graphical representation of one aspect of a control signal in the form of a current pulse waveform measured at the generator with SW1 closed and a zero ohm cable/connector impedance.

A second transistor M2 provides a substantial low impedance path to short out the resistor network R1, R2, R3, $R_{n+1}$ in order for the ADC to make an initial reference measurement. The drain terminal of transistor M2 is connected to the anode of diode D2 and one end of resistors R1, R2, R3, and $R_{n+1}$. The source terminal of transistor M2 is connected to the SR terminal of the surgical device 1600. In the illustrated embodiment, transistor M2 is also a p-channel MOSFET transistor, although in other embodiments, any suitable transistor can be employed. During a positive phase of the current pulse, transistor M2 turns on and applies a substantial low impedance path across the HS/RS terminals of the surgical device 1600 for a relatively short duration of time as defined by an RC time constant on the gate terminal of transistor M2, where the RC time constant is determined by resistor R4 and gate capacitor C2, each of which is coupled to the gate to transistor M2. Resistor R4 provides a discharge path and timing for the voltage decay of gate capacitor C2. Gate capacitor C2 charges during the positive phase of the current pulse, when transistor M2 is cut off or open circuit. Eventually, the voltage on gate capacitor C2 is sufficient to negatively bias the gate-source and turns on the transistor M2 during the negative phase of the current pulse. A first measurement is then obtained by the ADC of the signal conditioning circuit 202 in the generator 102, which is referred to herein as the "ADC_NEG1" measurement, as shown in FIG. 90, for example.

Diode D3 provides a current path during the positive phase of the current pulse and enables gate capacitor C2 to charge quickly while bypassing resistor R4, which provides the discharge path for gate capacitor C2. In one embodiment, transistor M2 may be selected due to a well defined minimum and maximum gate threshold to provide better characterization of ON/OFF timing for the differential measurement. In one embodiment, transistor M2 component may be provided as a stand alone discrete component or in the same package as transistor M1. Resistor R4 may be selected based on the 1% tolerance, 100 ppm temperature coefficient, and small package size. The identified component selection criterion is provided merely as a non-limiting example. Any suitable component may be substituted to perform the desired functionality.

As previously discussed, resistor network R1, R2, R3, and $R_{n+1}$ is configured by the switches SW1, SW2, $SW_n$ to present a different resistance (e.g., impedance) to the ADC of the generator 102. Resistor R1 sets the maximum resistance used for switch detection, e.g., when all switches SW1, SW2, SW, are open ("off"). When SW1 is closed ("on"), resistor R2 is located in parallel with the other switch detection resistors, as shown in Table 8, for example. When SW2 is closed ("on"), resistor R3 is located in parallel with other switch detection resistors, as shown in Table 8, for example. Each of the resistors R1, R2, R3, $R_{n+1}$ can be selected based on a 1% tolerance, 100 ppm temperature coefficient, and small package size, without limitation. Capacitor C1 may be located in parallel with the resistors R1, R2, R3, and $R_{n+1}$ to provide high frequency filtering from conducted and/or radiated noise, for example. In one embodiment, capacitor C1 may be a ceramic capacitor, without excluding other capacitor types.

Resistor R5 provides a relatively low impedance path to rapidly turn on transistor M2 during the start of the negative phase of the current pulse. Gate capacitor C2 charges in conjunction with resistor R4 to increases the gate voltage above the turn on threshold of transistor M2 for a short duration. The value of resistor R5 also may be selected to provide a sufficient supply voltage to the one or more EEPROM(s) during the positive phase of the current pulse.

Figure 88:
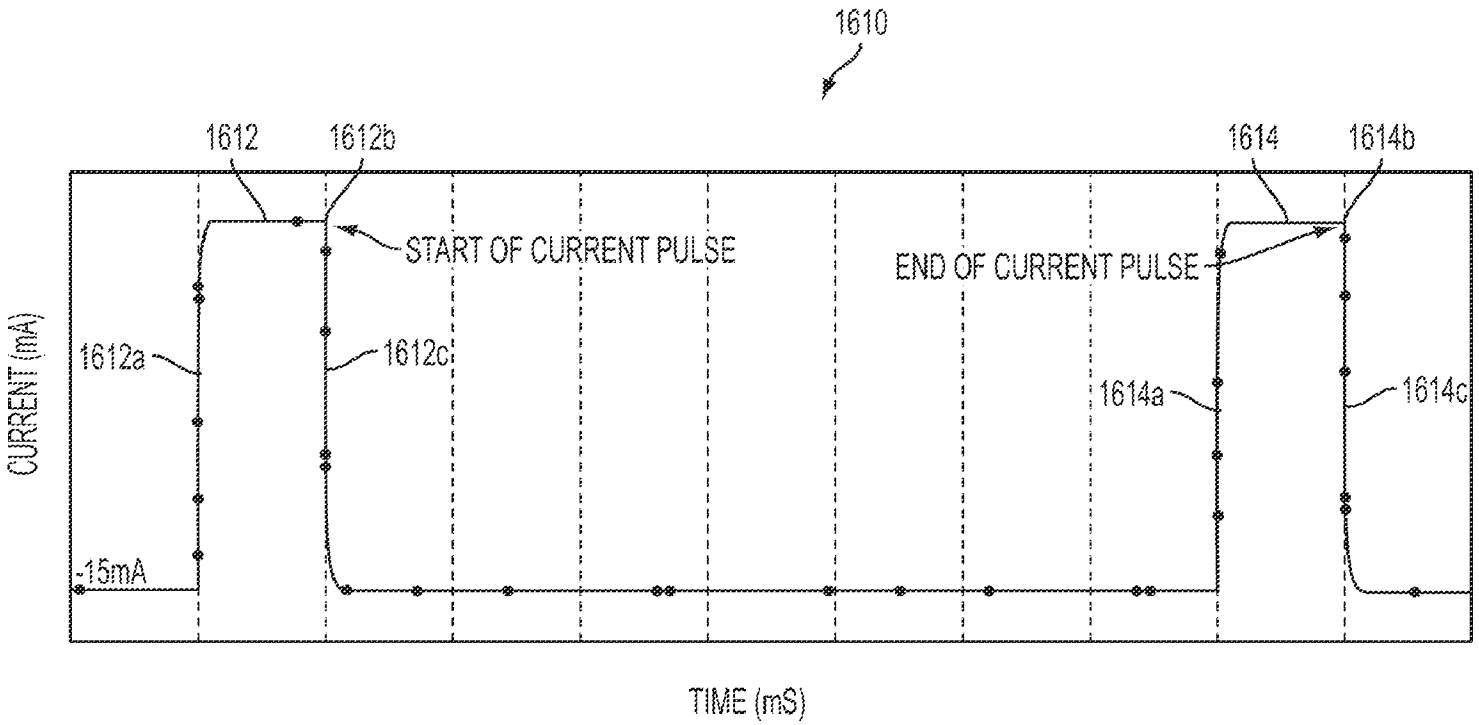
FIG. 88 is a graphical representation of one aspect of a control signal in the form of a constant current pulse waveform that may be generated by the signal conditioning circuit of the generator as shown in FIG. 10.

FIG. 88 is a graphical representation of one aspect of a control signal in the form of a constant current pulse waveform 1610 that may be generated by the signal conditioning circuit 202 of the generator 102 as shown in FIG. 10. Time, in milliseconds (mS), is shown along the horizontal axis and Current, in milliamps (mA), is shown along the vertical axis. In the embodiment illustrated in FIG. 88, periodic constant current pulses 1612, 1614, each having a first phase shown as positive transitions 1612a, 1614a and a second phase shown as negative transitions 1612c, 1614c, at +/−15 mA are produced by a current source generator located at the generator 102 side. The current source generator is coupled to the HS/SR input terminals of the surgical device 1600/control circuit 1602 via the cable 112, 128. Other constant current amplitudes may be employed. In the illustrated embodiment, the control circuit 1602 utilizes both pulse polarities to detect up to $2^n$ unique combinations of switches SW1, SW2, $SW_n$ and also supports communication to the one-wire EEPROM(s).

Figure 88A:
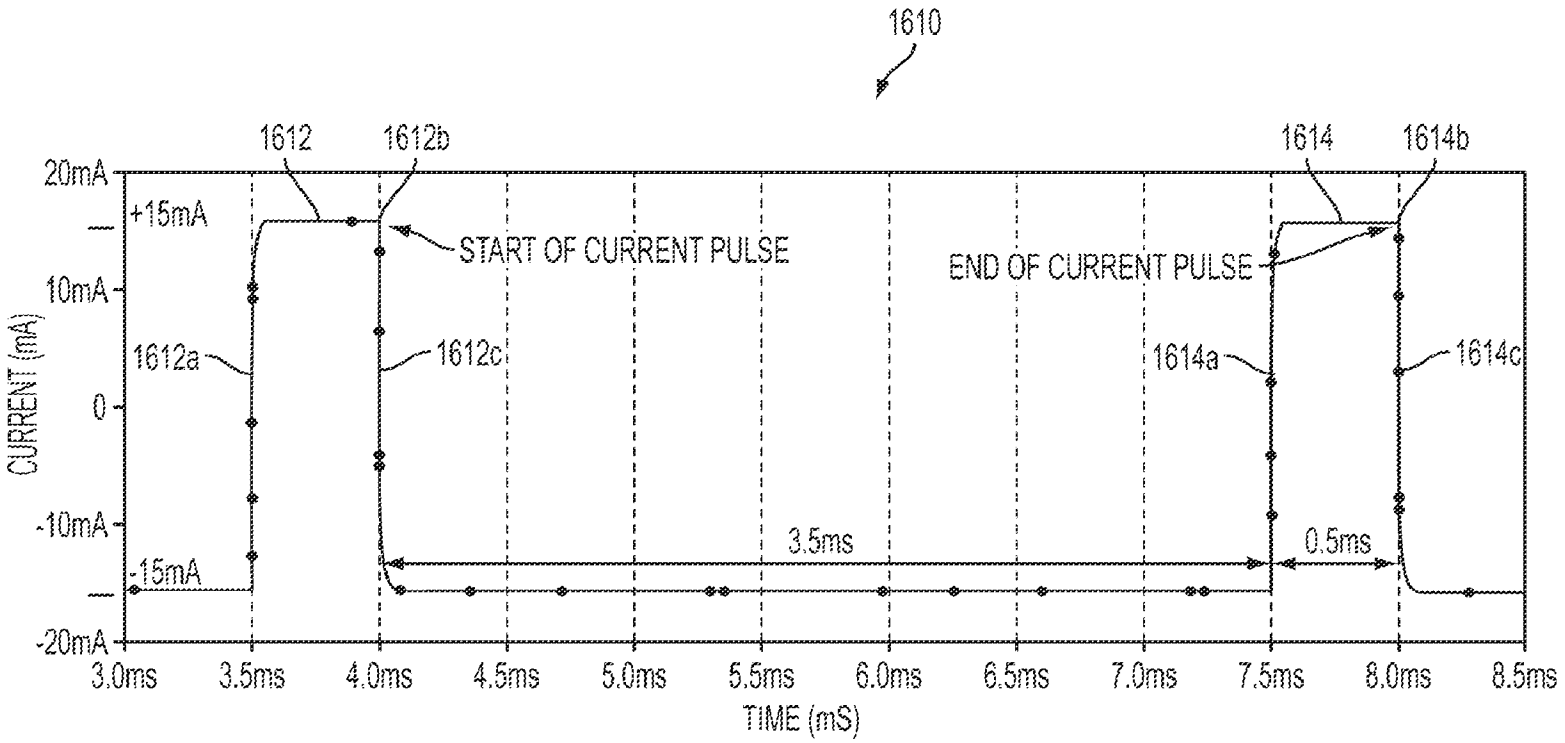
FIG. 88A is a graphical representation of one aspect of a control signal in the form of the constant current pulse waveform of FIG. 88 showing numerical values of various features of the waveform according to one example embodiment.

FIG. 88A is a graphical representation of one aspect of a control signal in the form of the constant current pulse waveform 1610 of FIG. 88 showing numerical values of various features of the waveform 1610 according to one example embodiment. In the example embodiment of FIG. 88A, time on the horizontal axis is shown in milliseconds (mS) while current along the horizontal axis is shown in milliamps (mA). Also, in the example embodiment of FIG. 88A, the current pulses 1612, 1614 may have an amplitude of +/−15 mA.

It will be appreciated that although the current pulse is characterized as having a first phase that is a positive transition and a second phase is a negative transition, the scope of the present disclosure includes embodiments where the current pulse is characterized as having the opposite polarity. For example, the current pulse can be characterized as having a first phase that is a negative transition and a second phase is a positive transition. It will also be appreciated that the selection of the components of any of the control circuits disclosed herein can be suitably adapted and configured to operate using a current pulse characterized as having a first phase that is a negative transition and a second phase is a positive transition. Also, although the present disclosure describes the control signal as a differential current pulse, the scope of the present disclosure includes embodiments where the control signal is characterized as a voltage pulse. Accordingly, the disclosed embodiments of the control circuits are not limited in the context of the differential current pulse described in connection with FIG. 88.

With reference now to both FIGS. 87 and 88, in one embodiment, the control circuit 1602 operates on a differential pulse with parallel resistors R1, R2, R3, and $R_{n+1}$ configured by the switches SW1, SW2, $SW_n$. Additionally, high speed data communication is provided through transistor M1 to the at least one memory device 1604. In one embodiment, the control circuit 1602 uses a variable resistance dictated by the closure of one or more pushbutton switches SW1, SW2, $SW_n$. Both positive edges 1612a, 1614a and negative edges 1612c, 1614c of the current pulses 1612, 1614 are used to derive a measurement that will allow for compensation of an unknown series cable 112, 128 and contamination resistance of the switches SW1, SW2, $SW_n$ contacts within a predetermined range. Initially a positive current pulse 1612a charges gate capacitor C2 and subsequently a negative current pulse 1612c enables transistor M2 to turn for a brief time period defined by the RC time constant of gate capacitor C2 and resistor R4. During the first phase of the negative current pulse 1612c, transistor M2 is placed in a saturated state creating a very low impedance path through the surgical device 1600 between terminals HS/SR. After a time period defined by the RC time constant pair of R4 and C2, gate capacitor C2 discharges through resistor R4 and the FET channel of transistor M2 opens causing the total current to be steered through the resistor R1, R2, R3, $R_{n+1}$ path based on the state of the pushbutton switches SW1, SW2, $SW_n$. The low impedance state when transistor M2 is in closed (saturation mode) and the state of the resistor network R1, R2, R3, $R_{n+1}$ when transistor M2 is in an open (cutoff mode) state are the two impedance states in the time domain that are used for detecting the activation of pushbutton switches SW1, SW2, $SW_n$. This provides the ability to compensate for an external path resistance (handpiece contacts, cabling, connector resistance) by comparing the difference between the two states.

With reference back to FIG. 88, each of the combination of switches SW1, SW2, $SW_n$ creates a unique resistance presented to the ADC at the generator 102 during the negative phase of the current pulse. The constant current pulses 1612, 1624 transmitted from the generator 102 to the surgical device 1600 presents a unique voltage back to an ADC in the generator 102 that is proportional to the resistance selected by the switches SW1, SW2, $SW_n$. Transistor M1 gate capacitor C2 charges during the positive current pulse phase 1612a, 1614a. When the current pulse waveform changes from positive to negative at 1612b, 1614b, the voltage on gate capacitor C2 turns on transistor M2, which effectively shorts the surgical device 1600 control circuit 1602 between the terminals HS/SR. The short circuit exists for a short duration that is set by the time constant defined by resistor R4 and gate capacitor C2 coupled to the gate of transistor M2. After gate capacitor C2 has fully discharged through resistor R4, the control circuit 1602 transitions to an impedance that represents the state of pushbutton switches SW1, SW2, $SW_n$. Using these two measurements for each time period when transistor M2 is in an open circuit state and a short circuit state, allows the control circuit 1602 system to tolerate resistance variations due to cable wiring affects, connector contact resistance, and pushbutton switch resistance. Additionally, as previously discussed, using p-Channel MOSFET transistor M1 rather than a diode is an effective means to facilitate high speed EEPROM communications without adversely affecting the hand switch detection capability.

Figure 89:
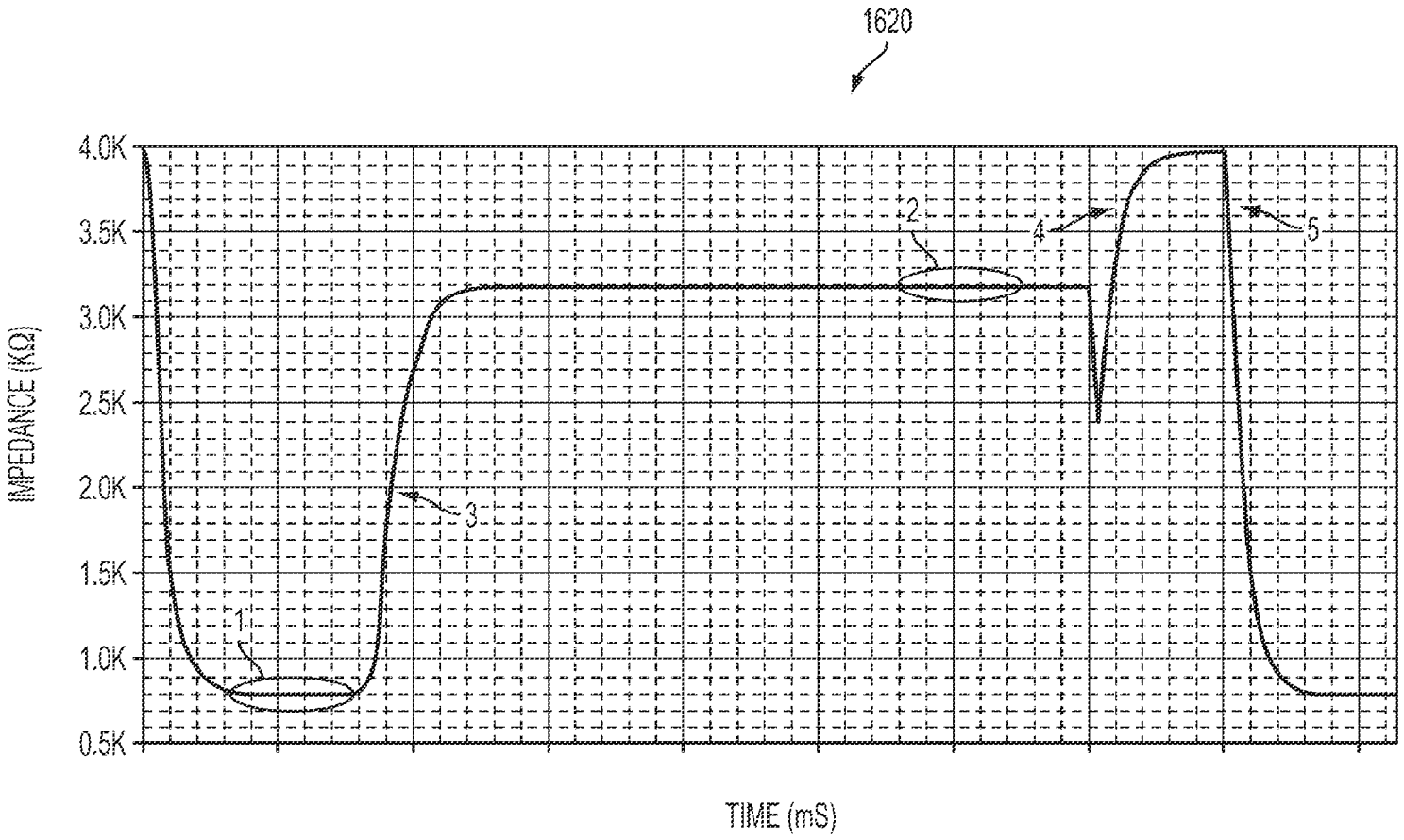
FIG. 89 is a graphical representation of various detection regions associated with the aspect of the control signal shown in FIG. 88.

FIG. 89 is a graphical representation 1620 of various detection regions associated with the aspect of the control signal shown in FIG. 88. Time in "mS" is shown along the horizontal axis and Impedance in "kΩ" is shown along the vertical axis. Five detections regions (1-5) are depicted in the graphical representation 1620. With reference also to FIGS. 87 and 88, region 1 represents the state of transistor M2 when it is in saturation mode during the negative phase 1612c of the current pulse 1612 creating a low resistance path through the surgical device 1600. This is the baseline ADC measurement that represents series resistor R1 except for pushbutton switch SW1, SW2, $SW_n$ detection resistance. Region 2 represents the state of transistor M2 after gate capacitor C2 has fully discharged through resistor R4 over a time constant defined by R4 and C2. In region 2, the surgical device 1600 will present a resistance that represents a unique pushbutton switch SW1, SW2, $SW_n$ state. The amplitude in region 2 changes depending on the states of pushbutton switches SW1, SW2, $SW_n$. Region 3 represents the ohmic region of transistor M2 when it is transitioning from saturation mode to cutoff mode. Region 4 represents the rising positive edge 1612a of the current pulse 1612 to charge gate capacitor C2 coupled to the gate of transistor M2. Diode D3 with its anode also coupled to the gate of transistor M2 allows gate capacitor C2 to be charged quickly in order to be within a predetermined total timing budget. Region 5 represents the falling or negative edge 1612c of the current pulse 1612 when transistor M2 is transitioning from cutoff mode to saturation mode.

FIG. 90 is a graphical representation of one aspect of a control signal in the form of a current pulse waveform 1630 measured at the generator 102 with SW1 closed and a zero ohm cable/connector 112, 128 impedance. The current pulse waveform 1630 shows a first current pulse 1632 followed by a second current pulse 1634. Gate capacitor C2, which is coupled to the gate of transistor M2, charges during the initial positive edge 1632a. During the negative edge 1632b of the current pulse 1632, transistor M2 goes into a saturated (on) state creating a very low impedance external to the surgical device 1600 between terminals HS/SR. During a first sample period 1636 the ADC makes a first "reference" impedance measurement labeled as "ADC_NEG1" on the waveform 1630. After a time period T defined by the time constant set by R4 and C2, gate capacitor C2 discharges through resistor R4 and the FET channel of transistor M2 opens causing the total current to be steered through the parallel combination of resistors R1 and R3 (R1||R3) since SW1 is in the closed position. Accordingly, with transistor M2 in the off state, the impedance external to the surgical device 1600 is measured during a second sample period 1638 by the ADC and is labeled as "ADC_NEG2" on the waveform 1630. A third sample period 1639 may be reserved for legacy instrument detection and occurs after a subsequent positive edge 1634a of the current pulse 1634 and is labeled ADC_POS.

Figure 90A:
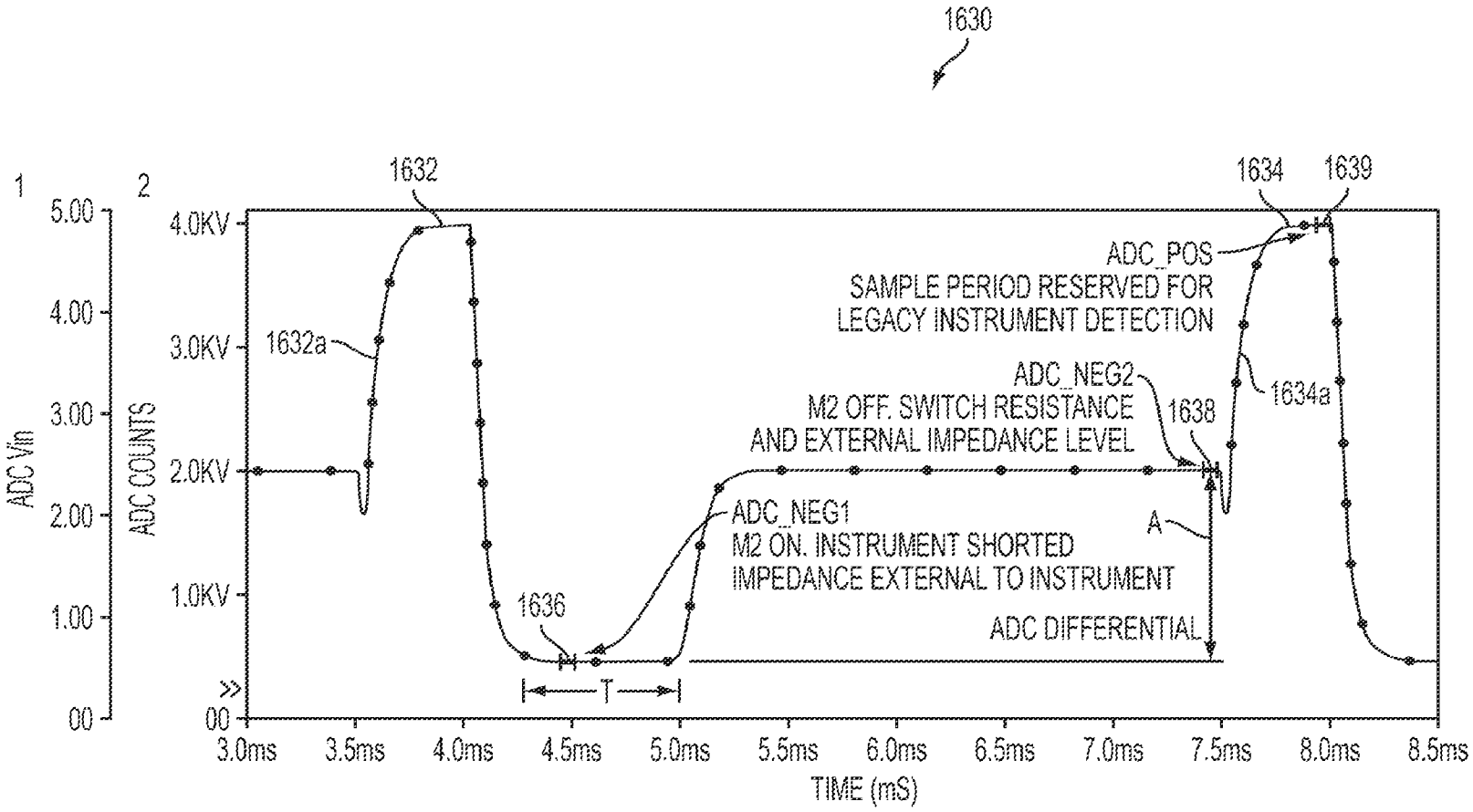
FIG. 90A is a graphical representation of one aspect of a control signal in the form of the current pulse waveform of FIG. 90 showing numerical values of various features of the waveform according to one example embodiment.

FIG. 90A is a graphical representation of one aspect of a control signal in the form of the current pulse waveform 1630 of FIG. 90 showing numerical values of various features of the waveform 1630 according to one example embodiment. Time in "mS" is shown along the horizontal axis and ADC Counts is shown along the inner vertical axis and ADC $V_{in}$ in volts (V) shown along the outer vertical axis.

Figure 91:
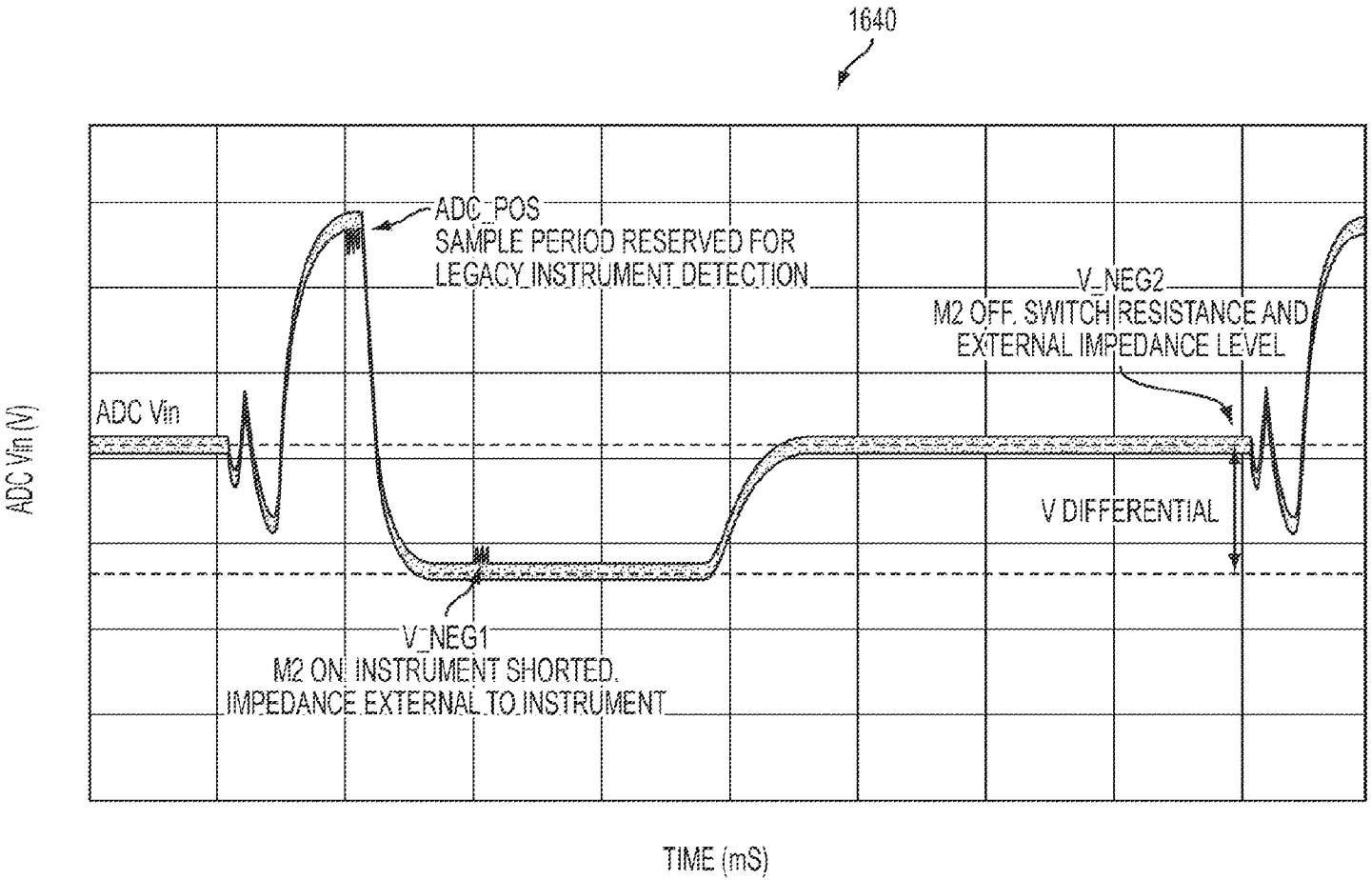
FIG. 91 is an oscilloscope trace of an actual measured analog-to-digital (ADC) input waveform using a generator and a control circuit.

FIG. 91 is an oscilloscope trace of an actual measured ADC input waveform 1640 using a generator 102 and a control circuit 1602. Time in "mS" is shown along the horizontal axis and ADC $V_{in}$ in volts (V) is shown along the vertical axis. The actual waveform 1640 shape shown in FIG. 90 is very similar to the simulated waveform shape 1630 shown in FIG. 90.

Figure 92:
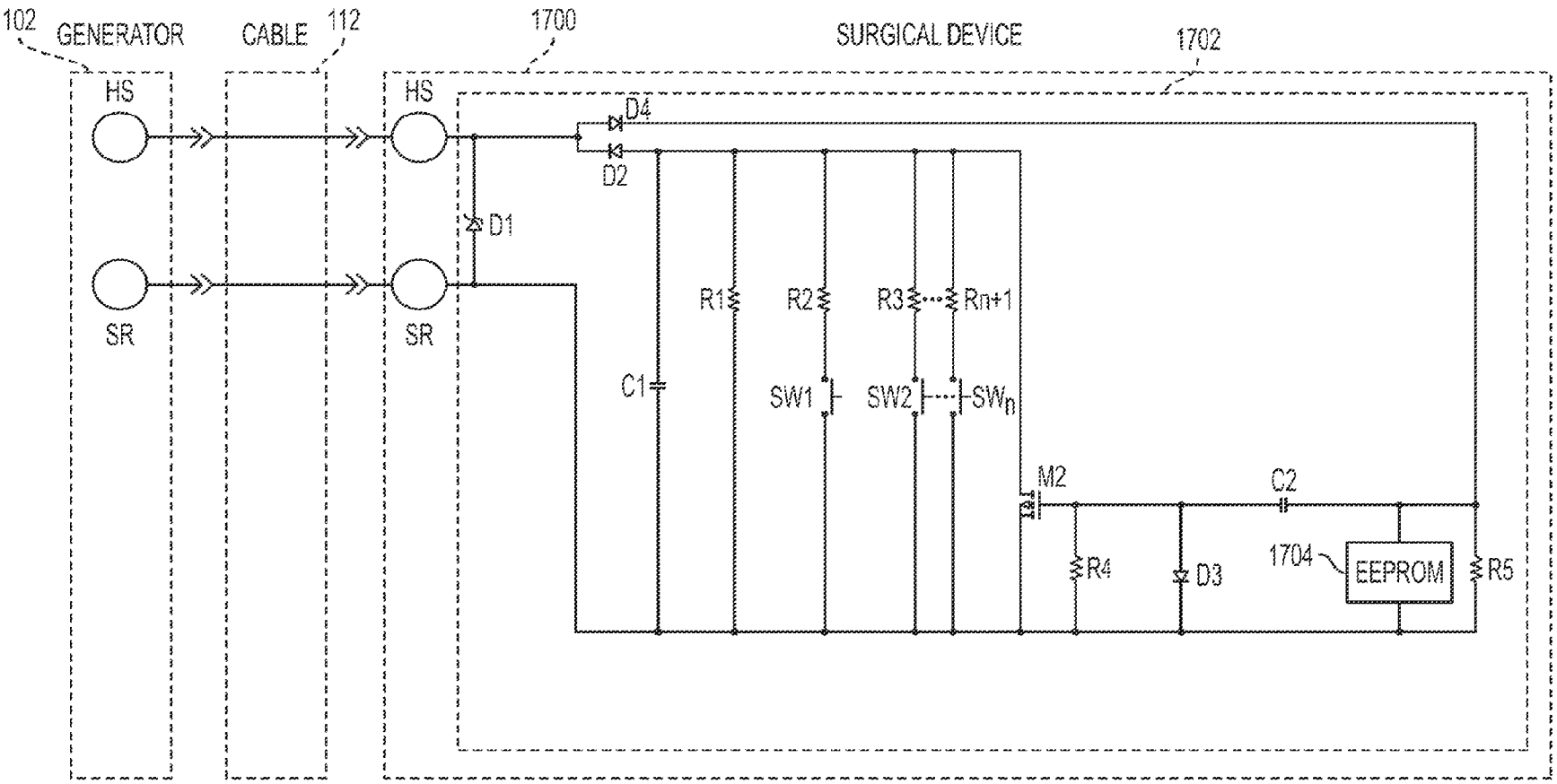
FIG. 92 illustrates another embodiment of a control circuit comprising parallel switched resistance circuit and at least one data element comprising at least one memory device memory device.

FIG. 92 illustrates another embodiment of a control circuit 1702 comprising parallel switched resistance circuit and at least one data element comprising at least one memory device memory device. In one embodiment, the control circuit 1702 is operable by a control signal in the form of a differential current pulse. As previously discussed with respect to the control circuit 1602 shown in FIG. 87, the control circuit 1702 interfaces with a current source (generator), which outputs periodic positive and negative constant current pulses at +/−15 mA, as shown in FIG. 88, for example. The control circuit 1702 design utilizes both pulse polarities to detect up to $2^n$ unique switch combinations and also supports communication to one or more memory devices 1704, such as, for example a one-wire EEPROM(s).

In one embodiment, the control circuit 1702 may be connected to the generator 102 to receive an interrogation signal (e.g., a bipolar interrogation signal at a predetermined frequency, such as 2 kHz, for example) from the signal conditioning circuit 202 (e.g., from generator terminals HS and SR shown in FIG. 10 via a conductive pair of cable 112, 128). The control circuit 1702 may be coupled to a predetermined number of n switches to provide an indication of the configuration and/or operation of a surgical device 1700 (e.g., an ultrasonic device 104, an electrosurgical device 106, or a combined ultrasonic/electrosurgical device 104/106). The control circuit 1702 shown in FIG. 92 is substantially similar in structure and operation to the control circuit 1602 described in connection with FIGS. 87-91, except that transistor M1 is replaced with diode D4. Otherwise, the two control circuits 1602 and 1702 function in a substantially similar manner.

As shown in FIG. 92, during the positive phase of the current pulse, as shown in FIG. 88, diode D2 is reversed biased and diode D4 is forward biased to enable gate capacitor C2 to charge through diode D3. During the negative phase of the current pulse, diode D4 is reversed biased and diode D2 is forward biased to connect resistors R1, R2, R3, $R_{n+1}$ in parallel in a configuration determined by the state of switches SW1, SW2, $SW_n$. During an initial period of the negative phase of the current pulse, transistor M2 is in saturation mode due to the voltage on charged gate capacitor C2 and provides a low impedance path to the external generator 102 for a period equal to the time constant defined by R4 and C2. During this period, the ADC makes an initial impedance measurement "ADC_NEG1" as shown in the waveform 1630 of FIG. 90. Once gate capacitor C2 discharges through resistor R4, transistor M2 turns off and the ADC sees the impedance configured by the parallel combination of resistors R1 and any of the other resistors R2, R3, $R_{n+1}$ that may be switched by corresponding switches SW1, SW2, $SW_n$, as previously described in connection with FIGS. 87-91. The detection region is similar to that shown in FIG. 89.

Figure 93:
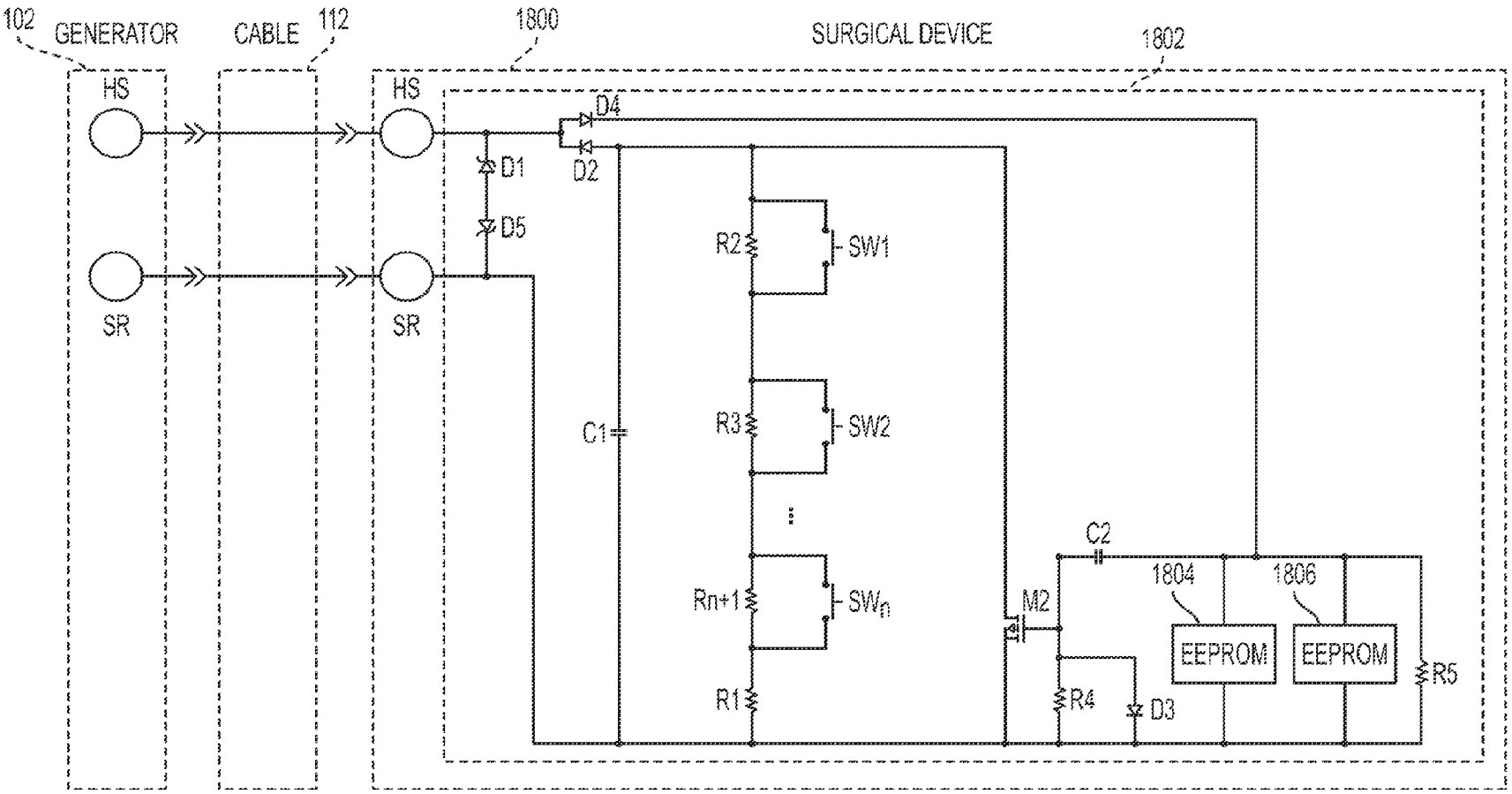
FIG. 93 illustrates one embodiment of a control circuit comprising a serial switched resistance circuit and at least one data element comprising at least one memory device.

FIG. 93 illustrates one embodiment of a control circuit 1802 comprising a serial switched resistance circuit and at least one data element comprising at least one memory device. In one embodiment, the control circuit 1802 is operable by a control signal in the form of a differential current pulse. As previously discussed with respect to the control circuits 1602, 1702 shown in FIGS. 87, 92, the control circuit 1802 interfaces with a current source (generator), which outputs periodic positive and negative constant current pulses at +/−15 mA, as shown in FIG. 88, for example. The control circuit 1802 utilizes both pulse polarities to detect up to $2^n$ unique switch combinations and also supports communication to one or more memory devices 1804, 1806, such as, for example, two one-wire EEPROM(s).

In one embodiment, the control circuit 1802 may be connected to the generator 102 to receive an interrogation signal (e.g., a bipolar interrogation signal at a predetermined frequency, such as 2 kHz, for example) from the signal conditioning circuit 202 (e.g., from generator terminals HS and SR shown in FIG. 10 via a conductive pair of cable 112, 128). The control circuit 1802 may be coupled to a predetermined number of n switches to provide an indication of the configuration and/or operation of a surgical device 1800 (e.g., an ultrasonic device 104, an electrosurgical device 106, or a combined ultrasonic/electrosurgical device 104/106).

In one embodiment, the control circuit 1802 employs a series variable resistance configurable by up to n pushbutton switches SW1, SW2, $SW_n$. Both positive and negative current pulses can be used to derive a measurement that will allow for compensation of an unknown series cable and contamination resistance within a given range. Initially a positive phase of a current pulse reverse biases diode D2 and forward biases diode D4 to charge gate capacitor C2 through diode D3. During a subsequent negative phase of the current pulse, diode D2 is forward biased and diode D4 is reversed biased. Accordingly, diode D2 now couples series resistors R1, R2, R3, $R_{n+1}$, in a configuration determined by the state of pushbutton switches SW1, SW2, $SW_n$, to the external ADC in the generator 102. During the first portion of the negative phase of the current pulse, transistor M2 is in saturation mode due to the voltage on charged gate capacitor C2, thus creating a very low impedance path through the surgical device 1800. After a time period defined by the time constant set by resistor R4 and C2, gate capacitor C2 discharges and the FET channel of transistor M2 opens to steer the total current through the series resistors path defined by resistors R1, R2, R3, $R_{n+1}$, in a configuration determined by the state of pushbutton switches SW1, SW2, $SW_n$. The initial shorted state of transistor M2 and the subsequent impedance state of the series resistor path are the only two impedance states in the time domain that are used for detecting the state of pushbutton switches SW1, SW2, $SW_n$. This provides the ability to compensate for an external path resistance (handpiece contacts, cabling, connector resistance) by comparing the difference between these two states. The detection region is similar to that shown in FIG. 89.

Depending on the open or closed state of switches SW1, SW2, $SW_n$ for example, the signal conditioning circuit 202 (e.g., from generator terminals HS and SR shown in FIG. 10 via a conductive pair of the cable 112, 128) would see a different impedance (e.g., resistance). For the embodiment where n=3, and the control circuit 1802 includes three switches SW1, SW2, SW3, for example, there are eight unique switch configurable impedances that can be detected by the signal conditioning circuit 202 based on the states of switches SW1, SW2, SW3, as described in Table 9, below:

TABLE 9

| SW1 | SW2 | SW3 | Impedance |
|---|---|---|---|
| Open | Open | Open | R1 + R2 + R3 + R4 |
| Open | Open | Closed | R1 + R2 + R3 |
| Open | Closed | Open | R1 + R2 + R4 |
| Open | Closed | Closed | R1 + R2 |
| Closed | Open | Open | R1 + R3 + R4 |
| Closed | Open | Closed | R1 + R3 |
| Closed | Closed | Open | R1 + R4 |
| Closed | Closed | Closed | R1 |

The dual protection diodes D1 and D5 placed across the HS/RS terminals of the control circuit 1802 are used to clamp ESD and/or transients coming from the surgical device 1800 and the generator 102 when the surgical device 1800 is connected and disconnected to the generator 102.

Figure 94:
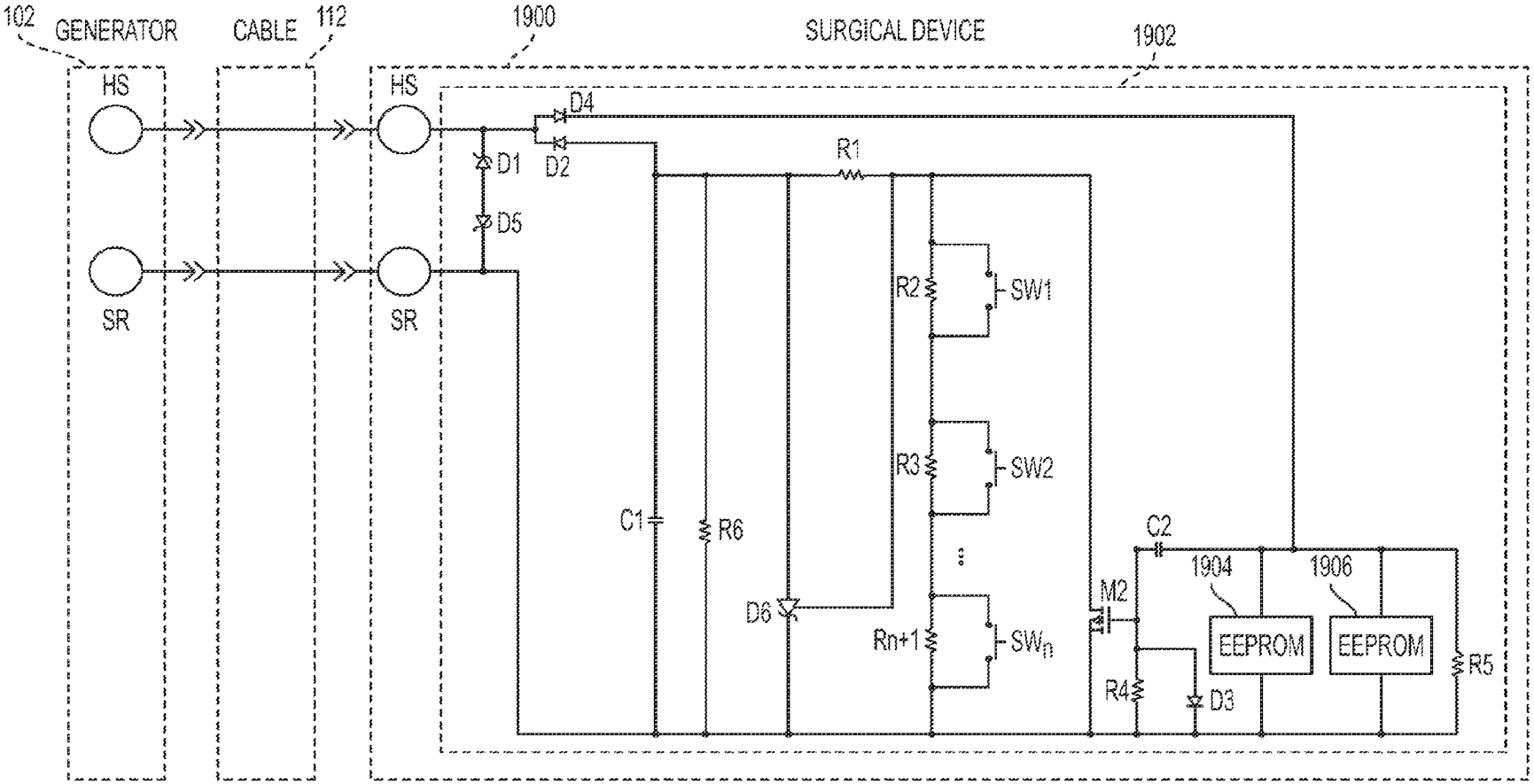
FIG. 94 illustrates one embodiment of a control circuit comprising a serial switched resistance circuit with a precision voltage reference and at least one data element comprising at least one memory device.

FIG. 94 illustrates one embodiment of a control circuit 1902 comprising a serial switched resistance circuit with a precision voltage reference and at least one data element comprising at least one memory device. In one embodiment, the control circuit 1902 is operable by a control signal in the form of a differential current pulse. As previously discussed with respect to the control circuits 1602, 1702, 1802 shown in FIGS. 87, 92, 93, the control circuit 1902 interfaces with a current source (generator), which outputs periodic positive and negative constant current pulses at +/−15 mA, as shown in FIG. 88, for example. The control circuit 1902 utilizes both pulse polarities to detect up to $2^n$ unique switch combinations and also supports communication to one or more memory devices 1904, 1906, such as, for example, two one-wire EEPROM(s).

In one embodiment, the control circuit 1902 may be connected to the generator 102 to receive an interrogation signal (e.g., a bipolar interrogation signal at a predetermined frequency, such as 2 kHz, for example) from the signal conditioning circuit 202 (e.g., from generator terminals HS and SR shown in FIG. 10 via a conductive pair of cable 112, 128). The control circuit 1902 may be coupled to a predetermined number of n switches to provide an indication of the configuration and/or operation of a surgical device 1900 (e.g., an ultrasonic device 104, an electrosurgical device 106, or a combined ultrasonic/electrosurgical device 104/106).

In one embodiment, the control circuit 1902 employs a series variable resistance configurable by up to n pushbutton switches SW1, SW2, $SW_n$. The control circuit 1902 in FIG. 94, however, comprises an additional shunt voltage reference implemented with zener diode D6, which allows higher resistance values to be used for switch detection. Higher resistance values are better suited when a low pushbutton contact resistance cannot be maintained (i.e., silver ink flex circuits). In other respects, the control circuit 1902 is substantially similar in operation to the control circuit 1802 described in connection with FIG. 93, except that the switch configurable impedance is in parallel with resistor R6.

Depending on the open or closed state of switches SW1, SW2, $SW_n$ for example, the signal conditioning circuit 202 (e.g., from generator terminals HS and SR shown in FIG. 10 via a conductive pair of the cable 112, 128) would see a different impedance (e.g., resistance). For the embodiment where n=3 and the control circuit 1902 includes three switches SW1, SW2, SW3, for example, there are eight unique switch configurable impedances that can be detected by the signal conditioning circuit 202 based on the states of switches SW1, SW2, SW3, as described in Table 10, below:

TABLE 10

| SW1 | SW2 | SW3 | Impedance |
|---|---|---|---|
| Open | Open | Open | R6 ‖ (R1 + R2 + R3 + R4) |
| Open | Open | Closed | R6 ‖ (R1 + R2 + R3) |

TABLE 10-continued

| SW1 | SW2 | SW3 | Impedance |
|---|---|---|---|
| Open | Closed | Open | R6 ‖ (R1 + R2 + R4) |
| Open | Closed | Closed | R6 ‖ (R1 + R2) |
| Closed | Open | Open | R6 ‖ (R1 + R3 + R4) |
| Closed | Open | Closed | R6 ‖ (R1 + R3) |
| Closed | Closed | Open | R6 ‖ (R1 + R4) |
| Closed | Closed | Closed | R6 ‖ R1 |

Figure 95:
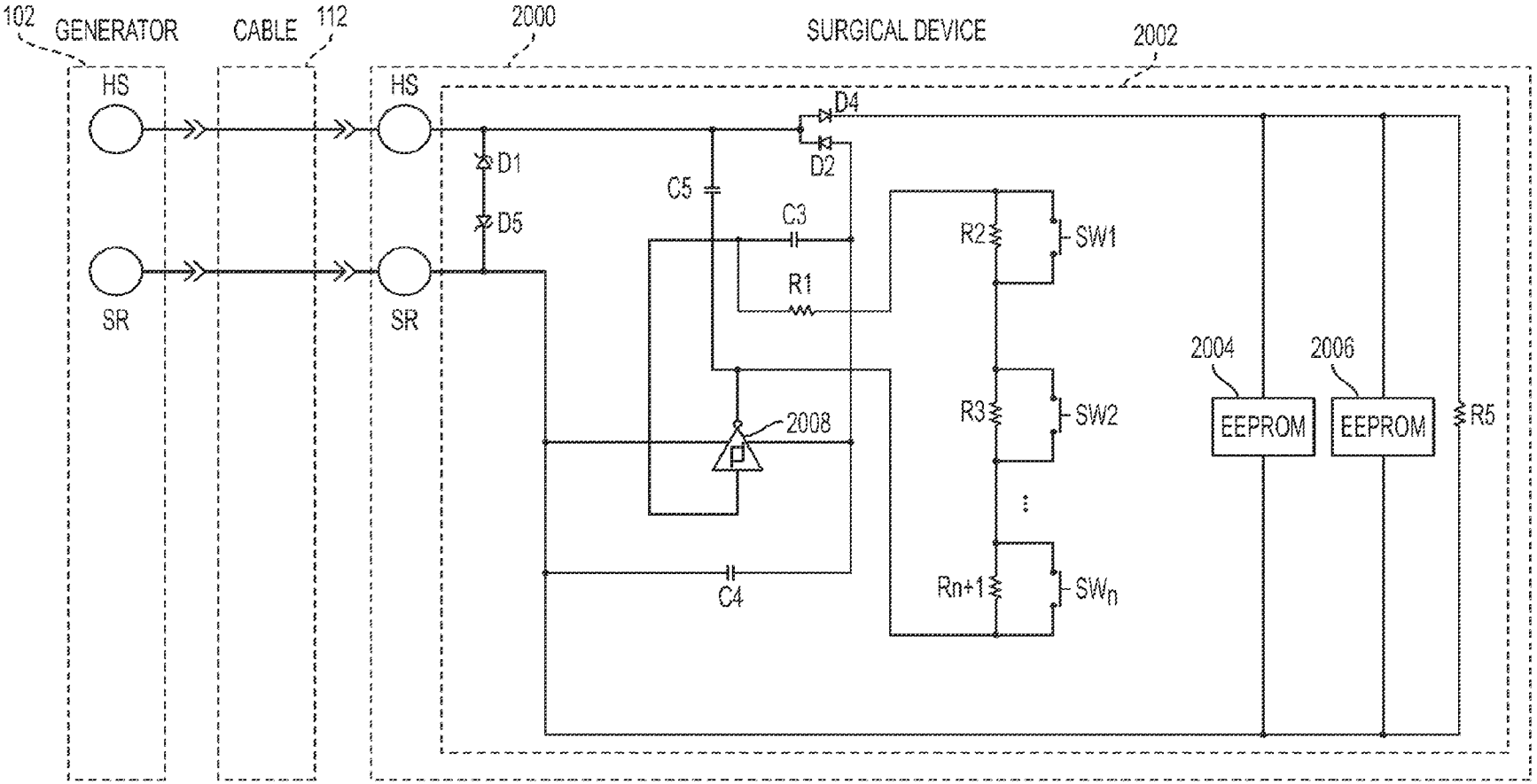
FIG. 95 illustrates one embodiment of a control circuit comprising a variable frequency switched resistance circuit and at least one data element comprising at least one memory device.

FIG. 95 illustrates one embodiment of a control circuit 2002 comprising a variable frequency switched resistance circuit and at least one data element comprising at least one memory device. As previously discussed with respect to the control circuits 1602, 1702, 1802, 1902 shown in FIGS. 87, 92, 93, 94, the control circuit 2002 interfaces with a current source (generator), which outputs periodic positive and negative constant current pulses at +/−15 mA as shown in FIG. 88, for example. The control circuit 2002 utilizes both pulse polarities to detect up to $2^n$ unique switch combinations and also supports communication to one or more memory devices 2004, 2006, such as, for example, two one-wire EEPROM(s).

In one embodiment, the control circuit 2002 may be connected to the generator 102 to receive an interrogation signal (e.g., a bipolar interrogation signal at a predetermined frequency, such as 2 kHz, for example) from the signal conditioning circuit 202 (e.g., from generator terminals HS and SR shown in FIG. 10 via a conductive pair of cable 112, 128). The control circuit 2002 may be coupled to a predetermined number of n switches to provide an indication of the configuration and/or operation of a surgical device 2000 (e.g., an ultrasonic device 104, an electrosurgical device 106, or a combined ultrasonic/electrosurgical device 104/106).

The switched resistance configuration control circuit 2002 employs variable pulse frequency to determine the states of pushbutton switches SW1, SW2, $SW_n$. The control circuit 2002 utilizes both pulse polarities to detect up to $2^n$ unique switch combinations and also supports communication to one or more memory devices 2004, 2006, such as, for example, two one-wire EEPROM(s). The use of variable frequency allows the detection method employed by the control circuit 2002 to be independent of external variable series resistance. A Schmitt trigger circuit 2008 is configured as an RC oscillator, where the frequency of oscillation is determined by the RC time constant set by the pushbutton switch configured resistors R1, R2, R3, $R_{n+1}$ and capacitor C3. An initial negative current pulse charges bulk capacitor C4 to be used as a power supply in order to freewheel between current source pulses. Then the current source generator is configured for zero current during frequency measurement. The output pulses are capacitive coupled by C5 back to the generator comparator. From here the oscillator frequency can be processed to determine the states of the switches SW1, SW2, $SW_n$.

Depending on the open or closed state of switches SW1, SW2, $SW_n$ for example, the signal conditioning circuit 202 (e.g., from generator terminals HS and SR shown in FIG. 10 via a conductive pair of the cable 112, 128) would see a different frequency ($f_0$) based on the switch selectable resistance. For an embodiment where n=3 and the control circuit 2002 includes three switches SW1, SW2, SW3, for example, there are eight unique switch configurable frequencies determined by the RC time constant for the Schmitt trigger 2008 based oscillator set by the by the pushbutton switch configured resistors R1, R2, R3, R4 and capacitor C3. The frequency ($f_0$) seen by the signal conditional conditioning circuit 202 based on the states of switches SW1, SW2, SW3, as described in Table 11, below:

TABLE 11

| SW1 | SW2 | SW3 | RC Time Constant | Frequency (Hz) |
|---|---|---|---|---|
| Open | Open | Open | (R1 + R2 + R3 + R4)C3 | $f_1$ |
| Open | Open | Closed | (R1 + R2 + R3)C3 | $f_2$ |
| Open | Closed | Open | (R1 + R2 + R4)C3 | $f_3$ |
| Open | Closed | Closed | (R1 + R2)C3 | $f_4$ |
| Closed | Open | Open | (R1 + R3 + R4)C3 | $f_5$ |
| Closed | Open | Closed | (R1 + R3)C3 | $f_6$ |
| Closed | Closed | Open | (R1 + R4)C3 | $f_7$ |
| Closed | Closed | Closed | R1C3 | $f_8$ |

Figure 96:
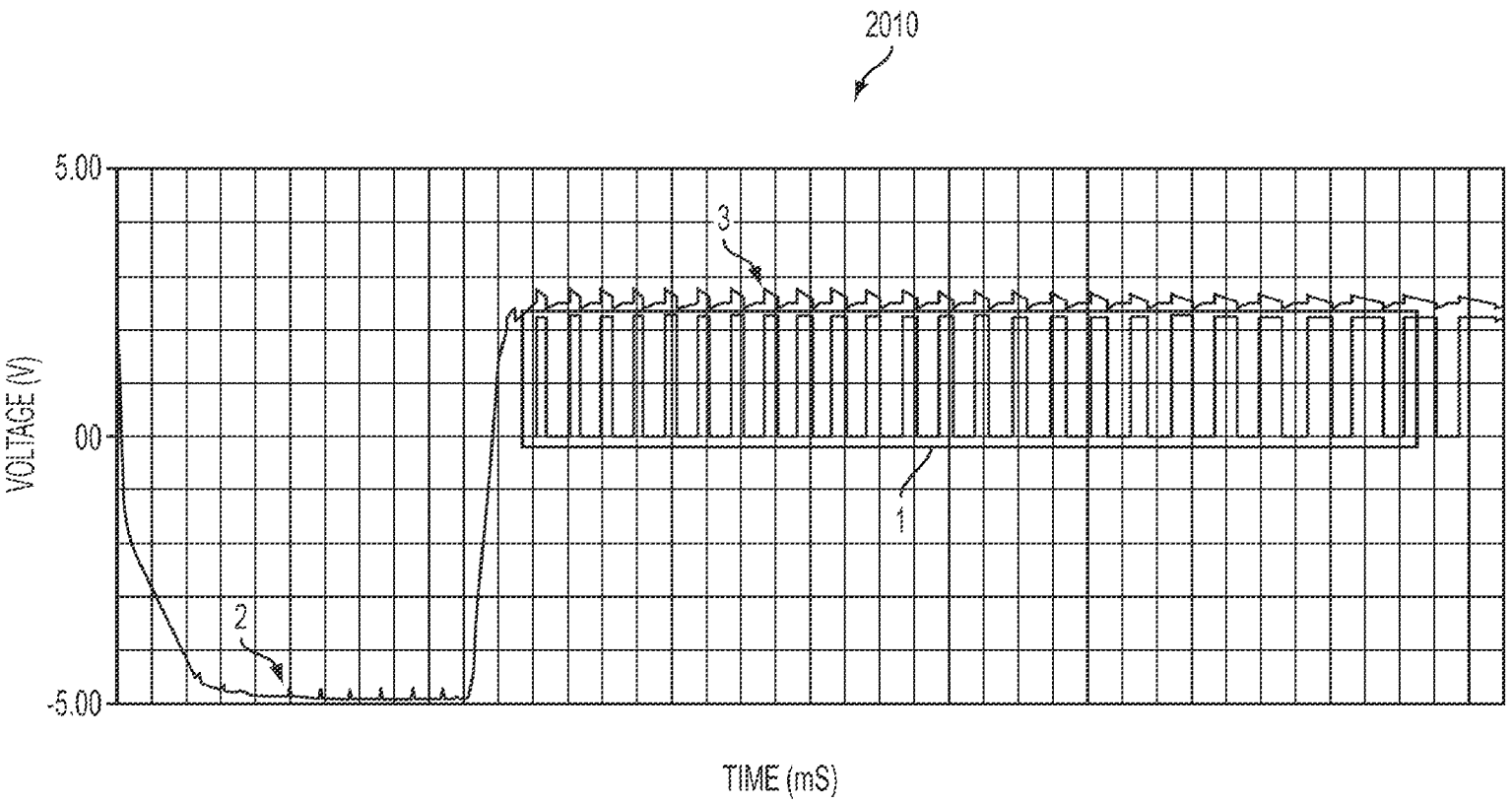
FIG. 96, is a graphical representation of one embodiment of a detection method showing detection regions for the control circuit comprising a variable frequency switched resistance circuit and a memory device, as described in connection with FIG. 95.

FIG. 96, is a graphical representation 2010 of one embodiment of a detection method showing detection regions for the control circuit 2002 comprising a variable frequency switched resistance circuit and a memory device, as described in connection with FIG. 95. Time (mS) is shown along the horizontal axis and Voltage (V) is shown along the vertical axis. As shown in FIG. 96, region 1 shows a pulse output of the generator 102 comparator circuit derived from the RC based oscillator circuit 2008 of control circuit 2001. As shown in Table 11, for n=3, there would be eight unique frequencies representing that state of each pushbutton switch SW1, SW2, SW3. Region 2 shows bulk supply capacitor C4 for the oscillator circuit 2008 being charged by a negative current pulse. Region 3 shows a pulse waveform on the generator 102 comparator input.

Figure 97:
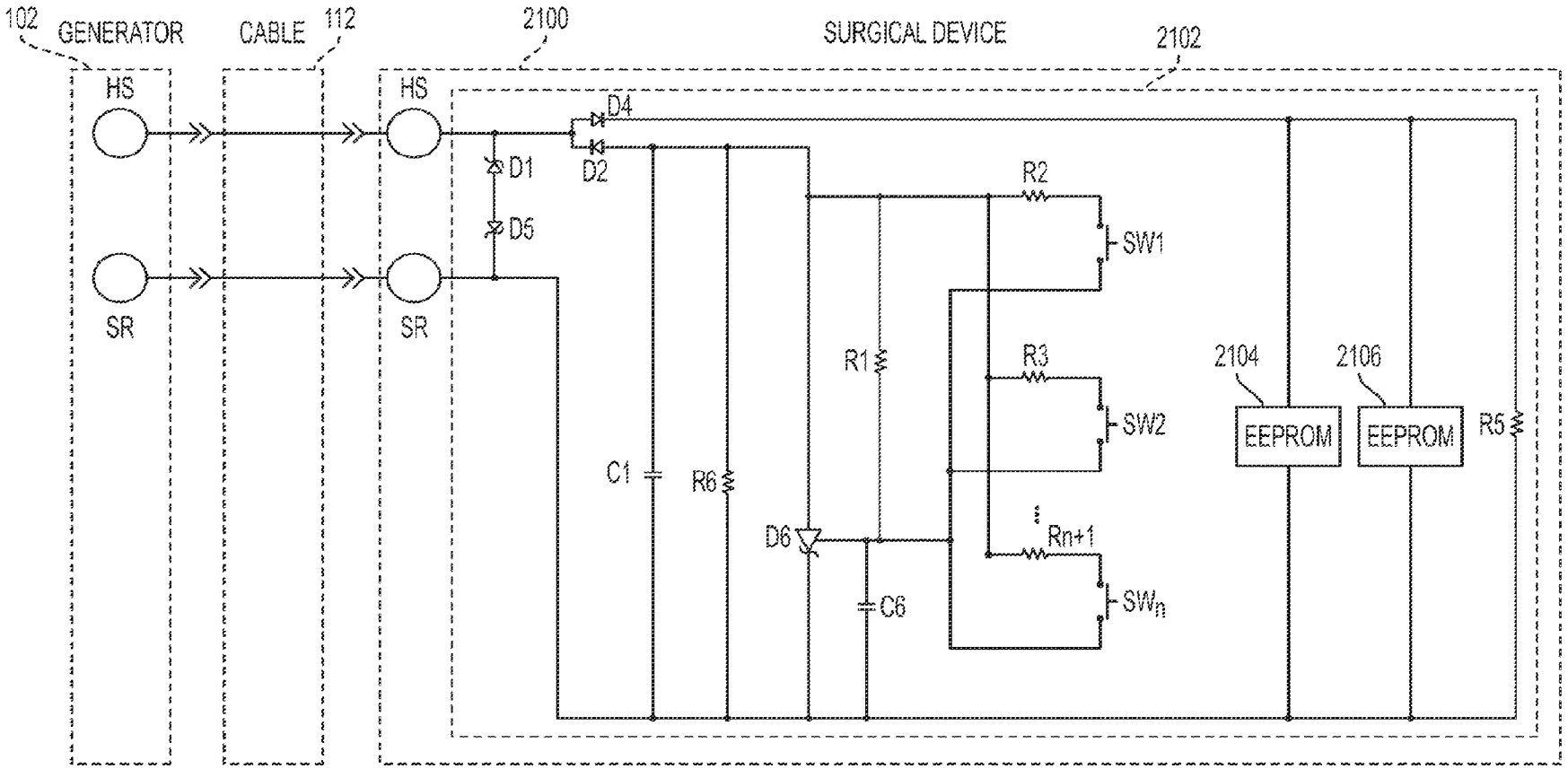
FIG. 97 illustrates one embodiment of a control circuit comprising a parallel switched resistance circuit with a precision voltage reference and at lease one data element comprising at least one memory device employing a variable slope waveform to determine switch states.

FIG. 97 illustrates one embodiment of a control circuit 2102 comprising a parallel switched resistance circuit with a precision voltage reference and at lease one data element comprising at least one memory device employing a variable slope waveform to determine switch states. In one embodiment, the control circuit 2102 is operable by a control signal in the form of a differential current pulse. As previously discussed with respect to the control circuits 1602, 1702, 1802, 1902, 2002 shown in FIGS. 87, 92, 93, 94, and 95, the control circuit 2102 interfaces with a current source (generator), which outputs periodic positive and negative constant current pulses at +/−15 mA as shown in FIG. 88, for example. The control circuit 2102 utilizes both pulse polarities to detect up to $2^n$ unique switch combinations and also supports communication to one or more memory devices 2104, 2106, such as, for example. two one-wire EEPROM(s).

In one embodiment, the control circuit 2102 may be connected to the generator 102 to receive an interrogation signal (e.g., a bipolar interrogation signal at a predetermined frequency, such as 2 kHz, for example) from the signal conditioning circuit 202 (e.g., from generator terminals HS and SR shown in FIG. 10 via a conductive pair of cable 112, 128). The control circuit 2102 may be coupled to a predetermined number of n switches to provide an indication of the configuration and/or operation of a surgical device 2100 (e.g., an ultrasonic device 104, an electrosurgical device 106, or a combined ultrasonic/electrosurgical device 104/106).

Figure 98:
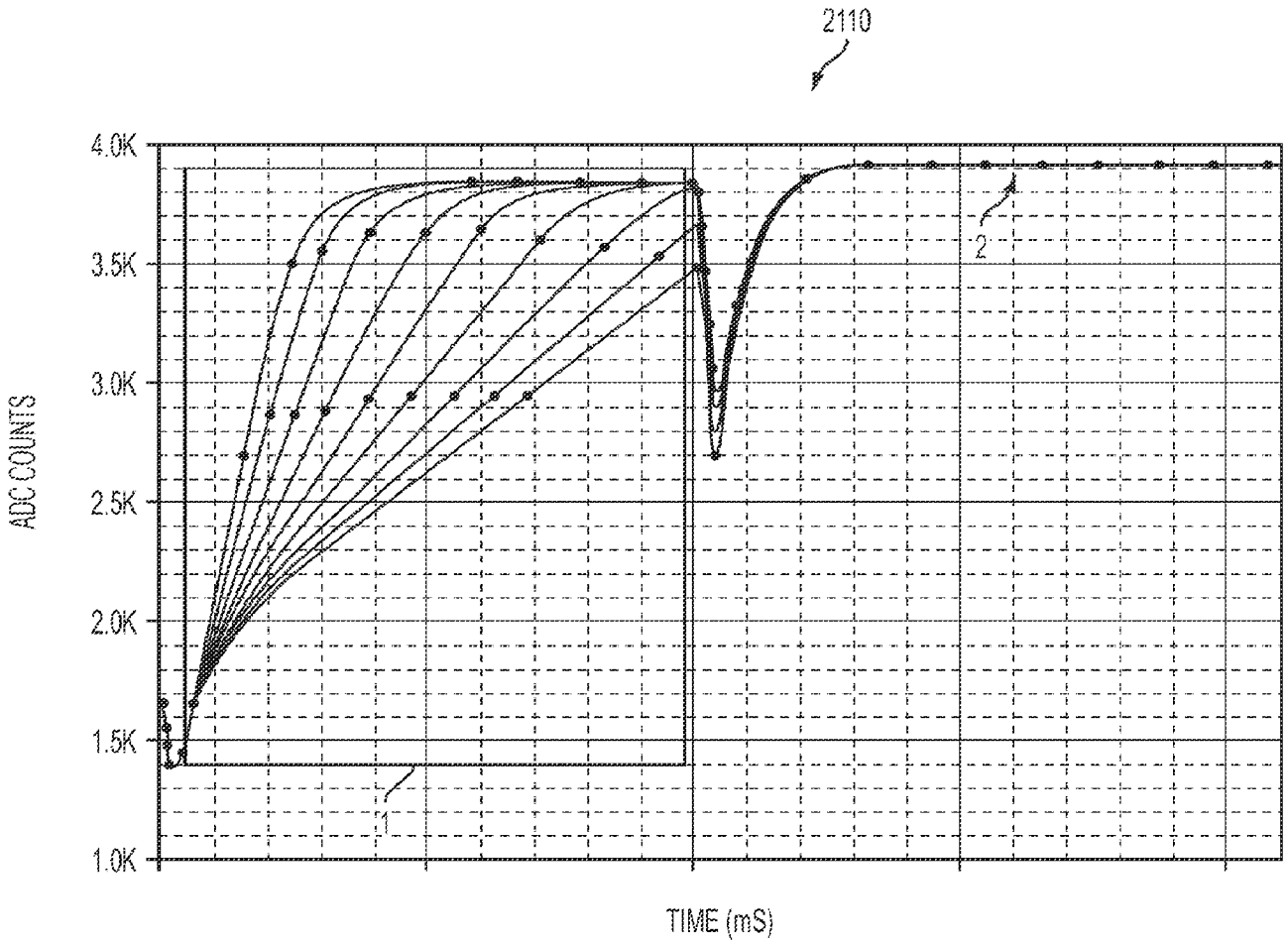
FIG. 98 is a graphical representation of one embodiment of a detection method showing detection regions for the control circuit comprising a variable ramp/slope switched resistance circuit and a memory device, as described in connection with FIG. 97.

The control circuit 2102 employs a variable slope waveform to determine the states of pushbutton switches SW1, SW2, $SW_n$. A constant current pulse source drives a current into a capacitive load, e.g., capacitor C6 to generate a slope dependent on the capacitance value of capacitor C6. Using a shunt regulator D6 and charged capacitor combination creates an active circuit that varies the slope by varying the switch configurable resistance R1, R2, R3, $R_{n+1}$ rather than varying the capacitance C6. Each pushbutton switch SW1, SW2, $SW_n$ state creates a unique ramp slope as shown in FIG. 98 based on a unique time constant determined by a combination of capacitor C6 and resistance R1, R2, R3, $R_{n+1}$ as selected by switches SW1, SW2, $SW_n$.

Depending on the open or closed state of switches SW1, SW2, $SW_n$ for example, the signal conditioning circuit 202 (e.g., from generator terminals HS and SR shown in FIG. 10 via a conductive pair of the cable 112, 128) would see a different ramp slope based on a unique time constant based on the switch selectable resistance. For an embodiment where n=3 and the control circuit 2102 includes three switches SW1, SW2, SW3, for example, there are eight unique switch configurable ramp slopes determined by the RC time constant determined by the pushbutton switch configured resistors R1, R2, R3, R4 and capacitor C6. The ramp slope seen by the signal conditional conditioning circuit 202 based on the state of each switch combination SW1, SW2, SW3, as described in Table 12, below:

TABLE 12

| SW1 | SW2 | SW3 | RC Time Constant | Ramp Slope (V/t) |
|---|---|---|---|---|
| Open | Open | Open | R1C6 | $Ramp/Slope_1$ |
| Open | Open | Closed | (R1 ‖ R4)C6 | $Ramp/Slope_2$ |
| Open | Closed | Open | (R1 ‖ R3)C6 | $Ramp/Slope_3$ |
| Open | Closed | Closed | (R1 ‖ R3 ‖ R4)C6 | $Ramp/Slope_4$ |
| Closed | Open | Open | (R1 ‖ R2)C6 | $Ramp/Slope_5$ |
| Closed | Open | Closed | (R1 ‖ R2 ‖ R4)C6 | $Ramp/Slope_6$ |
| Closed | Closed | Open | (R1 ‖ R2 ‖ R3)C6 | $Ramp/Slope_7$ |
| Closed | Closed | Closed | (R1 ‖ R2 ‖ R3 ‖ R4)C3 | $Ramp/Slope_8$ |

FIG. 98 is a graphical representation 2110 of one embodiment of a detection method showing detection regions for the control circuit 2102 comprising a variable ramp/slope switched resistance circuit and a memory device, as described in connection with FIG. 97. Time (mS) is shown along the horizontal axis and ADC counts is shown along the vertical axis. Region 1 shows the variable slope controlled by the time constant determined by capacitor C6 and switch SW1, SW2, SW3 configurable resistance R1, R2, R3, R4. Each switch SW1, SW2, SW3 state provides a unique slope. Region 2 is the time region to reset the RC time constant. Simulation modeling confirmed immunity to very high contact corrosion resistance. Nevertheless, time based measurement may be susceptible to cable inductance and capacitance due to fast transient edges of signaling. Accordingly, compensation circuits for cable inductance and capacitance due to fast transient edges of signaling are contemplated within this disclosure. Slope detection would minimize risk of false switch state detection. The current pulse rising and falling edges may need to be slower than the lowest resonance frequency of the cable, for example. The embodiments, however, are not limited in this context.

Figure 99:
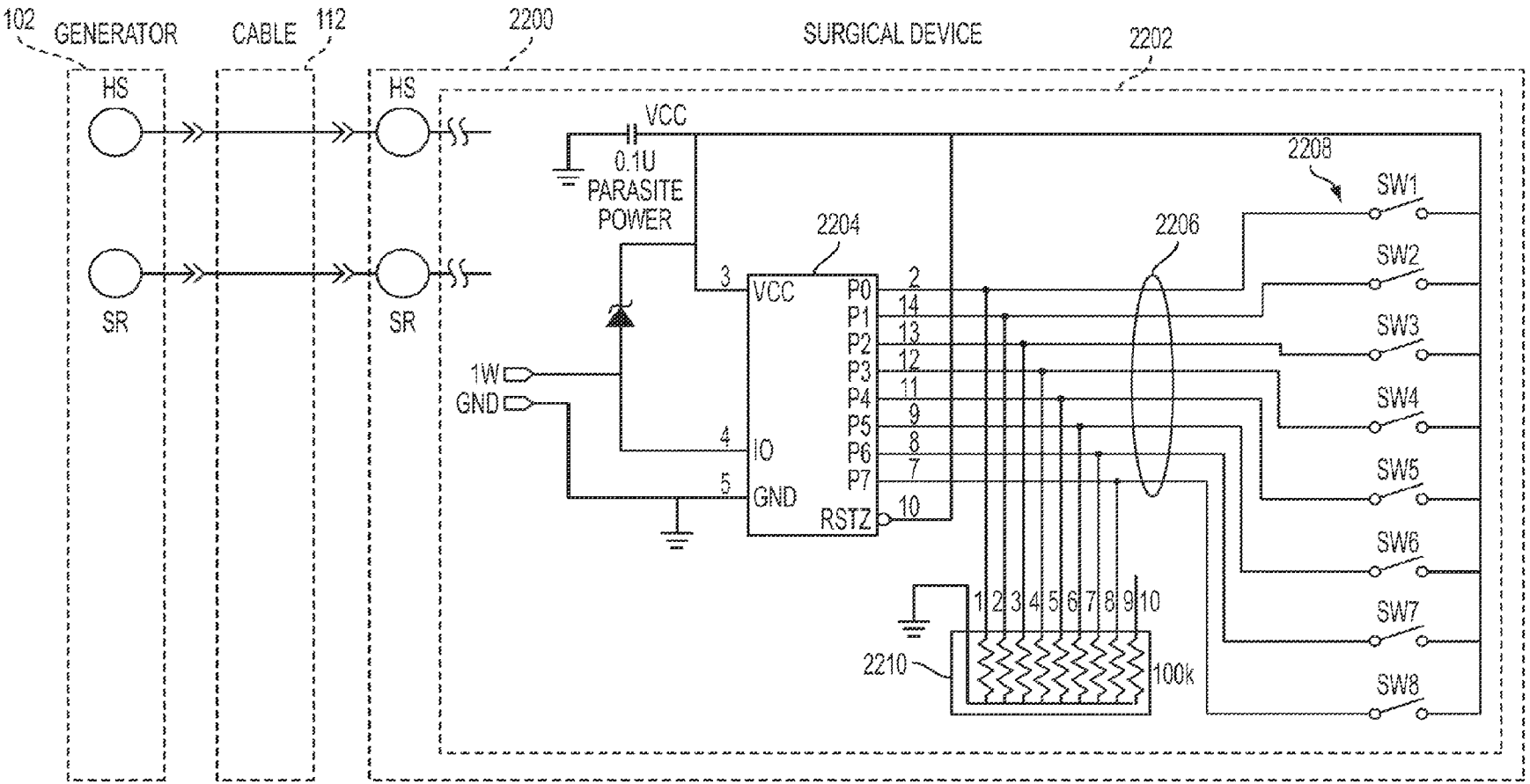
FIG. 99 illustrates one embodiment of a control circuit comprising a one-wire multi-switch input device.

FIG. 99 illustrates one embodiment of a control circuit 2202 comprising a one-wire multi-switch input device. As previously discussed with respect to the control circuits 1602, 1702, 1802, 1902, 2002, 2102 shown in FIGS. 87, 92, 93, 94, 95, and 97, the control circuit 2202 interfaces with a current source (generator), which outputs periodic positive and negative constant current pulses at +/−15 mA as shown in FIG. 88, for example. The control circuit 2202 utilizes both pulse polarities to detect up to $2^n$ unique switch combinations and also supports communication to one or more memory devices, such as, for example, two one-wire EEPROM(s), which are not shown in FIG. 99 for conciseness and clarity, but may be included in various aspects of this embodiment. Also, diode pair D2/D4 for bidirectional power are not shown in FIG. 99 for conciseness and clarity, but may be included in various aspects of this embodiment.

In one embodiment, the control circuit 2202 may be connected to the generator 102 to receive an interrogation signal (e.g., a bipolar interrogation signal at a predetermined frequency, such as 2 kHz, for example) from the signal conditioning circuit 202 (e.g., from generator terminals HS and SR shown in FIG. 10 via a conductive pair of cable 112, 128). The control circuit 2202 may be coupled to a predetermined number of n switches to provide an indication of the configuration and/or operation of a surgical device 2200 (e.g., an ultrasonic device 104, an electrosurgical device 106, or a combined ultrasonic/electrosurgical device 104/106).

In one embodiment, the one-wire multi-switch input device of the control circuit 2202 employs a one-wire port expansion device 2204 such as a Maxim DS2408 8-channel, programmable I/O one-wire integrated circuit available from Maxim Integrated Products, Inc., Sunnyvale, Calif., or equivalents thereof, known under the trade name "1-Wire." The port expansion device 2204 may be powered from the negative current pulse of the generator 102. The port expansion device 2204 complies with the one-wire communication protocol to accommodate up to eight switch inputs 2208. The port expansion device 2204 outputs are configured as open-drain and provide an on resistance of 100Ω max. A robust channel-access communication protocol ensures that the output-setting changes occur error-free. A data-valid strobe output can be used to latch port expansion device 2204 logic states into external circuitry such as a D/A converter (DAC) or microcontroller data bus. The port expansion device 2204 selects one of eight switches SW1-SW8 to select one of eight corresponding resistors 1-8 in resistor bank 2210. In one embodiment, for example, a detection method comprises reading any one of switches SW1-SW8 state using the one-wire communication protocol of the control circuit 2202 utilizing the same software functionality used to read the surgical device 2200 EEPROMs. In other embodiments, the control circuit 2202 can be expanded to read additional switch inputs. In one embodiment, cyclic redundancy code (CRC) error checking may be employed to eliminate or minimize uncertainty of switch states. It may be possible that one-wire communications may be susceptible to activation noise from other electrosurgical instruments, accordingly, compensation circuits and techniques to minimize interference from such electrosurgical instruments are contemplated within this disclosure.

Although the various embodiments of the devices have been described herein in connection with certain disclosed embodiments, many modifications and variations to those embodiments may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

We claim:

1. A surgical device, the surgical device comprising:

[an end effector to act on tissue; and]

a control circuit configured for communication with a surgical generator, the control circuit comprising:

a conductor pair to communicate with the surgical generator;

a first circuit portion comprising:

a first switch configured to switch between an open state and a closed state;

a first resistor coupled in parallel with the first switch;

a second switch configured to switch between an open state and a closed state; and a second resistor coupled in parallel with the second switch, wherein a combination of the first switch and the first resistor is coupled [in series] with a combination of the second switch and the second resistor;

[a voltage reference coupled in parallel with the first circuit portion.]

wherein the control circuit is configured to receive from the generator and over the conductor pair an interrogation signal, wherein a state of at least one of the first switch or the second switch is determined from at least one characteristic of the interrogation signal;

a capacitor coupled in parallel with the first circuit portion;

a resistor coupled in [series] *parallel* with the first circuit portion; and a memory device coupled to the first circuit portion.

2. The surgical device of claim 1, wherein the state of the first switch is determinable based on a slope of a voltage on the capacitor.

3. The surgical device of claim 1, comprising an oscillator in communication with the at least one switch, wherein the state of the at least one switch is determinable based on a frequency of the oscillator.

4. The surgical device of claim 1, comprising a one-wire multi-switch input device coupled to the at least one switch, wherein the state of the at least one switch is communicated to the generator over a one-wire communication protocol.

5. The surgical device of claim 1, wherein the interrogation signal is a differential constant current pulse having a positive phase and a negative phase.

6. The surgical device of claim 1, wherein the memory device comprises at least one one-wire electrically erasable programmable read only memory (EEPROM).

7. The surgical device of claim 5, wherein the positive phase of the interrogation signal is a positive transition of the differential constant current pulse and the negative phase of the differential constant current pulse is a negative transition of the differential constant current pulse.

*8. The surgical device of claim 1, further comprising an end effector to act on tissue.*

*9. The surgical device of claim 1, wherein the first resistor is coupled in series with a combination of the second switch and the second resistor.*

*10. The surgical device of claim 1, further comprising a rectifier coupled in parallel with the first circuit portion.*

*11. The surgical device of claim 1, further comprising a voltage reference.*

*12. The surgical device of claim 1, further comprising a resister coupled in series with the first circuit portion.*

*13. A surgical device, the surgical device comprising:*

*a control circuit configured for communication with a surgical generator, the control circuit comprising:*

*a conductor pair to communicate with the surgical generator;*

*a first circuit portion comprising:*

*a first switch configured to switch between an open state and a closed state;*

*a first resistor coupled with the first switch;*

*a second switch configured to switch between an open state and a closed state; and a second resistor coupled with the second switch, wherein a combination of the first switch and the first resistor is coupled with a combination of the second switch and the second resistor;*

*wherein the control circuit is configured to receive from the generator and over the conductor pair an interrogation signal, wherein a state of at least one of the first switch or the second switch is determined from at least one characteristic of the interrogation signal;*

*a capacitor coupled in parallel with the first circuit portion;*

*a resistor coupled in parallel with the first circuit portion; and*

*a memory device coupled to the first circuit portion.*

*14. The surgical device of claim 13, further comprising a rectifier coupled in parallel with the first circuit portion.*

*15. The surgical device of claim 13, wherein the state of the first switch is determinable based on a slope of a voltage on the capacitor.*

*16. The surgical device of claim 13, comprising an oscillator in communication with the at least one switch, wherein the state of the at least one switch is determinable based on a frequency of the oscillator.*

*17. The surgical device of claim 13, comprising a one-wire multi-switch input device coupled to the at least one switch, wherein the state of the at least one switch is communicated to the generator over a one-wire communication protocol.*

*18. The surgical device of claim 13, wherein the interrogation signal is a differential constant current pulse having a positive phase and a negative phase.*

*19. The surgical device of claim 13, wherein the memory device comprises at least one one-wire electrically erasable programmable read only memory (EEPROM).*

*20. The surgical device of claim 18, wherein the positive phase of the interrogation signal is a positive transition of the differential constant current pulse and the negative phase of the differential constant current pulse is a negative transition of the differential constant current pulse.*

*21. A surgical device, the surgical device comprising:*

*a control circuit configured for communication with a surgical generator, the control circuit comprising:*

*a conductor pair to communicate with the surgical generator;*

*a first circuit portion comprising:*

*a first switch configured to switch between an open state and a closed state;*

*a first resistor coupled in parallel with the first switch;*

*a second switch configured to switch between an open state and a closed state; and*

*a second resistor coupled in parallel with the second switch, wherein at least one of the first switch or the*

*first resistor is coupled in series with at least one of the second switch or the second resistor;*

*wherein the control circuit is configured to receive from the generator and over the conductor pair an interrogation signal, wherein a state of at least one of the first switch or the second switch is determined from at least one characteristic of the interrogation signal;*

*a capacitor coupled in parallel with the first circuit portion;*

*a resistor coupled in parallel with the first circuit portion; and*

*a memory device coupled to the first circuit portion.*

*22. The surgical device of claim 21, further comprising a rectifier coupled in parallel with the first circuit portion.*

*23. The surgical device of claim 21, wherein the state of the first switch is determinable based on a slope of a voltage on the capacitor.*

*24. The surgical device of claim 21, comprising an oscillator in communication with the at least one switch, wherein the state of the at least one switch is determinable based on a frequency of the oscillator.*

*25. The surgical device of claim 21, comprising a one-wire multi-switch input device coupled to the at least one switch, wherein the state of the at least one switch is communicated to the generator over a one-wire communication protocol.*

*26. The surgical device of claim 21, wherein the interrogation signal is a differential constant current pulse having a positive phase and a negative phase.*

*27. The surgical device of claim 21, wherein the memory device comprises at least one one-wire electrically erasable programmable read only memory (EEPROM).*

*28. The surgical device of claim 27, wherein the positive phase of the interrogation signal is a positive transition of the differential constant current pulse and the negative phase of the differential constant current pulse is a negative transition of the differential constant current pulse.*

* * * * *